United States Patent
Zhao et al.

(10) Patent No.: US 10,323,023 B2
(45) Date of Patent: *Jun. 18, 2019

(54) RHO-ASSOCIATED PROTEIN KINASE INHIBITOR, PHARMACEUTICAL COMPOSITION COMPRISING THE SAME, AS WELL AS PREPARATION METHOD AND USE THEREOF

(71) Applicant: Beijing Tide Pharmaceutical Co., Ltd., Beijing (CN)

(72) Inventors: Yanping Zhao, Beijing (CN); Hongjun Wang, Beijing (CN); Gong Li, Beijing (CN); Yuanyuan Jiang, Beijing (CN); Xiang Li, Beijing (CN); Liying Zhou, Beijing (CN); Yanan Liu, Beijing (CN)

(73) Assignee: Beijing Tide Pharmaceutical Co., Ltd., Beijing (CN)

( * ) Notice: Subject to any disclaimer, the term of this patent is extended or adjusted under 35 U.S.C. 154(b) by 0 days.

This patent is subject to a terminal disclaimer.

(21) Appl. No.: 15/719,934

(22) Filed: Sep. 29, 2017

(65) Prior Publication Data

US 2019/0002442 A1  Jan. 3, 2019

Related U.S. Application Data

(63) Continuation-in-part of application No. PCT/CN2017/091086, filed on Jun. 30, 2017.

(51) Int. Cl.

| | |
|---|---|
| *C07D 403/14* | (2006.01) |
| *C07D 487/04* | (2006.01) |
| *C07D 405/14* | (2006.01) |
| *C07D 413/14* | (2006.01) |
| *A61K 31/506* | (2006.01) |
| *A61K 31/517* | (2006.01) |
| *A61K 31/519* | (2006.01) |
| *C07D 409/14* | (2006.01) |
| *C07D 417/14* | (2006.01) |
| *C07D 495/04* | (2006.01) |
| *C07D 471/04* | (2006.01) |
| *A61K 31/53* | (2006.01) |

(52) U.S. Cl.
CPC .......... *C07D 403/14* (2013.01); *A61K 31/506* (2013.01); *A61K 31/517* (2013.01); *A61K 31/519* (2013.01); *A61K 31/53* (2013.01); *C07D 405/14* (2013.01); *C07D 409/14* (2013.01); *C07D 413/14* (2013.01); *C07D 417/14* (2013.01); *C07D 471/04* (2013.01); *C07D 487/04* (2013.01); *C07D 495/04* (2013.01)

(58) Field of Classification Search
CPC ............................ C07D 403/14; C07D 487/04
See application file for complete search history.

(56) References Cited

U.S. PATENT DOCUMENTS 9,783,536 B2  10/2017  Furuyama et al.
2012/0202793 A1  8/2012  Sweetnam et al.

FOREIGN PATENT DOCUMENTS

| CN | 101228161 | 7/2008 |
|---|---|---|
| CN | 104334553 | 2/2015 |
| CN | 104903320 | 9/2015 |
| CN | 106478651 | 3/2017 |
| EP | 2433636 | 3/2012 |
| WO | 2001/040215 | 6/2001 |
| WO | 02/22607 | 3/2002 |
| WO | 02/057259 | 7/2002 |
| WO | 02/076976 | 10/2002 |
| WO | 03/030909 | 4/2003 |
| WO | 03/059913 | 7/2003 |
| WO | 2004/046118 | 6/2004 |
| WO | 2004/048365 | 6/2004 |
| WO | 2006/105081 | 10/2006 |
| WO | 2006127587 | 11/2006 |
| WO | 2006/135383 | 12/2006 |
| WO | 2007/076161 | 7/2007 |
| WO | 2008/054599 | 5/2008 |
| WO | 2012/040499 | 3/2012 |
| WO | 2013156608 | 10/2013 |
| WO | 2014/052699 | 4/2014 |
| WO | 2014/055996 | 4/2014 |
| WO | 2014109414 | 7/2014 |
| WO | 2015/054317 | 4/2015 |
| WO | 2015/157556 | 10/2015 |
| WO | 2016/057834 | 4/2016 |
| WO | 2016/138335 | 9/2016 |
| WO | 2016/160833 | 10/2016 |

(Continued)

OTHER PUBLICATIONS

Zhao et al., "Rho-associated protein kinase inhibitor, pharmaceutical composition comprising the same, as well as preparation method and use thereof." U.S. Appl. No. 15/719,867, filed Sep. 29, 2017.

(Continued)

*Primary Examiner* — Golam M Shameem
(74) *Attorney, Agent, or Firm* — Robin L. Teskin; LeClairRyan PLLC

(57) ABSTRACT

The present invention relates to a Rho-associated protein kinase inhibitor of Formula (I), a pharmaceutical composition comprising the same, a preparation method thereof, and use thereof for the prevention or treatment of a disease mediated by the Rho-associated protein kinase (ROCK).

Formula (I)

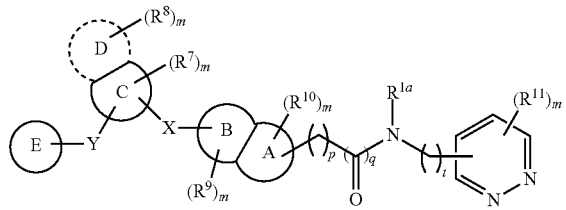

29 Claims, No Drawings

(56) References Cited

FOREIGN PATENT DOCUMENTS

| WO | 2016/210330 | 12/2016 |
|----|-------------|---------|
| WO | 2016/210331 | 12/2016 |
| WO | 2017/048675 | 3/2017  |
| WO | 2017/205536 | 11/2017 |
| WO | 2018/039539 | 3/2018  |

OTHER PUBLICATIONS

Wolff, ME, Burger's Medicinal Chemistry, Drug Discovery, and Development, 5th Edition., vol. 1: Principles and Practice, John Wiley & Sons, 1995, 975-76. (Year: 1996). 4 pages.

Banker, GS, et al. Modern Pharmaceutics, Marcel Dekker, New York, 1996, pp. 596 and 451 (Year: 1996). 3 pages.

West, AR. Solid State Chemistry and Its Applications, Wiley, New York, 1988. 358 and 365. (Year: 1988). 3 pages.

RHO-ASSOCIATED PROTEIN KINASE INHIBITOR, PHARMACEUTICAL COMPOSITION COMPRISING THE SAME, AS WELL AS PREPARATION METHOD AND USE THEREOF

RELATED APPLICATIONS

This application is a continuation-in-part of PCT Application No. PCT/CN2017/091086, filed Jun. 30, 2017, the disclosure of which is herein incorporated by reference in its entirety.

FIELD OF THE INVENTION

The present invention relates to a Rho-associated protein kinase inhibitor, a pharmaceutical composition comprising the same, a preparation method thereof, and use thereof for the prevention or treatment of a disease mediated by the Rho-associated protein kinase (ROCK).

BACKGROUND OF THE INVENTION

Rho-associated protein kinase (ROCK) is a serine/threonine kinase from the AGC kinase family, and comprises two isoforms, ROCK1 and ROCK2. ROCK1 and ROCK2 are expressed and regulated differently in specific tissues. For example, ROCK1 is ubiquitously expressed at a relatively high level, while ROCK2 is preferentially expressed in heart, brain and skeletal muscle. ROCK is the first downstream effector of the Rho protein discovered, and its biological function is achieved by phosphorylating the downstream effector proteins (MLC, Lin-11, Isl-1, LIMK, ERM, MARCKS, CRMP-2 etc.). Studies have shown that various diseases (e.g., pulmonary fibrosis, cardiac-cerebral vascular disease, neurological disease and cancer etc.) are related to the pathways mediated by ROCK. As such, ROCK is considered as an important target in the development of novel drugs.

However, at present, only Fasudil is approved as a ROCK inhibitor for the treatment of cerebral vasospasm and ischemia in Japan. Although various small molecule ROCK inhibitors have been reported by now, most of them are for topical ophthalmic application, and no small molecule ROCK inhibitor suitable for systemic administration is available.

SUMMARY OF THE INVENTION

The present invention provides a compound for use as a ROCK (preferably ROCK2) inhibitor, it has superior properties, such as excellent inhibitory activity on ROCK (preferably ROCk2), good selectivity (higher selectivity towards ROCK2 as compared with ROCK1), better physicochemical properties (e.g., solubility, physical and/or chemical stability), improved pharmacokinetic properties (e.g., improved bioavailability, proper half-life and duration of action), improved safety (low toxicity and/or less side effects, wide therapeutic window), and the like.

According to an aspect of the present invention, a compound or a pharmaceutically acceptable salt, ester, stereoisomer, polymorph, solvate, N-oxide, isotopically labeled compound, metabolite or prodrug thereof is provided, wherein the compound has the structure of Formula (I):

Formula (I)

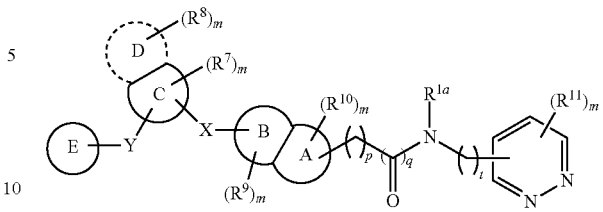

wherein:

X and Y are each independently selected from the group consisting of a direct bond, $C(=O)$, $O$, $S(=O)_i$ and $NR$;

R is selected from the group consisting of H, $C_{1-6}$ alkyl, $C_{2-6}$ alkenyl, $C_{2-6}$ alkynyl, saturated or partially unsaturated $C_{3-10}$ cyclic hydrocarbyl, saturated or partially unsaturated 3- to 10-membered heterocyclyl, $C_{6-10}$ aryl, 5- to 14-membered heteroaryl and $C_{6-12}$ aralkyl, and at most 2 ring members in the cyclic hydrocarbyl and heterocyclyl are $C(=O)$;

ring A and ring B are each independently selected from the group consisting of saturated or partially unsaturated $C_{3-10}$ hydrocarbon ring, saturated or partially unsaturated 3- to 10-membered heterocycle, $C_{6-10}$ aromatic ring and 5- to 14-membered heteroaromatic ring, and at most 2 ring members in the hydrocarbon ring and heterocycle are $C(=O)$;

ring C is selected from the group consisting of saturated or partially unsaturated $C_{3-10}$ hydrocarbon ring, saturated or partially unsaturated 3- to 10-membered heterocycle, $C_{6-10}$ aromatic ring and 5- to 14-membered heteroaromatic ring, and at most 2 ring members in the hydrocarbon ring and heterocycle are $C(=O)$;

ring D is absent, or is selected from the group consisting of saturated or partially unsaturated $C_{3-10}$ hydrocarbon ring, saturated or partially unsaturated 3- to 10-membered heterocycle, $C_{6-10}$ aromatic ring and 5- to 14-membered heteroaromatic ring, and at most 2 ring members in the hydrocarbon ring and heterocycle are $C(=O)$;

ring E is selected from the group consisting of

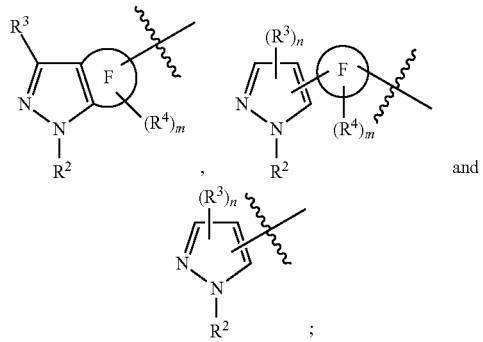

ring F is selected from the group consisting of saturated or partially unsaturated $C_{3-10}$ hydrocarbon ring, saturated or partially unsaturated 3- to 10-membered heterocycle, $C_{6-10}$ aromatic ring and 5- to 14-membered heteroaromatic ring, and at most 2 ring members in the hydrocarbon ring and heterocycle are $C(=O)$;

$R^{1a}$ is selected from the group consisting of H, halogen, amino, cyano, nitro, $C_{1-6}$ alkyl, $C_{2-6}$ alkenyl, $C_{2-6}$ alkynyl, $C_{3-10}$ cyclic hydrocarbyl, 3- to 10-membered heterocyclyl, $C_{6-10}$ aryl, 5- to 14-membered heteroaryl, $C_{6-12}$ aralkyl, —C(=O)R$^5$, —OC(=O)R$^5$, —C(=O)OR$^5$, —OR$^5$, —SR$^5$, —S(=O)R$^5$, —S(=O)$_2$R$^5$, —S(=O)$_2$NR$^5$R$^6$, —NR$^5$R$^6$, —C(=O)NR$^5$R$^6$, —NR$^5$—C(=O)R$^6$, —NR$^5$—C(=O)OR$^6$, —NR$^5$—S(=O)$_2$—R$^6$, —NR$^5$—C(=O)—NR$^5$R$^6$, —C$_{1-6}$ alkylene-NR$^5$R$^6$, —C$_{1-6}$ alkylene-OR$^5$ and —O—C$_{1-6}$ alkylene-NR$^5$R$^6$;

R$^2$, R$^3$, R$^4$, R$^7$, R$^8$, R$^9$, R$^{10}$ and R$^{11}$, at each occurrence, are each independently selected from the group consisting of H, halogen, amino, cyano, nitro, $C_{1-6}$ alkyl, $C_{2-6}$ alkenyl, $C_{2-6}$ alkynyl, $C_{3-10}$ cyclic hydrocarbyl, 3- to 10-membered heterocyclyl, $C_{6-10}$ aryl, 5- to 14-membered heteroaryl, $C_{6-12}$ aralkyl, —C(=O)R$^5$, —OC(=O)R$^5$, —C(=O)OR$^5$, —OR$^5$, —SR$^5$, —S(=O)R$^5$, —S(=O)$_2$R$^5$, —S(=O)$_2$NR$^5$R$^6$, —NR$^5$R$^6$, —C(=O)NR$^5$R$^6$, —NR$^5$—C(=O)R$^6$, —NR$^5$—C(=O)OR$^6$, —NR$^5$—S(=O)$_2$—R$^6$, —NR$^5$—C(=O)—NR$^5$R$^6$, —C$_{1-6}$ alkylene-NR$^5$R$^6$ and —O—C$_{1-6}$ alkylene-NR$^5$R$^6$;

alternatively, when the pyridazine ring in Formula (I) is substituted with two R$^{11}$, and the two R$^{11}$ are at ortho positions on the pyridazine ring, the two R$^{11}$ together with the carbon atoms to which they are attached form $C_{4-10}$ cyclic hydrocarbyl, 4- to 10-membered heterocyclyl, $C_{6-10}$ aryl, or 5- to 14-membered heteroaryl;

R$^5$ and R$^6$, at each occurrence, are each independently selected from the group consisting of H, $C_{1-6}$ alkyl, $C_{3-10}$ cyclic hydrocarbyl, 3- to 10-membered heterocyclyl, $C_{6-10}$ aryl, 5- to 14-membered heteroaryl and $C_{6-12}$ aralkyl;

the above alkyl, alkylene, alkenyl, alkynyl, cyclic hydrocarbyl, hydrocarbon ring, heterocyclyl, heterocycle, aryl, aromatic ring, heteroaryl, heteroaromatic ring and aralkyl, at each occurrence, are each optionally substituted with one or more substituents independently selected from the group consisting of: halogen, hydroxyl, oxo, amino, cyano, nitro, $C_{1-6}$ alkyl, $C_{3-6}$ cyclic hydrocarbyl, 3- to 10-membered heterocyclyl, $C_{6-10}$ aryl, 5- to 14-membered heteroaryl, $C_{6-12}$ aralkyl, —C(=O)R$^5$, —OC(=O)R$^5$, —C(=O)OR$^5$, —OR$^5$, —SR$^5$, —S(=O)R$^5$, —S(=O)$_2$R$^5$, —S(=O)$_2$NR$^5$R$^6$, —NR$^5$R$^6$, —C(=O)NR$^5$R$^6$, —NR$^5$—C(=O)R$^6$, —NR$^5$—C(=O)OR$^6$, —NR$^5$—S(=O)$_2$—R$^6$, —NR$^5$—C(=O)—NR$^5$R$^6$, —C$_{1-6}$ alkylene-NR$^5$R$^6$ and —O—C$_{1-6}$ alkylene-NR$^5$R$^6$, and the alkyl, cyclic hydrocarbyl, heterocyclyl, aryl, heteroaryl and aralkyl are further optionally substituted with one or more substituents independently selected from the group consisting of: halogen, hydroxyl, oxo, amino, cyano, nitro, $C_{1-6}$ alkyl, $C_{3-6}$ cyclic hydrocarbyl, 3- to 10-membered heterocyclyl, $C_{6-10}$ aryl, 5- to 14-membered heteroaryl and $C_{6-12}$ aralkyl;

m, at each occurrence, is each independently an integer of 0, 1, 2 or 3;

n is an integer of 0, 1 or 2;

i is an integer of 0, 1 or 2;

p is an integer of 0, 1, 2 or 3;

q is an integer of 0 or 1; and t is an integer of 0, 1, 2 or 3.

According to another aspect of the invention, a pharmaceutical composition comprising a prophylactically or therapeutically effective amount of the compound of the present invention or a pharmaceutically acceptable salt, ester, stereoisomer, polymorph, solvate, N-oxide, isotopically labeled compound, metabolite or prodrug thereof and one or more pharmaceutically acceptable carriers is provided, and the pharmaceutical composition is preferably in the form of a solid, semi-solid, liquid, or gas preparation.

According to another aspect of the invention, use of the compound of the present invention or a pharmaceutically acceptable salt, ester, stereoisomer, polymorph, solvate, N-oxide, isotopically labeled compound, metabolite or prodrug thereof or the pharmaceutical composition of the present invention in the preparation of a medicament for use as a Rho-associated protein kinase (ROCK) inhibitor, preferably a selective ROCK2 inhibitor, is provided.

According to another aspect of the invention, the compound of the present invention or a pharmaceutically acceptable salt, ester, stereoisomer, polymorph, solvate, N-oxide, isotopically labeled compound, metabolite or prodrug thereof or the pharmaceutical composition of the present invention for use as a Rho-associated protein kinase (ROCK) inhibitor, preferably a selective ROCK2 inhibitor, is provided.

According to another aspect of the invention, a method for the prevention or treatment of a disease mediated by the Rho-associated protein kinase (ROCK) is provided, wherein the method comprises administering to a subject in need thereof an effective amount of the compound of the present invention or a pharmaceutically acceptable salt, ester, stereoisomer, polymorph, solvate, N-oxide, isotopically labeled compound, metabolite or prodrug thereof or the pharmaceutical composition of the present invention.

According to another aspect of the invention, a method for the preparation of the compound of the present invention is provided.

DETAILED DESCRIPTION OF THE INVENTION

Definition

Unless otherwise defined in the context, all technical and scientific terms used herein are intended to have the same meaning as commonly understood by a person skilled in the art. References to techniques employed herein are intended to refer to the techniques as commonly understood in the art, including variations on those techniques or substitutions of equivalent techniques which would be apparent to a person skilled in the art. While it is believed that the following terms will be readily understood by a person skilled in the art, the following definitions are nevertheless put forth to better illustrate the present invention.

The terms "contain", "include", "comprise", "have", or "relate to", as well as other variations used herein are inclusive or open-ended, and do not exclude additional, unrecited elements or method steps.

As used herein, the term "alkylene" refers to a saturated divalent hydrocarbyl, preferably refers to a saturated divalent hydrocarbyl having 1, 2, 3, 4, 5 or 6 carbon atoms, e.g., methylene, ethylene, propylene or butylene.

As used herein, the term "alkyl" is defined as a linear or branched saturated aliphatic hydrocarbon. In some embodiments, alkyl has 1-12, e.g., 1-6, carbon atoms. For example, as used herein, the term "$C_{1-6}$ alkyl" refers to a linear or branched group having 1-6 carbon atoms (such as methyl, ethyl, n-propyl, isopropyl, n-butyl, isobutyl, sec-butyl, tert-butyl, n-pentyl, isopentyl, neopentyl, or n-hexyl), which is optionally substituted with one or more (e.g., 1 to 3) suitable substituents such as halogen (in which case the group may be referred to as "haloalkyl") (e.g., $CH_2F$, $CHF_2$, $CF_3$, $CCl_3$, $C_2F_5$, $C_2Cl_5$, $CH_2CF_3$, $CH_2Cl$ or —$CH_2CH_2CF_3$ etc.). The term "$C_{1-4}$ alkyl" refers to a linear or branched aliphatic hydrocarbon chain having 1-4 carbon atoms (i.e., methyl, ethyl, n-propyl, isopropyl, n-butyl, isobutyl, sec-butyl or tert-butyl).

As used herein, the term "alkenyl" refers to a linear or branched monovalent hydrocarbyl having a double bond and 2-6 carbon atoms ("$C_{2-6}$ alkenyl"). The alkenyl is e.g., vinyl, 1-propenyl, 2-propenyl, 2-butenyl, 3-butenyl, 2-pentenyl, 3-pentenyl, 4-pentenyl, 2-hexenyl, 3-hexenyl, 4-hexenyl, 5-hexenyl, 2-methyl-2-propenyl and 4-methyl-3-pentenyl. When the compound of the present invention contains an alkenylene group, the compound may exist as the pure E (entgegen) form, the pure Z (zusammen) form, or any mixture thereof.

As used herein, the term "alkynyl" refers to a monovalent hydrocarbyl containing one or more triple bond, and preferably having 2, 3, 4, 5 or 6 carbon atoms, e.g., ethynyl or propynyl.

As used herein, the term "cycloalkyl" refers to a saturated monocyclic or polycyclic (e.g., bicyclic) hydrocarbon ring (e.g., monocyclic, such as cyclopropyl, cyclobutyl, cyclopentyl, cyclohexyl, cycloheptyl, cyclooctyl, or cyclononyl, or bicyclic, including spiro, fused or bridged cyclic system (such as bicyclo[1.1.1]pentyl, bicyclo[2.2.1]heptyl, bicyclo[3.2.1]octyl or bicyclo[5.2.0]nonyl, or decahydronaphthalene etc.)), which is optionally substituted with one or more (e.g., 1 to 3) suitable substituents. The cycloalkyl has 3 to 15 carbon atoms. For example, the term "$C_{3-6}$ cycloalkyl" refers to a saturated monocyclic or polycyclic (e.g., bicyclic) hydrocarbon ring having 3 to 6 ring forming carbon atoms (e.g., cyclopropyl, cyclobutyl, cyclopentyl, or cyclohexyl), which is optionally substituted with one or more (e.g., 1 to 3) suitable substituents, e.g., methyl substituted cyclopropyl.

As used herein, the terms "cyclic hydrocarbylene", "cyclic hydrocarbyl" and "hydrocarbon ring" refer to a saturated (i.e., "cycloalkylene" and "cycloalkyl") or unsaturated (i.e., having one or more double and/or triple bonds in the ring) monocyclic or polycyclic hydrocarbon ring having e.g., 3-10 (suitably having 3-8, and more suitably having 3-6) ring carbon atoms, including but not limited to cyclopropyl(ene) (ring), cyclobutyl(ene) (ring), cyclopentyl(ene) (ring), cyclohexyl(ene) (ring), cycloheptyl(ene) (ring), cyclooctyl(ene) (ring), cyclononyl(ene) (ring), cyclohexenyl(ene) (ring), and the like.

As used herein, the terms "heterocyclyl", "heterocyclylene" and "heterocycle" refer to a saturated (i.e., heterocycloalkyl) or partially unsaturated (i.e., having one or more double and/or triple bonds in the ring) cyclic group having e.g. 3-10 (suitably having 3-8, and more suitably having 3-6) ring atoms, wherein at least one ring atom is a heteroatom selected from the group consisting of N, O and S, and the remaining ring atoms are C. For example, "3- to 10-membered heterocyclyl(ene)" of "3- to 10-membered heterocycle" refers to saturated or partially unsaturated heterocyclyl(ene) or heterocycle having 2-9 (e.g., 2, 3, 4, 5, 6, 7, 8 or 9) ring carbon atoms and one or more (e.g., 1, 2, 3, or 4) heteroatoms independently selected from the group consisting of N, O and S. Examples of heterocyclylene, heterocyclyl and heterocycle include, but are not limited to oxiranyl(ene), aziridinyl(ene), azetidinyl(ene), oxetanyl(ene), tetrahydrofuranyl(ene), dioxolinyl(ene), pyrrolidinyl(ene), pyrrolidonyl(ene), imidazolidinyl(ene), pyrazolidinyl(ene), pyrrolinyl(ene), tetrahydropyranyl(ene), piperidinyl(ene), morpholinyl(ene), dithianyl(ene), thiomorpholinyl(ene), piperazinyl(ene) or trithianyl(ene). Said group also encompasses a bicyclic system, including a spiro, fused, or bridged system (e.g., 8-azaspiro[4.5]decane, 3,9-diazaspiro[5.5]undecane, 2-azabicyclo[2.2.2]octane, etc.). Heterocyclylene, heterocyclyl and heterocycle may optionally be substituted with one or more (e.g. 1, 2, 3 or 4) suitable substituents.

As used herein, the terms "aryl(ene)" and "aromatic ring" refer to an all-carbon monocyclic or fused-ring polycyclic aromatic group having a conjugated π electron system. For example, as used herein, the terms "$C_{6-10}$ aryl(ene)" and "$C_{6-10}$ aromatic ring" refer to an aromatic group containing 6 to 10 carbon atoms, such as phenyl(ene) (benzene ring) or naphthyl(ene) (naphthalene ring). Aryl(ene) or aromatic ring is optionally substituted with one or more (such as 1 to 3) suitable substituents (e.g., halogen, —OH, —CN, —NO₂, and $C_{1-6}$ alkyl, etc.).

As used herein, the terms "heteroaryl(ene)" and "heteroaromatic ring" refer to a monocyclic, bicyclic or tricyclic aromatic ring system having 5, 6, 8, 9, 10, 11, 12, 13 or 14 ring atoms, particularly 1 or 2 or 3 or 4 or 5 or 6 or 9 or 10 carbon atoms, and containing at least one heteroatom (such as O, N, or S), which can be same to different. Moreover, in each case, it can be benzo-fused. In particular, "heteroaryl(ene)" or "heteroaromatic ring" is selected from the group consisting of thienyl(ene), furyl(ene), pyrrolyl(ene), oxazolyl(ene), thiazolyl(ene), imidazolyl(ene), pyrazolyl(ene), isoxazolyl(ene), isothiazolyl(ene), oxadiazolyl(ene), triazolyl(ene), thiadiazolyl(ene) etc., and benzo derivatives thereof; or pyridinyl(ene), pyridazinyl(ene), pyrimidinyl(ene), pyrazinyl(ene), triazinyl(ene), etc., and benzo derivatives thereof.

As used herein, the term "aralkyl" preferably means aryl or heteroaryl substituted alkyl, wherein aryl, heteroaryl and alkyl are as defined herein. Normally, the aryl group may have 6-14 carbon atoms, the heteroaryl group may have 5-14 ring atoms, and the alkyl group may have 1-6 carbon atoms. Exemplary aralkyl group includes, but is not limited to, benzyl, phenylethyl, phenylpropyl, phenylbutyl.

As used herein, the term "halo" or "halogen" are defined to include F, Cl, Br, or I.

As used herein, the term "nitrogen containing heterocycle" refers to a saturated or unsaturated monocyclic or bicyclic group having 2, 3, 4, 5, 6, 7, 8, 9, 10, 11, 12 or 13 carbon atoms and at least one nitrogen atom in the ring, which may further optionally comprise one or more (e.g., one, two, three or four) ring members selected from the group consisting of N, O, C=O, S, S=O and $S(=O)_2$. The nitrogen containing heterocycle is attached to the rest of the molecule through the nitrogen atom and any other ring atom in said nitrogen containing heterocycle. The nitrogen containing heterocycle is optionally benzo-fused, and is preferably attached to the rest of the molecule through the nitrogen atom in said nitrogen containing heterocycle and any carbon atom in the fused benzene ring.

The term "substituted" means that one or more (e.g., one, two, three, or four) hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds.

If a substituent is described as being "optionally substituted," the substituent may be either (1) not substituted, or (2) substituted. If a carbon of a substituent is described as being optionally substituted with one or more of a list of substituents, one or more of the hydrogens on the carbon (to the extent there are any) may separately and/or together be replaced with an independently selected optional substituent. If a nitrogen of a substituent is described as being optionally substituted with one or more of a list of substituents, one or more of the hydrogens on the nitrogen (to the extent there are any) may each be replaced with an independently selected optional substituent.

If substituents are described as being "independently selected" from a group, each substituent is selected independent of the other(s). Each substituent therefore may be identical to or different from the other substituent(s).

As used herein, the term "one or more" means one or more than one (e.g., 2, 3, 4, 5 or 10) as reasonable.

As used herein, unless specified, the point of attachment of a substituent can be from any suitable position of the substituent.

When a bond to a substituent is shown to cross a bond connecting two atoms in a ring, then such substituent may be bonded to any of the ring-forming atoms in that ring that are substitutable.

The present invention also includes all pharmaceutically acceptable isotopically labeled compounds, which are identical to those of the present invention except that one or more atoms are replaced by an atom having the same atomic number, but an atomic mass or mass number different from the atomic mass or mass number which predominates in nature. Examples of isotopes suitable for inclusion in the compound of the present invention include, but are not limited to, isotopes of hydrogen, such as $^2$H, $^3$H; carbon, such as $^{11}$C, $^{13}$C, and $^{14}$C; chlorine, such as $^{36}$Cl; fluorine, such as $^{18}$F; iodine, such as $^{123}$I and $^{125}$I; nitrogen, such as $^{13}$N and $^{15}$N; oxygen, such as $^{15}$O, $^{17}$O, and $^{18}$O; phosphorus, such as $^{32}$P; and sulfur, such as $^{35}$S. Certain isotopically labeled compounds of the present invention, for example those incorporating a radioactive isotope, are useful in drug and/or substrate tissue distribution studies (e.g., assays). The radioactive isotopes tritium, i.e., $^3$H, and carbon-14, i.e., $^{14}$C, are particularly useful for this purpose in view of their ease of incorporation and ready means of detection. Substitution with positron-emitting isotopes, such as $^{11}$C, $^{18}$F, $^{15}$O and $^{13}$N, can be useful in positron emission tomography (PET) studies for examining substrate receptor occupancy. Isotopically labeled compounds of the present invention can generally be prepared by processes analogous to those described in the accompanying Schemes and/or in the Examples and Preparations, by using an appropriate isotopically labeled reagent in place of the non-labeled reagent previously employed. Pharmaceutically acceptable solvates in accordance with the invention include those wherein the solvent of crystallization may be isotopically substituted, e.g., D$_2$O, acetone-d$_6$, or DMSO-d$_6$.

The term "stereoisomer" refers to isomers with at least one asymmetric center. A compound having one or more (e.g., one, two, three or four) asymmetric centers can give rise to a racemic mixture, single enantiomer, diastereomer mixture and individual diastereomer. Certain individual molecules may exist as geometric isomers (cis/trans). Similarly, the compound of the present invention may exist as a mixture of two or more structurally different forms in rapid equilibrium (generally referred to as tautomer). Typical examples of a tautomer include a keto-enol tautomer, phenol-keto tautomer, nitroso-oxime tautomer, imine-enamine tautomer and the like. It is to be understood that all such isomers and mixtures thereof in any proportion (such as 60%, 65%, 70%, 75%, 80%, 85%, 90%, 95%, 96%, 97%, 98%, and 99%) are encompassed within the scope of the present invention.

The carbon-carbon bonds of the compound of the present invention may be depicted herein using a solid line (-), a solid wedge ( ▬ ), or a dotted wedge ( ⋯⋯ ). The use of a solid line to depict bonds to asymmetric carbon atoms is meant to indicate that all possible stereoisomers (e.g., specific enantiomers, racemic mixtures, etc.) at that carbon atom are included. The use of either a solid or dotted wedge to depict bonds to asymmetric carbon atoms is meant to indicate that the stereoisomer shown is present. When present in racemic compounds, solid and dotted wedges are used to define relative stereochemistry, rather than absolute stereochemistry. Unless stated otherwise, it is intended that the compound of the present invention can exist as stereoisomers, which include cis and trans isomers, optical isomers such as R and S enantiomers, diastereomers, geometric isomers, rotational isomers, conformational isomers, atropisomers, and mixtures thereof. The compound of the present invention may exhibit more than one type of isomerism, and consist of mixtures thereof (such as racemates and diastereomeric pairs).

The present invention includes all possible crystalline forms or polymorphs of the compound of the present invention, either as a single polymorph, or as a mixture of more than one polymorphs, in any ratio.

It also should be understood that, certain compounds of the present invention can be used for the treatment in a free from, or where appropriate, in a form of a pharmaceutically acceptable derivative. In the present invention, the pharmaceutically acceptable derivative includes, but is not limited to a pharmaceutically acceptable salt, ester, solvate, N-oxide, metabolite or prodrug, which can directly or indirectly provide the compound of the present invention or a metabolite or residue thereof after being administered to a patient in need thereof. Therefore, "the compound of the present invention" mentioned herein also means to encompass various derivative forms of the compound as mentioned above.

A pharmaceutically acceptable salt of the compound of the present invention includes an acid addition salt and a base addition salt thereof.

A suitable acid addition salt is formed from an acid which forms a pharmaceutically acceptable salt. Specific examples include acetate, adipate, aspartate, benzoate, besylate, bicarbonate/carbonate, bisulfate/sulfate, borate, camphorsulfonate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts.

A suitable base addition salt is formed from a base which forms a pharmaceutically acceptable salt. Specific examples include aluminum, arginine, benzathine, calcium, choline, diethylamine, diolamine, glycine, lysine, magnesium, meglumine, olamine, potassium, sodium, tromethamine and zinc salts.

For a review on suitable salts, see "Hand book of Pharmaceutical Salts: Properties, Selection, and Use" by Stahl and Wermuth (Wiley-VCH, 2002). The method for preparing a pharmaceutically acceptable salt of the compound of the present invention is known to a person skilled in the art.

As used herein, the term "ester" refers to those derived from the compounds of the various formulae in the present application, which include physiologically-hydrolyzable esters (which may be hydrolyzed under physiological conditions to release the compounds of the present invention in the form of free acids or alcohols). The compound of the present invention itself may be an ester as well.

The compound of the present invention can exist as a solvate (preferably a hydrate), wherein the compound of the present invention contains a polar solvent, in particular water, methanol or ethanol for example, as a structural element of the crystal lattice of the compound. The amount of the polar solvent, in particular water, may exist in a stoichiometric or non-stoichiometric ratio.

As can be appreciated by a person skilled in the art, not all nitrogen containing heterocycles can form N-oxides since the nitrogen requires an available lone-pair electron for oxidation to the oxide; a person skilled in the art will recognize those nitrogen containing heterocycles which can form N-oxides. A person skilled in the art will also recognize that tertiary amines can form N-oxides. Synthetic methods for the preparation of N-oxides of heterocycles and tertiary amines are well known to a person skilled in the art, and they include the oxidation of heterocycles and tertiary amines with peroxy acids such as peracetic acid and m-chloroperbenzoic acid (MCPBA), hydrogen peroxide, alkyl hydroperoxides such as tert-butyl hydroperoxide, sodium perborate, and dioxiranes such as dimethyldioxirane. These methods for the preparation of N-oxides have been extensively described and reviewed in literatures, see e.g., T. L. Gilchrist, *Comprehensive Organic Synthesis*, vol. 7, pp 748-750; A. R. Katritzky and A. J. Boulton, Eds., Academic Press; and G. W. H. Cheeseman and E. S. G. Werstiuk, *Advances in Heterocyclic Chemistry*, vol. 22, pp 390-392, A. R. Katritzky and A. J. Boulton, Eds., Academic Press.

The metabolite of the compound of the present invention, namely a substance formed in vivo upon administration of the compound of the present invention, is also included within the scope of the present invention. Such a product may result e.g., from the oxidation, reduction, hydrolysis, amidation, de-amidation, esterification, enzymolysis, and the like, of the administered compound. Accordingly, the present invention encompasses the metabolite of the compound of the present invention, including a compound produced by a method comprising contacting the compound of the present invention with a mammal for a period of time sufficient to result in a metabolic product thereof.

Also within the scope of the present invention is a prodrug of the compound of the invention, which is certain derivative of the compound of the invention that may have little or no pharmacological activity itself, but can, when administered into or onto the body, be converted into the compound of the invention having the desired activity, for example, by hydrolytic cleavage. In general, such prodrug will be a functional derivative of the compound which is readily converted in vivo into the compound with desired therapeutic activity. Further information on the use of the prodrug may be found in "Pro-drugs as Novel Delivery Systems, Vol. 14, ACS Symposium Series (T. Higuchi and V. Stella). The prodrug in accordance with the invention can, for example, be produced by replacing appropriate functionalities present in the compound of the present invention with certain moieties known to those skilled in the art as "pro-moieties" as described, for example, in "Design of Prodrugs" by H. Bundgaard (Elsevier, 1985).

The present invention further encompasses the compound of the present invention having a protecting group. During any of the processes for preparation of the compound of the present invention, it may be necessary and/or desirable to protect sensitive or reactive groups on any of the molecules concerned, thereby resulting in the chemically protected form of the compound of the present invention. This may be achieved by means of conventional protecting groups, e.g., those described in T. W. Greene & P. GM. Wuts, Protective Groups in Organic Synthesis, John Wiley & Sons, 1991, which is incorporated herein by reference. The protecting groups may be removed at a convenient subsequent stage using methods known from the art.

The term "about" refers to a range within ±10%, preferably within ±5%, and more preferably within ±2% of the specified value.

Specific Embodiments

Compound

In some embodiments, the present invention provides a compound or a pharmaceutically acceptable salt, ester, stereoisomer, polymorph, solvate, N-oxide, isotopically labeled compound, metabolite or prodrug thereof, wherein the compound has the structure of Formula (I):

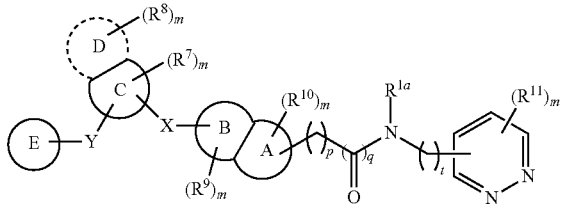

Formula (I)

wherein:

X and Y are each independently selected from the group consisting of a direct bond, $C(=O)$, O, $S(=O)_i$ and NR;

R is selected from the group consisting of H, $C_{1-6}$ alkyl, $C_{2-6}$ alkenyl, $C_{2-6}$ alkynyl, saturated or partially unsaturated $C_{3-10}$ cyclic hydrocarbyl, saturated or partially unsaturated 3- to 10-membered heterocyclyl, $C_{6-10}$ aryl, 5- to 14-membered heteroaryl and $C_{6-12}$ aralkyl, and at most 2 ring members in the cyclic hydrocarbyl and heterocyclyl are $C(=O)$;

ring A and ring B are each independently selected from the group consisting of saturated or partially unsaturated $C_{3-10}$ hydrocarbon ring, saturated or partially unsaturated 3- to 10-membered heterocycle, $C_{6-10}$ aromatic ring and 5- to 14-membered heteroaromatic ring, and at most 2 ring members in the hydrocarbon ring and heterocycle are $C(=O)$;

ring C is selected from the group consisting of saturated or partially unsaturated $C_{3-10}$ hydrocarbon ring, saturated or partially unsaturated 3- to 10-membered heterocycle, $C_{6-10}$ aromatic ring and 5- to 14-membered heteroaromatic ring, and at most 2 ring members in the hydrocarbon ring and heterocycle are $C(=O)$;

ring D is absent, or is selected from the group consisting of saturated or partially unsaturated $C_{3-10}$ hydrocarbon ring, saturated or partially unsaturated 3- to 10-membered heterocycle, $C_{6-10}$ aromatic ring and 5- to 14-membered heteroaromatic ring, and at most 2 ring members in the hydrocarbon ring and heterocycle are $C(=O)$;

ring E is selected from the group consisting of

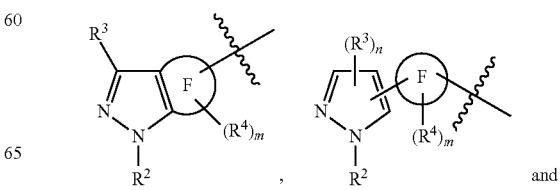

and

-continued

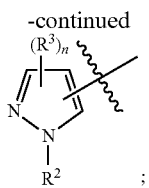

ring F is selected from the group consisting of saturated or partially unsaturated $C_{3-10}$ hydrocarbon ring, saturated or partially unsaturated 3- to 10-membered heterocycle, $C_{6-10}$ aromatic ring and 5- to 14-membered heteroaromatic ring, and at most 2 ring members in the hydrocarbon ring and heterocycle are C(=O);

$R^{1a}$ is selected from the group consisting of H, halogen, amino, cyano, nitro, $C_{1-6}$ alkyl, $C_{2-6}$ alkenyl, $C_{2-6}$ alkynyl, $C_{3-10}$ cyclic hydrocarbyl, 3- to 10-membered heterocyclyl, $C_{6-10}$ aryl, 5- to 14-membered heteroaryl, $C_{6-12}$ aralkyl, —C(=O)R$^5$, —OC(=O)R$^5$, —C(=O)OR$^5$, —OR$^5$, —SR$^5$, —S(=O)R$^5$, —S(=O)$_2$R$^5$, —S(=O)$_2$NR$^5$R$^6$, —NR$^5$R$^6$, —C(=O)NR$^5$R$^6$, —NR$^5$—C(=O)R$^6$, —NR$^5$—C(=O)OR$^6$, —NR$^5$—S(=O)$_2$—R$^6$, —NR$^5$—C(=O)—NR$^5$R$^6$, —$C_{1-6}$ alkylene-NR$^5$R$^6$, —$C_{1-6}$ alkylene-OR$^5$ and —O—$C_{1-6}$ alkylene-NR$^5$R$^6$;

$R^2$, $R^3$, $R^4$, $R^7$, $R^8$, $R^9$, $R^{10}$ and $R^{11}$, at each occurrence, are each independently selected from the group consisting of H, halogen, amino, cyano, nitro, $C_{1-6}$ alkyl, $C_{2-6}$ alkenyl, $C_{2-6}$ alkynyl, $C_{3-10}$ cyclic hydrocarbyl, 3- to 10-membered heterocyclyl, $C_{6-10}$ aryl, 5- to 14-membered heteroaryl, $C_{6-12}$ aralkyl, —C(=O)R$^5$, —OC(=O)R$^5$, —C(=O)OR$^5$, —OR$^5$, —SR$^5$, —S(=O)R$^5$, —S(=O)$_2$R$^5$, —S(=O)$_2$NR$^5$R$^6$, —NR$^5$R$^6$, —C(=O)NR$^5$R$^6$, —NR$^5$—C(=O)R$^6$, —NR$^5$—C(=O)OR$^6$, —NR$^5$—S(=O)$_2$—R$^6$, —NR$^5$—C(=O)—NR$^5$R$^6$, —$C_{1-6}$ alkylene-NR$^5$R$^6$ and —O—$C_{1-6}$ alkylene-NR$^5$R$^6$;

alternatively, when the pyridazine ring in Formula (I) is substituted with two $R^{11}$, and the two $R^{11}$ are at ortho positions on the pyridazine ring, the two $R^{11}$ together with the carbon atoms to which they are attached form $C_{4-10}$ cyclic hydrocarbyl, 4- to 10-membered heterocyclyl, $C_{6-10}$ aryl, or 5- to 14-membered heteroaryl;

$R^5$ and $R^6$, at each occurrence, are each independently selected from the group consisting of H, $C_{1-6}$ alkyl, $C_{3-10}$ cyclic hydrocarbyl, 3- to 10-membered heterocyclyl, $C_{6-10}$ aryl, 5- to 14-membered heteroaryl and $C_{6-12}$ aralkyl;

the above alkyl, alkylene, alkenyl, alkynyl, cyclic hydrocarbyl, hydrocarbon ring, heterocyclyl, heterocycle, aryl, aromatic ring, heteroaryl, heteroaromatic ring and aralkyl, at each occurrence, are each optionally substituted with one or more substituents independently selected from the group consisting of: halogen, hydroxyl, oxo, amino, cyano, nitro, $C_{1-6}$ alkyl, $C_{3-6}$ cyclic hydrocarbyl, 3- to 10-membered heterocyclyl, $C_{6-10}$ aryl, 5- to 14-membered heteroaryl, $C_{6-12}$ aralkyl, —C(=O)R$^5$, —OC(=O)R$^5$, —C(=O)OR$^5$, —OR$^5$, —SR$^5$, —S(=O)R$^5$, —S(=O)$_2$R$^5$, —S(=O)$_2$NR$^5$R$^6$, —NR$^5$R$^6$, —C(=O)NR$^5$R$^6$, —NR$^5$—C(=O)R$^6$, —NR$^5$—C(=O)OR$^6$, —NR$^5$—S(=O)$_2$—R$^6$, —NR$^5$—C(=O)—NR$^5$R$^6$, —$C_{1-6}$ alkylene-NR$^5$R$^6$ and —O—$C_{1-6}$ alkylene-NR$^5$R$^6$, and the alkyl, cyclic hydrocarbyl, heterocyclyl, aryl, heteroaryl and aralkyl are further optionally substituted with one or more substituents independently selected from the group consisting of: halogen, hydroxyl, oxo, amino, cyano, nitro, $C_{1-6}$ alkyl, $C_{3-6}$ cyclic hydrocarbyl, 3- to 10-membered heterocyclyl, $C_{6-10}$ aryl, 5- to 14-membered heteroaryl and $C_{6-12}$ aralkyl;

m, at each occurrence, is each independently an integer of 0, 1, 2 or 3;

n is an integer of 0, 1 or 2;

i is an integer of 0, 1 or 2;

p is an integer of 0, 1, 2 or 3;

q is an integer of 0 or 1; and t is an integer of 0, 1, 2 or 3.

In some embodiments, the present invention provides a compound or a pharmaceutically acceptable salt, ester, stereoisomer, polymorph, solvate, N-oxide, isotopically labeled compound, metabolite or prodrug thereof, wherein X and Y are each independently selected from the group consisting of a direct bond, C(=O), O, S, S(=O), S(=O)$_2$ and NH, and preferably, at least one of X and Y is a direct bond.

In some embodiments, the present invention provides a compound or a pharmaceutically acceptable salt, ester, stereoisomer, polymorph, solvate, N-oxide, isotopically labeled compound, metabolite or prodrug thereof, wherein at least one of ring A and ring B is selected from the group consisting of saturated or partially unsaturated 3- to 10-membered heterocycle and 5- to 14-membered heteroaromatic ring, at most 2 ring members in the heterocycle are C(=O), and when ring B is a heterocycle containing a nitrogen atom, ring B is not attached to X via the nitrogen atom.

In some embodiments,

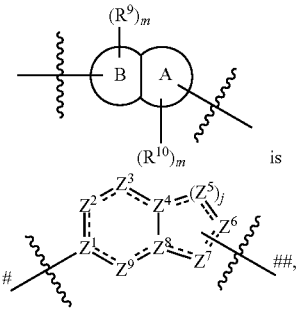

is preferably

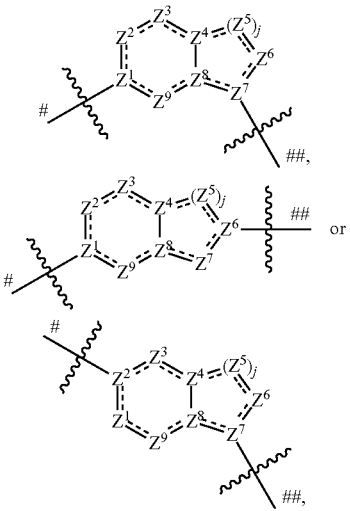

the above group is attached to X at either of the two positions labeled # or ##, and is attached to

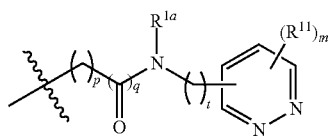

at the other position,
wherein:
═ represents either a single or a double bond, and the adjacent bonds are not double bonds simultaneously;

$Z^1$, $Z^2$, $Z^3$, $Z^4$, $Z^5$, $Z^6$, $Z^7$, $Z^8$ and $Z^9$, at each occurrence, are each independently selected from the group consisting of C, $CR^9$, $C(R^9)_2$, $CR^{10}$, $C(R^{10})_2$, $C(=O)$, N, $NR^9$, $NR^{10}$, O and S; preferably, $Z^1$, $Z^2$, $Z^3$, $Z^4$, $Z^5$, $Z^6$, $Z^7$, $Z^8$ and $Z^9$, at each occurrence, are each independently selected from the group consisting of C, CH, $CCH_3$, $CH_2$, $C(=O)$, N, NH, $NCH_3$, $NCH_2CH_2-N(CH_3)_2$, O and S; and j is 0, 1, 2, 3 or 4;

provided that at most two groups among $Z^1$-$Z^9$ are simultaneously $C(=O)$, and the atom attached to X is not a nitrogen atom.

In more preferred embodiments,

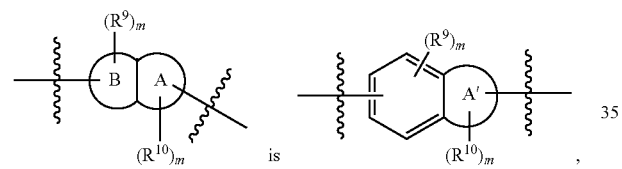 is

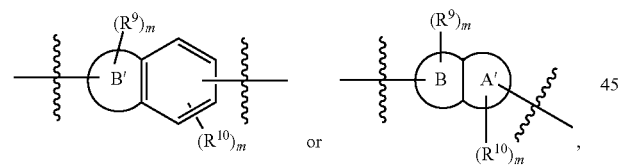 or wherein ring A' and ring B' are each independently selected from the group consisting of saturated or partially unsaturated 3- to 10-membered heterocycle and 5- to 14-membered heteroaromatic ring, and at most 2 ring members in the heterocycle are $C(=O)$; provided that when ring B' is a heterocycle containing a nitrogen atom, ring B' is not attached to X via the nitrogen atom.

In some embodiments,

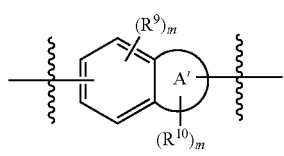

is preferably

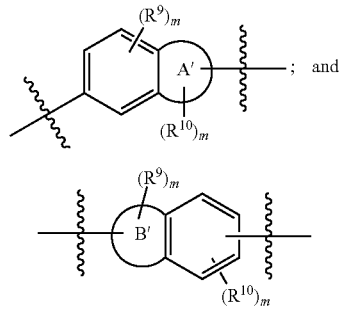; and is preferably

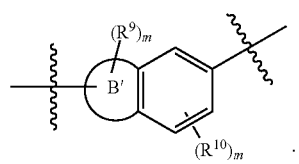

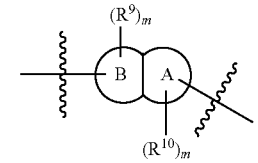

In preferred embodiments, $R^9$ and $R^{10}$, at each occurrence, are each independently selected from the group consisting of methyl, ethyl, propyl and $-CH_2CH_2-N(CH_3)_2$.

In the most preferred embodiments,

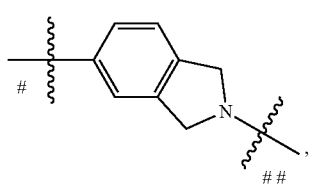

is selected from the group consisting of

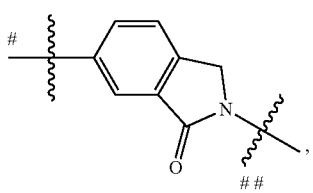

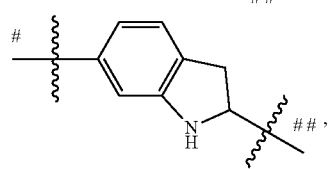

-continued
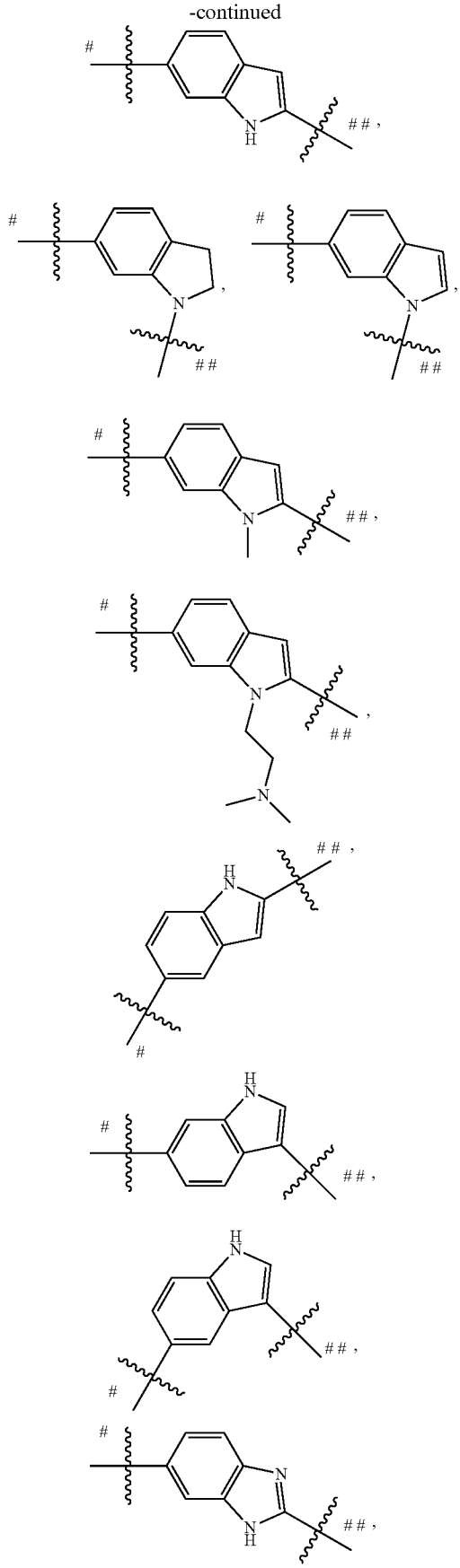
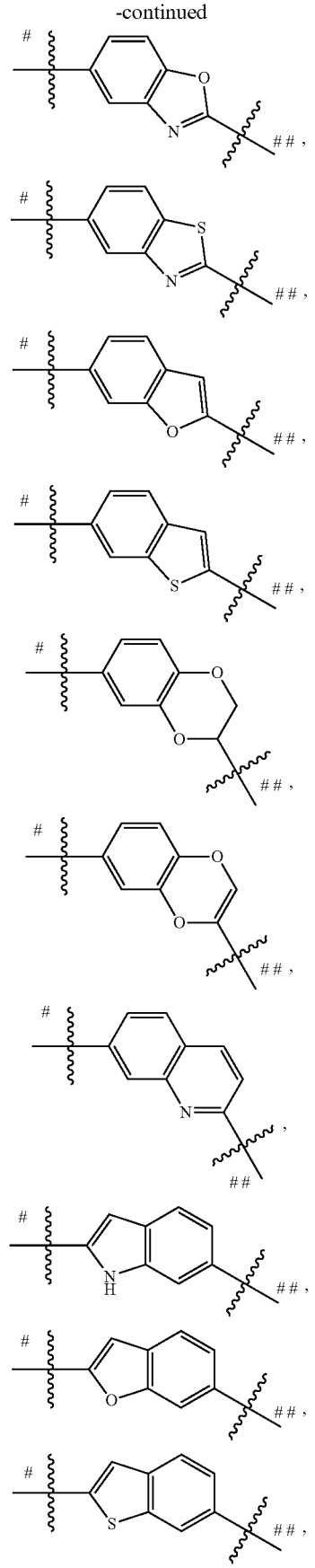

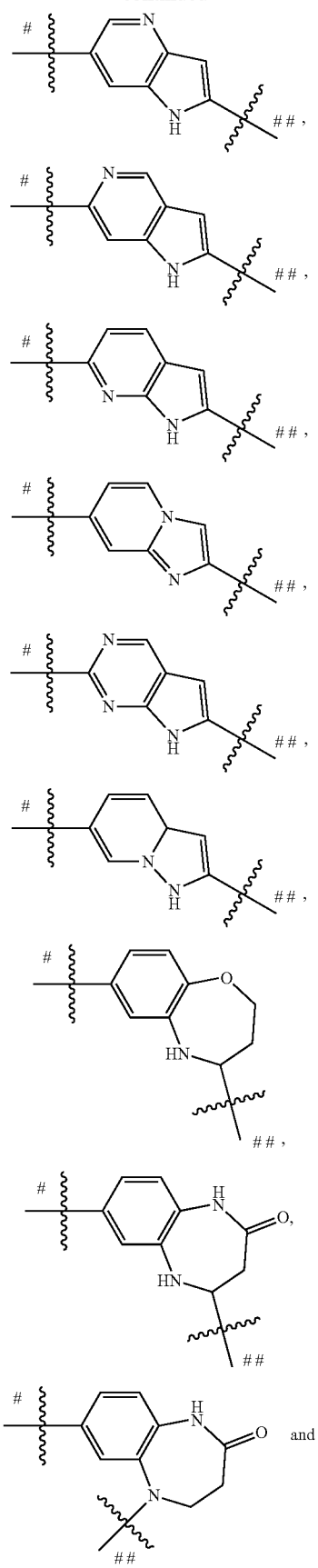

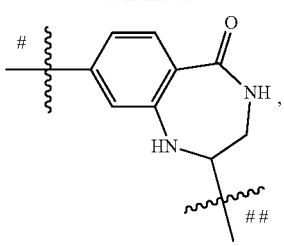

the above group is attached to X at either of the two positions labeled # or ##, and is attached to

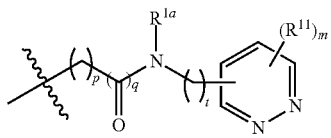

at the other position, provided that the atom attached to X is not a nitrogen atom.

In some embodiments, the present invention provides a compound or a pharmaceutically acceptable salt, ester, stereoisomer, polymorph, solvate, N-oxide, isotopically labeled compound, metabolite or prodrug thereof, wherein

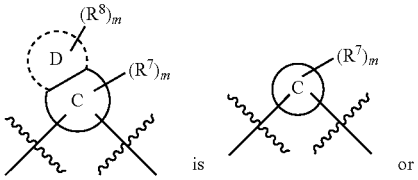 is 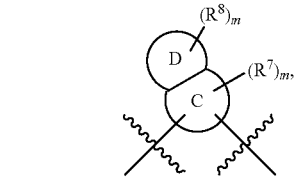 or

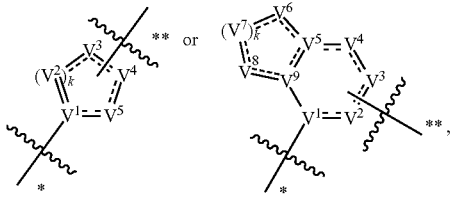

more preferably and more preferably

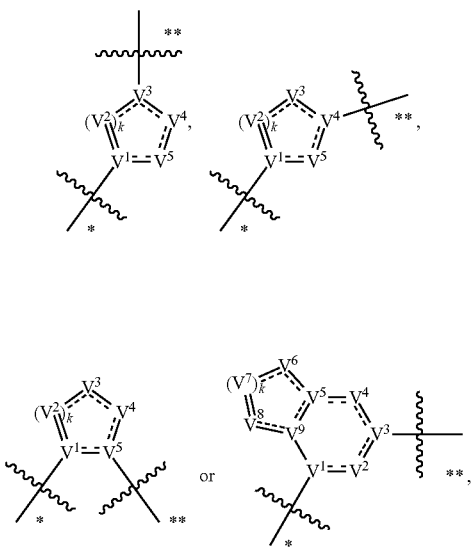

the above group is attached to Y at either of the two positions labeled * or **, and is attached to X at the other position, wherein:

═ represents either a single or a double bond, and the adjacent bonds are not double bonds simultaneously;

$V^1$, $V^2$, $V^3$, $V^4$, $V^5$, $V^6$, $V^7$, $V^8$ and $V^9$, at each occurrence, are each independently selected from the group consisting of C, $CR^7$, $C(R^7)_2$, $CR^8$, $C(R^8)_2$, C(=O), N, $NR^7$, $NR^8$, O and S; preferably, $V^1$, $V^2$, $V^3$, $V^4$, $V^5$, $V^6$, $V^7$, $V^8$ and $V^9$, at each occurrence, are each independently selected from the group consisting of C, CH, CF, CCN, $CCH_3$, $CCF_3$, —C—O—$CH_2CH_2$—$N(CH_3)_2$, $CH_2$, C(=O), N, NH, $NCH_3$, N-Ph, —N—$CH_2CH_2$—$N(CH_3)_2$, O and S; and k is 0, 1, 2, 3 or 4;

provided that at most two groups among $V^1$-$V^9$ are simultaneously C(=O).

In preferred embodiments,

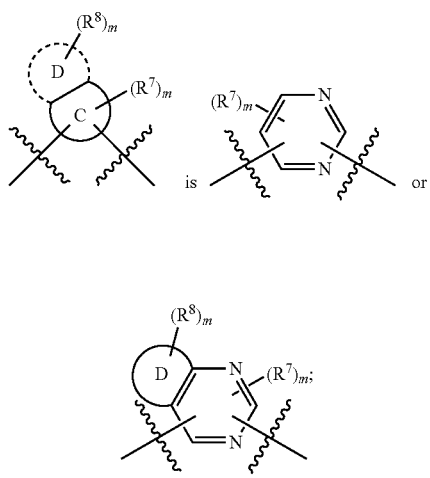

more preferably

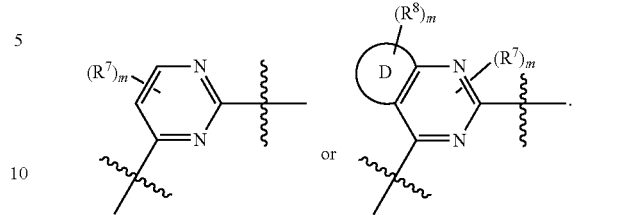

In preferred embodiments, $R^7$ and $R^8$, at each occurrence, are each independently selected from the group consisting of F, Cl, Br, I, cyano, methyl, ethyl, propyl, trifluoromethyl, phenyl, —O—$CH_2CH_2$—$N(CH_3)_2$ and —$CH_2CH_2$—$N(CH_3)_2$.

In the most preferred embodiments,

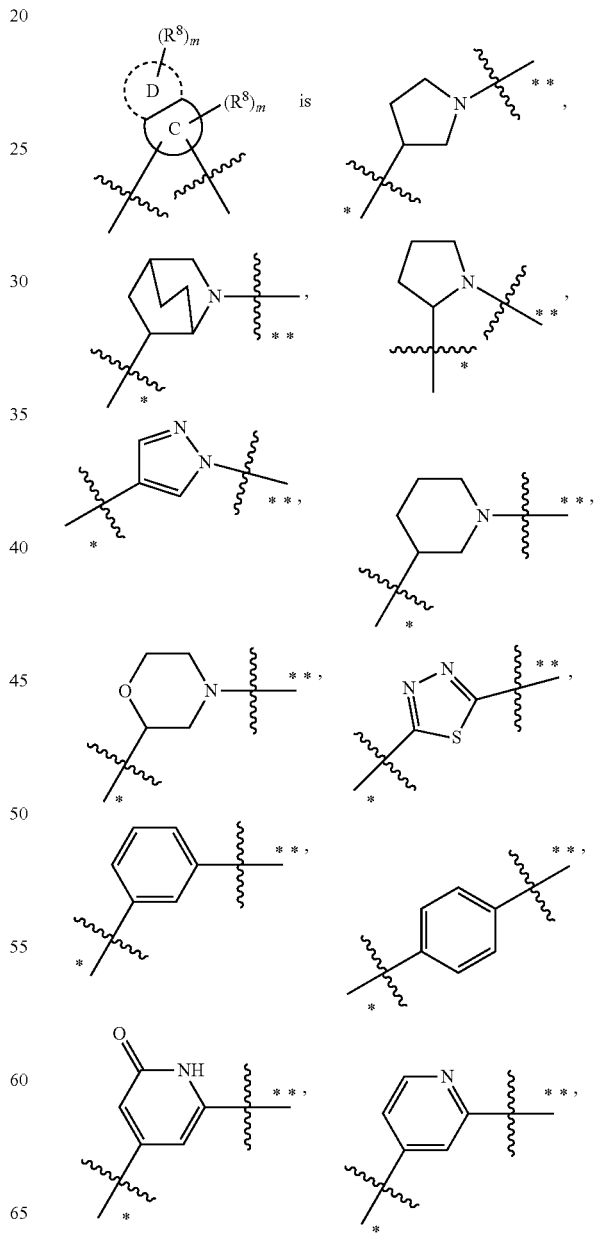

-continued
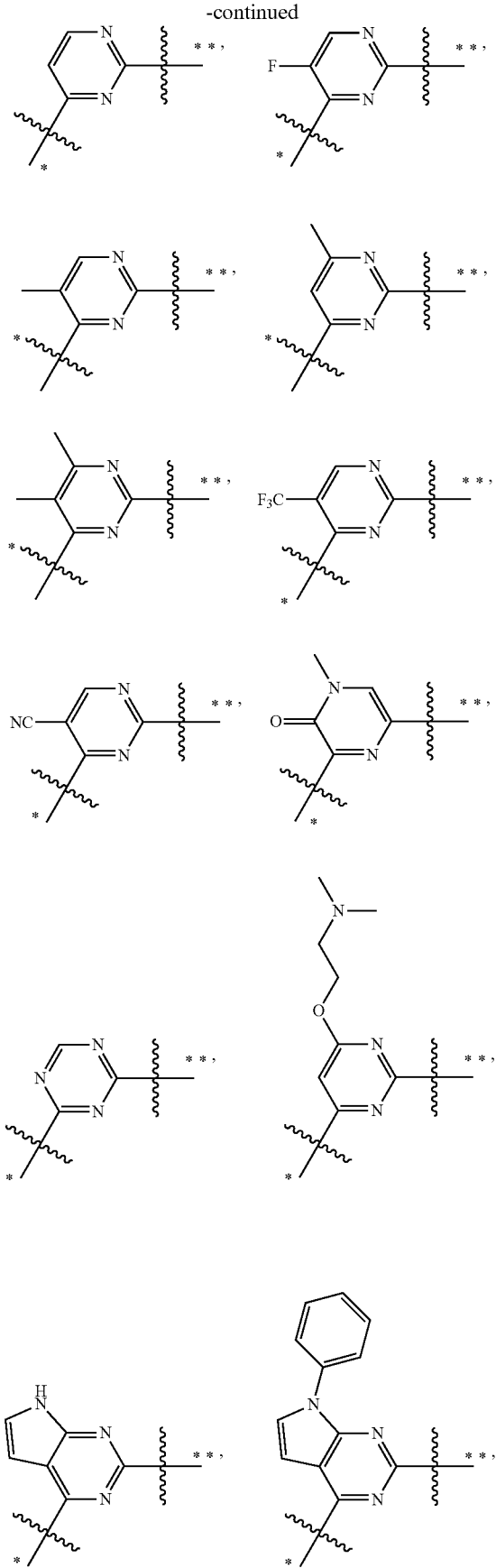
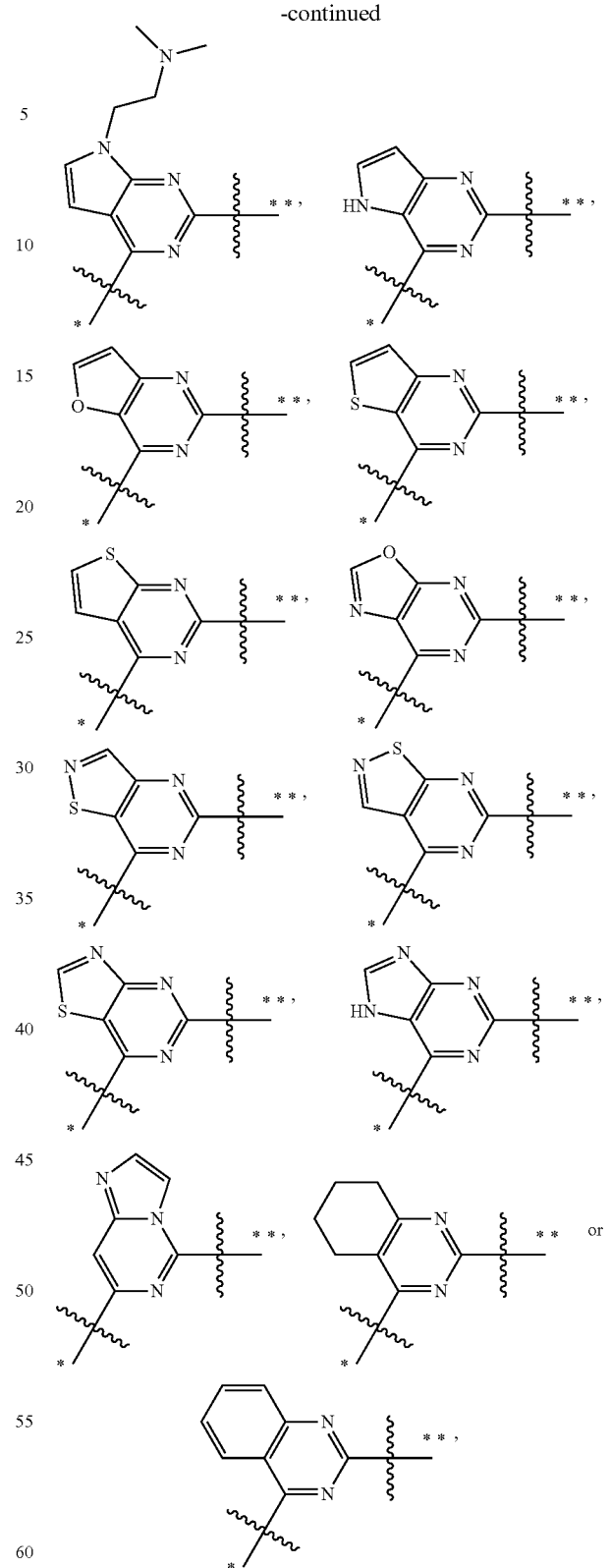
the above group is attached to Y at either of the two positions labeled * or **, and is attached to X at the other position.
In some embodiments, the present invention provides a compound or a pharmaceutically acceptable salt, ester, stereoisomer, polymorph, solvate, N-oxide, isotopically labeled compound, metabolite or prodrug thereof, wherein ring E is

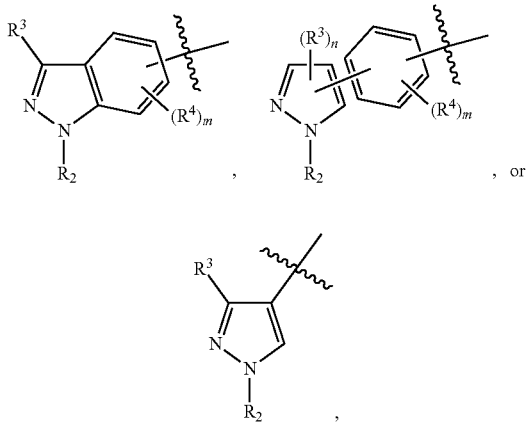

preferably

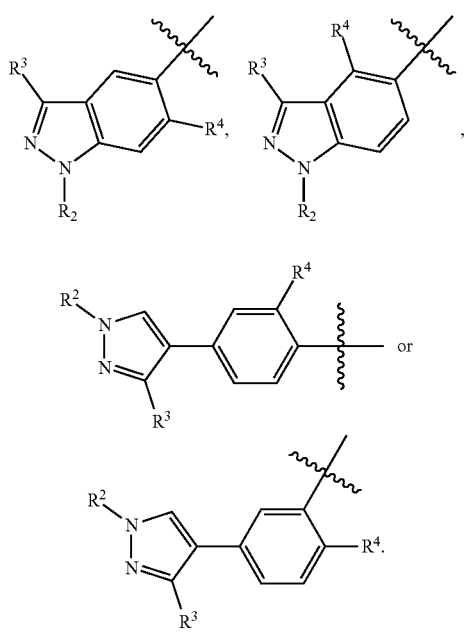

In some embodiments, $R^3$ and $R^4$, at each occurrence, are each independently selected from the group consisting of H, F, Cl, Br, I, methyl, ethyl, propyl, methoxy, —O-ethylene-N(CH$_3$)$_2$.

In preferred embodiments, ring E is

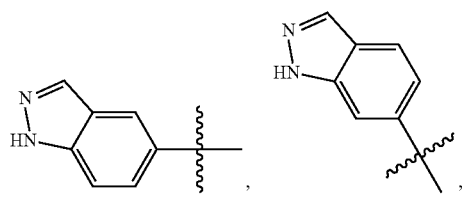

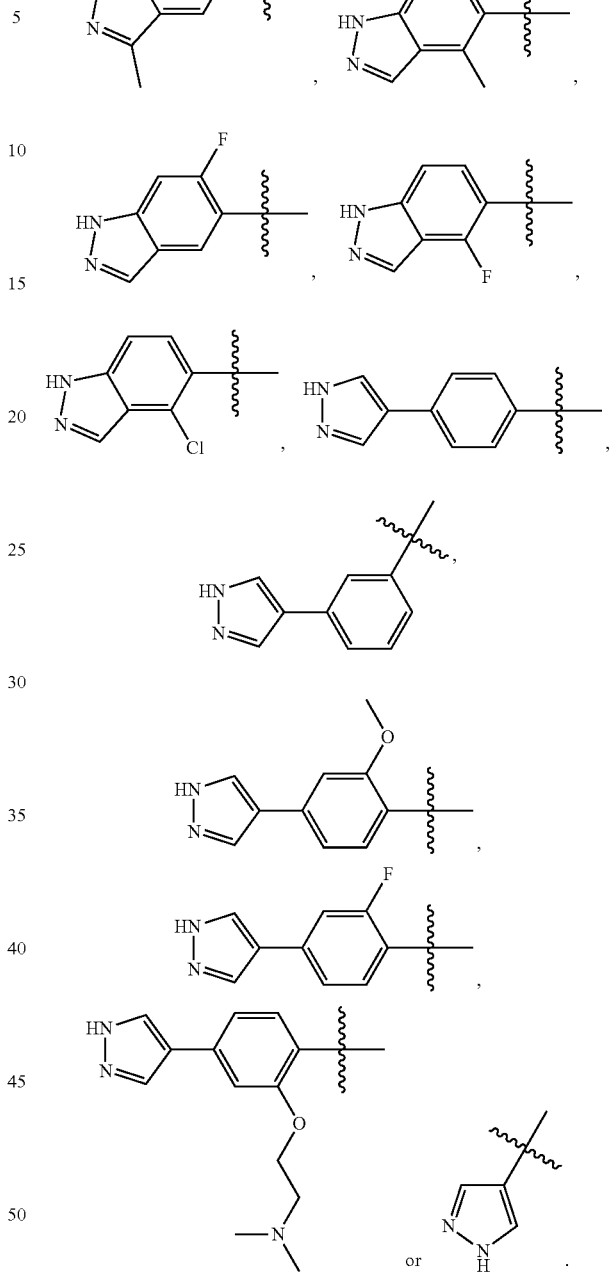

In some embodiments, the present invention provides a compound or a pharmaceutically acceptable salt, ester, stereoisomer, polymorph, solvate, N-oxide, isotopically labeled compound, metabolite or prodrug thereof, wherein

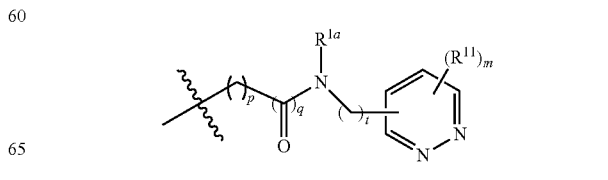

is selected form the group consisting of

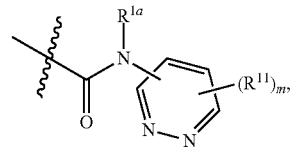

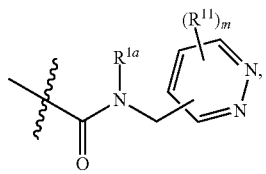

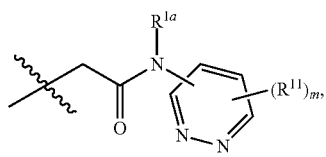

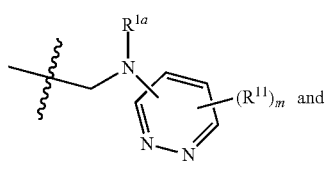

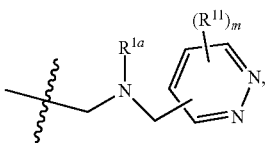

preferably is

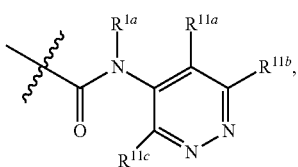

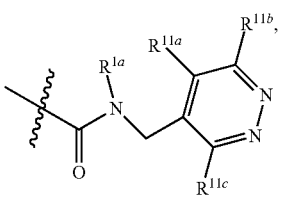

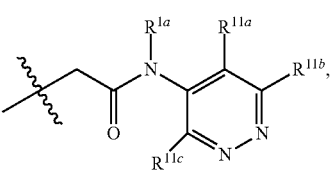

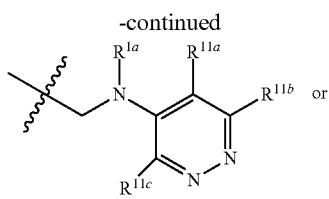

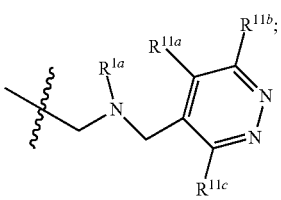

$R^{11a}$, $R^{11b}$ and $R^{11c}$ are each independently selected from the group consisting of H, halogen, amino, cyano, nitro, $C_{1-6}$ alkyl, $C_{2-6}$ alkenyl, $C_{2-6}$ alkynyl, $C_{3-10}$ cyclic hydrocarbyl, 3- to 10-membered heterocyclyl, $C_{6-10}$ aryl, 5- to 14-membered heteroaryl, $C_{6-12}$ aralkyl, —C(=O)R$^5$, —OC(=O)R$^5$, —C(=O)OR$^5$, —OR$^5$, —SR$^5$, —S(=O)R$^5$, —S(=O)$_2$R$^5$, —S(=O)$_2$NR$^5$R$^6$, —NR$^5$R$^6$, —C(=O)NR$^5$R$^6$, —NR$^5$—C(=O)R$^6$, —NR$^5$—C(=O)OR$^6$, —NR$^5$—S(=O)$_2$—R$^6$, —NR$^5$—C(=O)—NR$^5$R$^6$, —C$_{1-6}$ alkylene-NR$^5$R$^6$ and —O—C$_{1-6}$ alkylene-NR$^5$R$^6$;

alternatively, $R^{11a}$ and $R^{11b}$ together with the carbon atoms to which they are attached form $C_{4-10}$ cyclic hydrocarbyl, 4- to 10-membered heterocyclyl, $C_{6-10}$ aryl, or 5- to 14-membered heteroaryl.

In some embodiments, the present invention provides a compound or a pharmaceutically acceptable salt, ester, stereoisomer, polymorph, solvate, N-oxide, isotopically labeled compound, metabolite or prodrug thereof, wherein $R^{11a}$, $R^{11b}$ and $R^{11c}$ are each independently selected from the group consisting of H, F, Cl, Br, methyl, trifluoromethyl, methoxy, N-methylpiperazinyl, and dimethylamino;

alternatively, $R^{11a}$ and $R^{11b}$ together with the carbon atoms to which they are attached form phenyl.

In some embodiments, the present invention provides a compound or a pharmaceutically acceptable salt, ester, stereoisomer, polymorph, solvate, N-oxide, isotopically labeled compound, metabolite or prodrug thereof, wherein the compound has the structure of any of the following formulae:

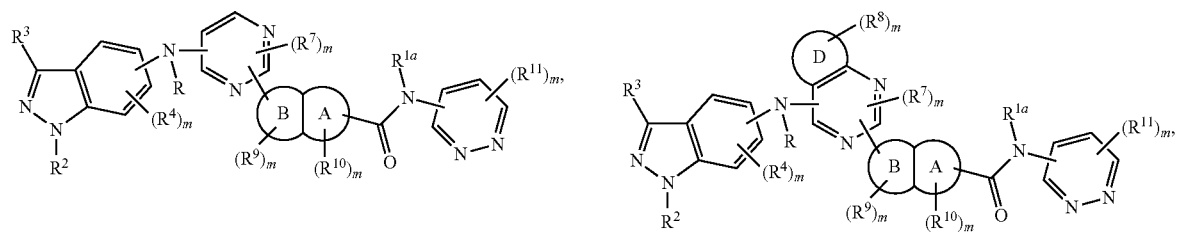
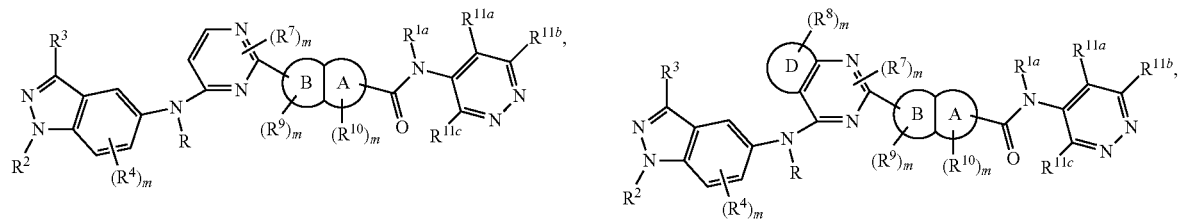
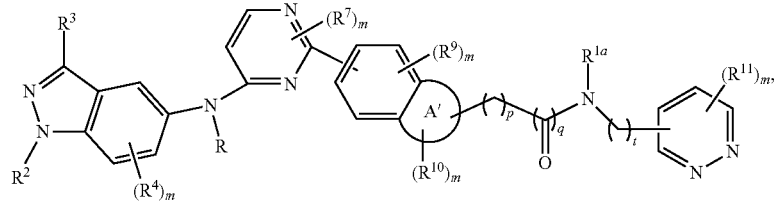
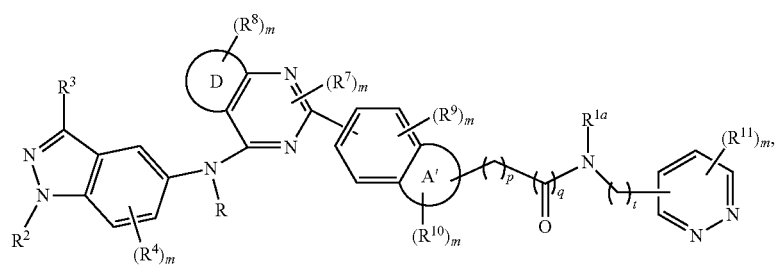
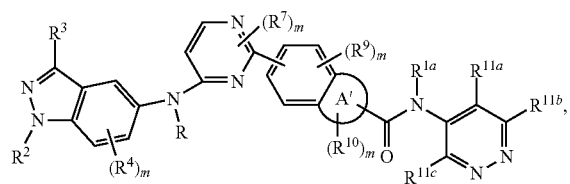
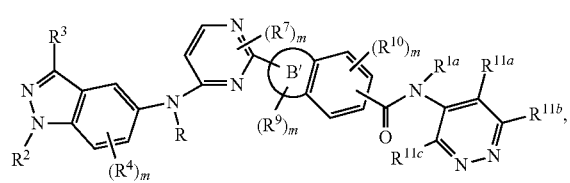
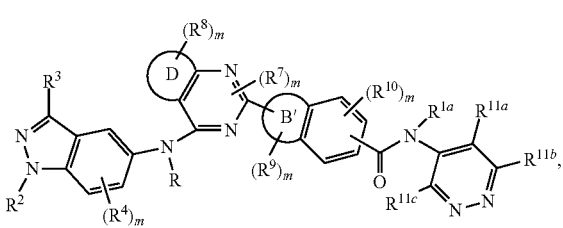

(VII)
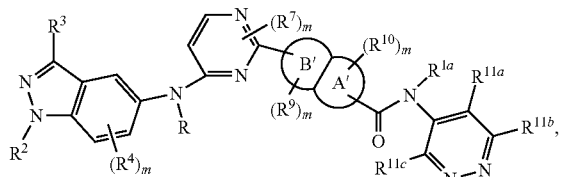

(VII')
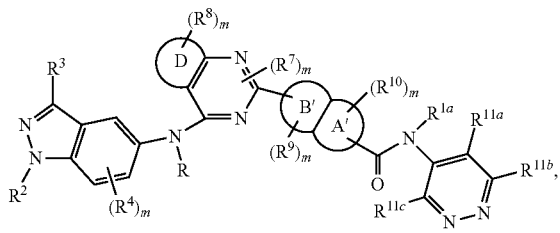

(VIII)
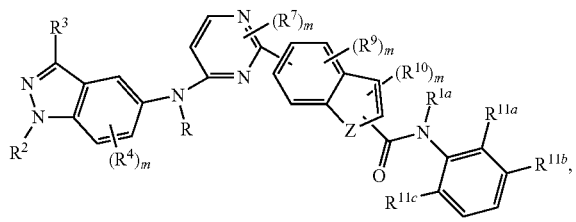

(VIII')
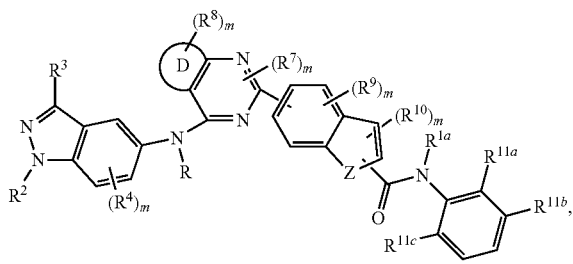

(IX)
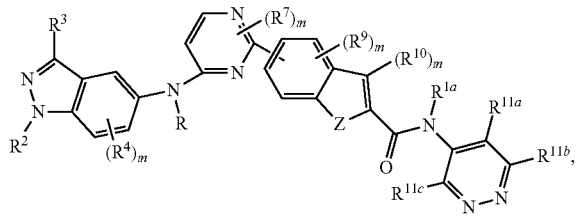

(IX')
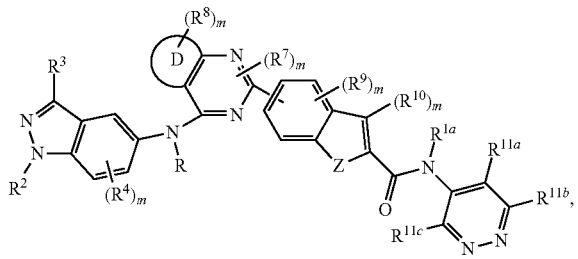

(X)
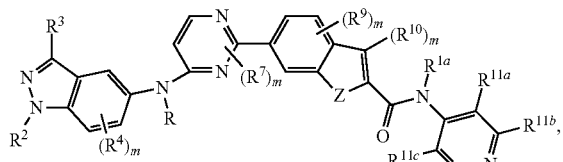

(X')
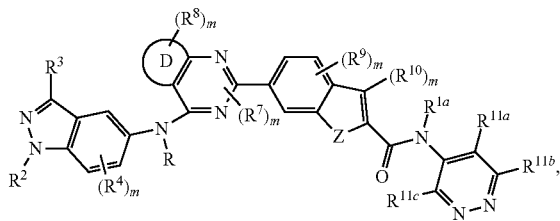

(XI)
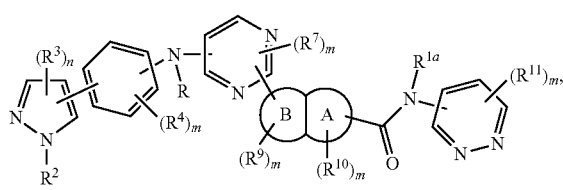

(XI')
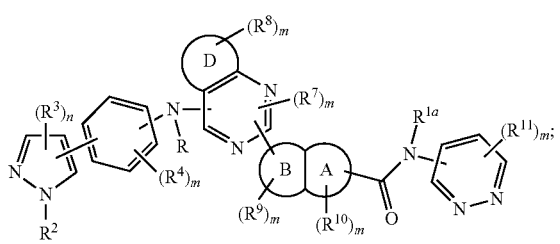

wherein:

Z is selected from the group consisting of O, S(=O)$_i$ and NR;

each of the remaining groups is as defined above.

The compound obtained by any combination of the various embodiments is encompassed by the invention.

In some embodiments, the present invention provides a compound or a pharmaceutically acceptable salt, ester, stereoisomer, polymorph, solvate, N-oxide, isotopically labeled compound, metabolite or prodrug thereof, wherein the structure and characterization data of the compound is as follows:

| Serial Number | No. | Compound Structure | MS m/z (ESI): [M + H] |
|---|---|---|---|
| 1. | TDI01116 | 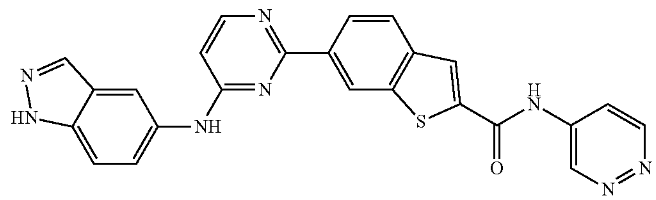 | 465.1 |
| 2. | TDI01152 | 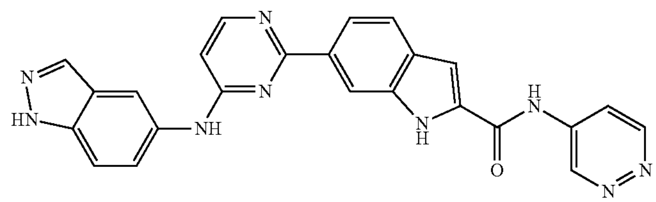 | 448.2 |
| 3. | TDI01154 | 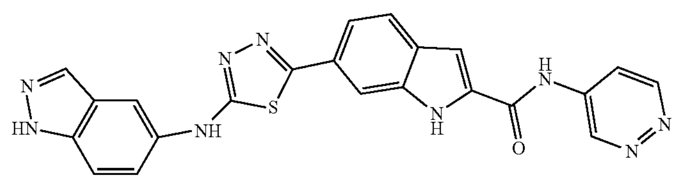 [SMILES: O=C(Nc1ccnnc1)c1cc2ccc(-c3nnc(Nc4ccc5[nH]ncc5c4)s3)cc2[nH]1] | 454.1 |
| 4. | TDI01162 | 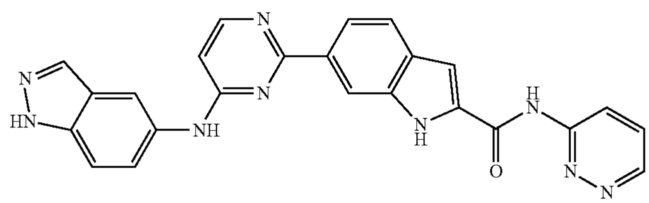 [SMILES: O=C(Nc1cccnn1)c1cc2ccc(-c3nccc(Nc4ccc5[nH]ncc5c4)n3)cc2[nH]1] | 448.2 |
| 5. | TDI01164 | 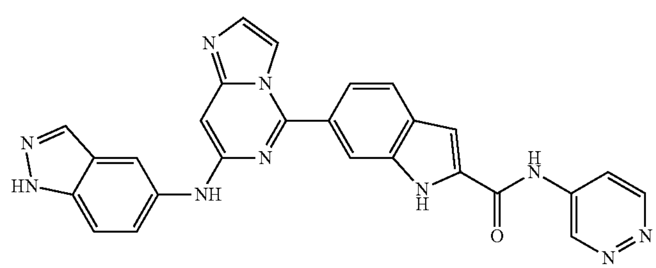 [SMILES: O=C(Nc1ccnnc1)c1cc2ccc(-c3nc(Nc4ccc5[nH]ncc5c4)cc4nccn34)cc2[nH]1] | 487.1 |
| 6. | TDI01165 | 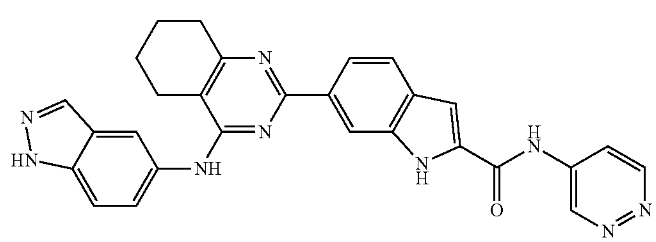 | 502.2 |
| 7. | TDI01166 | 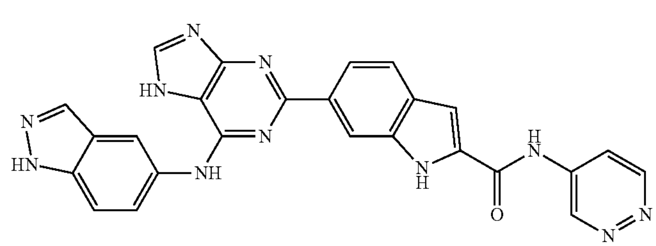 [SMILES: O=C(Nc1ccnnc1)c1cc2ccc(-c3nc(Nc4ccc5[nH]ncc5c4)c4[nH]cnc4n3)cc2[nH]1] | 488.2 |

-continued

| Serial Number | No. | Compound Structure | MS m/z (ESI): [M + H] |
|---|---|---|---|
| 8. | TDI01167 | 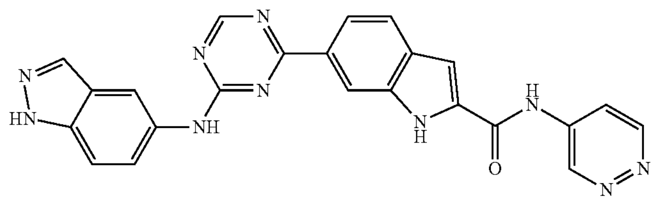 [SMILES: O=C(Nc1ccnnc1)c1cc2ccc(-c3ncnc(Nc4ccc5[nH]ncc5c4)n3)cc2[nH]1] | 449.3 |
| 9. | TDI01168 | 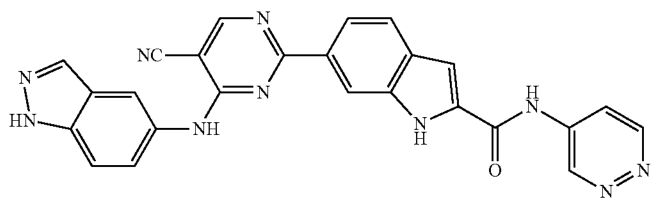 [SMILES: N#Cc1cnc(-c2ccc3cc(C(=O)Nc4ccnnc4)[nH]c3c2)nc1Nc1ccc2[nH]ncc2c1] | 473.2 |
| 10. | TDI01169 | 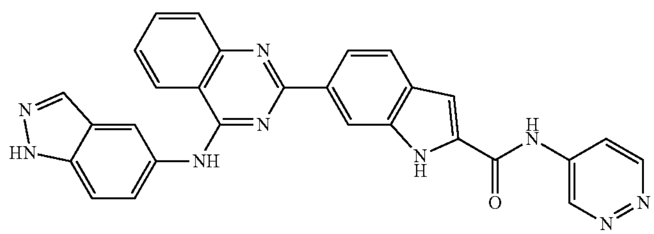 [SMILES: O=C(Nc1ccnnc1)c1cc2ccc(-c3nc(Nc4ccc5[nH]ncc5c4)c4ccccc4n3)cc2[nH]1] | 498.1 |
| 11. | TDI01172 | 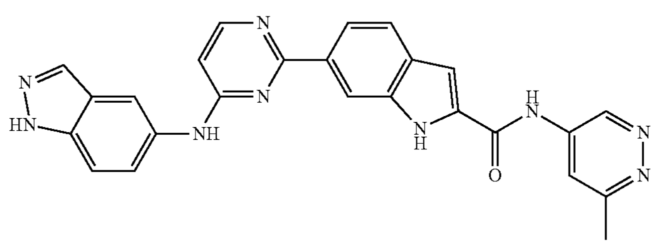 [SMILES: Cc1cc(NC(=O)c2cc3ccc(-c4nccc(Nc5ccc6[nH]ncc6c5)n4)cc3[nH]2)cnn1] | 462.2 |
| 12. | TDI01174 | 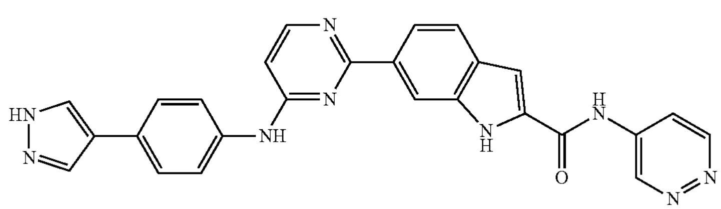 [SMILES: O=C(Nc1ccnnc1)c1cc2ccc(-c3nccc(Nc4ccc(-c5cn[nH]c5)cc4)n3)cc2[nH]1] | 474.1 |
| 13. | TDI01175 | 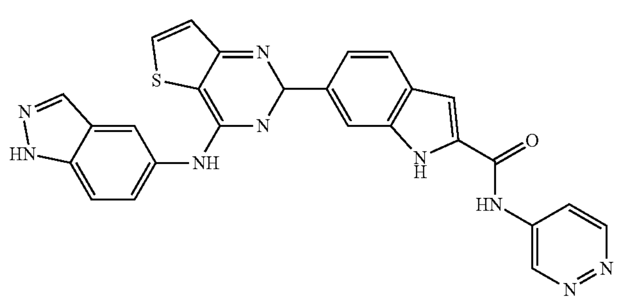 [SMILES: O=C(Nc1ccnnc1)c1cc2ccc(C3N=c4ccsc4=C(Nc4ccc5[nH]ncc5c4)N3)cc2[nH]1] | 504.1 |

| Serial Number | No. | Compound Structure | MS m/z (ESI): [M + H] |
|---|---|---|---|
| 14. | TDI01178 | 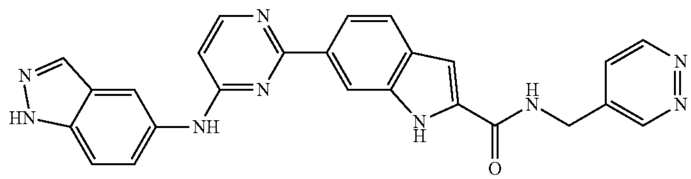 [SMILES: O=C(NCc1ccnnc1)c1cc2ccc(-c3nccc(Nc4ccc5[nH]ncc5c4)n3)cc2[nH]1] | 462.1 |
| 15. | TDI01179 | 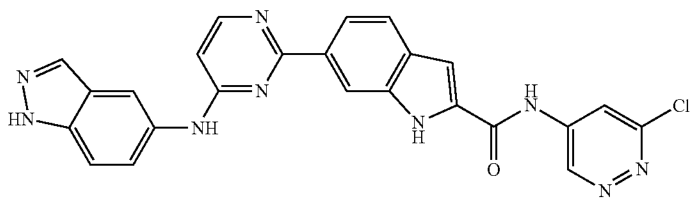 [SMILES: O=C(Nc1cnnc(Cl)c1)c1cc2ccc(-c3nccc(Nc4ccc5[nH]ncc5c4)n3)cc2[nH]1] | 482.1 |
| 16. | TDI01180 | 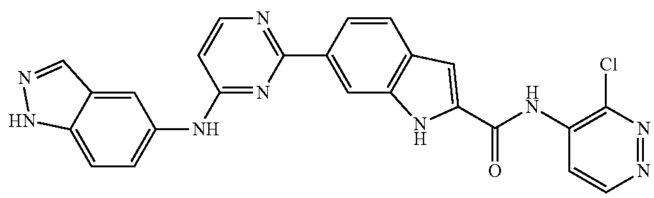 [SMILES: O=C(Nc1ccnnc1Cl)c1cc2ccc(-c3nccc(Nc4ccc5[nH]ncc5c4)n3)cc2[nH]1] | 482.1 |
| 17. | TDI01181 | 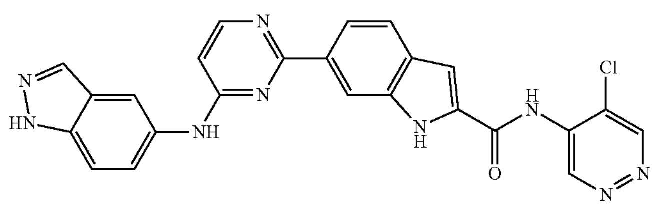 [SMILES: O=C(Nc1cnncc1Cl)c1cc2ccc(-c3nccc(Nc4ccc5[nH]ncc5c4)n3)cc2[nH]1] | 482.2 |
| 18. | TDI01185 | 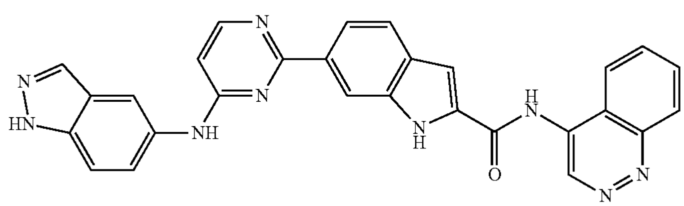 [SMILES: O=C(Nc1cnnc2ccccc12)c1cc2ccc(-c3nccc(Nc4ccc5[nH]ncc5c4)n3)cc2[nH]1] | 498.2 |
| 19. | TDI01187 | 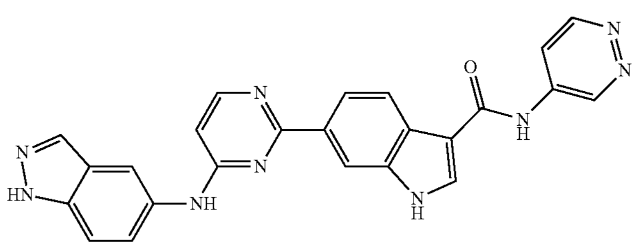 [SMILES: O=C(Nc1ccnnc1)c1c[nH]c2cc(-c3nccc(Nc4ccc5[nH]ncc5c4)n3)ccc12] | 448.2 |
| 20. | TDI01188 | 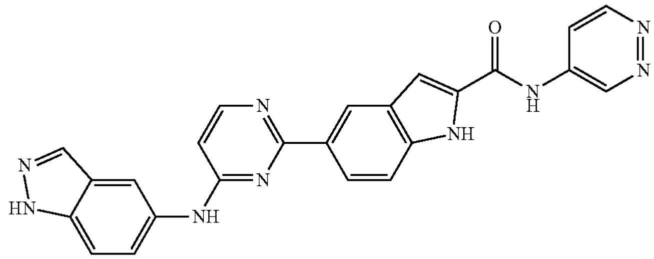 [SMILES: O=C(Nc1ccnnc1)c1cc2cc(-c3nccc(Nc4ccc5[nH]ncc5c4)n3)ccc2[nH]1] | 448.2 |

-continued

| Serial Number | No. | Compound Structure | MS m/z (ESI): [M + H] |
|---|---|---|---|
| 21. | TDI01189 | 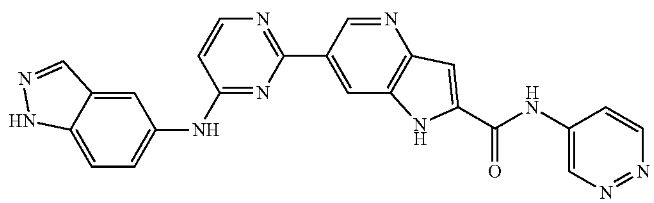 | 449.1 |
| 22. | TDI01190 | 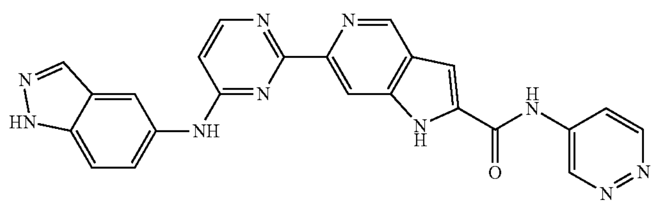 [SMILES: O=C(Nc1ccnnc1)c1cc2cnc(-c3nccc(Nc4ccc5[nH]ncc5c4)n3)cc2[nH]1] | 449.2 |
| 23. | TDI01191 | 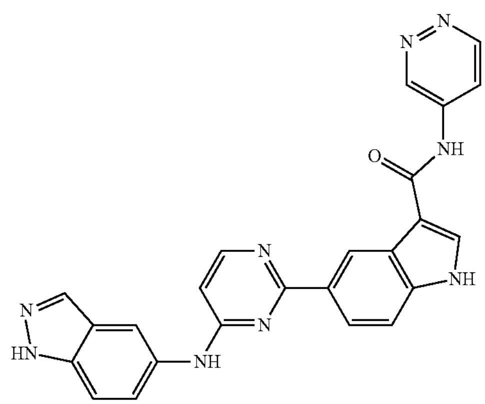 [SMILES: O=C(Nc1ccnnc1)c1c[nH]c2ccc(-c3nccc(Nc4ccc5[nH]ncc5c4)n3)cc12] | 448.2 |
| 24. | TDI01192 | 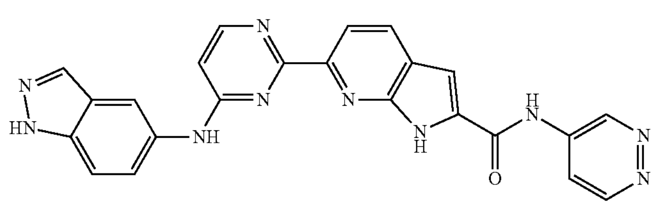 | 449.2 |
| 25. | TDI01193 | 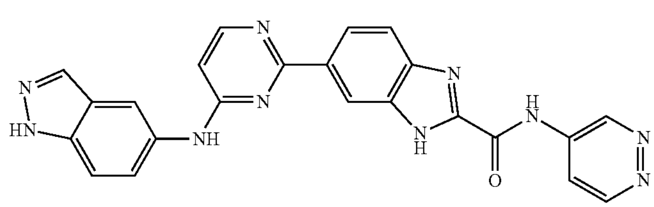 [SMILES: O=C(Nc1ccnnc1)c1nc2ccc(-c3nccc(Nc4ccc5[nH]ncc5c4)n3)cc2[nH]1] | 449.0 |
| 26. | TDI01194 | 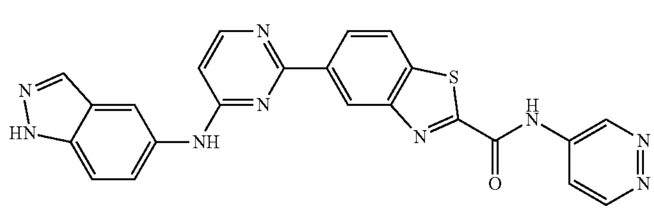 | 466.1 |

-continued

| Serial Number | No. | Compound Structure | MS m/z (ESI): [M + H] |
|---|---|---|---|
| 27. | TDI01195 | 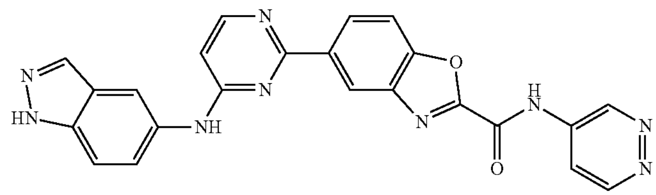 [SMILES: O=C(Nc1ccnnc1)c1nc2cc(-c3nccc(Nc4ccc5[nH]ncc5c4)n3)ccc2o1] | 450.1 |
| 28. | TDI01196 | 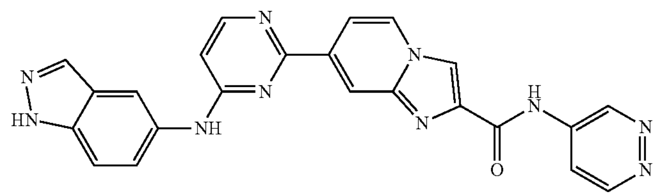 | 449.2 |
| 29. | TDI01197 | 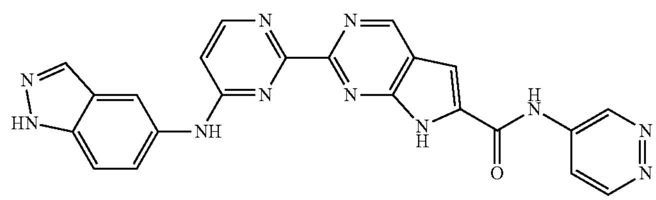 | 450.1 |
| 30. | TDI01198 | 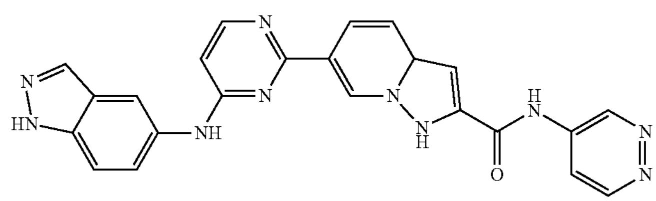 [SMILES: O=C(Nc1ccnnc1)C1=CC2C=CC(c3nccc(Nc4ccc5[nH]ncc5c4)n3)=CN2N1] | 451.2 |
| 31. | TDI01201 | 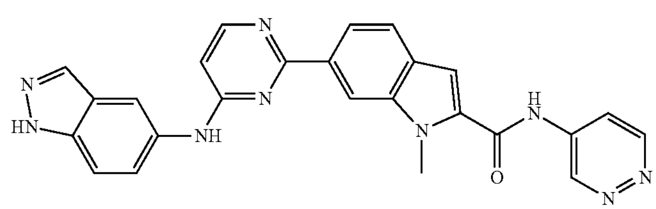 | 462.2 |
| 32. | TDI01209 | 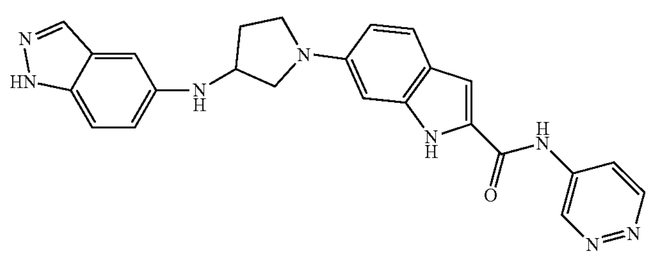 [SMILES: O=C(Nc1ccnnc1)c1cc2ccc(N3CCC(Nc4ccc5[nH]ncc5c4)C3)cc2[nH]1] | 439.1 |
| 33. | TDI01211 | 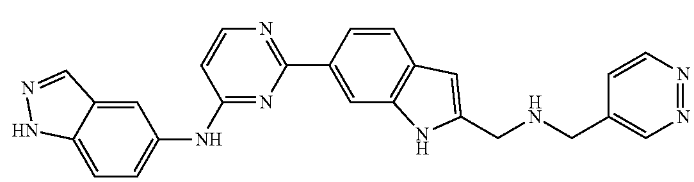 [SMILES: c1cc(CNCc2cc3ccc(-c4nccc(Nc5ccc6[nH]ncc6c5)n4)cc3[nH]2)cnn1] | 448.2 |

-continued

| Serial Number | No. | Compound Structure | MS m/z (ESI): [M + H] |
|---|---|---|---|
| 34. | TDI01212 | 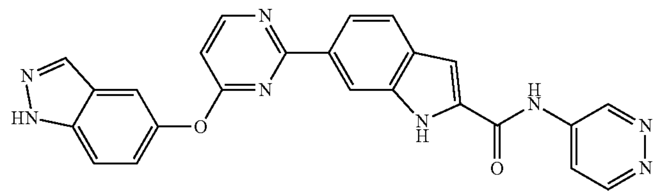 [SMILES: O=C(Nc1ccnnc1)c1cc2ccc(-c3nccc(Oc4ccc5[nH]ncc5c4)n3)cc2[nH]1] | 449.1 |
| 35. | TDI01213 | 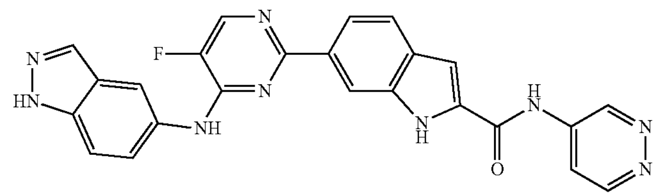 [SMILES: O=C(Nc1ccnnc1)c1cc2ccc(-c3ncc(F)c(Nc4ccc5[nH]ncc5c4)n3)cc2[nH]1] | 466.1 |
| 36. | TDI01214 | 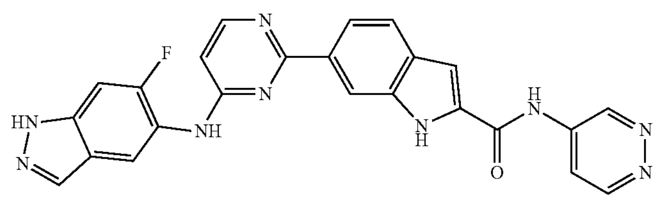 [SMILES: O=C(Nc1ccnnc1)c1cc2ccc(-c3nccc(Nc4cc5cn[nH]c5cc4F)n3)cc2[nH]1] | 466.1 |
| 37. | TDI01216 | 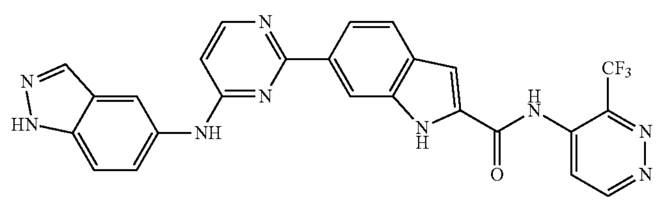 [SMILES: O=C(Nc1ccnnc1C(F)(F)F)c1cc2ccc(-c3nccc(Nc4ccc5[nH]ncc5c4)n3)cc2[nH]1] | 516.1 |
| 38. | TDI01217 | 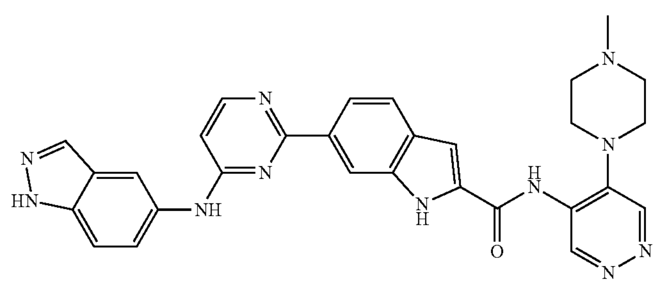 [SMILES: CN1CCN(c2cnncc2NC(=O)c2cc3ccc(-c4nccc(Nc5ccc6[nH]ncc6c5)n4)cc3[nH]2)CC1] | 546.2 |
| 39. | TDI01223 | 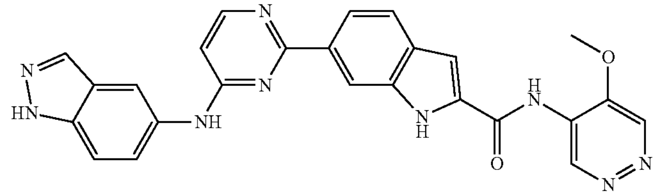 | 478.2 |
| 40. | TDI01224 | 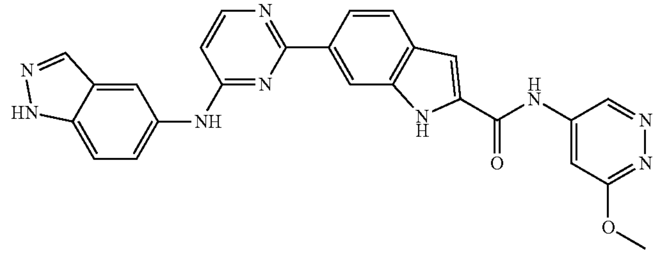 [SMILES: COc1cc(NC(=O)c2cc3ccc(-c4nccc(Nc5ccc6[nH]ncc6c5)n4)cc3[nH]2)cnn1] | 478.2 |

-continued

| Serial Number | No. | Compound Structure | MS m/z (ESI): [M + H] |
|---|---|---|---|
| 41. | TDI01225 | 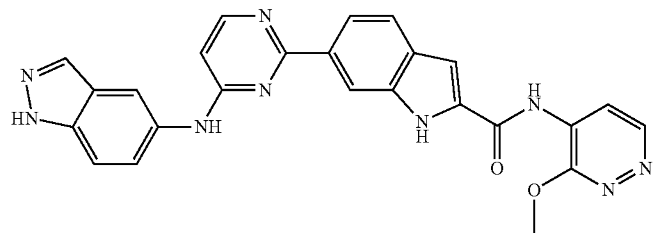 [SMILES: COc1nnccc1NC(=O)c1cc2ccc(-c3nccc(Nc4ccc5[nH]ncc5c4)n3)cc2[nH]1] | 478.2 |
| 42. | TDI01226 | 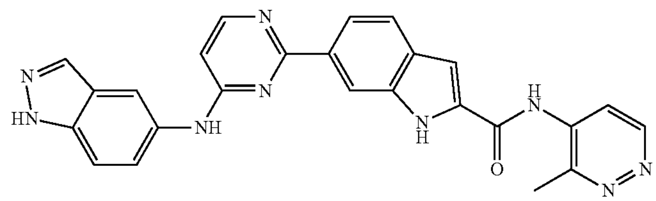 | 462.2 |
| 43. | TDI01227 | 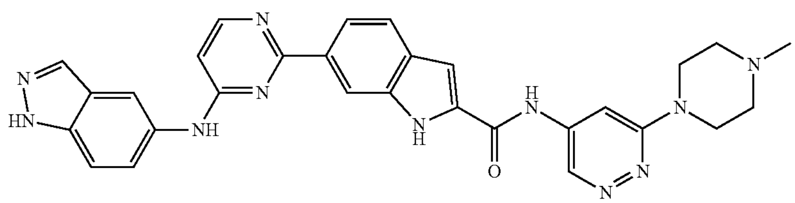 [SMILES: CN1CCN(c2cc(NC(=O)c3cc4ccc(-c5nccc(Nc6ccc7[nH]ncc7c6)n5)cc4[nH]3)cnn2)CC1] | 546.2 |
| 44. | TDI01228 | 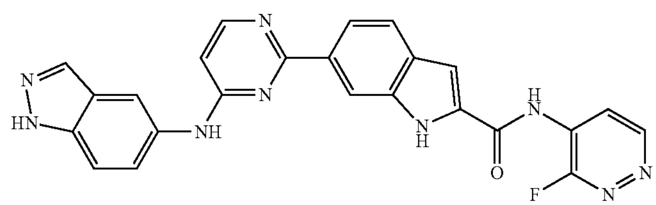 | 466.1 |
| 45. | TDI01231 | 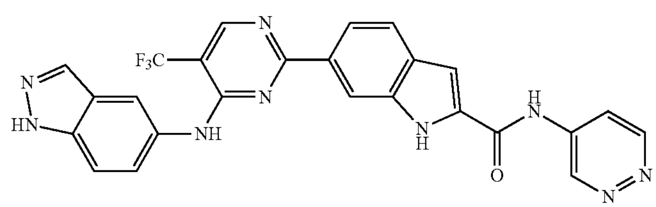 | 516.2 |
| 46. | TDI01232 | 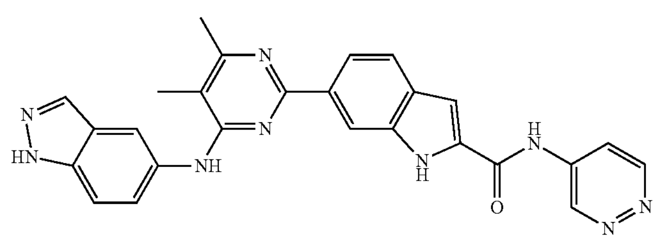 [SMILES: Cc1nc(-c2ccc3cc(C(=O)Nc4ccnnc4)[nH]c3c2)nc(Nc2ccc3[nH]ncc3c2)c1C] | 476.3 |
| 47. | TDI01233 | 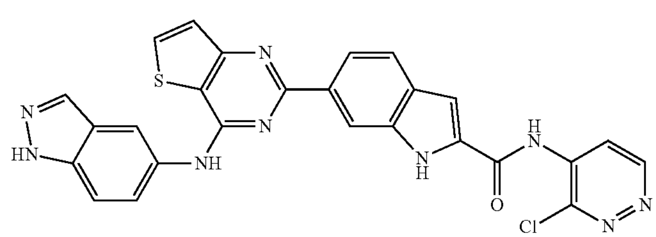 [SMILES: O=C(Nc1ccnnc1Cl)c1cc2ccc(-c3nc(Nc4ccc5[nH]ncc5c4)c4sccc4n3)cc2[nH]1] | 538.1 |

| Serial Number | No. | Compound Structure | MS m/z (ESI): [M + H] |
|---|---|---|---|
| 48. | TDI01234 | 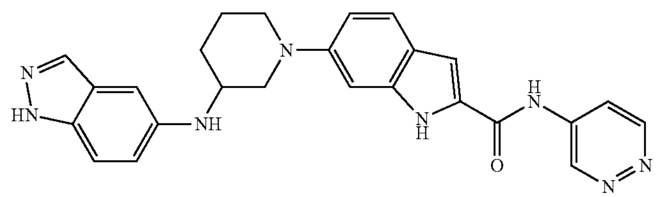 [SMILES: O=C(Nc1ccnnc1)c1cc2ccc(N3CCCC(Nc4ccc5[nH]ncc5c4)C3)cc2[nH]1] | 451.3 |
| 49. | TDI01235 | 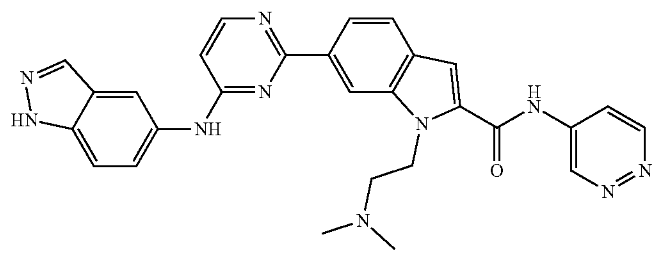 [SMILES: CN(C)CCn1c(C(=O)Nc2ccnnc2)cc2ccc(-c3nccc(Nc4ccc5[nH]ncc5c4)n3)cc21] | 519.2 |
| 50. | TDI01236 | 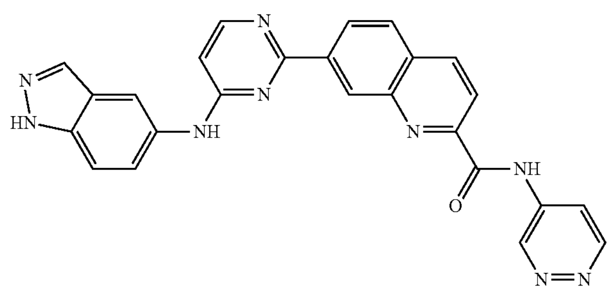 [SMILES: O=C(Nc1ccnnc1)c1ccc2ccc(-c3nccc(Nc4ccc5[nH]ncc5c4)n3)cc2n1] | 460.3 |
| 51. | TDI01237 | 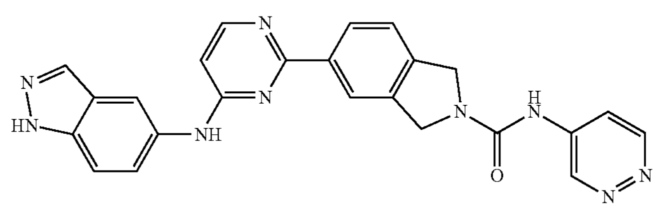 [SMILES: O=C(Nc1ccnnc1)N1Cc2ccc(-c3nccc(Nc4ccc5[nH]ncc5c4)n3)cc2C1] | 450.2 |
| 52. | TDI01238 | 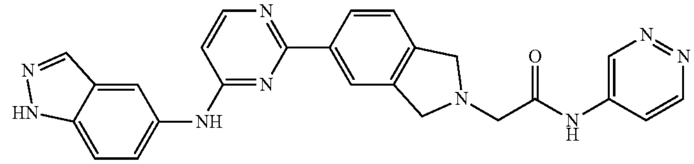 [SMILES: O=C(CN1Cc2ccc(-c3nccc(Nc4ccc5[nH]ncc5c4)n3)cc2C1)Nc1ccnnc1] | 464.3 |
| 53. | TDI01239 | 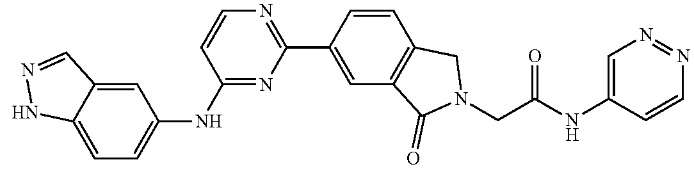 [SMILES: O=C(CN1Cc2ccc(-c3nccc(Nc4ccc5[nH]ncc5c4)n3)cc2C1=O)Nc1ccnnc1] | 478.2 |
| 54. | TDI01240 | 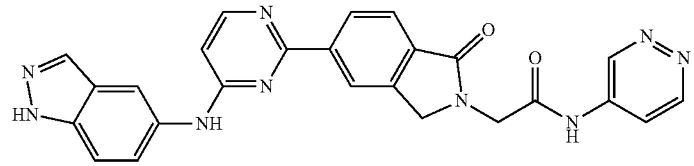 [SMILES: O=C(CN1Cc2cc(-c3nccc(Nc4ccc5[nH]ncc5c4)n3)ccc2C1=O)Nc1ccnnc1] | 478.2 |

-continued

| Serial Number | No. | Compound Structure | MS m/z (ESI): [M + H] |
|---|---|---|---|
| 55. | TDI01242 | 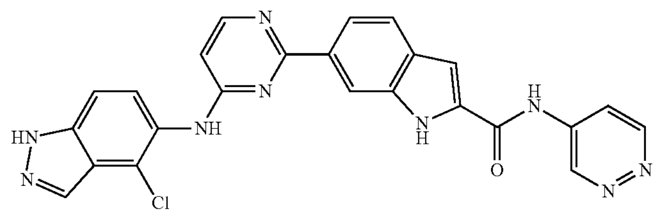 [SMILES: O=C(Nc1ccnnc1)c1cc2ccc(-c3nccc(Nc4ccc5[nH]ncc5c4Cl)n3)cc2[nH]1] | 482.1 |
| 56. | TDI01243 | 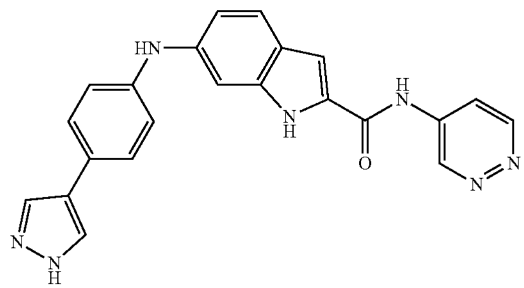 [SMILES: O=C(Nc1ccnnc1)c1cc2ccc(Nc3ccc(-c4cn[nH]c4)cc3)cc2[nH]1] | 396.1 |
| 57. | TDI01244 | 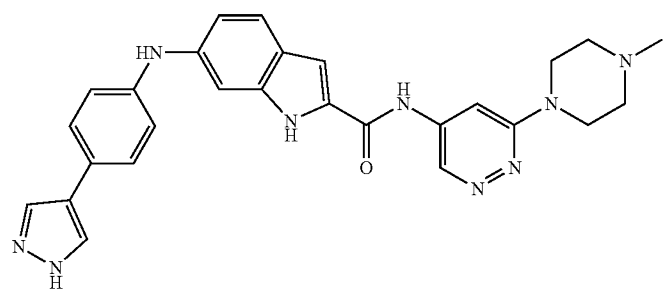 [SMILES: CN1CCN(c2cc(NC(=O)c3cc4ccc(Nc5ccc(-c6cn[nH]c6)cc5)cc4[nH]3)cnn2)CC1] | 494.2 |
| 58. | TDI01245 | 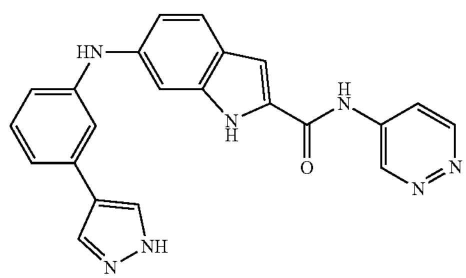 [SMILES: O=C(Nc1ccnnc1)c1cc2ccc(Nc3cccc(-c4cn[nH]c4)c3)cc2[nH]1] | 396.2 |
| 59. | TDI01246 | 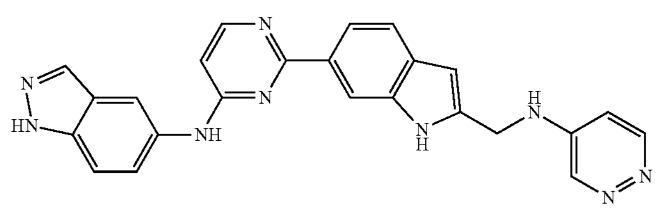 [SMILES: c1cc(NCc2cc3ccc(-c4nccc(Nc5ccc6[nH]ncc6c5)n4)cc3[nH]2)cnn1] | 434.2 |
| 60. | TDI01249 | 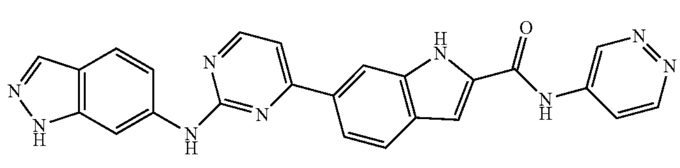 [SMILES: O=C(Nc1ccnnc1)c1cc2ccc(-c3ccnc(Nc4ccc5cn[nH]c5c4)n3)cc2[nH]1] | 448.0 |

-continued

| Serial Number | No. | Compound Structure | MS m/z (ESI): [M + H] |
|---|---|---|---|
| 61. | TDI01250 | 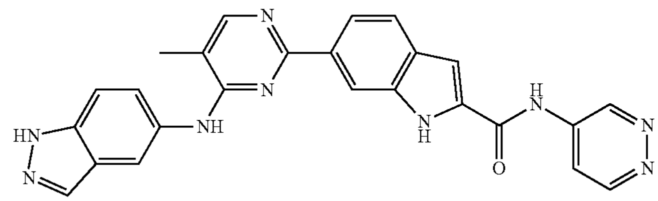 | 462.3 |
| 62. | TDI01251 | 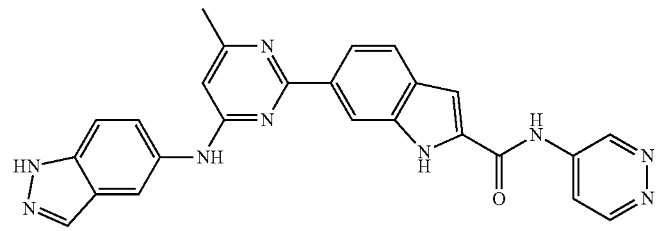 [SMILES: Cc1cc(Nc2ccc3[nH]ncc3c2)nc(-c2ccc3cc(C(=O)Nc4ccnnc4)[nH]c3c2)n1] | 462.1 |
| 63. | TDI01257 | 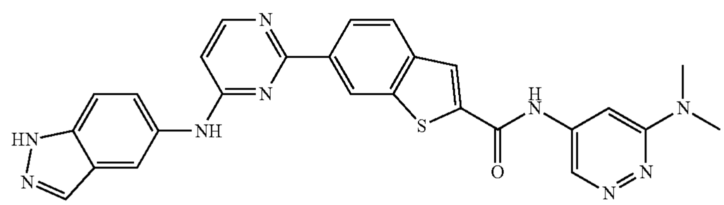 [SMILES: CN(C)c1cc(NC(=O)c2cc3ccc(-c4nccc(Nc5ccc6[nH]ncc6c5)n4)cc3s2)cnn1] | 508.2 |
| 64. | TDI01261 | 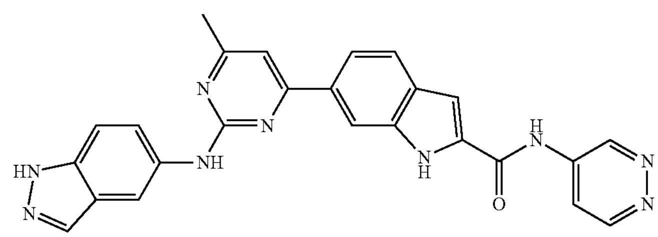 [SMILES: Cc1cc(-c2ccc3cc(C(=O)Nc4ccnnc4)[nH]c3c2)nc(Nc2ccc3[nH]ncc3c2)n1] | 462.1 |
| 65. | TDI01275 | 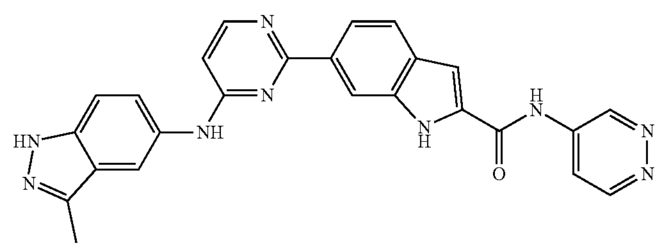 [SMILES: Cc1n[nH]c2ccc(Nc3ccnc(-c4ccc5cc(C(=O)Nc6ccnnc6)[nH]c5c4)n3)cc12] | 462.2 |
| 66. | TDI01276 | 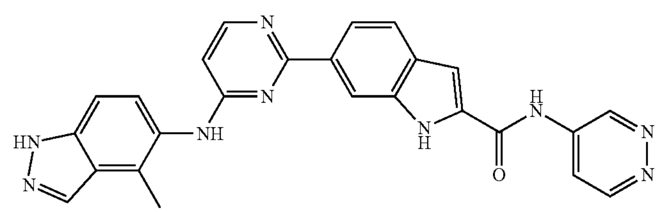 [SMILES: Cc1c(Nc2ccnc(-c3ccc4cc(C(=O)Nc5ccnnc5)[nH]c4c3)n2)ccc2[nH]ncc12] | 462.2 |
| 67. | TDI01277 | 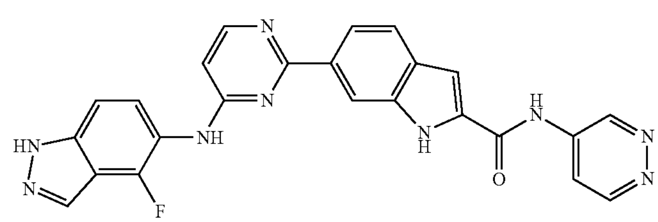 [SMILES: O=C(Nc1ccnnc1)c1cc2ccc(-c3nccc(Nc4ccc5[nH]ncc5c4F)n3)cc2[nH]1] | 466.1 |

| Serial Number | No. | Compound Structure | MS m/z (ESI): [M + H] |
|---|---|---|---|
| 68. | TDI01278 | 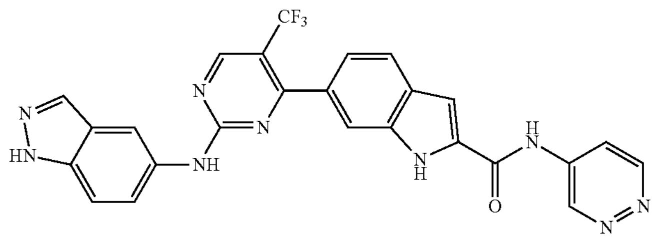 [SMILES: O=C(Nc1ccnnc1)c1cc2ccc(-c3nc(Nc4ccc5[nH]ncc5c4)ncc3C(F)(F)F)cc2[nH]1] | 516.2 |
| 69. | TDI01282 | 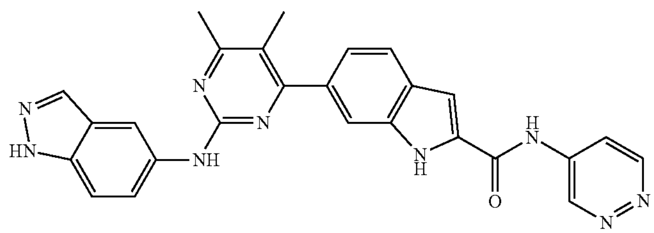 [SMILES: Cc1nc(Nc2ccc3[nH]ncc3c2)nc(-c2ccc3cc(C(=O)Nc4ccnnc4)[nH]c3c2)c1C] | 476.3 |
| 70. | TDI01314 | 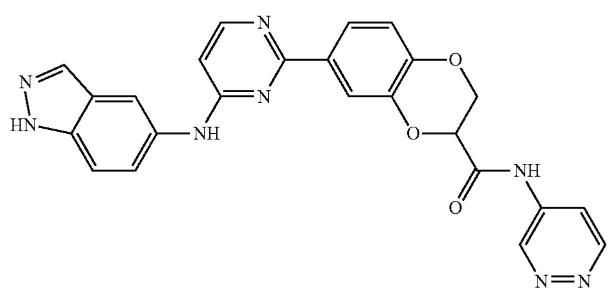 [SMILES: O=C(Nc1ccnnc1)C1COc2ccc(-c3nccc(Nc4ccc5[nH]ncc5c4)n3)cc2O1] | 467.2 |
| 71. | TDI01347 | 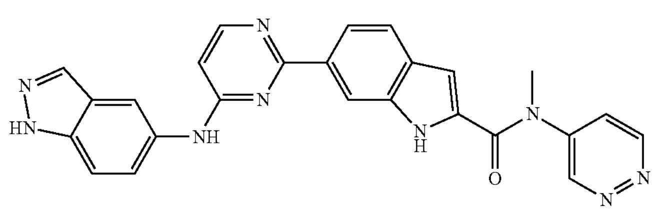 [SMILES: CN(C(=O)c1cc2ccc(-c3nccc(Nc4ccc5[nH]ncc5c4)n3)cc2[nH]1)c1ccnnc1] | 462.2 |
In some embodiments, the present invention provides a method for the preparation of a compound of Formula (II), wherein the method comprises the following steps:
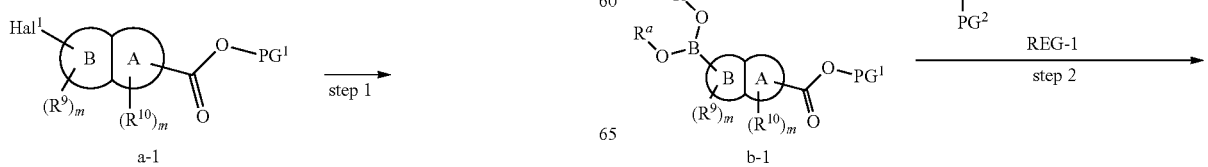

-continued

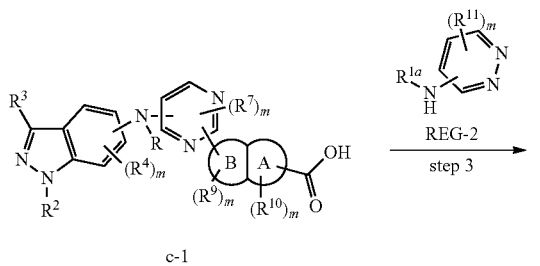

c-1

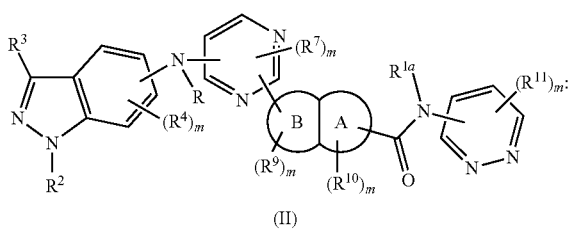

(II)

wherein:
R² is H;
Hal¹ and Hal² are same or different halogens, e.g., F, C, Br or I;
PG¹ is a carboxy protecting group, preferably $C_{1-6}$ alkyl;
PG² is H or an amino protecting group, preferably tert-butyloxycarbonyl (Boc);
$R^a$ and $R^{a'}$, at each occurrence, are each independently selected from the group consisting of H and $C_{1-6}$ alkyl; or $R^a$ and $R^{a'}$ together with the group to which they are attached form a 5- to 10-membered ring system;
the remaining groups are as defined above;
the reaction conditions for each step are as follows:
step 1: reacting compound a-1 with a boric acid or borate under the catalysis of a palladium catalyst (preferably in the presence of a base), to obtain compound b-1;
step 2: reacting compound b-1 with compound REG-1 under the catalysis of a palladium catalyst (preferably in the presence of a base), to obtain compound c-1; and
step 3: reacting compound c-1 with compound REG-2 (preferably in the presence of an appropriate condensation agent and an appropriate base), to obtain the compound of Formula (II);
alternatively, the method comprises the following steps:

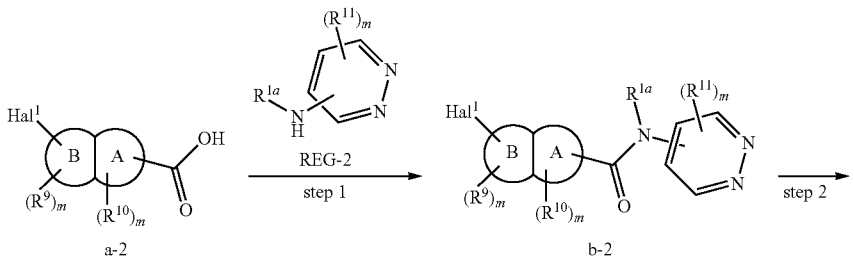

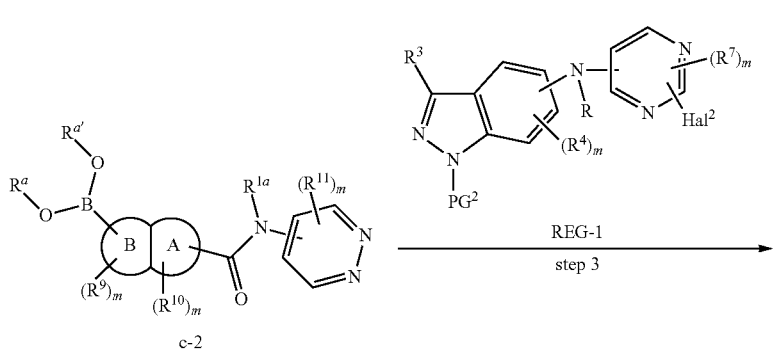

c-2

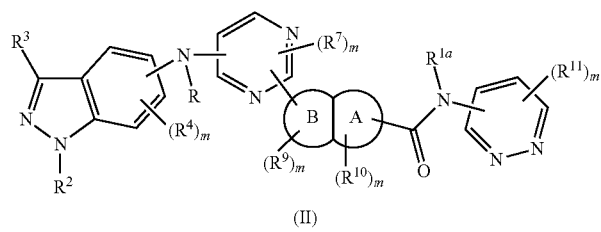

(II)

wherein each of the groups is as defined above;

the reaction conditions for each step are as follows:

step 1: reacting compound a-2 with compound REG-2 (preferably in the presence of an appropriate condensation agent and an appropriate base), to obtain compound b-2;

step 2: reacting compound b-2 with a boric acid or borate under the catalysis of a palladium catalyst (preferably in the presence of a base), to obtain compound c-2; and step 3: reacting compound c-2 with compound REG-1 under the catalysis of a palladium catalyst (preferably in the presence of a base), to obtain the compound of Formula (II);

alternatively, the method comprises the following steps:

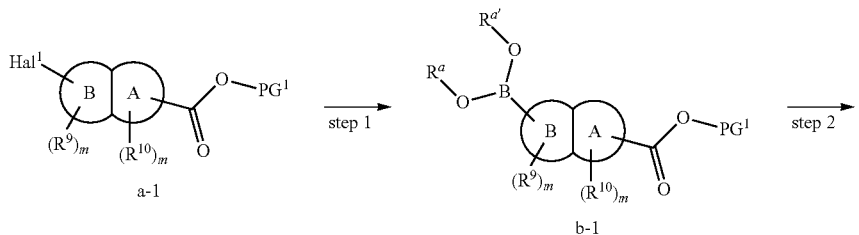

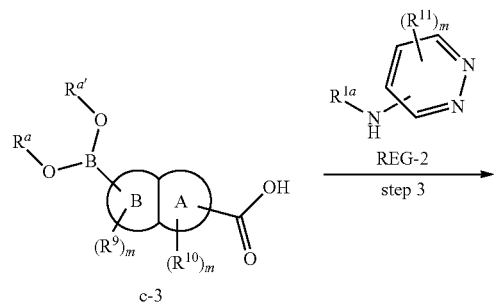

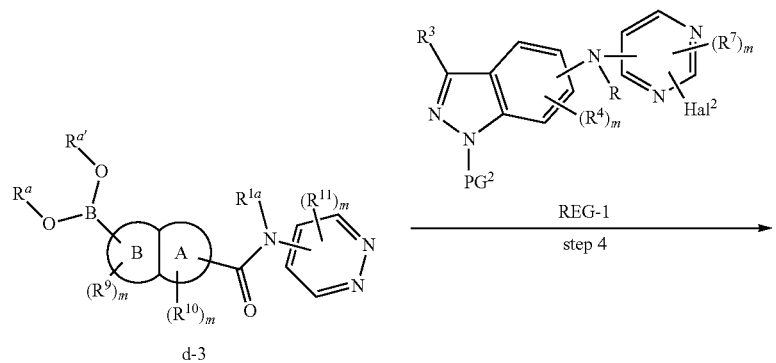

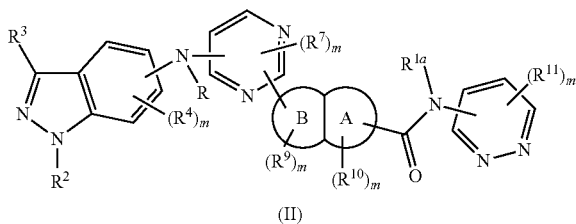

wherein each of the groups is as defined above;
the reaction conditions for each step are as follows:
step 1: reacting compound a-1 with a boric acid or borate under the catalysis of a palladium catalyst (preferably in the presence of a base), to obtain compound b-1;
step 2: deprotecting compound b-1 under a condition corresponding to $PG^1$, to obtain compound c-3;
step 3: reacting compound c-3 with compound REG-2 (preferably in the presence of an appropriate condensation agent and an appropriate base), to obtain compound d-3; and
step 4: reacting compound d-3 with compound REG-1 under the catalysis of a palladium catalyst (preferably in the presence of a base), to obtain the compound of Formula (II);

In some embodiments, the present invention provides a method for the preparation of a compound of Formula (XI), wherein the method comprises the following steps:

$PG^1$ is a carboxy the protecting group, preferably $C_{1-6}$ alkyl;
$PG^2$ is H or an amino protecting group, preferably tert-butyloxycarbonyl (Boc);
$R^a$ and $R^{a'}$, at each occurrence, are each independently selected from the group consisting of H and $C_{1-6}$ alkyl; or $R^a$ and $R^{a'}$ together with the group to which they are attached form a 5- to 10-membered ring system;
the remaining groups are as defined above;
the reaction conditions for each step are as follows:
step 1: reacting compound a-1 with a boric acid or borate under the catalysis of a palladium catalyst (preferably in the presence of a base), to obtain compound b-1; and
step 2: reacting compound b-1 with compound REG-1' under the catalysis of a palladium catalyst (preferably in the presence of a base), to obtain compound c-1'; and

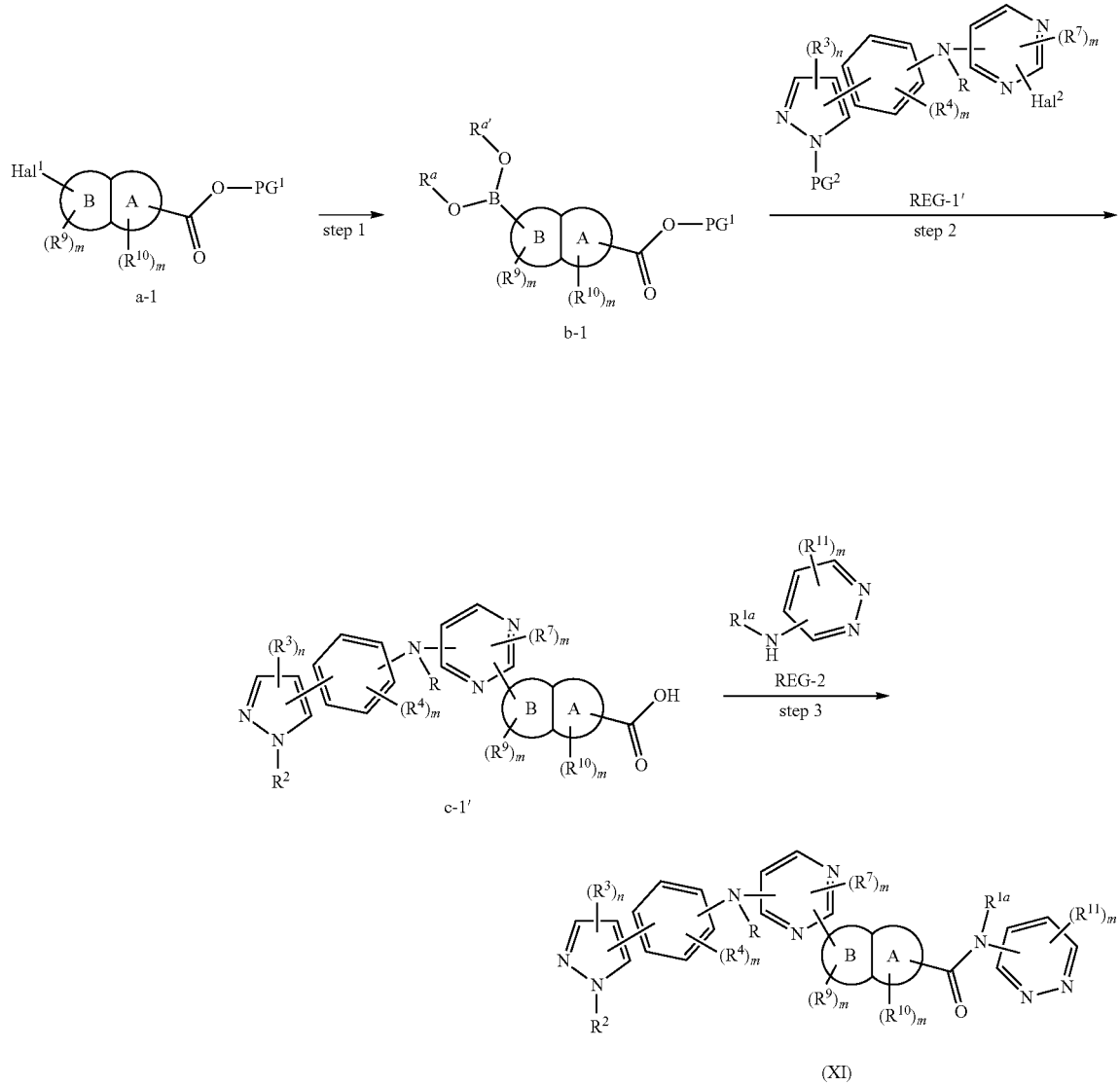

(XI)

wherein:
$R^2$ is H;
$Hal^1$ and $Hal^2$ are same or different halogens, e.g., F, Cl, Br or I;

step 3: reacting compound c-1' with compound REG-2 (preferably in the presence of an appropriate condensation agent and an appropriate base), to obtain the compound of Formula (XI);

alternatively, the method comprises the following steps:

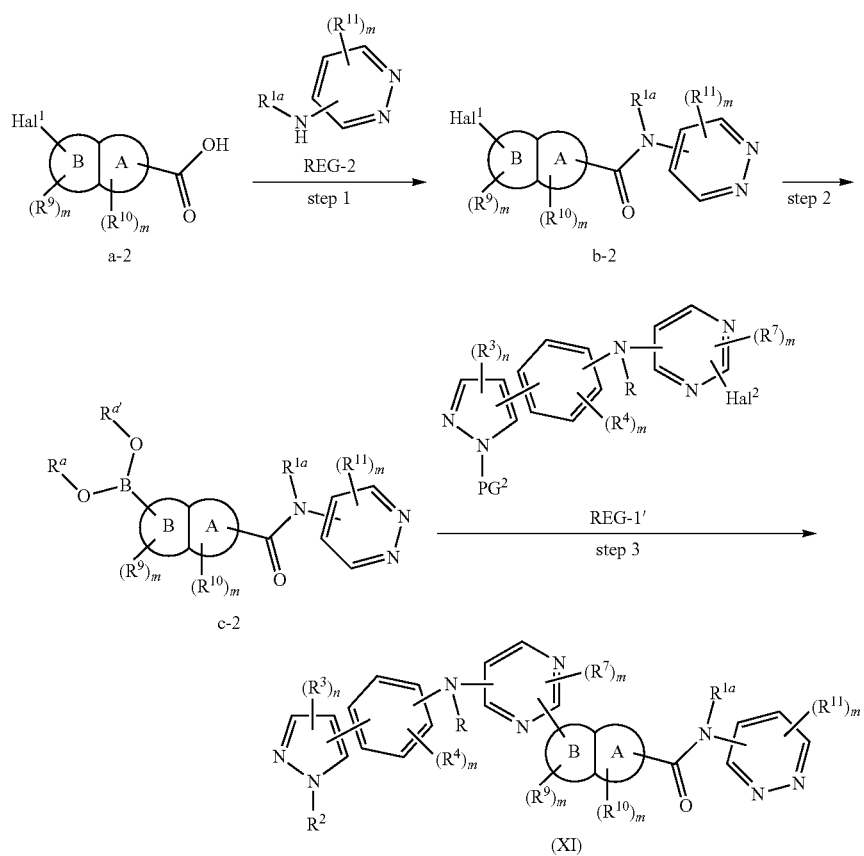

wherein each of the groups is as defined above;

the reaction conditions for each step are as follows:

step 1: reacting compound a-2 with compound REG-2 (preferably in the presence of an appropriate condensation agent and an appropriate base), to obtain compound b-2;

step 2: reacting compound b-2 with a boric acid or borate under the catalysis of a palladium catalyst (preferably in the presence of a base), to obtain compound c-2; and step 3: reacting compound c-2 with compound REG-1' under the catalysis of a palladium catalyst (preferably in the presence of a base), to obtain the compound of Formula (XI);

alternatively, the method comprises the following steps:

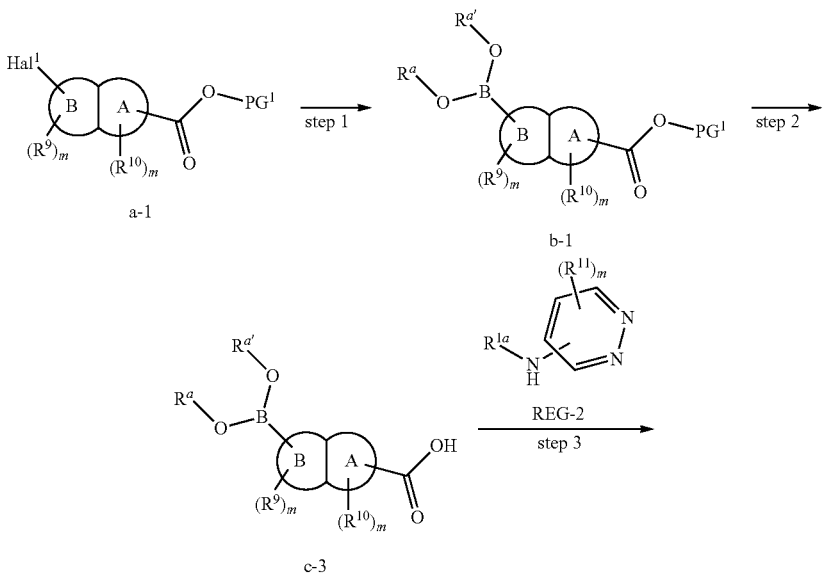

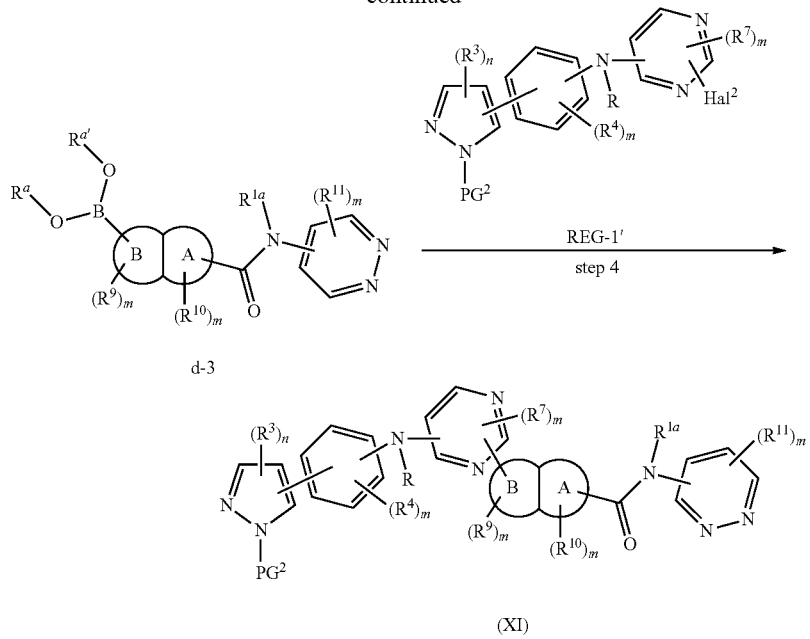

wherein each of the groups is as defined above;
the reaction conditions for each step are as follows:
step 1: reacting compound a-1 with a boric acid or borate under the catalysis of a palladium catalyst (preferably in the presence of a base), to obtain compound b-1;
step 2: deprotecting compound b-1 under a condition corresponding to $PG^1$, to obtain compound c-3;
step 3: reacting compound c-3 with compound REG-2 (preferably in the presence of an appropriate condensation agent and an appropriate base), to obtain compound d-3; and
step 4: reacting compound d-3 with compound REG-1' under the catalysis of a palladium catalyst (preferably in the presence of a base), to obtain the compound of Formula (XI).

In preferred embodiments, the boric acid or borate is e.g., bis(pinacolato)diboron.

In preferred embodiments, the palladium catalyst is e.g., $Pd(dppf)Cl_2$, $Pd(PPh_3)_4$, $Pd(OAc)_2$ or $Pd(PPh_3)_2Cl_2$.

In preferred embodiments, the condensation agent is e.g., DCC, EDCI, HATU, PyBOP.

In preferred embodiments, the appropriate base is e.g., diisopropylethylamine, triethylamine, pyridine, sodium carbonate, potassium acetate, potassium carbonate, potassium hydroxide, cesium carbonate.

Pharmaceutical Composition and Therapeutic Method

In some embodiments, the present invention provides a pharmaceutical composition comprising a prophylactically or therapeutically effective amount of the compound of the present invention or a pharmaceutically acceptable salt, ester, stereoisomer, polymorph, solvate, N-oxide, isotopically labeled compound, metabolite or prodrug thereof and one or more pharmaceutically acceptable carriers, and the pharmaceutical composition is preferably in the form of a solid, semi-solid, liquid, or gas preparation. In some embodiments, the pharmaceutical composition can further comprise one or more additional therapeutic agents.

In some embodiments, the present invention provides use of the compound of the present invention or a pharmaceutically acceptable salt, ester, stereoisomer, polymorph, solvate, N-oxide, isotopically labeled compound, metabolite or prodrug thereof or the pharmaceutical composition of the present invention in the preparation of a medicament for use as a Rho-associated protein kinase (ROCK) inhibitor, preferably a selective ROCK2 inhibitor.

In some embodiments, the present invention provides the compound of the present invention or a pharmaceutically acceptable salt, ester, stereoisomer, polymorph, solvate, N-oxide, isotopically labeled compound, metabolite or prodrug thereof or the pharmaceutical composition of the present invention for use as a Rho-associated protein kinase (ROCK) inhibitor, preferably a selective ROCK2 inhibitor.

In some embodiments, the present invention provides a method for the prevention or treatment of a disease mediated by the Rho-associated protein kinase (ROCK), wherein the method comprises administering to a subject in need thereof an effective amount of the compound of the present invention or a pharmaceutically acceptable salt, ester, stereoisomer, polymorph, solvate, N-oxide, isotopically labeled compound, metabolite or prodrug thereof or the pharmaceutical composition of the present invention.

In some embodiments, the disease mediated by the Rho-associated protein kinase (ROCK) includes an autoimmune disorder (comprising rheumatoid arthritis, systemic lupus erythematosus (SLE; lupus), psoriasis, Crohn's disease, atopic dermatitis, eczema, or graft-versus-host disease (GVHD)); a cardiovascular disorder (comprising hypertension, atherosclerosis, restenosis, cardiac hypertrophy, cerebral ischemia, cerebral vasospasm, or erectile dysfunction); inflammation (comprising asthma, cardiovascular inflammation, ulcerative colitis, or renal inflammation); a central nervous system disorder (comprising neuronal degeneration or spinal cord injury; and the central nervous system disorder is preferably Huntington's disease, Parkinson's disease, Alzheimer's disease, Amyotrophic lateral sclerosis (ALS), or multiple sclerosis); an arterial thrombotic disorder (comprising platelet aggregation, or leukocyte aggregation); a fibrotic disorder (comprising liver fibrosis, lung fibrosis, or kidney fibrosis); a neoplastic disease (comprising a lymphoma, carcinoma (e.g., squamous cell cancer, small-cell lung cancer, pituitary cancer, esophageal cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, bladder cancer, liver cancer, breast cancer, colon cancer, colorectal cancer, endometrial or uterine carcinoma, salivary gland carcinoma, kidney cancer, prostate cancer, vulval cancer, thyroid cancer, brain cancer, endometrial cancer, testis cancer, cholangiocarcinoma, gallbladder carcinoma, gastric cancer, melanoma, or head and neck cancer), leukemia, astrocytoma, soft tissue sarcoma, sarcoma, or blastoma); a metabolic syndrome; insulin resistance; hyperinsulinemia; type 2 diabetes; glucose intolerance; osteoporosis; an ocular disorder (comprising ocular hypertension, age related macular degeneration (AMD), choroidal neovascularization (CNV), diabetic macular edema (DME), iris neovascularization, uveitis, glaucoma (comprising primary open-angle glaucoma, acute angle-closure glaucoma, pigmentary glaucoma, congenital glaucoma, normal tension glaucoma, secondary glaucoma or neo vascular glaucoma), or retinitis of prematurity (ROP)).

In some embodiments, the disease mediated by the Rho-associated protein kinase (ROCK) includes lupus nephritis, atherosclerosis, rheumatoid arthritis (RA), hemangioma, angiofibroma, lung fibrosis, psoriasis, corneal graft rejection, insulin-dependent diabetes mellitus, multiple sclerosis, myasthenia gravis, Chron's disease, autoimmune nephritis, primary biliary cirrhosis, acute pancreatitis, allograph rejection, allergic inflammation, contact dermatitis, delayed hypersensitivity, inflammatory bowel disease, septic shock, osteoporosis, osteoarthritis, neuronal inflammation, Osier-Weber syndrome, restenosis, fungal infection, parasitic infection, and viral infection.

The term "pharmaceutically acceptable carrier" in the present invention refers to a diluent, auxiliary material, excipient, or vehicle with which a therapeutic is administered, and it is, within the scope of sound medical judgment, suitable for contact with the tissues of human beings and animals without excessive toxicity, irritation, allergic response, or other problem or complication, commensurate with a reasonable benefit/risk ratio.

The pharmaceutically acceptable carrier which can be employed in the pharmaceutical composition of the present invention includes, but is not limited to sterile liquids, such as water and oils, including those of petroleum, animal, vegetable or synthetic origin, such as peanut oil, soybean oil, mineral oil, sesame oil and the like. Water is an exemplary carrier when the pharmaceutical composition is administered intravenously. Physiological salines as well as aqueous dextrose and glycerol solutions can also be employed as liquid carriers, particularly for injectable solutions. Suitable pharmaceutical excipients include starch, glucose, lactose, sucrose, gelatin, maltose, chalk, silica gel, sodium stearate, glycerol monostearate, talc, sodium chloride, dried skim milk, glycerol, propylene glycol, water, ethanol and the like. The pharmaceutical composition, if desired, can also contain minor amounts of wetting or emulsifying agents, or pH buffering agents. Oral formulations can include standard carriers such as pharmaceutical grades of mannitol, lactose, starch, magnesium stearate, sodium saccharine, cellulose, magnesium carbonate, etc. Examples of suitable pharmaceutical carriers are described in e.g. Remington's Pharmaceutical Sciences (1990).

The pharmaceutical composition of the present invention can act systemically and/or topically. To this end, it can be administered through a suitable route, such as through injection, (intravenous, intraarterial, subcutaneous, intraperitoneal, intramuscular injection, including dripping), or transdermal administration, or administered via oral, buccal, nasal, transmucosal, topical, as an ophthalmic formulation, or via inhalation.

For these routes of administration, the pharmaceutical composition of the present invention can be administered in a suitable dosage form.

Such dosage forms include, but are not limited to tablets, capsules, lozenges, hard candies, powders, sprays, creams, salves, suppositories, gels, pastes, lotions, ointments, aqueous suspensions, injectable solutions, elixirs, and syrups.

As used herein, the term "effective amount" refers to the amount of a compound being administered which will relieve to some extent one or more of the symptoms of the disorder being treated.

Dosage regimens may be adjusted to provide the optimum desired response. For example, a single bolus may be administered, several divided doses may be administered over time, or the dose may be proportionally reduced or increased as indicated by the exigencies of the therapeutic situation. It is to be noted that dosage values may vary with the type and severity of the condition to be alleviated, and may include single or multiple doses. It is to be further understood that for any particular subject, specific dosage regimens should be adjusted over time according to the individual need and the professional judgment of the person administering or supervising the administration of the composition.

The amount of the compound of the present invention administered will be dependent on the subject being treated, the severity of the disorder or condition, the rate of administration, the disposition of the compound and the discretion of the prescribing physician. Generally, an effective dosage is in the range of about 0.0001 to about 50 mg per kg body weight per day, for example about 0.01 to about 10 mg/kg/day, in single or divided doses. For a 70 kg human, this would amount to about 0.007 mg to about 3500 mg/day, for example about 0.7 mg to about 700 mg/day. In some instances, dosage levels below the lower limit of the aforesaid range may be more than adequate, while in other cases, still larger doses may be employed without causing any harmful side effect, provided that such larger doses are first divided into several small doses for administration throughout the day.

The content or dosage of the compound of the present invention in the pharmaceutical composition is about 0.01 mg to about 1000 mg, suitably 0.1-500 mg, preferably 0.5-300 mg, more preferably 1-150 mg, particularly preferably 1-50 mg, e.g., 1.5 mg, 2 mg, 4 mg, 10 mg, 25 mg, etc.

Unless otherwise indicated, the term "treating" or "treatment", as used herein, means reversing, alleviating, inhibiting the progress of, or preventing the disorder or condition to which such term applies, or one or more symptoms of such disorder or condition.

As used herein, the term "subject" includes a human or non-human animal. An exemplary human subject includes a human subject having a disease (such as one described herein) (referred to as a patient), or a normal subject. The term "non-human animal" as used herein includes all vertebrates, such as non-mammals (e.g. birds, amphibians, reptiles) and mammals, such as non-human primates, livestock and/or domesticated animals (such as sheep, dog, cat, cow, pig and the like).

In some embodiments, the pharmaceutical composition of the present invention can further comprise one or more additional therapeutic agents or prophylactic agents.

Examples

The present invention is further described with reference to the following examples, which are not provided to limit the scope of the present invention.

The structure of the compound was confirmed by nuclear magnetic resonance spectrum ($^1$H NMR) or mass spectrum (MS).

Chemical shifts (δ) are expressed in parts per million (ppm). $^1$HNMR was recorded on a Bruker BioSpin GmbH 400 spectrometer, the test solvent was deuterated methanol ($CD_3OD$), deuterated chloroform ($CDCl_3$) or hexadeuterated dimethyl sulfoxide (DMSO-$d_6$), and the internal standard was tetramethylsilane (TMS).

The LC-MS assay was conducted on Shimadzu LC-MS-2020 liquid chromatography-mass spectrometer (Manufacturer: Shimadzu, Model: Shimadzu LC-MS-2020).

Preparative high-performance liquid chromatography was conducted on Waters 2767 (waters sunfire, C18, 19×250 mm 10 um chromatographic column).

Thin layer chromatography (TLC) was performed with Huanghai HSGF 254 (5×20 cm) silica gel plates, and preparative thin layer chromatography was performed with GF 254 (0.4~0.5 nm) silica gel plates produced in Yantai.

The reaction was monitored by thin layer chromatography (TLC) or LC-MS, the developing solvent system included dichloromethane and methanol system, hexane and ethyl acetate system, as well as petroleum ether and ethyl acetate system, and was adjusted (by adjusting the volume ratio the solvents, or by adding triethylamine, etc.) according to the polarity of the compound to be separated.

The microwave reaction was conducted by Biotagelnitiator+ (400 W, RT~300° C.) microwave reactor.

Silica gel (200~300 mesh) produced by Yucheng Chemical Co., Ltd was normally employed as a stationary phase in column chromatography. The eluent system included dichloromethane and methanol system, as well as hexane and ethyl acetate system, and was adjusted (by adjusting the volume ratio the solvents, or by adding triethylamine, etc.) according to the polarity of the compound to be separated.

In the following examples, unless otherwise specified, the reaction temperature was room temperature (20° C.~30° C.).

The reagents employed in the Examples were purchased from companies such as Acros Organics, Aldrich Chemical Company, or Bide Pharmatech Ltd. etc.

The abbreviations as used in the present invention have the following meanings:

| Abbreviation | Meaning |
|---|---|
| ACN | acetonitrile |
| AcOH | acetic acid |
| AcOK/KOAc | potassium acetate |
| aq. | aqueous solution |
| BINAP | (±)-2,2'-Bis(diphenylphosphino)-1,1'-binaphthalene |
| $Boc_2O$ | Di-tert-butyl dicarbonate |
| $Cs_2CO_3$ | cesium carbonate |
| $Cu(AcO)_2$ | copper acetate |
| CuCN | cuprous cyanide |
| DCC | Dicyclohexylcarbodiimide |
| DCE | 1,2-dichloroethane |
| DCM | dichloromethane |
| DIAD | diisopropyl azodiformate |
| DIEA/DIPEA | N,N-diisopropylethylamine |
| DMAP | dimethylaminopyridine |
| DMF | N,N-dimethylformamide |
| DMSO | dimethyl sulfoxide |
| EDCI | 1-ethyl-(3-dimethylaminopropyl)carbodiimide hydrochloride |
| $Et_3N$ | triethylamine |
| EtOH | ethanol |
| HATU | O-(7-azabenzotriazol-1-yl)-N,N,N',N'-tetramethyluronium hexafluorophosphate |
| HCl | hydrochloric acid |
| $H_2O$ | water |
| IPA | isopropanol |
| $K_2CO_3$ | potassium carbonate |
| $KMnO_4$ | potassium permanganate |
| KOH | potassium hydroxide |
| KTB | potassium tert-butoxide |
| $LiAlH_4$ | lithium aluminium hydride |
| $LiOH \cdot H_2O$ | lithium hydroxide monohydrate |
| m-CPBA | metachloroperbenzoic acid |
| MeCN | acetonitrile |
| MeOH | methanol |
| $MgCl_2$ | magnesium chloride |
| $Mg_2SO_4$ | magnesium sulfate |
| $MnO_2$ | manganese dioxide |
| MsCl | methylsulfonyl chloride |
| MTBE | methyl tert-butyl ether |
| $NaBH_4$ | sodium borohydride |
| $NaBH(OAc)_3$ | sodium triacetoxyborohyride |
| $Na_2CO_3$ | sodium carbonate |
| NaH | sodium hydride |
| NaOH | sodium hydroxide |
| NBS | N-bromosuccinimide |
| $NH_4Cl$ | ammonium chloride |
| $N_2H_4 \cdot H_2O$ | hydrazine hydrate |
| NMP | N-methylpyrrolidone |
| $O_2$ | oxygen |
| Pd/C | palladium/carbon |
| $Pd_2(dba)_3$ | tris(dibenzylideneacetone)dipalladium |
| $Pd(dppf)Cl_2$ | [1,1'-bis(diphenylphosphino)ferrocene]dichloropalladium |
| $Pd(OAc)_2$ | palladium acetate |
| $Pd(PPh_3)_4$ | tetrakis(triphenylphosphine)palladium |
| $Pd(PPh_3)_2Cl_2$ | dichlorobis(triphenylphosphine)palladium |
| $Pin_2B_2$ | bis(pinacolato)diboron |
| $PPh_3$ | triphenylphosphine |
| PyBOP | Benzotriazol-1-yl-oxytripyrrolidinophosphonium hexafluorophosphate |
| $SOCl_2$ | thionyl chloride |
| t-BuXPhos | 2-di-tert-butylphosphino-2',4',6'-triisopropylbiphenyl |
| TEA | triethylamine |
| TFA | trifluoroacetic acid |
| THF | tetrahydrofuran |
| TsCl | 4-toluenesulfonyl chloride |
| Zn | zinc |

Preparation of Intermediates

Intermediate Example 1

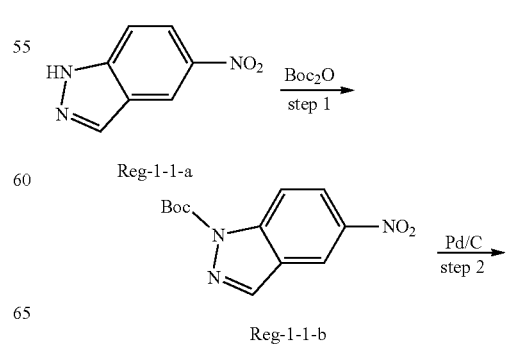

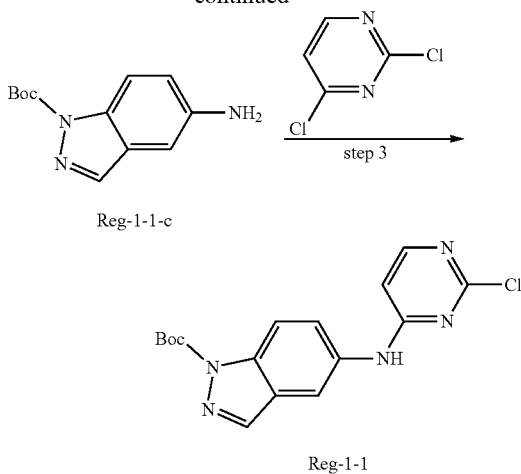

Reg-1-1-c

Reg-1-1

Step 1:

Compound Reg-1-1-a (26 g, 159.38 mmol) and tetrahydrofuran (400 mL) were added to a 1 L flask, and ethylamine (45 mL, 324.6 mmol) and 4-dimethylaminopyridine (2.92 g, 23.91 mmol) were added, followed by slowly dropwise addition of Boc$_2$O (41.74 g, 191.25 mmol). The reaction was performed overnight at room temperature. Thin layer chromatography (petroleum ether:ethyl acetate=3:1) indicated the reaction was complete. The reaction mixture was concentrated to obtain a crude product, which was dissolved in dichloromethane (400 mL), and the organic phase was washed three times with 0.5M dilute hydrochloric acid. The organic phase was then washed with saturated brine, dried over anhydrous sodium sulfate, filtered and concentrated to afford compound Reg-1-1-b (39 g, brown solid, yield: 92.95%).

$^1$H NMR (400 MHz, CDCl$_3$) δ 8.70 (d, J=2.1 Hz, 1H), 8.42 (dd, J=9.1, 2.1 Hz, 1H), 8.34 (d, J=9.6 Hz, 2H), 1.75 (s, 9H). MS m/z (ESI): 164.2 [M-Boc+H].

Step 2:

Compound Reg-1-1-b (38 g, 144.35 mmol) was dissolved in methanol (700 mL), Pd/C (3.8 g, 10% water) was added, purge with hydrogen was performed for three times, and the reaction was performed under a hydrogen atmosphere overnight. Thin layer chromatography (petroleum ether:ethyl acetate=3:1) indicated the reaction was complete. The reaction solution was filtered through Celite to afford compound Reg-1-1-c (33.2 g, brown solid, yield: 98.6%).

$^1$H NMR (400 MHz, CDCl$_3$) δ 7.97 (d, J=10.8 Hz, 2H), 7.00-6.87 (m, 2H), 3.74 (s, 2H), 1.71 (s, 9H).

Step 3:

Compound Reg-1-1-c (4 g, 17.14 mmol) and 2,4-dichloropyrimidine (5.1 g, 34.28 mmol) were dissolved in N,N-dimethylformamide (60 mL), diisopropylethylamine (11.08 g, 85.8 mmol) was added, and the reaction was placed in an oil bath at 80° C., and allowed to proceed overnight. Thin layer chromatography (petroleum ether:ethyl acetate=2:1) indicated the reaction was complete. The reaction solution was cooled to room temperature, concentrated under reduced pressure to give a crude product, which was separated through preparative chromatography (petroleum ether:ethyl acetate=100:1-1.5:1) to afford compound Reg-1-1 (3 g, yellow solid, yield: 50.60%).

$^1$H NMR (400 MHz, CDCl$_3$) δ 9.50-9.23 (m, 1H), 8.52-7.91 (m, 4H), 7.89-7.45 (m, 1H), 7.28-6.51 (m, 1H), 1.73 (s, 9H). MS m/z (ESI): 346.1 [M+H].

The following intermediates were prepared according to methods similar to that described in Intermediate Example 1:

| No. | Structure of Intermediate | Characterization Data |
|---|---|---|
| Reg-1-2 | (structure shown) | $^1$H NMR (400 MHz, CDCl$_3$) δ 8.41 (s, 1H), 8.24-8.22 (m, 2H), 7.91-7.87 (m, 2H), 7.86-7.82 (m, 1H), 7.74 (s, 1H), 7.67 (d, J = 8.8 Hz, 1H), 7.59 (t, J = 7.6 Hz, 1H), 1.75 (s, 9H). |
| Reg-1-3 | (structure shown) | $^1$H NMR (400 MHz, CDCl$_3$) δ 8.28 (s, 1H), 8.21 (d, J = 8.0 Hz, 2H), 7.79 (d, J = 2.0 Hz, 1H), 7.60 (d, J = 8.8 Hz, 1H), 7.27 (s, 1H), 6.87 (d, J = 2.0 Hz, 1H), 1.74 (s, 9H). |
| Reg-1-4 | (structure shown) | $^1$H NMR (400 MHz, DMSO-d$_6$) δ 10.35 (s, 1H), 8.48 (s, 1H), 8.28 (d, J = 5.2 Hz, 1H), 8.22 (s, 1H), 8.11 (d, J = 9.2 Hz, 1H), 7.83 (d, J = 9.2 Hz, 1H), 7.43 (d, J = 5.2 Hz, 1H), 1.67 (s, 9H). MS m/z (ESI): 402.1 [M + H]. |

| No. | Structure of Intermediate | Characterization Data |
|---|---|---|
| Reg-1-5 | | MS m/z (ESI): 402.1 [M + H]. |
| Reg-1-6 | | $^1$H NMR 1H NMR (400 MHz, DMSO-d$_6$) δ 11.99 (s, 1H), 10.06 (s, 1H), 8.46-8.41 (m, 2H), 8.06 (d, J = 8.0 Hz, 1H), 7.93 (d, J = 8.0 Hz, 1H), 7.24 (s, 1H), 6.86 (s, 1H). MS m/z (ESI): 385.2 [M + H]. |
| Reg-1-7 | | $^1$H NMR (400 MHz, DMSO-d$_6$) δ 10.84 (s, 1H), 9.42 (s, 1H), 8.49 (s, 1H), 8.33 (d, J = 1.2 Hz, 1H), 8.07 (d, J = 8.8 Hz, 1H), 7.97 (dd, J = 8.8, 1.6 Hz, 1H), 1.67 (s, 9H). |
| Reg-1-8 | | $^1$H NMR (400 MHz, DMSO-d$_6$) δ 10.08 (s, 1H), 8.49 (s, 1H), 8.34 (s, 1H), 8.24 (d, J = 1.5 Hz, 1H), 8.14-8.11 (m, 1H), 7.87 (dd, J = 9.0, 1.9 Hz, 1H), 7.64 (d, J = 0.9 Hz, 1H), 7.14 (s, 1H), 1.67 (s, 10H). MS m/z (ESI): 385.0 [M + H]. |
| Reg-1-9 | | $^1$H NMR (400 MHz, CDCl$_3$) δ 8.21 (s, 1H), 8.19 (s, 1H), 8.04 (s, 1H), 7.56 (dd, J = 8.9, 1.8 Hz, 1H), 7.26 (s, 2H), 7.21 (s, 1H), 6.97 (d, J = 3.6 Hz, 1H), 5.81 (d, J = 2.9 Hz, 1H), 4.30 (t, J = 6.4 Hz, 2H), 2.33 (s, 6H), 1.73 (d, J = 13.8 Hz, 9H). MS m/z (ESI): 454.1 [M − H]. |

-continued

| No. | Structure of Intermediate | Characterization Data |
| --- | --- | --- |
| Reg-1-10* | [structure: Boc-indazole-NH linked to 7-phenyl-pyrrolopyrimidine with Cl] | $^1$H NMR (400 MHz, MeOD) δ 8.13 (d, J = 3.7 Hz, 1H), 8.05 (s, 1H), 7.86 (d, J = 8.9 Hz, 1H), 7.51 (m, 6H), 7.04 (m, 3H), 6.65 (d, J = 9.0 Hz, 1H). MS m/z (ESI): 361.1 [M + H]. |
| Reg-1-11 | [structure: Boc-indazole-NH linked to chloro-triazine] | $^1$H NMR (400 MHz, CDCl$_3$) δ 8.49 (d, J = 24.0 Hz, 1H), 8.21-8.03 (m, 3H), 7.69 (d, J = 40.0 Hz, 1H), 7.46 (dd, J = 8.8, 4.0 Hz, 1H), 1.66 (s, 9H). MS m/z (ESI): 347.1 [M + H]. |
| Reg-1-12 | [structure: Boc-indazole-NH linked to 5-fluoro-2-chloropyrimidine] | $^1$H NMR (400 MHz, DMSO-d$_6$) δ 10.20 (s, 1H), 8.47 (s, 1H), 8.35 (d, J = 3.6 Hz, 1H), 8.21 (d, J = 1.2 Hz, 1H), 8.07 (d, J = 8.8 Hz, 1H), 7.82 (dd, J = 8.8, 2.0 Hz, 1H), 1.66 (s, 9H). |
| Reg-1-15 | [structure: Boc-indazole-NH linked to 6-methyl-2-chloropyrimidine] | $^1$H NMR (400 MHz, DMSO-d$_6$) δ 10.07 (s, 1H), 8.44 (s, 1H), 8.16 (s, 1H), 8.05 (d, J = 9.2 Hz, 1H), 7.63 (d, J = 8.8 Hz, 1H), 6.61 (s, 1H), 2.29 (s, 3H), 1.66 (s, 9H). MS m/z (ESI): 360.0 [M + H]. |
| Reg-1-30 | [structure: Boc-indazole-NH linked to 4,6-dichloropyrimidine] | $^1$H NMR (400 MHz, CDCl$_3$) δ 8.25 (d, J = 8.8 Hz, 1H), 8.20 (s, 1H), 7.76 (s, 1H), 7.54 (s, 1H), 7.43 (d, J = 8.8 Hz, 1H), 6.48 (s, 1H), 1.73 (s, 9H). |

The reagent employed in step 3 for the preparation of Reg-1-10 was prepared according to the following reaction:

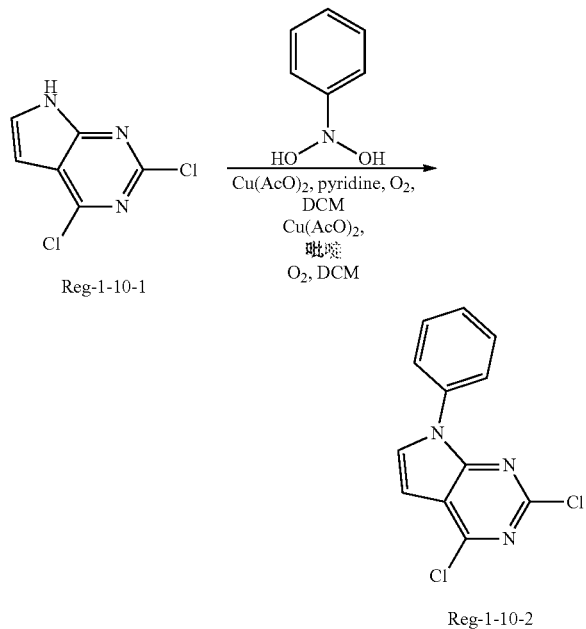

Compound Reg-1-10-1 (1.0 g, 5.32 mmol), phenylboronic acid (972.79 mg, 7.98 mmol) and pyridine (2.52 g, 31.86 mmol) were dissolved in dichloromethane (30 mL), followed by addition of copper acetate (0.966 g, 4.99 mmol) and molecular sieve (0.5 g), and then the reaction was performed under an oxygen atmosphere for 12 h. LC-MS indicated the reaction was complete. The reaction solution was filtered, and the filtrate was concentrated under reduced pressure to give a crude product, which was separated and purified through a medium pressure preparative column (petroleum ether:ethyl acetate=100:1~3:1) to afford compound Reg-1-10-2 (0.9 g, white solid, yield: 64.07%). MS m/z (ESI): 264.0 [M+H].

Intermediate Example 2

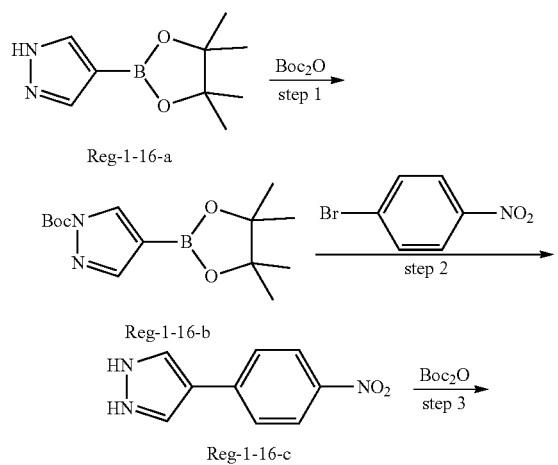

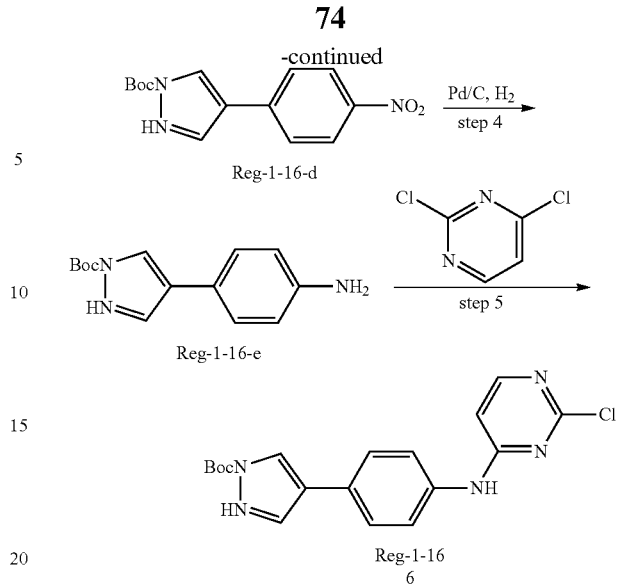

Step 1:

Compound Reg-1-16-a (4.5 g, 2.58 mmol) and dichloromethane (200 mL) were added to a 100 mL flask, diisopropylethylamine (5.99 g, 46.38 mmol) and 4-dimethylaminopyridine (424 mg, 3.48 mmol) were added, followed by slow dropwise addition of Boc$_2$O (7.59 g, 34.79 mmol). The reaction was performed overnight at room temperature. Thin layer chromatography (petroleum ether:ethyl acetate=3:1) indicated the reaction was complete. The reaction solution was concentrated to give a crude product, which was dissolved in dichloromethane (100 mL), and the organic phase was then washed three times with 0.5M dilute hydrochloric acid. The organic phase was further washed with saturated brine, dried over anhydrous sodium sulfate, filtered, and concentrated to obtain Reg-1-16-b (6.8 g, colorless oil, yield: 99.68%). MS m/z (ESI): 195.2 [M-Boc+H].

Step 2:

Compound Reg-1-16-b (6.8 g, 23.12 mmol) and 1-bromo-4-nitrobenzene (7.0 g, 34.68 mmol) were dissolved in a mixture of 1,4-dioxane/water (4:1) (200 mL), followed by addition of potassium carbonate (9.58 g, 69.35 mmol) and Pd(dppf)Cl$_2$ (0.9 g, 1.16 mmol). Purge with argon was performed for 3 times, and the reaction was placed in an oil bath at 80° C. overnight. LC-MS indicated the reaction was complete. The reaction solution was cooled to room temperature, filtered, and concentrated under reduced pressure to afford compound Reg-1-16-c (12 g, brown solid). The crude was used directly in the next reaction. MS m/z (ESI): 190.1 [M+H].

Step 3:

Compound Reg-1-16-c (4.5 g, 2.58 mmol) and dichloromethane (200 mL) were added to a 250 mL flask, and diisopropylethylamine (8.54 mL, 52.86 mmol) and 4-dimethylaminopyridine (484 mg, 3.96 mmol) were added, followed by slow dropwise addition of BOC$_2$O (8.65 g, 39.65 mmol). The reaction was performed overnight at room temperature. Thin layer chromatography (petroleum ether:ethyl acetate=3:1) indicated the reaction was complete. The reaction solution was concentrated to give a crude product, which was purified through flash column chromatography (petroleum ether:ethyl acetate=100:1 to 1.5:1) to afford compound Reg-1-16-d (6 g, light yellow oil, yield: 78.47%).

¹H NMR (400 MHz, CDCl₃) δ 8.44 (s, 1H), 8.27 (d, J=8.8 Hz, 2H), 8.06 (s, 1H), 7.69 (d, J=8.8 Hz, 2H), 1.34-1.12 (m, 9H). MS m/z (ESI): 190.2 [M-Boc+H].

Step 4:

Compound Reg-1-16-d (6 g, 20 mmol) was dissolved in methanol (100 mL), Pd/C (10% water) was added, and purge with hydrogen was performed for 3 times. The reaction was performed under a hydrogen atmosphere overnight. LC-MS indicated the reaction was complete. The reaction solution was filtered through Celite, and concentrated to afford compound Reg-1-16-e (5 g, white solid, yield: 92.97%).

¹H NMR (400 MHz, CDCl₃) δ 7.74 (s, 1H), 7.49 (s, 1H), 6.89-6.82 (m, 2H), 6.25 (d, J=8.8 Hz, 2H), 1.43-1.08 (m, 9H). MS m/z (ESI): 260.2 [M+H].

Step 5:

Compound Reg-1-16-e (3.8 g, 14.65 mmol) and 2,4-dichloropyrimidine (4.37 g, 29.31 mmol) were dissolved in N,N-dimethylformamide (30 mL), diisopropylethylamine (7.22 mL, 43.98 mmol) was added, and the reaction was performed in an oil bath at 80° C. for 8 h. LC-MS indicated the reaction was complete. The reaction solution was cooled to room temperature, and concentrated under reduced pressure to afford a crude product, which was separated through preparative chromatography (dichloromethane/methanol=100:1-100:5) to afford compound Reg-1-16 (2.2 g, yellow solid, yield: 54.80%).

¹H NMR (400 MHz, CDCl₃) δ 8.31 (s, 1H), 8.16 (d, J=5.9 Hz, 1H), 7.99 (s, 1H), 7.57 (d, J=8.4 Hz, 2H), 7.38 (d, J=8.4 Hz, 2H), 6.98 (s, 1H), 6.62 (d, J=5.9 Hz, 1H), 1.69 (s, 9H). MS m/z (ESI): 372.1 [M+H].

The following intermediates were prepared according to methods similar to that described in Intermediate Example 2:

Intermediate Example 3

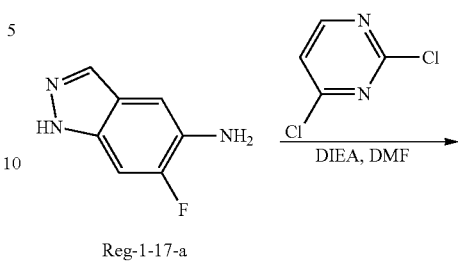

Reg-1-17-a

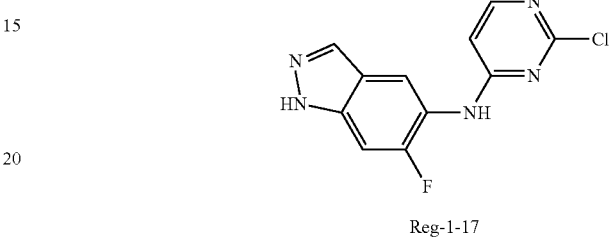

Reg-1-17

Compound Reg-1-17-a (650 mg, 4.30 mmol) and 2,4-dichloropyrimidine (1.28 g, 8.60 mmol) were dissolved in N,N-dimethylformamide (20 mL), diisopropylethylamine (2.22 g, 17.2 mmol) was added, and the reaction was performed in an oil bath at 80° C. overnight. Thin layer chromatography (petroleum ether:ethyl acetate=1:1) indicated the reaction was complete. The reaction solution was cooled to room temperature, diluted with ethyl acetate (80 mL), and was successively washed with a saturated aqueous

| No. | Structure of Intermediate | Characterization Data |
|---|---|---|
| Reg-1-33 | ![structure] | ¹H NMR (400 MHz, DMSO-d₆) δ 10.22 (s, 1H), 8.73 (s, 1H), 8.32 (s, 1H), 8.30 (d, J = 5.6 Hz, 1H), 7.80 (s, 1H), 7.76 (s, 1H), 7.66 (s, 1H), 7.43 (d, J = 5.6 Hz, 1H), 1.62 (s, 9H). MS m/z (ESI): 428.3 [M + H]. |
| Reg-1-34 | ![structure] | ¹H NMR (400 MHz, DMSO-d₆) δ 9.56 (s, 1H), 8.72 (s, 1H), 8.39 (s, 1H), 8.31 (s, 1H), 7.78 (d, J = 8.8 Hz, 2H), 7.65 (d, J = 8.8 Hz, 2H), 1.61 (s, 9H). MS m/z (ESI): 404.1 [M − H]. |
| Reg-1-36 | ![structure] | ¹H NMR (400 MHz, DMSO-d₆) δ 9.52 (s, 1H), 8.44 (s, 1H), 8.25 (s, 1H), 8.02 (d, J = 8.0 Hz, 1H), 7.96 (s, 1H), 7.85 (d, J = 8.0 Hz, 1H), 3.96 (s, 3H), 1.66 (s, 9H). MS m/z (ESI): 375.9 [M − H]. | solution of ammonium chloride (80 mL*2) and saturated brine (100 mL*2). The organic phase was dried over anhydrous sodium sulfate, filtered, concentrated under reduced pressure, and the crude was separated and purified by column chromatography (petroleum ether:ethyl acetate=10:1, 4:1 to 2:1) to afford compound Reg-1-17 (480 mg, yellow solid, yield: 42.5%).

$^1$H NMR (400 MHz, DMSO-$d_6$) δ 13.20 (s, 1H), 9.75 (s, 1H), 8.21-8.06 (m, 2H), 7.98 (d, J=7.6 Hz, 1H), 7.50 (d, J=12.0 Hz, 1H), 6.67 (s, 1H).

The following intermediates were prepared according to methods similar to that described in Intermediate Example 3:

| No. | Structure of Intermediate | Characterization Data |
|---|---|---|
| Reg-1-13 | | $^1$H NMR (400 MHz, DMSO-$d_6$) δ 8.81 (s, 1H), 8.06 (s, 1H), 7.85 (s, 1H), 7.53 (d, J = 8.8 Hz, 1H), 7.43 (d, J = 8.8 Hz, 1H), 2.32 (s, 3H), 2.16 (s, 3H). MS m/z (ESI): 274.0 [M + H]. |
| Reg-1-14 | | $^1$H NMR (400 MHz, DMSO-$d_6$) δ 13.07 (s, 1H), 8.92 (s, 1H), 8.08 (s, 1H), 8.00 (s, 1H), 7.93 (s, 1H), 7.56 (d, J = 8.8 Hz, 1H), 7.49 (dd, J = 8.9, 1.4 Hz, 1H), 2.18 (s, 3H). MS m/z (ESI): 260.1 [M + H]. |
| Reg-1-19 | | $^1$H NMR (400 MHz, DMSO-$d_6$) δ 13.20 (s, 1H), 9.75 (s, 1H), 8.21-8.06 (m, 2H), 7.98 (d, J = 7.6 Hz, 1H), 7.50 (d, J = 12.0 Hz, 1H), 6.67 (s, 1H). |
| Reg-1-20 | | $^1$H NMR (400 MHz, DMSO-$d_6$) δ 12.72 (s, 1H), 10.14 (s, 1H), 8.14 (d, J = 5.9 Hz, 1H), 8.00 (s, 1H), 7.93 (s, 1H), 7.52 (d, J = 8.8 Hz, 1H), 7.45 (d, J = 8.5 Hz, 1H), 2.51 (s, 3H). MS m/z (ESI): 260.1 [M + H]. |
| Reg-1-21 | | $^1$H NMR (400 MHz, DMSO-$d_6$) δ 13.10 (s, 1H), 9.99 (s, 1H), 8.13-8.06 (m, 2H), 7.99 (s, 1H), 7.57 (d, J = 8.8 Hz, 1H), 7.40 (d, J = 8.5 Hz, 1H), 6.70 (d, J = 5.8 Hz, 1H). |
| Reg-1-22 | | $^1$H NMR (400 MHz, DMSO-$d_6$) δ 12.98 (s, 1H), 9.69 (s, 1H), 8.20 (s, 1H), 8.01 (s, 1H), 7.50 (d, J = 15.6 Hz, 2H), 2.42 (s, 3H), 2.19 (s, 3H). MS m/z (ESI): 274.0 [M + H]. |

| No. | Structure of Intermediate | Characterization Data |
|---|---|---|
| Reg-1-26 | | $^1$H NMR (400 MHz, DMSO-$d_6$) δ 13.11 (s, 1H), 9.59 (s, 1H), 8.17 (s, 1H), 8.03 (d, J = 5.5 Hz, 1H), 7.41 (d, J = 8.6 Hz, 1H), 7.20 (d, J = 8.6 Hz, 1H), 2.40 (s, 3H). MS m/z (ESI): 260.1 [M + H]. |
| Reg-1-28 | | MS m/z (ESI): 302.1 [M + H]. |

Intermediate Example 4

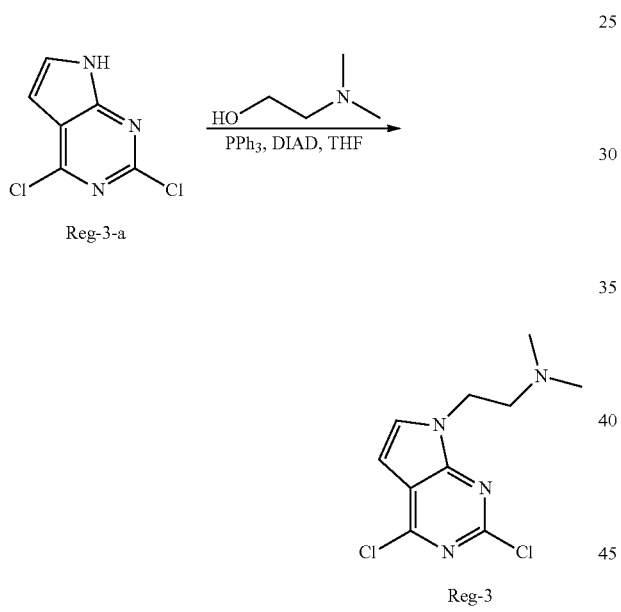

Compound Reg-3-a (3 g, 15.63 mmol), 2-(dimethylamino)ethanol (1.7 g, 19.11 mmol) and triphenylphosphine (5.01 g 19.11 mmol) were dissolved in tetrahydrofuran (200 mL), diisopropyl azodiformate (4.83 g, 23.89 mmol) was added at 0° C., purge with argon was performed for 3 times, and the reaction was performed at room temperature for 6 hours. LC-MS indicated the reaction was complete. 200 mL ethyl acetate was added to the reaction solution; the organic phase was washed with water (100 mL×3), dried, concentrated under reduced pressure, and the residue was purified by column chromatography (dichloromethane:methanol=100:1~20:1) to afford compound Reg-3 (3 g, brown solid, yield: 72.55%). MS m/z (ESI): 259.0 [M+H].

Intermediate Example 5

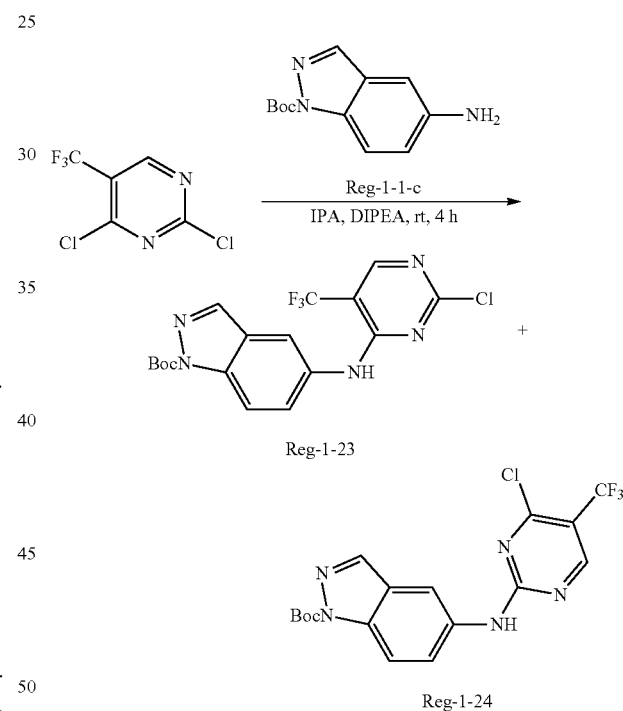

Compound 2,4-dichloro-5-(trifluoromethyl)pyrimidine (3 g, 13.825 mmol) and N,N-diisopropylethylamine (2.14 g, 16.59 mmol) were dissolved in isopropanol (100 mL), compound Reg-1-1-c (3.2 g, 13.825 mmol) was then added to the aforementioned solution in portions. The reaction was performed at room temperature for 16 hours. LC-MS indicated the reaction was complete. The reaction solution was filtered, and the filter cake was rinsed once with isopropanol to afford compound Reg-1-24 (2.3 g, pink solid, yield: 40.19%); the filtrate was washed with saturated brine, dried over anhydrous sodium sulfate, and then concentrated to dryness, to afford compound Reg-1-23 (1.84 g, dark red solid, yield: 32.15%). Characterization data of the compound are as follows:

| No. | Structure of Intermediate | Characterization Data |
|---|---|---|
| Reg-1-23 | 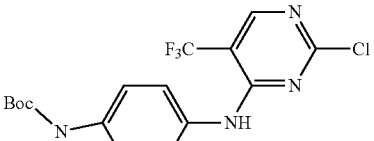 | $^1$H NMR (400 MHz, CDCl$_3$): δ 8.46 (s, 1H), 8.21 (m, 2H), 8.08 (d, 1H), 7.53 (dd, 1H), 7.20 (s, 1H), 1.74 (s, 9H). MS m/z (ESI): 414.1 [M + H]. |
| Reg-1-24 | 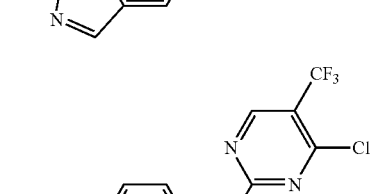 | $^1$H NMR (400 MHz, CDCl$_3$) δ 8.59 (s, 1H), 8.20 (m, 3H), 7.71 (s, 1H), 7.53 (dd, 1H), 1.73 (s, 9H). MS m/z (ESI): 414.1 [M + H]. |

Intermediate Example 6

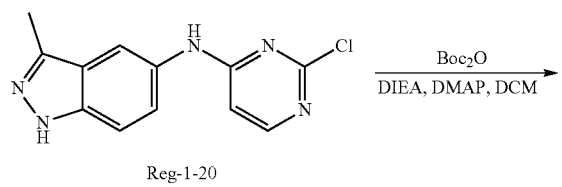

Reg-1-20

Compound Reg-1-20 (0.8 g, 3.09 mmol) was dissolved in dichloromethane (100 mL), DIEA (1.59 g, 12.36 mmol) and DMAP (188 mg, 1.55 mmol) were added, and Boc$_2$O (2.02 g, 9.27 mmol) was added after stir at room temperature for 10 minutes, the reaction was performed at room temperature for 3 hours. Thin layer chromatography (petroleum ether:ethyl acetate=2:1) indicated the reaction was complete. The reaction solution was dissolved in dichloromethane (400 ml), and successively washed with water (250 ml*3) and saturated brine (250 ml), the organic phase was dried over anhydrous sodium sulfate, concentrated under reduced pressure, and the residue was separated and purified by column chromatography (petroleum ether:ethyl acetate=1:0 to 5:1), to afford compound Reg-1-25 (2.01 g, white solid).

$^1$H NMR (400 MHz, CDCl$_3$) δ 8.45 (d, J=5.6 Hz, 1H), 8.15 (d, J=8.8 Hz, 1H), 7.96 (d, J=5.6 Hz, 1H), 7.41 (d, J=1.6 Hz, 1H), 7.29 (d, J=1.6 Hz, 1H), 2.59 (s, 3H), 1.74 (s, 9H), 1.41 (s, 9H). MS m/z (ESI): 460.3 [M+H].

The following intermediate was prepared according to a method similar to that described in Intermediate Example 6:

| No. | Structure of Intermediate | Characterization Data |
|---|---|---|
| Reg-1-27 | 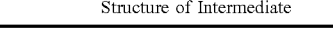 | $^1$H NMR (400 MHz, DMSO-d$_6$) δ 8.63 (d, J = 6.0 Hz, 1H), 8.45 (s, 1H), 8.13 (d, J = 8.8 Hz, 1H), 8.02 (d, J = 6.0 Hz, 1H), 7.82 (d, J = 2.0 Hz, 1H), 7.50 (dd, J = 8.8, 2.0 Hz, 1H), 1.67 (s, 9H), 1.36 (s, 9H). |

-continued

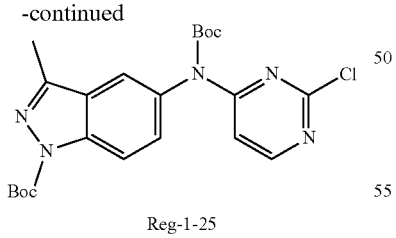

Reg-1-25

Intermediate Example 7

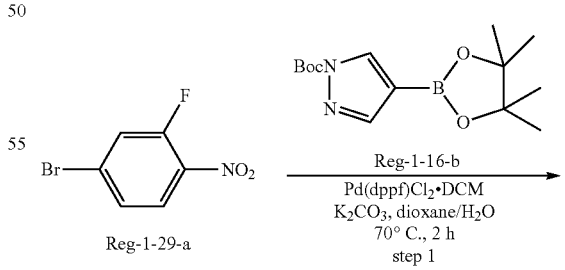

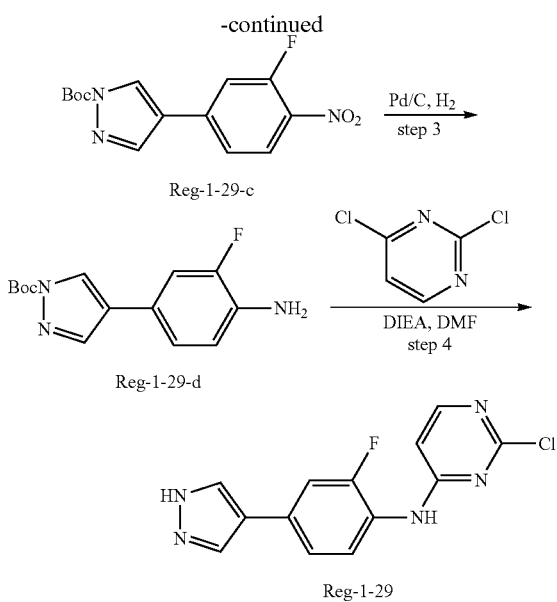

Step 1:
A solution of Reg-1-29-a (6.7 g, 30.612 mmol) and Reg-1-16-b (6.0 g, 20.408 mmol) dissolved in a mixture of dioxane and water (4:1) (84 mL) was added to a 250 mL single neck flask, potassium carbonate (11.28 g, 81.59 mmol) and [1,1'-bis(diphenylphosphino)ferrocene]dichloropalladium dichloromethane complex (833 mg, 1.020 mmol) were added, purge with argon was performed for 3 times, and the reaction was placed in an oil bath at 70° C. for 3 hours. The reaction was cooled to room temperature, water (50 ml) was added, and the solution was extracted three times with ethyl acetate (150 ml). The organic phase was dried over sodium sulfate, filtered, dried by rotary evaporation, and the residue was directly used in the next reaction. MS m/z (ESI): 208.2 [M+H].

Step 2:
Reg-1-29-b (4.58 g, 22.126 mmol) was dissolved in dichloromethane (50 ml), DMAP (270 mg, 2.213 mmol) and DIEA (5.7 g, 44.251 mmol) were added, followed by slow dropwise addition of Boc$_2$w (5.79 g, 26.551 mmol). The reaction was performed overnight at room temperature. After the reaction was complete, the reaction solution was concentrated under reduced pressure to afford a crude product, which was separated by medium pressure preparative chromatography to afford Reg-1-29-c (3.6 g, yellow solid, yield: 53.04%).

$^1$H NMR (400 MHz, CDCl$_3$) δ 8.44 (s, 1H), 8.17-8.10 (m, 1H), 8.03 (s, 1H), 7.43 (dt, J=6.5, 2.1 Hz, 2H), 1.69 (s, 9H). MS m/z (ESI): 206.1 [M-Boc−H].

Step 3:
Reg-1-29-c (3.6 g, 11.726 mmol) and methanol (100 ml) were added to a 250 mL single neck flask, and then Pd/C (10 wt %, 360 mg) was added. The reaction was performed under a hydrogen atmosphere overnight. After thin layer chromatography indicated completion of the reaction, the reaction solution was filtered through Celite to afford Reg-1-29-d (3.0 g, brown oil, yield: 92.36%).

$^1$H NMR (400 MHz, CDCl$_3$) δ 8.17 (s, 1H), 7.89 (s, 1H), 7.18-7.08 (m, 2H), 6.82-6.75 (m, 1H), 1.67 (s, 9H). MS m/z (ESI): 178.3 [M-Boc+H].

Step 4:
Reg-1-29-d (3.3 g, 12.74 mmol) and 2,4-dichloropyrimidine (3.8 g, 25.48 mmol) were dissolved in DMF (60 mL), DIEA (4.93 g, 38.22 mmol) was added, and the reaction was performed in an oil bath at 120° C. overnight. Thin layer chromatography indicated the reaction was complete. The reaction solution was cooled to room temperature, followed by addition of water (30 ml), and extraction with ethyl acetate (150 ml). The organic phase was dried over sodium sulfate, filtered, and dried by rotary evaporation to afford a crude product, which was separated by column chromatography to afford Reg-1-29 (1 g, yellow solid, yield: 29.52%).

$^1$H NMR (400 MHz, DMSO-d$_6$) δ 13.04 (s, 1H), 9.78 (s, 1H), 8.33-7.96 (m, 3H), 7.79-7.57 (m, 2H), 7.48 (dd, J=8.3, 1.5 Hz, 1H), 6.75 (d, J=5.3 Hz, 1H). MS m/z (ESI): 290.0 [M+H].

The following intermediates were prepared according to methods similar to that described in Intermediate Example 7:

| No. | Structure of Intermediate | Characterization Data |
|---|---|---|
| Reg-1-32 | | $^1$H NMR (400 MHz, DMSO-d$_6$) δ 12.99 (s, 1H), 9.48 (s, 1H), 9.23 (s, 1H), 8.53 (s, 1H), 8.17 (d, J = 5.9 Hz, 1H), 7.73 (d, J = 5.2 Hz, 1H), 7.61 (d, J = 5.2 Hz, 1H), 7.49 (dd, J = 8.2, 1.7 Hz, 1H), 7.28 (dd, J = 8.2, 1.7 Hz, 1H), 3.94 (s, 3H). MS m/z (ESI): 302.3 [M + H]. |
| Reg-1-37 | | $^1$H NMR (400 MHz, DMSO-d$_6$) δ 12.89 (s, 1H), 9.30 (s, 1H), 8.02 (s, 1H), 7.94 (s, 1H), 7.73 (d, J = 8.0 Hz, 2H), 7.58 (d, J = 8.0 Hz, 2H), 3.95 (s, 3H). MS m/z (ESI): 302.0 [M + H]. |

Intermediate Example 8

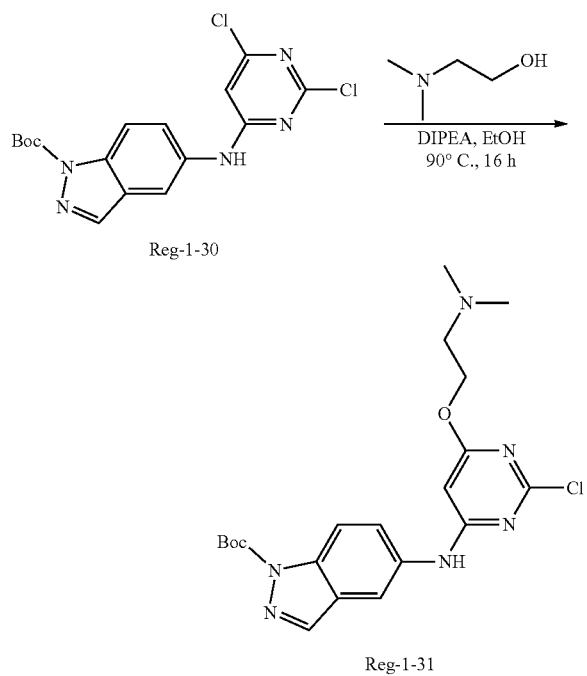

Compound Reg-1-30 (2.0 g, 5.26 mmol) was dissolved in anhydrous ethanol (20 mL), and dimethylaminoethanol (468 mg, 5.26 mmol) and DIPEA (905 mg, 5.26 mmol) were added. The obtained mixture was heated to 90° C., at which temperature the reaction was performed overnight. LC-MS indicated the starting material underwent complete reaction. The reaction solution was concentrated under reduced pressure, and ethyl acetate (40 mL) and water (40 mL) were added to the residue. The organic layer was separated, and Reg-1-31 was obtained after evaporation under reduced pressure to remove solvents. MS m/z (ESI): 432.9 [M+H].

Intermediate Example 9

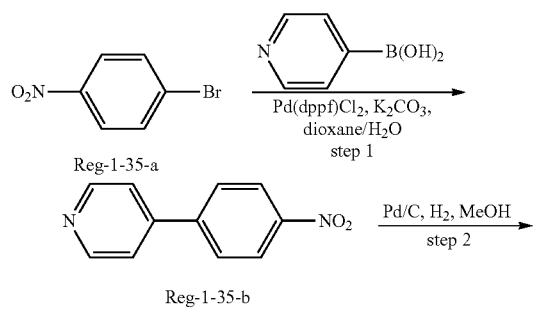

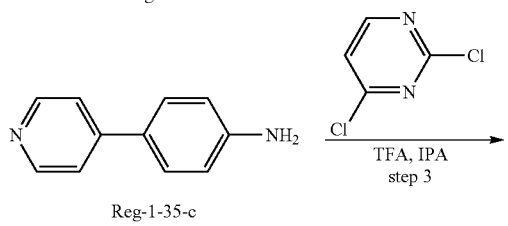

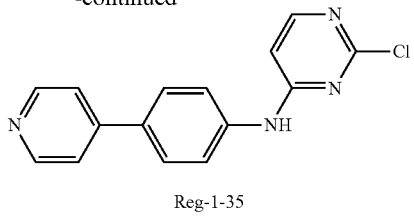

Step 1:

Compound Reg-1-35-a (3.0 g, 14.93 mmol) and pyridin-4-ylboronic acid (2.2 g, 17.91 mmol) were dissolved in dioxane:water (4:1, 50 mL), followed by addition of potassium carbonate (6.18 g, 44.79 mmol) and Pd(dppf)Cl$_2$ (1.09 g, 1.493 mmol), purge with argon was performed for 3 times, and the reaction was performed in an oil bath at 90° C. overnight. LC-MS indicated the reaction was complete. The reaction solution was concentrated under reduced pressure. The crude product was successively extracted with ethyl acetate (50 mL*3), and washed with saturated brine (50 mL*2). The organic phase was dried over anhydrous sodium sulfate, filtered, and concentrated to afford compound Reg-1-35-b (2.6 g, crude product).

$^1$H NMR (400 MHz, DMSO-d$_6$) δ 8.72 (d, J=6.0 Hz, 2H), 8.35 (d, J=8.8 Hz, 2H), 8.08 (d, J=8.8 Hz, 2H), 7.81 (dd, J=4.6, 1.5 Hz, 2H). MS m/z (ESI): 201.2 [M+H].

Step 2:

Compound Reg-1-35-b (2.5 g, 12.5 mmol) was dissolved in anhydrous methanol (100 mL), and Pd/C (10%, 250 mg) was added. The reaction solution was placed under a H$_2$ atmosphere, and the reaction was performed at room temperature overnight. LC-MS indicated the reaction was complete. The reaction solution was filtered with suction, the filter cake was washed, and the collected filter cake was concentrated under reduced pressure to dryness to afford compound Reg-1-35-c (2.0 g, crude product).

$^1$H NMR (400 MHz, DMSO-d$_6$) δ 8.47 (d, J=5.7 Hz, 2H), 7.57-7.52 (m, 4H), 6.67 (d, J=8.4 Hz, 2H), 5.50 (s, 2H). MS m/z (ESI): 171.4 [M+H].

Step 3:

Compound Reg-1-35-c (1.0 g, 5.85 mmol) and 2,4-dichloropyrimidine (1.75 g, 11.7 mmol) were dissolved in isopropanol (50 mL), trifluoroacetic acid (1.34 g, 11.7 mmol) was added, and the reaction was performed in an oil bath at 80° C. overnight. LC-MS indicated the reaction was complete. The reaction solution was cooled to room temperature, concentrated under reduced pressure, and the residue was added to ethyl acetate (150 mL*2), and filtered to afford compound Reg-1-35 (1.2 g, crude product). MS m/z (ESI): 283.3 [M+H].

Intermediate Example 10

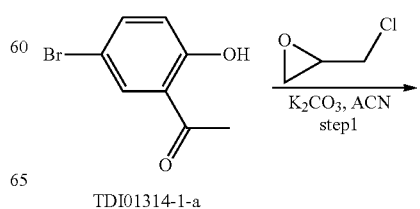

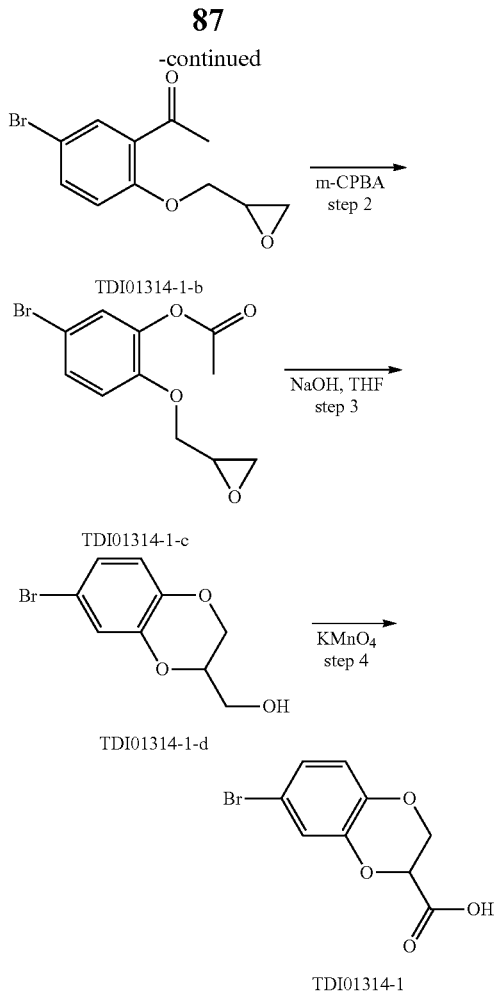

-continued

TDI01314-1-b

TDI01314-1-c

TDI01314-1-d

TDI01314-1

Step 1:

TDI01314-1-a (8.00 g, 37.20 mmol) and 2-(chloromethyl) oxirane (6.88 g, 74.40 mmol) were dissolved in acetonitrile (200 mL), potassium carbonate (15.42 g, 111.60 mmol) was added, and the reaction was performed at 80° C. overnight. Thin layer chromatography indicated the reaction was complete. The reaction solution was concentrated under reduced pressure, and the crude product was separated and purified by flash column chromatography to afford TDI01314-1-b (6 g, white solid, yield: 59.49%). MS m/z (ESI): 271.1; 273.1 [M+H].

Step 2:

TDI01314-1-b (6 g, 22.13 mmol) was dissolved in dichloromethane (100 mL), m-chloroperbenzoic acid (7.64 g, 44.26 mmol) was added, and the reaction was performed at 40° C. for 8 hours. Thin layer chromatography indicated the reaction was complete. The reaction solution was cooled to room temperature, and stirred for half an hour after addition of a saturated solution of sodium sulfite. The precipitated white solid was filtered, the organic phase was concentrated, and the crude product was separated and purified by column chromatography to afford TDI01314-1-c (3 g, white solid, yield: 47.21%). MS m/z (ESI): 287.1; 289.1 [M+H].

Step 3:

TDI01314-1-c (3 g, 10.45 mmol) was dissolved in tetrahydrofuran (100 mL) and water (10 mL), sodium hydroxide (835.85 mg, 20.90 mmol) was added, and the reaction was performed at ambient temperature overnight. Thin layer chromatography indicated the reaction was complete. The reaction solution was extracted with ethyl acetate, concentrated under reduced pressure, and the residue was separated and purified by column chromatography to afford TDI01314-1-d (2 g, colorless oil, yield: 78.1%).

$^1$H NMR (400 MHz, CDCl$_3$) δ 7.06 (dd, J=11.2, 2.3 Hz, 1H), 6.95 (dd, J=8.6, 2.3 Hz, 1H), 6.75 (d, J=8.6 Hz, 1H), 4.33-4.22 (m, 2H), 4.14-4.05 (m, 1H), 3.95-3.79 (m, 2H).

Step 4:

TDI01314-1-d (2 g, 8.16 mmol) was added to water (100 mL), followed by addition of potassium carbonate (2.26 g, 16.32 mmol) and potassium permanganate (2.58 g, 16.32 mmol), and the reaction was performed at ambient temperature for 12 hours. LC-MS assay indicated the reaction was complete. The reaction solution was filtered, and the filtrate was concentrated to give a crude product, which was then separated and purified by column chromatography to afford TDI01314-1 (1 g, white solid, yield: 47.3%).

$^1$H NMR (400 MHz, CDCl$_3$) δ 7.16 (d, J=2.3 Hz, 1H), 6.99 (dd, J=8.7, 2.3 Hz, 1H), 6.76 (d, J=8.6 Hz, 1H), 4.88 (dd, J=4.3, 3.0 Hz, 1H), 4.44 (dd, J=11.5, 4.4 Hz, 1H), 4.36 (dd, J=11.5, 2.9 Hz, 1H).

Intermediate Example 11

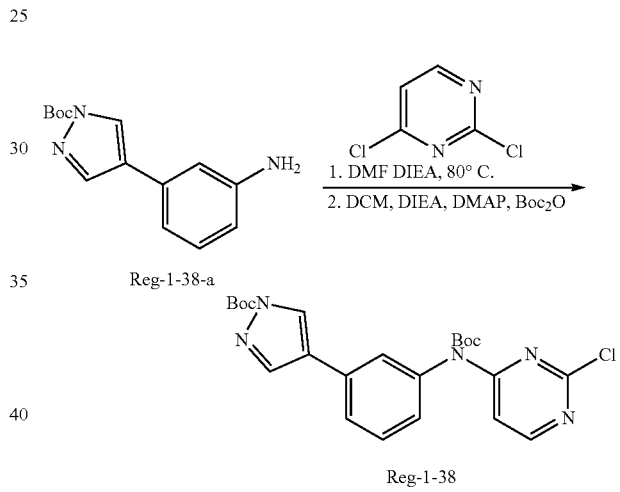

Reg-1-38-a

Reg-1-38

Compound Reg-1-38-a (320 mg, 1.24 mmol) and 2,4-dichloropyrimidine (221 mg, 1.48 mmol) were dissolved in N,N-dimethylformamide (20 mL), diisopropylethylamine (638 mg, 4.94 mmol) was added, and the reaction solution was slowly warmed to 80° C., and kept at this temperature for 16 hours. Thin layer chromatography (petroleum ether/ethyl acetate=2:1) indicated the reaction was complete. The reaction solution was dissolved in ethyl acetate (250 ml), and successively washed with water (250 ml*2) and saturated brine (250 ml). The organic phase was dried over anhydrous sodium sulfate, concentrated, and the crude product was directly used in the next reaction.

The crude product obtained from the last step was dissolved in dichloromethane (20 mL), diisopropylethylamine (417 mg, 3.24 mmol) and 4-dimethylaminopyridine (99 mg, 0.81 mmol) were added, and the reaction was stirred at room temperature for 10 minutes. Di-tert-butyl dicarbonate (705 mg, 3.24 mmol) was then added, and the reaction was performed at room temperature for 3 hours. Thin layer chromatography (petroleum ether/ethyl acetate=2:1) indicated the reaction was complete. The reaction solution was dissolved in dichloromethane (400 ml), and successively washed with water (250 ml*32) and saturated brine (250 ml). The organic phase was dried over anhydrous sodium sulfate, concentrated under reduced pressure, and the residue was separated and purified by column chromatography (petroleum ether dichloromethane=100:1 to 0:1) to afford compound Reg-1-38 (400 mg, light yellow oil).

$^1$H NMR (400 MHz, CDCl$_3$) δ 8.44 (d, J=5.6 Hz, 1H), 8.31 (s, 1H), 7.99 (s, 1H), 7.90 (d, J=5.6 Hz, 1H), 7.73 (dd, J=5.6, 3.2 Hz, 1H), 7.53 (dd, J=5.6, 3.2 Hz, 3H), 7.08 (d, J=7.6 Hz, 1H), 1.68 (s, 9H), 1.43 (s, 9H). MS m/z (ESI): 472.3 [M+H].

Preparation of Final Products

Example 1: Preparation of 6-(4-((1H-indazol-5-yl)amino)pyrimidin-2-yl)-N-(pyridazin-4-yl)benzo[b]thiophene-2-carboxamide (TDI01116)

concentrated under reduced pressure. The crude product was dissolved in dichloromethane (40 mL), and successively washed with saturated aqueous sodium carbonate (50 mL×2) and saturated brine (50 mL×2). The organic phase was dried over anhydrous sodium sulfate, filtered, and concentrated to afford compound TDI01116-2 (550 mg, yellow solid, crude product).

$^1$H NMR (400 MHz, CDCl$_3$) δ 8.01 (s, 2H), 7.73 (d, J=8.4 Hz, 1H), 7.51 (d, J=8.4 Hz, 1H), 3.95 (s, 3H).

Step 2:

Compound TDI01116-2 (550 mg, 2.04 mmol) and bis(pinacolato)diboron (621 mg, 2.44 mmol) were dissolved in dioxane (20 mL), potassium acetate (600 mg, 6.12 mmol) and Pd(dppf)Cl$_2$ (140 mg, 0.20 mmol) were added, purge with argon was performed for 3 times, and the reaction was placed in an oil bath at 80° C. overnight. Thin layer chromatography (petroleum ether:ethyl acetate=10:1) indi-

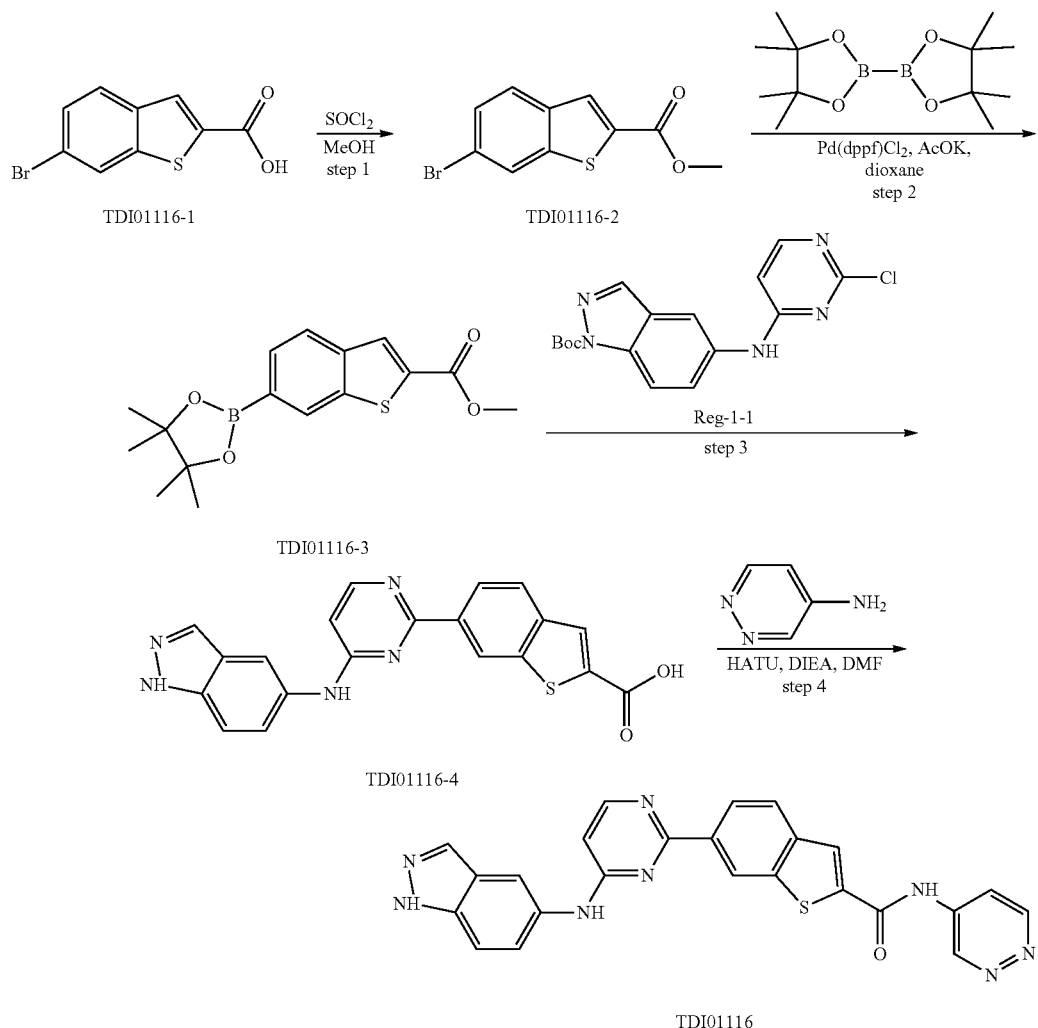

Step 1:

Compound TDI01116-1 (500 mg, 1.95 mmol) was dissolved in anhydrous methanol (20 mL), thionyl chloride (4 mL) was slowly added, and the reaction was performed at 70° C. for 2 hours. Thin layer chromatography (petroleum ether:ethyl acetate=5:1) indicated the reaction was complete. The reaction solution was cooled to room temperature, and cated the reaction was complete. The reaction solution was cooled to room temperature, and concentrated under reduced pressure. The residue was separated and purified by column chromatography (petroleum ether:ethyl acetate=20:1) to afford compound TDI01116-3 (600 mg, white solid, yield: 92.3%).

¹H NMR (400 MHz, CDCl₃) δ 8.35 (s, 1H), 8.06 (s, 1H), 7.87 (d, J=8.0 Hz, 1H), 7.80 (d, J=8.0 Hz, 1H), 3.95 (s, 3H), 1.38 (s, 12H).

Step 3:

Compound TDI01116-3 (600 mg, 1.90 mmol) and Reg-1-1 (546 mg, 1.58 mmol) were dissolved in a mixture of ethanol/water (10:1) (55 mL), sodium carbonate (335 mg, 3.16 mmol) and Pd(PPh₃)₂Cl₂ (112 mg, 0.16 mmol) were added, purge with argon was performed for 3 times, and the reaction mixture was placed in an oil bath at 110° C. overnight. Thin layer chromatography (ethyl acetate) indicated the reaction was complete. The reaction solution was cooled to room temperature, filtered, and concentrated under reduced pressure. The residue was dissolved in water (40 mL), extracted with ethyl acetate (50 mL×2). The pH of the aqueous phase was adjusted to 2 with 4N HCl, the precipitated solid was filtered, dissolved in methanol, and then concentrated to afford compound TDI01116-4 (700 mg, yellow solid, crude product).

¹H NMR (400 MHz, DMSO-d₆) δ 11.90 (s, 1H), 9.06 (s, 1H), 8.37 (d, J=6.4 Hz, 2H), 8.25-8.18 (m, 4H), 7.68 (d, J=8.0 Hz, 2H), 7.51 (d, J=7.6 Hz, 1H), 7.20 (s, 1H). MS m/z (ESI): 388.1 [M+H].

Step 4:

Compound TDI01116-4 (200 mg, 0.52 mmol) and pyridazin-4-amine (60 mg, 0.62 mmol) were dissolved in N,N-dimethylformamide (5 mL), HATU (240 mg, 0.62 mmol) and diisopropylethylamine (268 mg, 2.08 mmol) were added, and the reaction was performed at room temperature for 3 hours. LC-MS indicated the reaction was complete. The reaction solution was added with saturated ammonium chloride (30 mL), filtered with suction, and the filter cake was dissolved in methanol. The filtrate was extracted with (dichloromethane/methanol=10:1)(50 mL*2), and the combined organic phase was washed with saturated brine (50 mL*3), dried over anhydrous sodium sulfate, filtered, and concentrated under reduced pressure. The residue was purified by liquid chromatography to afford compound TDI01116 (16.61 mg, yellow solid, yield: 6.9%).

¹H NMR (400 MHz, DMSO-d₆) δ 13.16 (s, 1H), 11.28 (s, 1H), 10.18 (s, 1H), 9.56 (s, 1H), 9.18 (d, J=4.0 Hz, 1H), 8.98 (s, 1H), 8.53 (s, 1H), 8.41 (d, J=4.0 Hz, 2H), 8.24 (d, J=8.0 Hz, 1H), 8.17 (s, 2H), 8.14 (s, 1H), 7.63 (d, J=8.0 Hz, 1H), 7.60 (s, 1H), 6.80 (d, J=8.0 Hz, 1H). MS m/z (ESI): 465.1 [M+H].

The compounds in Table 1 were prepared according to methods similar to that described in Example 1.

TABLE 1

| No. | Compound Structure | Compound Name | Starting material or regent different from that in Example 1 | Characterization Data |
|---|---|---|---|---|
| TDI 01152 | 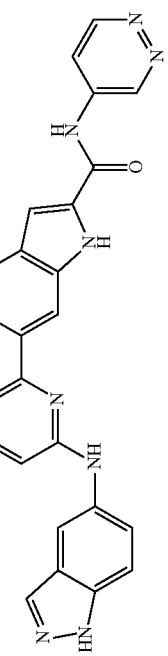 | 6-(4-((1H-indazol-5-yl)amino)pyrimidin-2-yl)-N-(pyridazin-4-yl)-1H-indole-2-carboxamide | in step 1 of Example 1 was replaced with <br> ; and <br> in step 4 was replaced with | ¹H NMR (400 MHz, DMSO-D₆) δ 9.60 (s, 1H), 9.27 (s, 1H), 8.83 (s, 1H), 8.54 (s, 1H), 8.35 (d, J = 15.6 Hz, 1H), 8.30 (s, 1H), 8.19-8.09 (m, 2H), 8.05-8.04 (m, 1H), 7.71 (d, J = 8.8 Hz, 1H), 7.64-7.58 (m, 2H), 7.21 (s, 1H), 6.65 (d, J = 5.6 Hz, 1H). MS m/z (ESI): 448.2 [M + H]. |
| TDI 01164 | 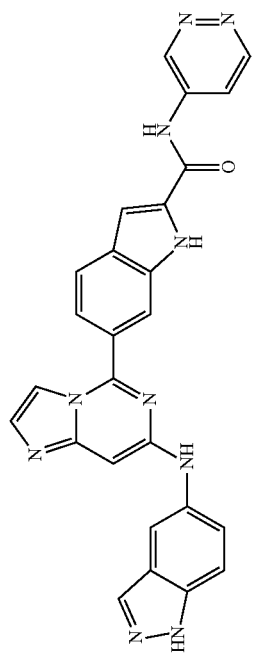 | 6-(7-((1H-indazol-5-yl)amino)imidazo[1,2-c]pyrimidin-5-yl)-N-(pyridazin-4-yl)-1H-indole-2-carboxamide | in step 1 of Example 1 was replaced with <br> ; <br> in step 3 was replaced with <br> (Reg-1-8); and | ¹H NMR (400 MHz, DMSO-d₆) δ 13.24 (s, 1H), 12.33 (s, 1H), 4P-97 (s, 1H), 10.31 (s, 1H), 9.59 (s, 1H), 9.14 (d, J = 5.8 Hz, 1H), 8.54 (s, 1H), 8.26 (s, 1H), 8.23 (s, 1H), 8.20-8.16 (m, 2H), 8.10 (s, 1H), 7.87 (s, 2H), 7.81 (d, J = 8.9 Hz, 1H), 7.77-7.71 (m, 2H), 7.59 (s, 1H). MS m/z (ESI): 487.1 [M + H]. |

TABLE 1-continued

| No. | Compound Structure | Compound Name | Starting material or regent different from that in Example 1 | Characterization Data |
|---|---|---|---|---|
| TDI 01167 | (structure shown) | 6-(4-((1H-indazol-5-yl)amino)-1,3,5-triazin-2-yl)-N-(pyridazin-4-yl)-1H-indole-2-carboxamide | in step 4 was replaced with 2-aminotetrahydrofuran and H₂N-pyridazine; in step 1 of Example 1 was replaced with 6-bromobenzothiophene-2-carboxylic acid and 6-bromo-1H-indole-2-carboxylic acid; in step 3 was replaced with 2-chloro-N-(1-Boc-indazol-5-yl)pyrimidin-4-amine and 2-chloro-N-(1-Boc-indazol-5-yl)-1,3,5-triazin-4-amine (Reg-1-11); and in step 4 was replaced with 2-aminotetrahydrofuran and H₂N-pyridazine | ¹H NMR (400 MHz, DMSO-d₆) δ 13.26-12.93 (m, 1H), 12.41 (s, 1H), 11.03 (s, 1H), 10.30 (s, 1H), 9.60 (s, 1H), 9.16 (d, J = 5.2 Hz, 1H), 8.81 (s, 1H), 8.64 (s, 1H), 8.21 (s, 4H), 7.89 (d, J = 8.4 Hz, 1H), 7.63 (s, 3H). MS m/z (ESI): 449.3 [M + H]. |

TABLE 1-continued

| No. | Compound Name | Compound Structure | Starting material or regent different from that in Example 1 | Characterization Data |
|---|---|---|---|---|
| TDI 01169 | 6-(4-((1H-indazol-5-yl)amino)quinazolin-2-yl)-N-(pyridazin-4-yl)-1H-indole-2-carboxamide | (structure shown) | 6-bromobenzothiophene-2-carboxylic acid in step 1 of Example 1 was replaced with 6-bromo-1H-indole-2-carboxylic acid; 2-chloro-N-(1-Boc-1H-indazol-5-yl)pyrimidin-4-amine in step 3 was replaced with 2-chloro-N-(1-Boc-1H-indazol-5-yl)quinazolin-4-amine (Reg-1-2); and 3-aminotetrahydrofuran in step 4 was replaced with 4-aminopyridazine | $^1$H NMR (400 MHz, DMSO-d$_6$) δ 12.54 (s, 1H), 11.15-11.07 (m, 2H), 9.60 (s, 1H), 9.16 (d, J = 4.8 Hz, 1H), 8.73 (d, J = 7.6 Hz, 1H), 8.48 (s, 1H), 8.24-8.22 (m, 3H), 8.06 (br. s, 3H), 7.86-7.73 (m, 4H), 7.64 (s, 1H). MS m/z (ESI): 498.1 [M + H]. |

TABLE 1-continued

| No. | Compound Name | Compound Structure | Starting material or regent different from that in Example 1 | Characterization Data |
|---|---|---|---|---|
| TDI 01174 | 6-(4-((4-(1H-pyrazol-4-yl)phenyl)amino)pyrimidin-2-yl)-N-(pyridazin-4-yl)-1H-indole-2-carboxamide | 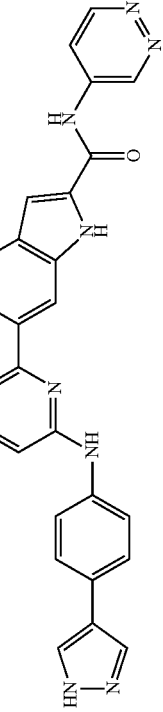 |  in step 1 of Example 1 was replaced with (Reg-1-16) was used to replace in step 3; and in step 4 was replaced with | $^1$H NMR (400 MHz, DMSO-d$_6$) δ 12.52 (s, 1H), 11.14 (s, 1H), 10.60 (s, 1H), 9.61 (s, 1H), 9.19 (d, J = 5.9 Hz, 1H), 8.52 (s, 1H), 8.39 (d, J = 6.5 Hz, 1H), 8.26 (dd, J = 5.9, 2.5 Hz, 1H), 8.09 (s, 2H), 8.05 (d, J = 8.4 Hz, 1H), 7.96 (d, J = 8.5 Hz, 1H), 7.81 (d, J = 7.6 Hz, 2H), 7.72 (d, J = 8.5 Hz, 2H), 7.66 (s, 1H), 6.86 (d, J = 6.5 Hz, 1H). MS m/z (ESI): 474.1 [M + H]. |

TABLE 1-continued

| No. | Compound Structure | Compound Name | Starting material or regent different from that in Example 1 | Characterization Data |
|---|---|---|---|---|
| TDI 01175 | 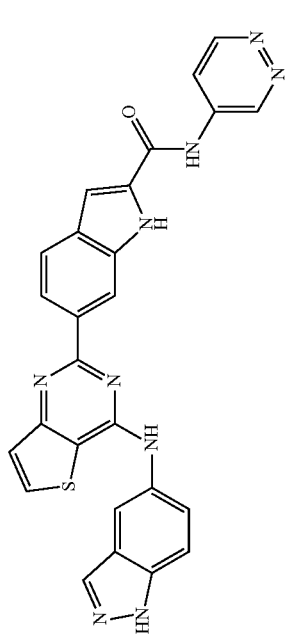 | 6-(4-((1H-indazol-5-yl)amino)thieno[3,2-d]pyrimidin-2-yl)-N-(pyridazin-4-yl)-1H-indole-2-carboxamide | (structures shown): 6-bromobenzothiophene-2-carboxylic acid in step 1 of Example 1 was replaced with 6-bromoindole-2-carboxylic acid; 2-chloro-N-(Boc)pyrimidine aniline replaced in step 3 with 2-chloro-thieno[3,2-d]-N-(Boc)pyrimidine aniline (Reg-1-4); and tetrahydrofuran-3-amine in step 4 was replaced with pyridazin-4-amine | $^1$H NMR (400 MHz, DMSO-d$_6$) δ 12.39 (s, 1H), 11.15 (s, 1H), 10.32 (s, 1H), 9.62 (s, 1H), 9.20 (d, J = 5.6 Hz, 1H), 8.56 (s, 1H), 8.30-8.26 (m, 2H), 8.19-9.17 (m, 3H), 7.88 (d, J = 8.4 Hz, 1H), 7.74 (d, J = 8.8 Hz, 1H), 7.38-7.64 (m, 2H), 7.56 (d, J = 5.4 Hz, 1H). MS m/z (ESI): 504.1 [M + H]. |

TABLE 1-continued

| No. | Compound Name | Starting material or regent different from that in Example 1 | Characterization Data |
|---|---|---|---|
| TDI 01178 | 6-(4-((1H-indazol-5-yl)amino)pyrimidin-2-yl)-N-(pyridazin-4-ylmethyl)-1H-indole-2-carboxamide | 6-bromobenzothiophene-2-carboxylic acid in step 1 of Example 1 was replaced with 6-bromo-1H-indole-2-carboxylic acid; and pyridazin-4-ylmethanamine·2HCl in step 4 was replaced with | $^1$H NMR (400 MHz, DMSO-d$_6$) δ 12.38 (s, 1H), 11.11 (s, 1H), 9.41 (t, J = 5.9 Hz, 1H), 9.28-9.15 (m, 2H), 8.30 (m, J = 40.4, 33.4 Hz, 5H), 7.91 (s, 2H), 7.72-7.60 (m, 3H), 7.34 (s, 1H), 6.89 (s, 1H), 4.62 (d, J = 5.8 Hz, 2H). MS m/z (ESI): 462.1 [M + H]. |
| TDI 01180 | 6-(4-((1H-indazol-5-yl)amino)pyrimidin-2-yl)-N-(3-chloropyridazin-4-yl)-1H-indole-2-carboxamide | 6-bromobenzothiophene-2-carboxylic acid in step 1 of Example 1 was replaced with 6-bromo-1H-indole-2-carboxylic acid; and 3-chloropyridazin-4-amine in step 4 was replaced with | $^1$H NMR (400 MHz, MeOD) δ 9.07 (d, J = 5.4 Hz, 1H), 8.61 (d, J = 5.4 Hz, 1H), 8.41 (s, 1H), 8.35-8.04 (m, 3H), 7.96 (d, J = 8.3 Hz, 1H), 7.90 (s, 1H), 7.70 (d, J = 7.5 Hz, 2H), 7.51 (s, 1H), 6.91 (s, 1H). MS m/z (ESI): 482.1 [M + H]. |

TABLE 1-continued

| No. | Compound Structure | Compound Name | Starting material or regent different from that in Example 1 | Characterization Data |
|---|---|---|---|---|
| TDI 01181 | (structure shown) | 6-(4-((1H-indazol-5-yl)amino)pyrimidin-2-yl)-N-(5-chloropyridazin-4-yl)-1H-indole-2-carboxamide | in step 1 of Example 1 was replaced with 6-bromobenzothiophene-2-carboxylic acid; and 6-bromo-1H-indole-2-carboxylic acid; in step 4 was replaced with 4-chloro-5-aminopyridazine | $^1$H NMR (400 MHz, DMSO-d$_6$) δ 13.2-13.10 (m, 1H), 12.49 (s, 1H), 10.66 (s, 1H), 9.64 (s, 1H), 9.44 (s, 1H), 8.49 (s, 1H), 8.35 (d, J = 6.4 Hz, 1H), 8.18 (s, 1H), 8.06 (d, J = 7.4 Hz, 1H), 7.91 (d, J = 8.0 Hz, 1H), 7.63 (s, 3H), 6.80 (s, 1H). MS m/z (ESI): 482.2 [M + H]. |
| TDI 01187 | (structure shown) | 6-(4-((1H-indazol-5-yl)amino)pyrimidin-2-yl)-N-(pyridazin-4-yl)-1H-indole-3-carboxamide | in step 1 of Example 1 was replaced with 6-bromobenzothiophene-2-carboxylic acid; and 6-bromo-1H-indole-3-carboxylic acid; in step 4 was replaced with 4-aminopyridazine | $^1$H NMR (400 MHz, MeOD) δ 9.55 (s, 1H), 9.23 (d, J = 5.0 Hz, 1H), 8.78 (d, J = 4.7 Hz, 1H), 8.58 (s, 1H), 8.50 (d, J = 8.5 Hz, 1H), 8.41 (s, 1H), 8.22 (d, J = 7.2 Hz, 2H), 8.16 (s, 1H), 8.04 (dd, J = 3.5, 1.4 Hz, 1H), 7.86-7.57 (m, 2H), 6.92 (s, 1H). MS m/z (ESI): 448.2 [M + H]. |

TABLE 1-continued

| No. | Compound Structure | Compound Name | Starting material or regent different from that in Example 1 | Characterization Data |
|---|---|---|---|---|
| TDI 01188 | (structure) | 5-(4-((1H-indazol-5-yl)amino)pyrimidin-2-yl)-N-(pyridazin-4-yl)-1H-indole-2-carboxamide | in step 1 of Example 1 was replaced with (6-bromobenzothiophene-2-carboxylic acid); and (5-bromo-1H-indole-2-carboxylic acid) and (3-aminotetrahydrofuran); in step 4 was replaced with (4-aminopyridazine) | $^1$H NMR (400 MHz, DMSO-$d_6$) δ 13.23 (s, 1H), 12.46 (s, 1H), 11.09 (s, 1H), 10.93 (s, 1H), 9.60 (d, J = 1.6 Hz, 1H), 9.17 (d, J = 6.0 Hz, 1H), 8.70 (s, 1H), 8.36 (d, J = 6.8 Hz, 1H), 8.21 (dt, J = 22.4, 7.2 Hz, 4H), 7.68 (dd, J = 28.8, 19.2 Hz, 4H), 6.86 (d, J = 6.4 Hz, 1H). MS m/z (ESI): 448.2 [M + H]. |
| TDI 01189 | (structure) | 6-(4-((1H-indazol-5-yl)amino)pyrimidin-2-yl)-N-(pyridazin-4-yl)-1H-pyrrolo[3,2-b]pyridine-2-carboxamide | in step 1 of Example 1 was replaced with (6-bromobenzothiophene-2-carboxylic acid); and (6-bromo-1H-pyrrolo[3,2-b]pyridine-2-carboxylic acid) and (3-aminotetrahydrofuran); in step 4 was replaced with (4-aminopyridazine) | $^1$H NMR (400 MHz, DMSO-$d_6$) δ 13.08 (s, 2H), 12.78 (s, 1H), 11.14 (s, 1H), 10.07 (s, 1H), 9.61 (s, 1H), 9.46 (s, 1H), 9.18 (d, J = 6.0 Hz, 1H), 8.83 (s, 1H), 8.40 (d, J = 6.1 Hz, 1H), 8.21 (d, J = 3.3 Hz, 1H), 8.15 (s, 1H), 7.76 (s, 1H), 7.61 (t, J = 8.4 Hz, 2H), 6.78 (d, J = 6.1 Hz, 1H). MS m/z (ESI): 449.1 [M + H]. |

TABLE 1-continued

| No. | Compound Structure | Compound Name | Starting material or regent different from that in Example 1 | Characterization Data |
|---|---|---|---|---|
| TDI 01191 | (structure) | 5-(4-((1H-indazol-5-yl)amino)pyrimidin-2-yl)-N-(pyridazin-4-yl)-1H-indole-3-carboxamide | in step 1 of Example 1 was replaced with 6-bromobenzothiophene-2-carboxylic acid; in step 4 was replaced with 5-bromo-1H-indole-3-carboxylic acid and 3-aminotetrahydrofuran; in step 4 was replaced with 4-aminopyridazine | $^{1}$H NMR (400 MHz, MeOD) δ 9.58 (s, 1H), 9.33 (s, 1H), 9.23 (d, J = 5.2 Hz, 1H), 8.59 (s, 1H), 8.54 (d, J = 4.8 Hz, 1H), 8.41 (s, 1H), 18.27-8.25 (m, 2H), 8.15 (d, J = 8.8 Hz, 1H), 7.78 (d, J = 8.8 Hz, 1H), 7.71 (d, J = 8.8 Hz, 1H), 7.63 (s, 1H), 6.93 (d, J = 6.0 Hz, 1H). MS m/z (ESI): 448.2 [M + H]. |
| TDI 01193 | (structure) | 6-(4-((1H-indazol-5-yl)amino)pyrimidin-2-yl)-N-4-(pyridazin-4-yl)-1H-benzo[d]imidazole-2-carboxamide | in step 1 of Example 1 was replaced with 6-bromobenzothiophene-2-carboxylic acid; 6-bromo-1H-benzimidazole-2-carboxylic acid and 3-aminotetrahydrofuran; in step 4 was replaced with 4-aminopyridazine | $^{1}$H NMR (400 MHz, MeOD) δ 9.68 (d, J = 2.3 Hz, 1H), 9.21 (d, J = 6.2 Hz, 1H), 8.68 (s, 1H), 8.54 (dd, J = 6.1, 2.6 Hz, 1H), 8.24 (m, 4H), 7.95 (d, J = 8.5 Hz, 1H), 7.72 (d, J = 8.3 Hz, 1H), 7.65 (s, 1H), 6.94 (d, J = 6.2 Hz, 1H). MS m/z (ESI): 449.0 [M + H]. |

TABLE 1-continued

| No. | Compound Structure | Compound Name | Starting material or regent different from that in Example 1 | Characterization Data |
|---|---|---|---|---|
| TDI 01201 | 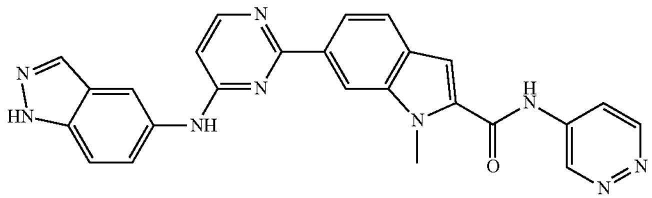 [SMILES: Cn1c(C(=O)Nc2ccnnc2)cc2ccc(-c3nccc(Nc4ccc5[nH]ncc5c4)n3)cc21] | 6-(4-((1H-indazol-5-yl)amino)pyrimidin-2-yl)-1-methyl-N-(pyridazin-4-yl)-1H-indole-2-carboxamide | The preparation started from step 3 of Example 1, [pinacol boronate ester of methyl benzothiophene-2-carboxylate]; in step 3 was replaced with [pinacol boronate ester of methyl 1-methyl-1H-indole-2-carboxylate]; and [3-aminotetrahydrofuran] NH₂; in step 4 was replaced with [4-aminopyridazine] H₂N-N | ¹H NMR (400 MHz, DMSO-d₆) δ 11.24 (s, 1H), 10.97 (s, 1H), 9.57 (s, 1H), 9.19 (d, J = 5.6 Hz, 1H), 8.54 (s, 1H), 8.40 (d, J = 6.4 Hz, 1H), 8.24 (s, 2H), 8.17 (s, 1H), 8.04 (d, J = 8.4 Hz, 1H), 7.95 (d, J = 8.4 Hz, 1H), 7.67 (d, J = 8.4 Hz, 1H), 7.61-7.57 (m, 2H), 6.89 (d, J = 6.0 Hz, 1H), 4.11 (s, 3H). MS m/z (ESI): 462.2 [M + H]. |
| TDI 01213 | 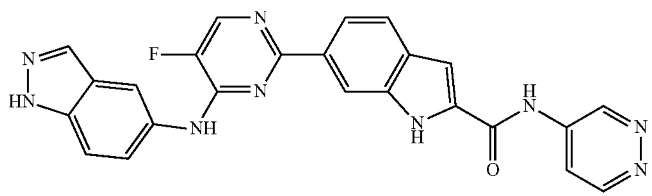 [SMILES: O=C(Nc1ccnnc1)c1cc2ccc(-c3ncc(F)c(Nc4ccc5[nH]ncc5c4)n3)cc2[nH]1] | 6-(4-((1H-indazol-5-yl)amino)-5-fluoropyrimidin-2-yl)-N-(pyridazin-4-yl)-1H-indole-2-carboxamide | in step 1 of Example 1 was replaced with [6-bromobenzothiophene-2-carboxylic acid] and [6-bromo-1H-indole-2-carboxylic acid]; [2-chloro-N-(Boc-indazolyl)pyrimidine derivative]; in step 3 was replaced with [2-chloro-5-fluoro-N-(Boc-indazolyl)pyrimidine derivative] (Reg-1-12); and | ¹H NMR (400 MHz, MeOD, DMSO-d₆) δ 9.64 (m, 1H), 9.19 (s, 1H), 8.53-8.47 (m, 2H), 8.41 (d, J = 3.6 Hz, 1H), 8.36 (s, 1H), 8.22 (s, 1H), 8.16 (d, J = 8.0 Hz, 1H), 7.85 (d, J = 8.8 Hz, 2H), 7.70 (d, J = 8.8 Hz, 1H), 7.57 (s, 1H). MS m/z (ESI): 466.1 [M + H]. |

TABLE 1-continued

| No. | Compound Structure | Compound Name | Starting material or regent different from that in Example 1 | Characterization Data |
|---|---|---|---|---|
| TDI 01214 | (structure shown) | 6-(4-((6-fluoro-1H-indazol-5-yl)amino)pyrimidin-2-yl)-N-(pyridazin-4-yl)-1H-indole-2-carboxamide | in step 4 was replaced with H₂N—(tetrahydrofuran-2-yl)amine; H₂N—(pyridazin-4-yl); in step 1 of Example 1 was replaced with 6-bromobenzothiophene-2-carboxylic acid; 6-bromo-1H-indole-2-carboxylic acid; in step 3 was replaced with 2-chloro-N-Boc-indazolyl amine; 2-chloro-4-(6-fluoro-1H-indazol-5-ylamino)pyrimidine (Reg-1-17); and in step 4 was replaced with H₂N—tetrahydrofuran-2-yl; H₂N—pyridazin-4-yl | ¹H NMR (400 MHz, DMSO-d₆) δ 12.35 (s, 1H), 11.02 (s, 1H), 9.91 (s, 1H), 9.60 (s, 1H), 9.14 (d, J = 5.2 Hz, 1H), 8.43 (s, 1H), 8.39 (d, J = 6.0 Hz, 1H), 8.27-8.14 (m, 3H), 8.02 (d, J = 8.0 Hz, 1H), 7.83 (d, J = 8.4 Hz, 1H), 7.60 (s, 1H), 7.55 (d, J = 10.8 Hz, 1H), 6.78 (d, J = 3.6 Hz, 1H). MS m/z (ESI): 466.1 [M + H]. |

| No. | Compound Structure | Compound Name | Starting material or regent different from that in Example 1 | Characterization Data |
|---|---|---|---|---|
| TDI 01231 | 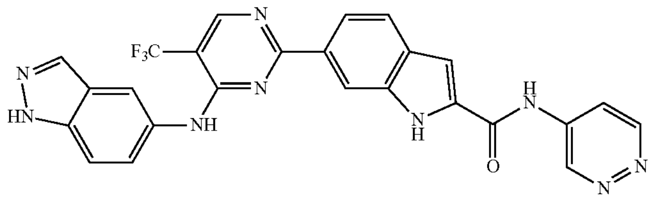 | 6-(4-((1H-indazol-5-yl)amino)-5-(trifluoromethyl)pyrimidin-2-yl)-N-(pyridazin-4-yl)-1H-indole-2-carboxamide | in step 1 of Example 1 was replaced with ; in step 3 was replaced with (Reg-1-23); and in step 4 was replaced with . | $^1$H NMR (400 MHz, DMSO-d$_6$) δ 13.16 (s, 1H), 12.31 (s, 1H), 11.06 (s, 1H), 9.58 (d, 1H), 9.17 (m, 2H), 8.75 (s, 1H), 8.45 (s, 1H), 8.26 (dd, 1H), 8.14 (s, 1H), 7.95 (dd, 1H), 7.88 (s, 1H), 7.76 (d, 1H), 7.60 (m, 3H). MS m/z (ESI): 516.2 [M + H]. |

TABLE 1-continued

| No. | Compound Structure | Compound Name | Starting material or regent different from that in Example 1 | Characterization Data |
|---|---|---|---|---|
| TDI 01232 | (structure) | 6-(4-((1H-indazol-5-yl)amino)-5,6-dimethylpyrimidin-2-yl)-N-(pyridazin-4-yl)-1H-indole-2-carboxamide | (structures) in step 1 of Example 1 was replaced with (structure); in step 3 was replaced with (Reg-1-13); and in step 4 was replaced with (structure) | $^1$H NMR (400 MHz, DMSO-d$_6$) δ 13.16 (s, 1H), 12.45 (s, 1H), 10.98 (s, 1H), 9.58 (s, 2H), 9.14 (s, 1H), 8.29 (s, 1H), 8.17 (s, 2H), 8.00 (s, 1H), 7.89 (d, J = 8.4 Hz, 2H), 7.64 (s, 2H), 7.59 (s, 1H), 2.58 (s, 3H), 2.31 (s, 3H). MS m/z (ESI): 476.3 [M + H]. |

TABLE 1-continued

| No. | Compound Name | Starting material or regent different from that in Example 1 | Characterization Data |
|---|---|---|---|
| TDI 01250 | 6-(4-((1H-indazol-5-yl)amino)-5-methyl-pyrimidin-2-yl)-N-(pyridazin-4-yl)-1H-indole-2-carboxamide | [6-bromobenzothiophene-2-carboxylic acid] in step 1 of Example 1 was replaced with [6-bromoindole-2-carboxylic acid with N-Boc]; [2-chloro-N-(1H-indazol-5-yl)pyrimidin-4-amine] in step 3 was replaced with [2-chloro-5-methyl-N-(1H-indazol-5-yl)pyrimidin-4-amine] (Reg-1-14); and [3-aminotetrahydrofuran] in step 4 was replaced with [pyridazin-4-amine] | $^1$H NMR (400 MHz, DMSO-d$_6$) δ 13.17 (br, 1H), 12.52 (s, 1H), 11.04 (s, 1H), 9.95 (br, 1H), 9.59 (d, J = 4.0 Hz, 1H), 9.16 (d, J = 8.0 Hz, 1H), 8.31 (d, J = 5.2 Hz, 2H), 8.22-8.18 (m, 2H), 8.05 (s, 1H), 7.91 (d, J = 8.6 Hz, 1H), 7.85 (d, J = 7.9 Hz, 1H), 7.68 (s, 2H), 7.61 (s, 1H), 2.36 (s, 3H). MS m/z (ESI): 462.3 [M + H]. |

TABLE 1-continued

| No. | Compound Structure | Compound Name | Starting material or regent different from that in Example 1 | Characterization Data |
|---|---|---|---|---|
| TDI 01251 | (structure shown) | 6-(4-((1H-indazol-5-yl)amino)-6-methyl-pyrimidin-2-yl)-N-(pyridazin-4-yl)-1H-indole-2-carboxamide | 6-bromobenzothiophene-2-carboxylic acid in step 1 of Example 1 was replaced with 6-bromo-1H-indole-2-carboxylic acid; N-Boc-2-chloro-N-(1H-indazol-5-yl)pyrimidin-4-amine in step 3 was replaced with N-Boc-2-chloro-6-methyl-N-(1H-indazol-5-yl)pyrimidin-4-amine (Reg-1-15); and 3-aminotetrahydrofuran in step 4 was replaced with pyridazin-4-amine | $^1$H NMR (400 MHz, DMSO-d$_6$) δ 13.20 (s, 1H), 12.55 (s, 1H), 11.11 (s, 1H), 10.78 (s, 1H), 9.62 (d, J = 2.0 Hz, 1H), 9.18 (d, J = 6.0 Hz, 1H), 8.43 (s, 1H), 8.20 (dt, J = 40.4, 13.2 Hz, 3H), 7.97 (d, J = 8.8 Hz, 2H), 7.71-7.47 (m, 3H), 6.71 (s, 1H), 2.54 (s, 3H). MS m/z (ESI): 462.1 [M + H]. |

TABLE 1-continued

| No. | Compound Structure | Compound Name | Starting material or regent different from that in Example 1 | Characterization Data |
|---|---|---|---|---|
| TDI 01275 | (structure: 3-methyl-1H-indazol-5-yl amino pyrimidine linked to N-(pyridazin-4-yl) 1H-indole-2-carboxamide) | 6-(4-((3-methyl-1H-indazol-5-yl)amino) pyrimidin-2-yl)-N-(pyridazin-4-yl)-1H-indole-2-carboxamide | (6-bromobenzothiophene-2-carboxylic acid) in step 1 of Example 1 was replaced with (6-bromo-N-Boc-indazole-2-carboxylic acid); (2-chloro-4-((3-methyl-1H-indazol-5-yl)amino-Boc)pyrimidine) in step 3 was replaced with (2-chloro-4-((3-methyl-1-Boc-indazol-5-yl)amino)pyrimidine) (Reg-1-25); and (3-aminotetrahydrofuran) in step 4 was replaced with (4-aminopyridazine). | $^1$H NMR (400 MHz, DMSO-d$_6$) δ 12.82-12.59 (m, 1H), 12.43 (s, 1H), 10.99 (s, 1H), 10.37 (s, 1H), 9.60 (s, 1H), 9.14 (d, J = 5.6 Hz, 1H), 8.50 (s, 1H), 8.35 (d, J = 6.4 Hz, 1H), 8.18 (d, J = 3.6 Hz, 2H), 8.09 (d, J = 8.4 Hz, 1H), 7.91 (d, J = 8.4 Hz, 1H), 7.62 (s, 1H), 7.55 (s, 1H), 6.78 (d, J = 5.6 Hz, 1H), 2.54 (s, 3H). MS m/z (ESI): 462.2 [M + H]. |

TABLE 1-continued

| No. | Compound Structure | Compound Name | Starting material or regent different from that in Example 1 | Characterization Data |
|---|---|---|---|---|
| TDI 01276 | (structure shown) | 6-(4-((4-methyl-1H-indazol-5-yl)amino)pyrimidin-2-yl)-N-(pyridazin-4-yl)-1H-indole-2-carboxamide | 6-bromobenzothiophene-2-carboxylic acid in step 1 of Example 1 was replaced with 6-bromoindole-2-carboxylic acid; BocN-protected indazolyl-aminopyrimidine (Reg-1-26) in step 3 was replaced with the chloropyrimidine-methylindazole intermediate; and tetrahydrofuran-3-amine in step 4 was replaced with 4-aminopyridazine. | $^1$H NMR (400 MHz, DMSO-$d_6$) δ 13.22 (s, 1H), 12.48 (s, 1H), 11.00 (s, 1H), 9.59 (d, J = 2.3 Hz, 1H), 9.15 (d, J = 6.0 Hz, 1H), 8.34 (s, 1H), 8.29 (d, J = 6.7 Hz, 1H), 8.24 (s, 1H), 8.20-8.16 (m, 1H), 7.90 (s, 2H), 7.61 (s, 1H), 7.50 (d, J = 8.7 Hz, 1H), 7.39 (s, d, J = 8.2 Hz, 1H), 2.50 (s, 3H). MS m/z (ESI): 462.2 [M + H]. |

TABLE 1-continued

| No. | Compound Structure | Compound Name | Starting material or regent different from that in Example 1 | Characterization Data |
|---|---|---|---|---|
| TDI 01278 | 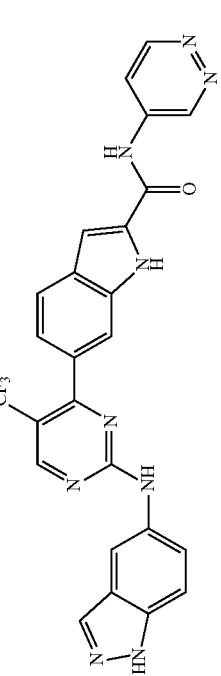 | 6-(2-((1H-indazol-5-yl)amino)-5-(trifluoromethyl)pyrimidin-4-yl)-N-(pyridazin-4-yl)-1H-indole-2-carboxamide | 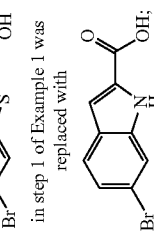 in step 1 of Example 1 was replaced with the second structure; in step 3 was replaced with (Reg-1-24); and in step 4 was replaced with 4-aminopyridazine | $^1$H NMR (400 MHz, DMSO-d$_6$) δ 12.98 (s, 1H), 12.26 (s, 1H), 11.04 (s, 1H), 10.34 (s, 1H), 9.59 (d, 1H), 9.17 (d, 1H), 8.86 (s, 1H), 8.24 (m, 2H), 8.03 (s, 1H), 7.88 (d, 1H), 7.76 (s, 1H), 7.63 (s, 2H), 7.50 (d, 1H), 7.34 (d, 1H). MS m/z (ESI): 516.2 [M + H]. |

TABLE 1-continued

| No. | Compound Structure | Compound Name | Starting material or regent different from that in Example 1 | Characterization Data |
|---|---|---|---|---|
| TDI 01282 | (structure shown) | 6-(2-((1H-indazol-5-yl)amino)-5,6-dimethylpyrimidin-4-yl)-N-(pyridazin-4-yl)-1H-indole-2-carboxamide | (6-bromobenzothiophene-2-carboxylic acid) in step 1 of Example 1 was replaced with (6-bromo-1H-indole-2-carboxylic acid); (2-chloro-N-(1-Boc-1H-indazol-5-yl)pyrimidin-4-amine) in step 3 was replaced with (4-chloro-5,6-dimethyl-N-(1H-indazol-5-yl)pyrimidin-2-amine) (Reg-1-22); and (3-aminotetrahydrofuran) in step 4 was replaced with (4-aminopyridazine) | $^1$H NMR (400 MHz, DMSO-d$_6$) δ 10.13 (s, 2H), 9.70 (s, 1H), 8.96 (s, 1H), 8.82 (s, 1H), 8.50 (s, 1H), 8.40-8.23 (m, 3H), 8.10 (d, J = 12.0 Hz, 3H), 7.93 (dd, 34.6, 8.8 Hz, 3H), 3.02 (s, 3H), 2.75 (s, 3H). MS m/z (ESI): 476.3 [M + H]. |

TABLE 1-continued

| No. | Compound Name | Compound Structure | Starting material or regent different from that in Example 1 | Characterization Data |
|---|---|---|---|---|
| TDI 01314 | 7-(4-((1H-indazol-5-yl)amino)pyrimidin-2-yl)-N-(pyridazin-4-yl)-2,3-dihydrobenzo[b][1,4]dioxine-2-carboxamide | (structure shown) | 6-bromobenzothiophene-2-carboxylic acid in step 1 of Example 1 was replaced with 7-bromo-2,3-dihydrobenzo[b][1,4]dioxine-2-carboxylic acid (TDI01314-1); and 3-aminotetrahydrofuran in step 4 was replaced with 4-aminopyridazine. | $^1$H NMR (400 MHz, MeOD) δ 9.40 (s, 1H), 9.15 (d, J = 6.1 Hz, 1H), 8.57 (d, J = 7.1 Hz, 1H), 8.47 (d, J = 3.1 Hz, 1H), 8.35 (d, J = 3.7 Hz, 1H), 8.18 (d, J = 7.2 Hz, 1H), 8.13 (s, 1H), 7.92 (s, 1H), 7.74 (s, 1H), 7.68 (d, J = 8.2 Hz, 1H), 7.15 (d, J = 8.6 Hz, 1H), 6.87 (s, 1H), 5.16 (s, 1H), 4.60 (d, J = 3.8 Hz, 2H). MS m/z (ESI): 467.2 [M + H]. |

TABLE 1-continued

| No. | Compound Structure | Compound Name | Starting material or regent different from that in Example 1 | Characterization Data |
|---|---|---|---|---|
| TDI 01347 | (structure) | 6-(4-((1H-indazol-5-yl)amino)pyrimidin-2-yl)-N-methyl-N-(pyridazin-4-yl)-1H-indole-2-carboxamide | (6-bromobenzothiophene-2-carboxylic acid structure) in step 1 of Example 1 was replaced with (6-bromoindole-2-carboxylic acid structure) and (3-aminotetrahydrofuran structure); in step 4 was replaced with (N-methyl-pyridazin-4-amine structure). | $^1$H NMR (400 MHz, DMSO-d$_6$) δ 12.33 (s, 1H), 10.61 (s, 1H), 9.28 (d, J = 2.1 Hz, 1H), 9.23 (d, J = 5.7 Hz, 1H), 8.43 (s, 1H), 8.34 (d, J = 6.5 Hz, 1H), 8.19 (d, J = 13.4 Hz, 2H), 7.95 (d, J = 8.6 Hz, 1H), 7.78 (dd, J = 5.7, 2.7 Hz, 1H), 7.70 (d, J = 8.5 Hz, 1H), 7.63 (q, J = 8.8 Hz, 2H), 6.82 (d, J = 6.5 Hz, 1H), 6.39 (s, 1H), 3.59 (s, 3H). MS m/z (ESI): 462.2 [M + H]. |

Example 2: Preparation of 6-(4-((1H-indazol-5-yl)oxy)pyrimidin-2-yl)-N-(pyridazin-4-yl)-1H-indole-2-carboxamide (TDI01212)

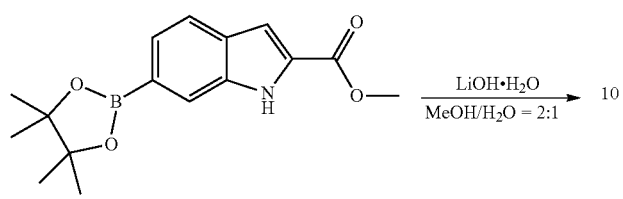

TDI01212-a

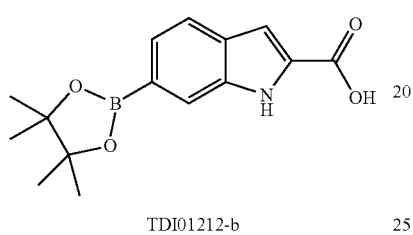

TDI01212-b

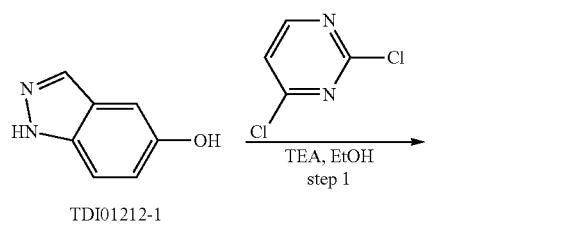

TDI01212-1

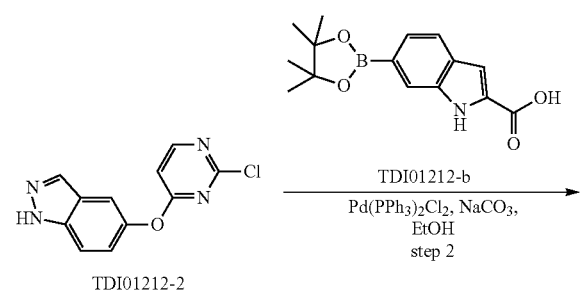

TDI01212-2

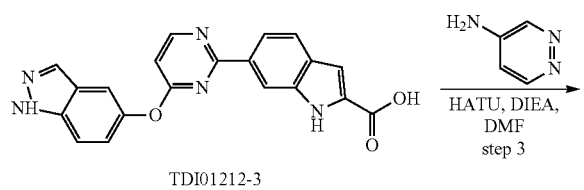

TDI01212-3

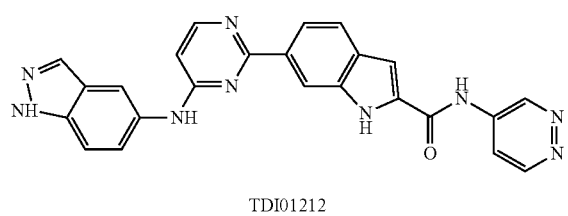

TDI01212

Preparation of Intermediate TDI01212-b

Intermediate TDI01212-a was prepared according to steps 1 and 2 of Example 1, wherein

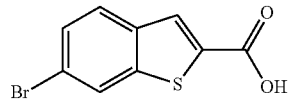

in step 1 was replaced with

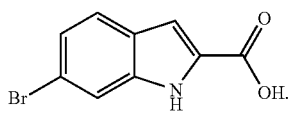

Intermediate TDI01212-a (3.00 g, 9.97 mmol) was dissolved in a mixture of methanol and water (2:1) (60 mL), lithium hydroxide monohydrate (4.19 g, 99.7 mmol) was added, and the reaction was performed at room temperature overnight. LC-MS indicated the reaction was complete. The reaction solution was concentrated under reduced pressure to remove methanol, the pH of the aqueous phase was adjusted to 3 with 6N HCl, a large amount of solid precipitated, and was stirred for 30 minutes before filtered to obtain intermediate TDI01212-b (2.1 g, yellow solid, yield: 73.2%).

$^1$H NMR (400 MHz, DMSO-$d_6$) δ 11.89 (s, 1H), 7.82 (s, 1H), 7.64 (d, J=8.0 Hz, 1H), 7.34 (d, J=8.0 Hz, 1H), 7.09 (s, 1H), 1.30 (s, 12H).

Step 1:

Compound TDI01212-1 (600 mg, 3.36 mmol), 2,4-dichloropyrimidine (736 mg, 3.70 mmol), TEA (1.36 g, 10 mmol) and anhydrous ethanol (20 mL) were added to a 50 mL flask, and the reaction was warmed to 80° C., and allowed to proceed overnight. Thin layer chromatography (methanol/dichloromethane=1:10) indicated the reaction was complete. The reaction solution was concentrated to give a crude product, and the crude product was added to 20 mL MTBE and 7.5 mL anhydrous ethanol. The mixture was warmed to 50° C., and triturated to afford TDI01212-2 (1.2 g, yellow solid, yield: 87%).

$^1$H NMR (400 MHz, DMSO-$d_6$) δ 13.33 (s, 1H), 8.61 (d, J=5.7 Hz, 1H), 8.11 (s, 1H), 7.67-7.63 (m, 2H), 7.25 (dd, J=9.0, 2.0 Hz, 1H), 7.14 (d, J=5.7 Hz, 1H). MS m/z (ESI): 247 [M+H].

Step 2:

Compound TDI01212-2 (1 g, 4 mmol), TDI01212-b (1.44 g, 4.8 mmol), Pd(PPh$_3$)$_2$Cl$_2$ (0.28 g, 0.4 mmol), Na$_2$CO$_3$ (0.85 g, 8 mmol), 40 mL ethanol and 5 mL water were added to a 100 mL flask, purge with argon was performed for 3 times, and the reaction was warmed to 105° C. and allowed to proceed for 4 h. The reaction was cooled to 50° C., 0.32 g sodium hydroxide was added, and the reaction was continued for 1 h. LC-MS indicated the reaction was complete. The reaction solution was concentrated under reduced pressure, the pH was adjusted to 3-4, and the solution was filtered to give a solid (1.5 g). 20 mL MTBE was added to obtain a slurry, and the slurry was dried to afford compound TDI01212-3 (0.4 g, yellow solid, yield: 27%).

$^1$H NMR (400 MHz, DMSO-$d_6$) δ 13.26 (s, 1H), 12.05 (s, 1H), 8.74 (d, J=5.7 Hz, 1H), 8.38 (s, 1H), 8.13 (s, 1H), 7.92 (d, J=8.6 Hz, 1H), 7.66 (d, J=8.6 Hz, 3H), 7.51 (d, J=6.9 Hz,

2H), 7.34 (d, J=9.2 Hz, 2H), 7.09 (s, 1H), 6.91 (d, J=5.7 Hz, 1H). MS m/z (ESI): 372 [M+H].

Step 3:

Compound TDI01212-3 (200 mg, 0.54 mmol), pyridazin-4-amine (61.6 mg, 0.64 mmol), HATU (244 mg, 0.64 mmol), DIEA (280 mg, 2.16 mmol) and 12 mL DMF were added to a 25 mL flask, and the reaction was performed at room temperature for 3 h. LC-MS indicated the reaction was complete. The reaction solution was cooled to room temperature, and added to 100 mL water. The precipitated solid was filtered and dried before purified by preparative liquid chromatography to afford TDI01212 (50 mg, yellow solid, yield: 13.8%).

$^1$H NMR (400 MHz, DMSO-$d_6$) δ 13.28 (s, 1H), 12.27 (s, 1H), 11.08 (s, 1H), 9.58 (d, J=2.0 Hz, 1H), 9.19 (d, J=6.2 Hz, 1H), 8.76 (d, J=5.7 Hz, 1H), 8.41 (s, 1H), 8.28 (dd, J=6.0, 2.5 Hz, 1H), 8.13 (s, 1H), 7.96 (d, J=8.5 Hz, 1H), 7.77 (d, J=8.5 Hz, 1H), 7.72-7.66 (m, 2H), 7.57 (s, 1H), 7.34 (dd, J=8.9, 2.1 Hz, 1H), 6.93 (d, J=5.7 Hz, 1H). MS m/z (ESI): 449.1 [M+H].

Example 3: Preparation of 7-(4-((1H-indazol-5-yl)amino)pyrimidin-2-yl)-N-(pyridazin-4-yl)quinoline-2-carboxamide (TDI01236)

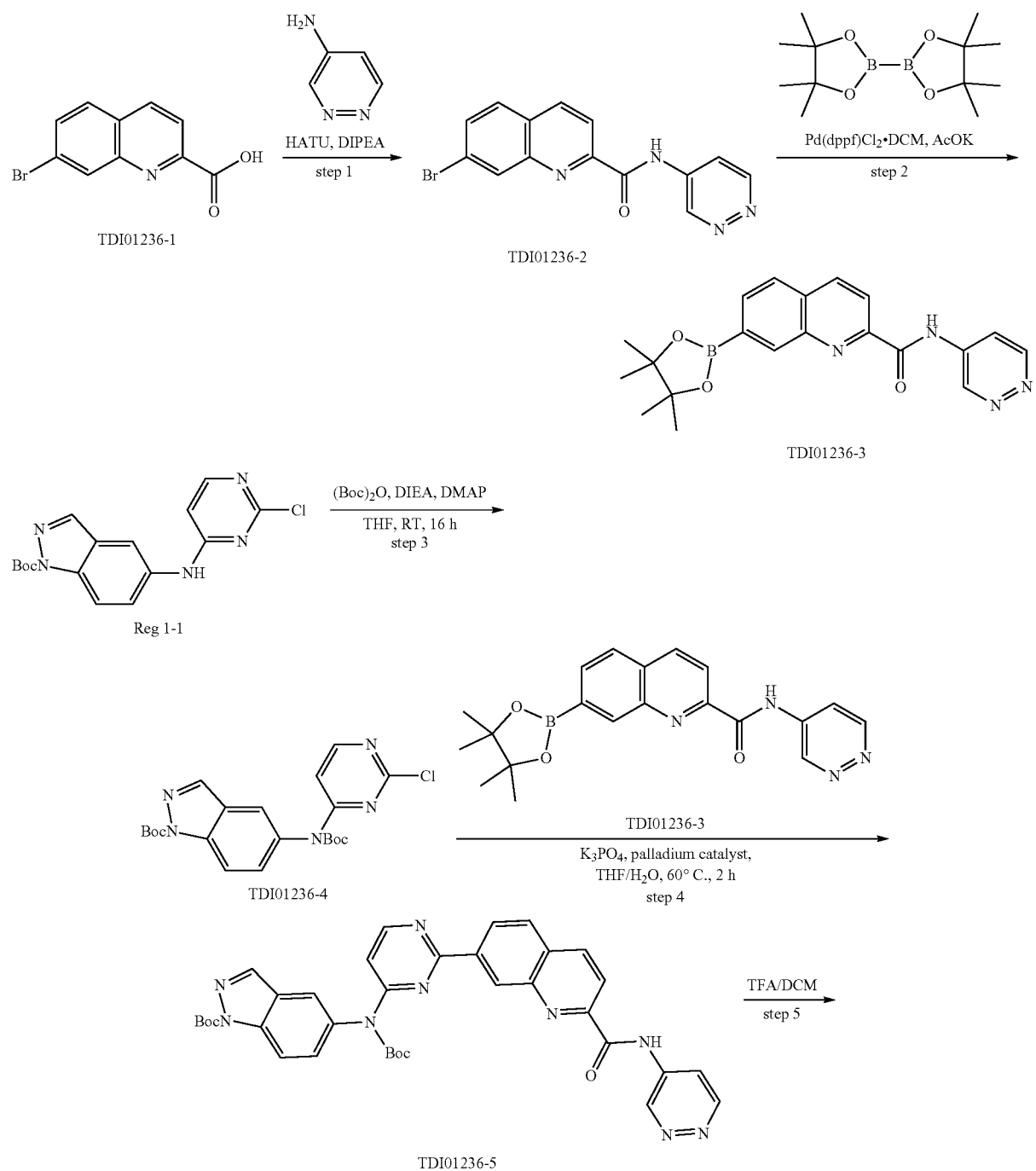

-continued

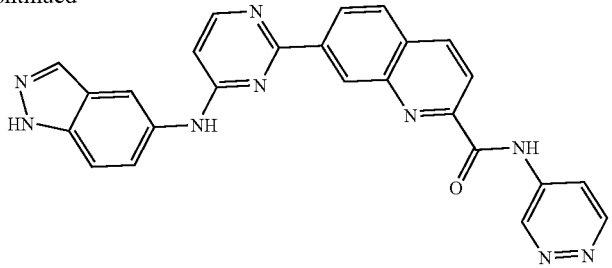

TDI01236

Step 1:

TDI01236-1 (700 mg, 2.78 mmol) and N,N-dimethylformamide (5 mL) were added to a 50 mL flask, HATU (1.59 g, 4.17 mmol) was cautiously added under stirring, and the reaction was stirred at room temperature for half an hour. Pyridazin-4-amino (290 mg, 3.16 mmol) and diisopropylethylamine (898 mg, 6.95 mmol) were then sequentially added, and the reaction was further stirred at room temperature for 4 h.

After the reaction was complete, the reaction solution was slowly added dropwise to water (20 mL) under stirring. A large amount of solid precipitated, and was filtered after being stirred for 30 min. The solid was successively washed with water (5 mL*2) and petroleum ether (5 mL*2), to afford TDI01236-2 (900 mg, yellow solid, yield: 98.4%)

$^1$H NMR (400 MHz, DMSO-$d_6$) δ 11.36 (s, 1H), 9.75 (d, J=2.0 Hz, 1H), 9.16 (d, J=5.9 Hz, 1H), 8.72 (d, J=8.5 Hz, 1H), 8.48 (s, 1H), 8.30-8.27 (m, 2H), 8.14 (d, J=8.8 Hz, 1H), 7.95 (dd, J=8.7, 1.8 Hz, 1H). MS m/z (ESI): 329.0 [M+H].

Step 2:

Compound TDI01236-2 (300 mg, 0.911 mmol), bis(pinacolato)diboron (457 mg, 1.822 mmol), potassium acetate (179 mg, 1.822 mmol), dioxane (12 mL) and dimethyl sulfoxide (1 drop) were sequentially added to a 50 mL flask, and purge with nitrogen was performed for 3 times. Under the protection of nitrogen, Pd(dppf)Cl$_2$.DCM (19 mg, 0.026 mmol) was cautiously added, and after the addition, the reaction was performed in an oil bath at 100° C. for 2 hours. After the reaction was complete, the reaction solution was cooled to room temperature, and insoluble was filtered off. The solution was washed with ethyl acetate (10 mL*2), and the filtrate was concentrated under reduced pressure to remove the solvent. The residue was purified by combi-flash (normal phase silica gel column, 12 g, petroleum ether:ethyl acetate=0-100%), to afford compound TDI01236-3 (240 mg, grey solid, yield: 70.2%).

$^1$H NMR (400 MHz, CDCl$_3$) δ 10.50 (s, 1H), 9.42 (d, J=2.2 Hz, 1H), 9.14 (d, J=5.8 Hz, 1H), 8.73 (s, 1H), 8.39 (q, J=8.5 Hz, 2H), 8.30 (dd, J=5.9, 2.8 Hz, 1H), 8.05 (d, J=8.1 Hz, 1H), 7.93 (d, J=8.2 Hz, 1H), 1.43 (s, 12H). MS m/z (ESI): 377.2 [M+H].

Step 3:

Reg-1-1 (6.00 g, 17.4 mmol) was dissolved in tetrahydrofuran (150 mL), and diisopropylethylamine (8.98 g, 69.6 mmol) and dimethylaminopyridine (212 mg, 1.74 mmol) were added. Di-tert-butyl dicarbonate (4.55 g, 20.9 mmol) was slowly added under stirring, and the reaction was performed at room temperature overnight. Thin lay chromatography (petroleum ether:ethyl acetate=1:1) indicated the reaction was complete. The reaction solution was diluted with water (80 mL), extracted with ethyl acetate (100 mL*2), the organic phase was combined, successively washed with 0.5M HCl (150 mL*2) and saturated brine (200 mL*2), dried over anhydrous sodium sulfate, filtered, and concentrated to afford compound TDI01236-4 (7.0 g, yellow solid, yield: 90.9%).

$^1$H NMR (400 MHz, DMSO-$d_6$) δ 8.63 (d, J=6.0 Hz, 1H), 8.45 (s, 1H), 8.13 (d, J=8.8 Hz, 1H), 8.02 (d, J=6.0 Hz, 1H), 7.82 (d, J=2.0 Hz, 1H), 7.50 (dd, J=8.8, 2.0 Hz, 1H), 1.67 (s, 9H), 1.36 (s, 9H).

Step 4:

TDI01236-3 (102 mg, 0.270 mmol), TDI01236-4 (100 mg, 0.225 mmol), potassium phosphate (95 mg, 0.450 mmol), tetrahydrofuran (3 mL) and water (1.5 mL) were sequentially added to a 10 mL single neck flask, purge with nitrogen was performed for 3 minutes, and chloro(2-dicyclohexylphosphino-2',4',6'-triisopropyl-1,1'-biphenyl)[2-(2'-amino-1,1'-biphenyl)]palladium (II) (3.5 mg, 0.0045 mmol) was cautiously added, and the reaction was performed in an oil bath at 60° C. for 2 hours. LC-MS indicated about 12% of the target product formed. The reaction solution was cooled to room temperature, poured to 10 mL water, and extracted with ethyl acetate (30 mL*2). The combined organic phase was washed with water (10 mL*2) and saturated brine (10 mL*2), dried over anhydrous sodium sulfate, filtered, and concentrated. The residue was purified by combi-flash (normal phase silica gel column, 12 g, petroleum ether:ethyl acetate=0-30%), to give a crude product (80 mg), which was then separated by preparative thin layer chromatography to afford TDI01236-5 (20 mg, yellow solid, yield: 13.5%).

MS m/z (ESI): 660.0 [M+H].

Step 5:

TDI01236-5 (20 mg, 0.03 mmol) and dichloromethane (1 mL) were added to a 10 mL single neck flask, trifluoroacetic acid (0.5 mL) was cautiously added dropwise under stirring, and after the dropwise addition, the reaction was stirred at room temperature for 1 hour. LC-MS indicated the reaction was complete. The solvent was removed by evaporation under reduced pressure, and the residue was purified by preparative HPLC, to afford TDI01236 (2.60 mg, yellow solid, yield: 19.0%)

$^1$H NMR (400 MHz, DMSO-$d_6$) δ 11.53 (s, 1H), 9.84 (d, J=18.4 Hz, 2H), 9.32 (s, 1H), 9.21 (s, 1H), 8.72 (t, J=10 Hz, 2H), 8.47 (d, J=5.9 Hz, 1H), 8.39 (s, 1H), 8.33-8.22 (m, 3H), 8.19 (s, 1H), 7.64 (s, 1H), 6.80 (d, J=5.8 Hz, 1H). MS m/z (ESI): 460.3 [M+H].

Example 4: Preparation of 6-(3-((1H-indazol-5-yl)amino)pyrrolidin-1-yl)-N-(pyridazin-4-yl)-1H-indole-2-carboxamide (TDI01209)

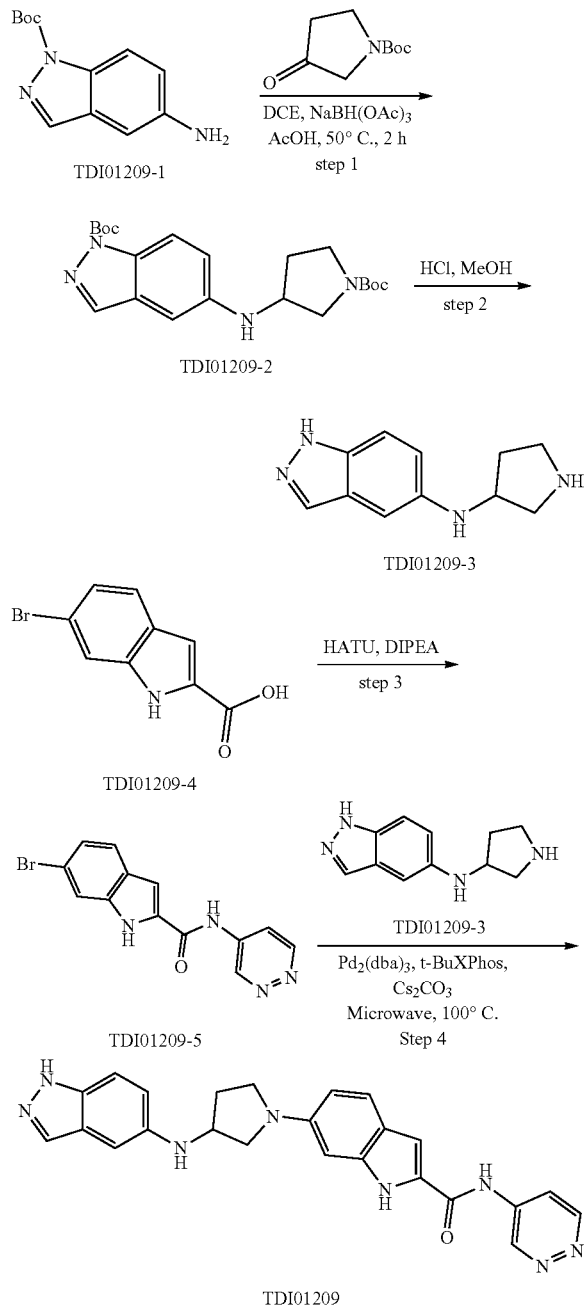

Step 1:

Compound TDI01209-1 (1.0 g, 4.3 mmol), tert-butyl 3-oxopyrrolidine-1-carboxylate (800 mg, 4.3 mmol), 1,2-dichloroethane (30 mL) and glacial acetic acid (8 drops) were added to a 50 mL single neck flask, and the reaction was performed at room temperature (15~25° C.) for 1.5 h. Sodium triacetoxyborohyride (2.73 g, 12.9 mmol) was then added, and the reaction was performed at 50° C. for 2 h. The reaction solution was added with 40 mL water, and extracted with dichloromethane (15 mL*2). The organic phase was combined, washed with saturated brine, dried over anhydrous sodium sulfate, and purified by column chromatography (petroleum ether:ethyl acetate=10:1-7:1) to afford TDI01209-2 (1.44 g, light yellow solid, yield: 83.7%).

$^1$H NMR (400 MHz, CDCl$_3$) δ 8.04-7.94 (m, 2H), 6.88 (dd, J=8.9, 2.1 Hz, 1H), 6.78 (d, J=1.9 Hz, 1H), 3.47 (s, 4H), 2.22 (s, 1H), 1.95 (d, J=9.0 Hz, 1H), 1.71 (s, 9H), 1.46 (s, 10H), 1.26 (t, J=7.1 Hz, 1H). MS m/z (ESI): 403.2 [M+H].

Step 2:

Compound TDI01209-2 (1.44 g, 3.58 mmol) and 30 mL hydrochloride methanol solution (3 mol/L) were added to a 50 mL single neck flask, and the reaction was warmed to 50° C., and allowed to proceed for 1 h. The reaction solution was concentrated under reduced pressure to remove methanol, followed by addition of methanol (20 mL), and sodium methoxide solid was added until the pH is basic. The reaction solution was filtered to collect filtrate, which was then evaporated to dryness to afford compound TDI01209-3 (1.14 g, grey solid, crude product).

$^1$H NMR (400 MHz, DMSO-d$_6$) δ 9.70 (s, 1H), 9.48 (s, 1H), 8.15 (s, 1H), 7.76 (s, 1H), 7.65 (d, J=8.9 Hz, 1H), 7.43 (d, J=8.5 Hz, 1H), 3.48 (ddd, J=19.5, 11.2, 5.2 Hz, 3H), 3.24 (dd, J=12.1, 6.2 Hz, 1H), 3.08-3.02 (m, 1H), 2.25-2.14 (m, 2H), 1.20 (t, J=7.3 Hz, 2H). MS m/z (ESI): 203.2 [M+H].

Step 3:

Compound TDI01209-4 (1 g, 4.167 mmol) and 4-aminopyridazine (475 mg, 4.999 mmol) were dissolved in N,N-dimethylformamide (40 mL), HATU (1.586 g, 4.167 mmol) and diisopropylethylamine (1.612 g, 12.501 mmol) were added, and the reaction was performed at room temperature for 16 h. After completion of the reaction, water (50 mL) was added, and a large amount of solid precipitated, and was filtered after being stirred for 30 min to afford compound TDI01209-5 (1.17 g, yellow solid, yield: 88.9%). MS m/z (ESI): 316.9 [M+H].

Step 4:

Compound TDI01209-5 (250 mg, 0.788 mmol), TDI01209-3 (175 mg, 0.867 mmol), Pd$_2$(dba)$_3$ (75 mg, 0.0788 mmol), t-BuXPhos (67 mg, 0.1576 mmol), cesium carbonate (770 mg, 2.364 mmol) and tert-butanol (10 mL) were added to a microwave tube, and the reaction was performed under microwave radiation at 110° C. for 2.5 h. The reaction solution was dissolved in methanol (20 mL), and concentrated to dryness after insoluble materials were filtered off. The residue was purified by high-performance liquid chromatography to afford TDI01209 (12.66 mg, yellow solid, yield: 3.7%).

$^1$H NMR (400 MHz, DMSO-d$_6$) δ 12.07 (s, 1H), 11.00 (s, 1H), 9.60 (d, J=2.1 Hz, 1H), 9.15 (d, J=6.0 Hz, 1H), 8.93 (s, 2H), 8.22 (dd, J=6.0, 2.7 Hz, 1H), 8.13 (s, 1H), 7.92 (d, J=8.6 Hz, 1H), 7.77 (s, 1H), 7.70 (d, J=9.0 Hz, 1H), 7.64 (d, J=1.3 Hz, 1H), 7.53 (dd, J=8.6, 1.8 Hz, 1H), 6.98 (dd, J=9.0, 2.0 Hz, 1H), 6.86 (d, J=1.8 Hz, 1H), 4.15 (m, 1H), 3.48 (m, 1H), 3.33 (m, 2H), 3.12 (m, 1H), 2.26 (dd, J=14.0, 7.7 Hz, 1H), 1.95 (m, 1H). MS m/z (ESI): 439.1 [M+H].

Example 5: Preparation of 6-((4-(1H-pyrazol-4-yl) phenyl)amino)-N-(pyridazin-4-yl)-1H-indole-2-carboxamide (TDI01243)

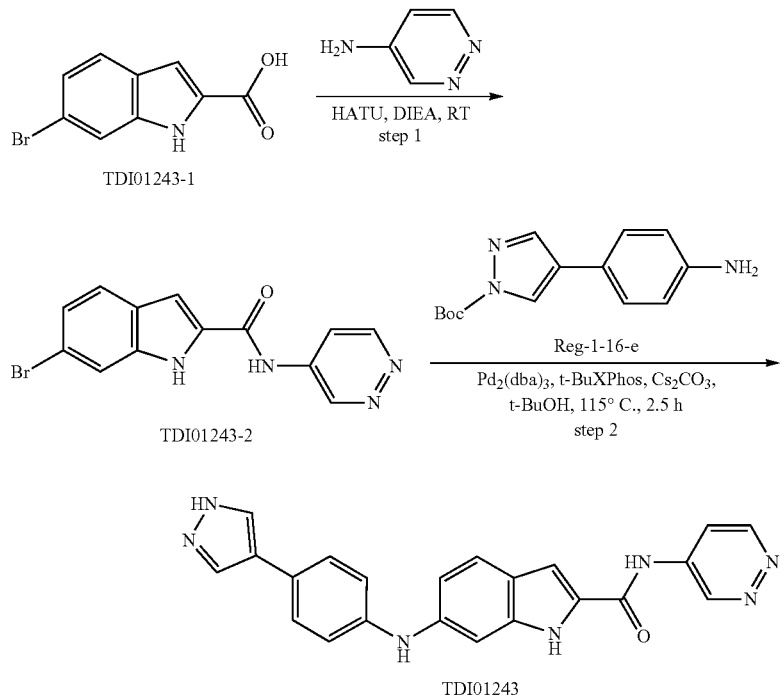

Step 1:

TDI01243-1 (1.0 g, 4.17 mmol) and N,N-dimethylformamide (10 mL) were successively added to a 50 mL single neck flask, HATU (2.38 g, 5.0 mmol) and DIEA (1.72 mL, 10.43 mmol) were cautiously added under stirring, and the reaction was performed in an oil bath at 50° C. for 1 h. After the reaction was complete, the reaction solution was slowly poured into water (20 mL) under stirring. A large amount of solid precipitated, and was filtered after being stirred for 30 min. The solid was washed with water as well as a mixed solvent of petroleum ether and ethyl acetate (v/v=20/1) for several times, to afford TDI01243-2 (1.26 g, grey-yellow solid, yield: 95.5%).

$^1$H NMR (400 MHz, DMSO-$d_6$) δ 12.08 (s, 1H), 10.83 (s, 1H), 9.56 (s, 1H), 9.10 (d, J=5.9 Hz, 1H), 8.12 (dd, J=5.5, 2.2 Hz, 1H), 7.73 (d, J=8.5 Hz, 1H), 7.66 (s, 1H), 7.54 (s, 1H), 7.25 (d, J=8.5 Hz, 1H). MS m/z (ESI): 317.0 [M+H].

Step 2:

Compound TDI01243-2 (190.3 mg, 0.6 mmol), Reg-1-16-e (130 mg, 0.5 mmol), Pd$_2$(dba)$_3$ (50 mg, 0.05 mmol), t-BuXPhos (106 mg, 0.25 mmol), cesium carbonate (325.8 mg, 1 mmol) and 10 mL tert-butanol were added to a 25 mL microwave tube, purge with argon was performed for 4 times, and the reaction was performed under microwave radiation at 115° C. for 2.5 h. LC-MS assay indicated the reaction was complete. The reaction solution was filtered, and concentrated under reduced pressure. The obtained solid was rinsed with 30 mL water and 30 mL dichloromethane to give 0.3 g solid, which was purified by preparative chromatography to afford TDI01243 (6.90 mg, dark brown solid, yield: 1.7%).

$^1$H NMR (400 MHz, DMSO-$d_6$) δ 11.51 (s, 1H), 10.64 (s, 1H), 9.56 (s, 1H), 9.06 (d, J=5.9 Hz, 1H), 8.28 (s, 1H), 8.12 (d, J=3.3 Hz, 1H), 7.96 (s, 2H), 7.57 (d, J=8.5 Hz, 1H), 7.50 (d, J=8.3 Hz, 2H), 7.45 (s, 1H), 7.17 (s, 1H), 7.13 (d, J=8.4 Hz, 2H), 6.89 (d, J=8.9 Hz, 1H), 6.57 (s, 1H). MS m/z (ESI): 396.1 [M+H].

Example 6: Preparation of 6-(2-((1H-indazol-6-yl) amino)pyrimidin-4-yl)-N-(pyridazin-4-yl)-1H-indole-2-carboxamide (TDI01249)

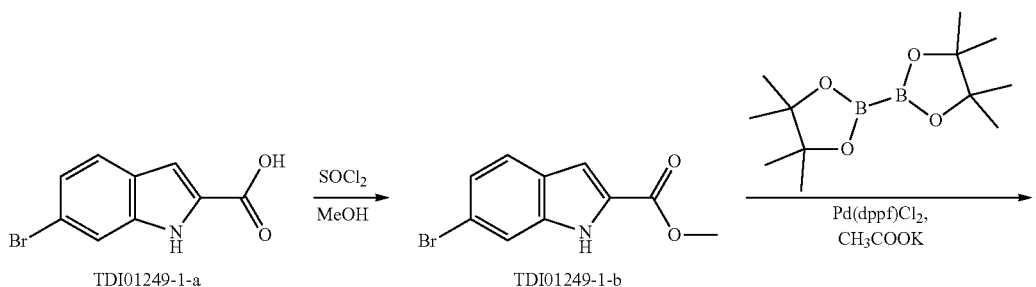

-continued
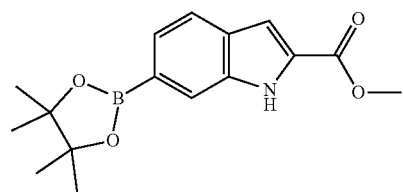
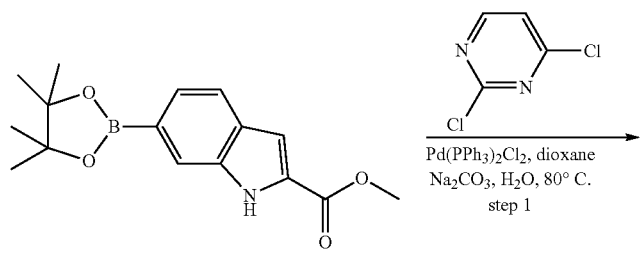
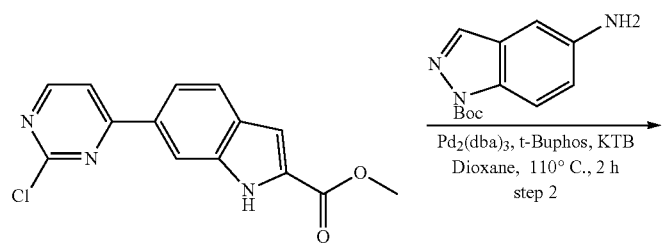
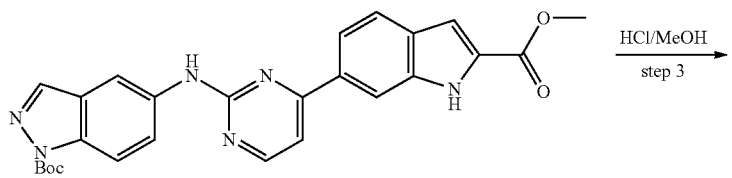
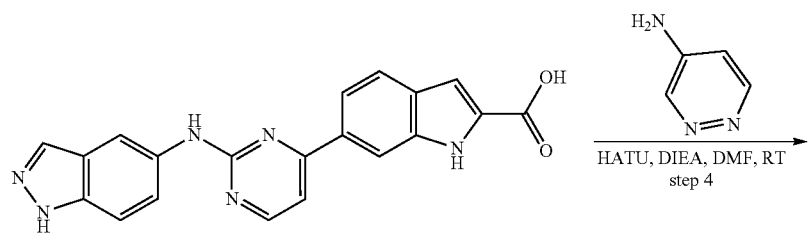
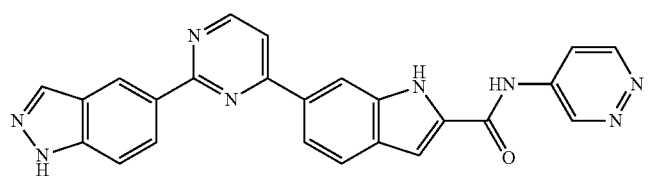

Preparation of TDI01249-1:

TDI01249-1-a (2 g, 8.33 mmol) and methanol (20 mL) were added to a 100 mL flask, thionyl chloride (1.98 g, 16.66 mmol) was added, and then the reaction was performed at 60° C. for 3 hours. Thin layer chromatography (petroleum ether:ethyl acetate=10:1) indicated the reaction was complete. The reaction solution was concentrated to give a crude product, and the crude product was dissolved in dichloromethane (100 mL). The dichloromethane phase was washed with a saturated aqueous solution of sodium hydrogen carbonate twice (50 ml for each time). The dichloromethane phase was then washed with saturated brine, dried over anhydrous sodium sulfate, filtered, and concentrated to obtain TDI01249-1-b (2.149 g, brown solid, yield: 100%).

$^1$H NMR (400 MHz, CDCl$_3$) δ 7.59 (s, 1H), 7.54 (d, J=8.5 Hz, 1H), 7.25 (d, J=8.6 Hz, 1H), 7.18 (s, 1H), 3.96 (s, 3H).

TDI01249-1-b (2 g, 7.87 mmol) and bis(pinacolato)diboron (3.0 g, 11.81 mmol) were dissolved in 1,4-dioxane (20 mL), potassium acetate (2.32 g, 23.61 mmol) and Pd(dppf)Cl$_2$ (130 mg, 0.157 mmol) were added, purge with argon was performed for 3 times, and the reaction was placed in an oil bath at 80° C. overnight. Thin layer chromatography (petroleum ether:ethyl acetate=20:1) indicated the reaction was complete. The reaction solution was cooled to room temperature, concentrated under reduced pressure, and the residue was separated and purified by column chromatography (petroleum ether:ethyl acetate=100:1 to 5:1) to afford TDI01249-1 (2.0 g, white solid, yield: 84.37%).

$^1$H NMR (400 MHz, CDCl$_3$) δ 9.08-8.93 (m, 1H), 7.97-7.86 (m, 1H), 7.69 (d, J=8.1 Hz, 1H), 7.61-7.52 (m, 1H), 7.21 (dd, J=2.1, 1.0 Hz, 1H), 3.95 (s, 3H), 1.37 (s, 12H). MS m/z (ESI): 302.2 [M+H].

Step 1:

Compound TDI01249-1 (2 g, 6.64 mmol), 2,4-dichloropyrimidine (1.08 g, 7.30 mmol), Pd(PPh$_3$)$_2$Cl$_2$ (47 mg, 0.07 mmol), sodium carbonate (1.40 g, 13.28 mmol), 60 mL dioxane and 15 mL water were added to a 250 mL single neck flask, purge with argon was performed for 4 times, and the reaction was warmed to 105° C., and allowed to proceed for 3 h. LC-MS indicated the reaction was complete. The reaction solution was cooled followed by concentration under reduced pressure to remove dioxane, 100 mL water was added, and the solution was stirred at room temperature for 1 h. The reaction mixture was filtered to give a yellow solid (2.3 g), which was rinsed with dichloromethane (80 mL*4) to afford TDI01249-2 (0.62 g, yellow solid, yield: 32.6%).

$^1$H NMR (400 MHz, DMSO-d$_6$) δ 12.33 (s, 1H), 8.78 (d, J=5.2 Hz, 1H), 8.34 (s, 1H), 8.13 (d, J=5.3 Hz, 1H), 7.89 (d, J=8.4 Hz, 1H), 7.83 (d, J=8.5 Hz, 1H), 7.24 (s, 1H), 3.91 (s, 3H). MS m/z (ESI): 288.0 [M+H].

Step 2:

Compound TDI01249-2 (400 mg, 1.39 mmol), tert-butyl 5-amino-1H-indazole-1-carboxylate (200 mg, 0.86 mmol), Pd$_2$(dba)$_3$ (85.6 mg, 0.09 mmol), 2-di-tert-butylphosphino-2',4',6'-triisopropyl-biphenyl (182.4 mg, 0.43 mmol), potassium tert-butoxide (193 mg, 1.72 mmol) and 80 mL dioxane were added to a 250 mL single neck flask, purge with argon was performed for 4 times, and the reaction was warmed to 110° C., and allowed to proceed for 3 h. 20 mg Pd$_2$(dba)$_3$, 40 mg 2-di-tert-butylphosphino-2',4',6'-triisopropyl-biphenyl and 50 mg potassium tert-butoxide were supplemented, and the reaction was continued for 1 h. LC-MS indicated the reaction was complete. The reaction solution was concentrated under reduced pressure to remove dioxane, 80 mL ethyl acetate was added, and filtered to obtain the filtrate, which was purified to afford TDI01249-3 (100 mg, yellow solid, yield: 24%).

$^1$H NMR (400 MHz, DMSO-d$_6$) δ 12.31 (s, 1H), 9.92 (s, 1H), 8.58 (d, J=5.2 Hz, 1H), 8.55 (d, J=1.5 Hz, 1H), 8.46 (s, 1H), 8.35 (s, 1H), 8.03 (s, 1H), 7.94 (dd, J=9.2, 1.8 Hz, 1H), 7.91-7.88 (m, 1H), 7.84 (s, 1H), 7.45 (d, J=5.3 Hz, 1H), 7.25 (d, J=1.2 Hz, 1H), 3.92 (s, 3H), 1.67 (s, 9H). MS m/z (ESI): 485.1 [M+H].

Step 3:

Compound TDI01249-3 (100 mg, 0.135 mmol) and 2 mol/L hydrochloric acid/methanol (5 mL) were added to a 100 mL single neck flask. The reaction was warmed to 60° C., and allowed to proceed for 1.5 h. LC-MS indicated the reaction was complete. The reaction solution was cooled to room temperature, 10 mL 2 mol/L aqueous solution of sodium hydroxide was added, and the reaction was warmed to 60° C., and allowed to proceed for 0.5 h. LC-MS indicated the reaction was complete. The reaction solution was cooled to room temperature, and the pH was adjusted to above 12 with concentrated hydrochloric acid. Methanol was removed through concentration under reduced pressure, 20 mL water was then added, and the reaction was filtered after stirring, the solid obtained after filtration was dried to afford compound TDI01249-4 (50 mg, yellow solid, yield: 23.8%).

$^1$H NMR (400 MHz, DMSO-d$_6$) δ 12.22 (s, 1H), 9.82 (s, 1H), 8.57 (d, J=5.4 Hz, 1H), 8.39 (s, 2H), 8.15 (s, 1H), 7.92 (d, J=1.1 Hz, 1H), 7.87 (s, 1H), 7.72 (dd, J=10.6, 9.0 Hz, 1H), 7.60 (s, 1H), 7.46 (d, J=5.4 Hz, 1H), 7.22 (s, 1H). MS m/z (ESI): 371.0 [M+H].

Step 4:

Compound TDI01249-4 (50 mg, 0.135 mmol), pyridazin-4-amine (15.4 mg, 0.162 mmol), HATU (61.7 mg, 0.162 mmol), DIEA (70 mg, 0.54 mmol) and 4 mL N,N-dimethylformamide were added to a 25 mL single neck flask, and the reaction was performed at room temperature for 0.5 h. LC-MS indicated the reaction was complete. The reaction solution was cooled to room temperature, and added to 20 mL water to give a solid, which was dried and purified by preparative chromatography to afford TDI01249 (14.38 mg, yellow solid, yield: 23.8%).

$^1$H NMR (400 MHz, DMSO-d$_6$) δ 12.89 (s, 1H), 12.33 (s, 1H), 10.94 (s, 1H), 9.62 (d, J=17.6 Hz, $^2$H), 9.14 (d, J=5.8 Hz, 1H), 8.54 (d, J=5.2 Hz, 1H), 8.36 (d, J=5.8 Hz, 2H), 8.18 (d, J=3.2 Hz, 1H), 8.08 (s, 1H), 7.90 (s, 2H), 7.69 (s, 1H), 7.61 (s, 1H), 7.51 (d, J=8.8 Hz, 1H), 7.38 (d, J=5.2 Hz, 1H). MS m/z (ESI): 448.0 [M+H].

Example 7: preparation of 6-(2-((1H-indazol-5-yl)amino)-6-methylpyrimidin-4-yl)-N-(pyridazin-4-yl)-1H-indole-2-carboxamide (TDI01261)

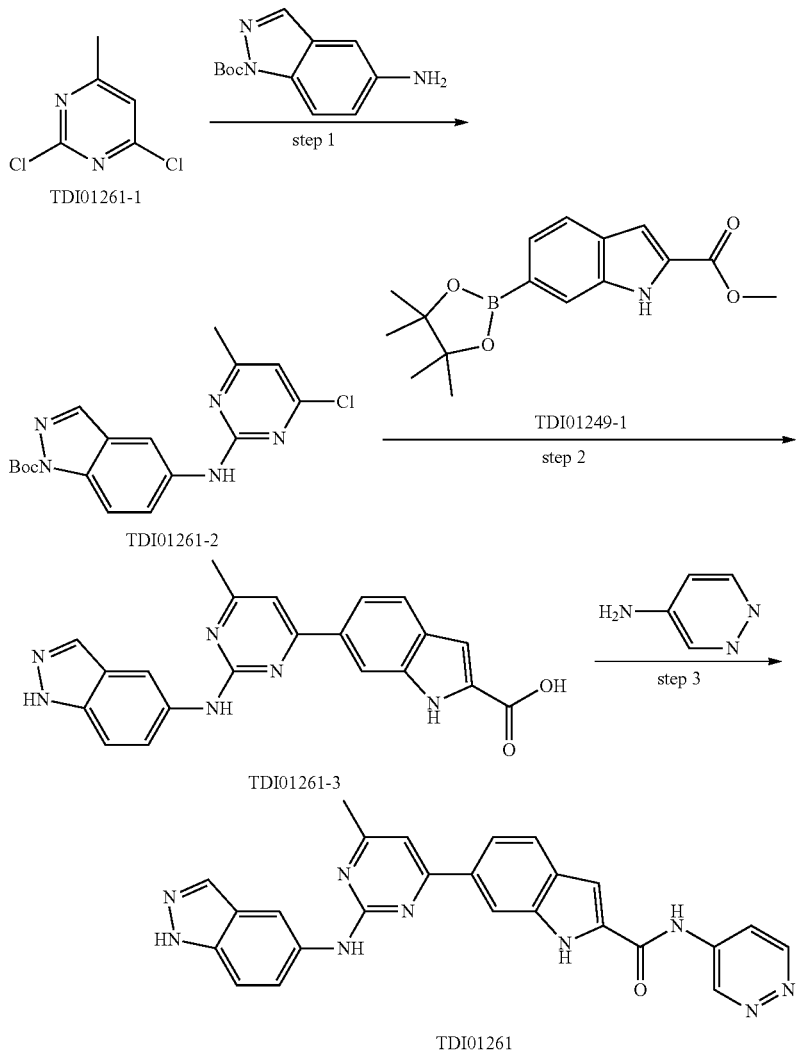

Step 1:
Compound TDI01261-1 (2.0 g, 8.58 mmol) and tert-butyl 5-amino-1H-indazole-1-carboxylate (1.68 g, 10.296 mmol) were dissolved in N,N-dimethylformamide (150 mL), diisopropylethylamine (4.427 g, 34.32 mmol) was added, and the reaction was slowly warmed to 100° C., and allowed to proceed at this temperature for 16 hours. Thin layer chromatography (petroleum ether:ethyl acetate=2:1) indicated the reaction was complete. The reaction solution was slowly poured into water (900 ml), stirred for 30 minutes followed by filtration. The residue was separated and purified by column chromatography (petroleum ether:ethyl acetate=1:0 to 1:1), to afford compound TDI01261-2 (300 mg, light yellow solid).

$^1$H NMR (400 MHz, DMSO-d$_6$) δ 10.18 (s, 1H), 8.40 (s, 1H), 8.37 (s, 1H), 7.98 (d, J=9.2 Hz, 1H), 7.77 (dd, J=9.2, 1.6 Hz, 1H), 6.92 (s, 1H), 2.40 (s, 3H), 1.65 (s, 8H). MS m/z (ESI): 360.0 [M+H].

Step 2:
Compound TDI01261-2 (300 mg, 0.836 mmol) and TDI01249-1 (299 mg, 1.672 mmol) were dissolved in a mixed solution of ethanol:water (10:1) (30 mL), sodium carbonate (177 mg, 1.672 mmol) and Pd(PPh$_3$)$_2$Cl$_2$ (59 mg, 0.0836 mmol) were added, purge with argon was performed for 3 times, and the reaction was perform in an oil bath at 110° C. overnight. LC-MS indicated the reaction was complete. The reaction solution was cooled to room temperature, filtered, and concentrated under reduced pressure. The residue was dissolved in dichloromethane (500 mL), washed with water (500 ml*3), the pH of the aqueous phase was adjusted to 2 with concentrated hydrochloric acid (3 mL), and compound TDI01261-3 (110 mg, yellow solid, yield: 32.7%) was obtained by filtration.

$^1$H NMR (400 MHz, DMSO-d$_6$) δ 12.20 (s, 1H), 9.90 (s, 1H), 8.33 (d, J=5.6 Hz, 2H), 8.12 (s, 1H), 7.87 (d, J=8.4 Hz, 1H), 7.81 (d, J=8.4 Hz, 1H), 7.71-7.66 (m, 1H), 7.56 (d, J=8.8 Hz, 1H), 7.42 (s, 1H), 7.17 (s, 1H), 2.09 (s, 3H). MS m/z (ESI): 385.1 [M+H].

Step 3:
Compound TDI01261-3 (100 mg, 0.26 mmol) and pyridazin-4-amine (30 mg, 0.313 mmol) were dissolved in N,N-dimethylformamide (10 mL), HATU (120 mg, 0.313 mmol) and diisopropylethylamine (130 mg, 1.04 mmol) were added, and the reaction was performed at room temperature overnight. LC-MS indicated the reaction was complete. The reaction solution was cooled to room temperature, filtered, concentrated under reduced pressure, and the residue was purified by liquid chromatography to afford compound TDI01261 (11.02 mg, yellow solid, yield: 10.2%).

$^1$H NMR (400 MHz, DMSO-d$_6$) δ 13.07-12.76 (m, 1H), 12.35 (s, 1H), 11.07 (s, 1H), 9.61 (s, 2H), 9.18 (d, J=5.6 Hz, 1H), 8.39 (d, J=20.0 Hz, 2H), 8.26 (d, J=3.6 Hz, 1H), 8.09 (s, 1H), 7.90 (s, 2H), 7.72 (d, J=8.8 Hz, 1H), 7.63 (s, 1H), 7.51 (d, J=8.8 Hz, 1H), 7.32 (s, 1H), 2.46 (s, 3H). MS m/z (ESI): 462.1 [M+H].

Example 8: Preparation of 6-(3-((1H-indazol-5-yl)amino)piperidin-1-yl)-N-(pyridazin-4-yl)-1H-indole-2-carboxamide (TDI01234)

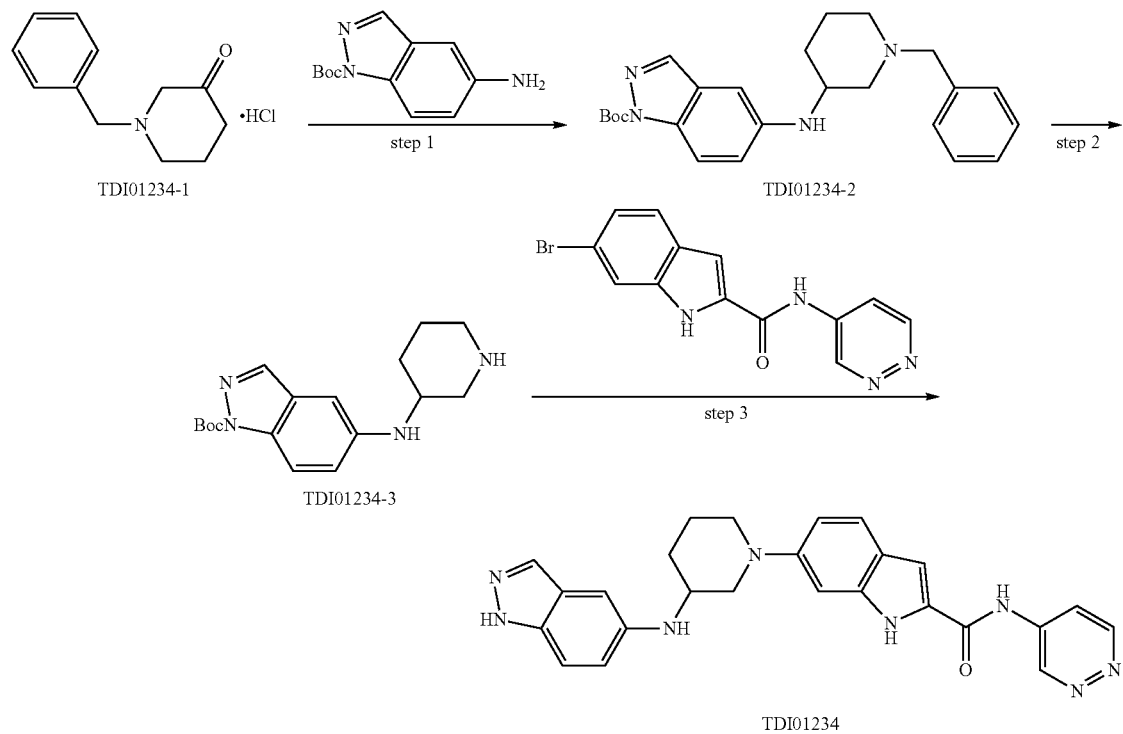

Step 1:
Compound TDI01234-1 (2.0 g, 8.86 mmol) was dissolved in 1,2-dichloroethane (150 mL), triethylamine (746 mg, 7.38 mmol) was added, and the reaction solution was warmed to 30° C. and stirred for 1.5 hours. Tert-butyl 5-amino-1H-indazole-1-carboxylate (1.72 g, 7.38 mmol) and acetic acid (443 mg, 7.38 mmol) were then added, after stir of 0.5 hour, sodium triacetoxyborohydride (4.69 g, 22.14 mmol) was added, and the reaction was maintained at 30° C. overnight. Thin layer chromatography (dichloromethane:methanol=60:1) assay indicated the reaction was complete. The reaction solution was dissolved in dichloromethane (1500 ml), successively washed with water (150 ml*2) and saturated brine (150 ml), and the organic phase was dried over anhydrous sodium sulfate, concentrated, and purified by column chromatography (dichloromethane:methanol=1:0 to 60:1), to afford compound TDI01234-2 (1.0 g, brown yellow solid).

$^1$H NMR (400 MHz, CDCl$_3$) δ 7.96 (s, 1H), 7.93 (d, J=8.8 Hz, 1H), 7.30 (dd, J=13.6, 5.2 Hz, 4H), 7.24 (dd, J=5.2, 3.2 Hz, 1H), 6.88 (dd, J=8.8, 2.1 Hz, 1H), 6.75 (d, J=1.6 Hz, 1H), 4.16 (s, 1H), 3.66-3.44 (m, 3H), 2.57 (d, J=120.0 Hz, 4H), 1.70 (s, 11H), 1.59 (s, 2H). MS m/z (ESI): 407.3 [M+H].

Step 2:
Compound TDI01234-2 (0.6 g, 1.478 mmol) was dissolved in methanol (50 mL), palladium/carbon (100 mg) was added, purge with hydrogen was performed for 3 times, and the reaction was placed in an oil bath at 35° C. overnight. LC-MS indicated the reaction was complete. The reaction solution was cooled to room temperature, filtered, concentrated under reduced pressure, and purified by column chromatography (dichloromethane:methanol=1:0 to 10:1), to afford compound TDI01234-3 (200 mg, off-white solid).

$^1$H NMR (400 MHz, CDCl$_3$) δ 7.98 (s, 1H), 7.93 (d, J=8.8 Hz, 1H), 6.94-6.88 (m, 1H), 6.83-6.78 (m, 1H), 4.09 (s, 1H), 3.56 (s, 1H), 3.33-3.19 (m, 1H), 2.99-2.90 (m, 1H), 2.81 (d, J=8.0 Hz, 1H), 2.68 (dd, J=11.2, 7.1 Hz, 1H), 1.84 (dd, J=13.6, 6.7 Hz, 2H), 1.71 (s, 9H), 1.59 (dd, J=19.2, 13.9 Hz, 3H). MS m/z (ESI): 317.3 [M+H].

Step 3:
Compound TDI01234-3 (400 mg, 1.27 mmol) and TDI01234-2 (400 mg, 1.27 mmol) were dissolved in dimethyl sulfoxide (10 mL). Pd$_2$(dba)$_3$ (120 mg, 0.127 mmol), t-BuXPhos (823 mg, 2.53 mmol) and cesium carbonate (268.4 mg, 0.63 mmol) were then added, and the reaction was performed under microwave radiation and the protection of argon for 2 hours. LC-MS indicated the reaction was complete. The reaction solution was cooled to room temperature, slowly added to water (80 ml), and filtered. The filter cake was rinsed with dichloromethane:ethyl acetate=1:1 (20 ml*2), and the residue was purified by liquid chromatography to afford compound TDI01234 (2.58 mg, yellow solid).

¹H NMR (400 MHz, DMSO-d₆) δ 12.06 (s, 1H), 11.05 (s, 1H), 10.20 (s, 1H), 9.61 (s, 1H), 9.10 (s, 2H), 8.95 (s, 1H), 8.18 (s, 1H), 8.07 (s, 1H), 7.87 (d, J=8.4 Hz, 1H), 7.76 (s, 1H), 7.66 (d, J=9.6 Hz, 1H), 7.51 (d, J=8.8 Hz, 1H), 6.98 (d, J=8.4 Hz, 1H), 6.89 (s, 1H), 3.24 (s, 1H), 2.87 (s, 1H), 1.95 (d, J=46.4 Hz, 3H), 1.74 (s, 2H), 1.52 (s, 2H). MS m/z (ESI): 451.3 [M–H].

Example 9: Preparation of 6-((3-(1H-pyrazol-4-yl)phenyl)amino)-N-(pyridazin-4-yl)-1H-indole-2-carboxamide (TDI01245)

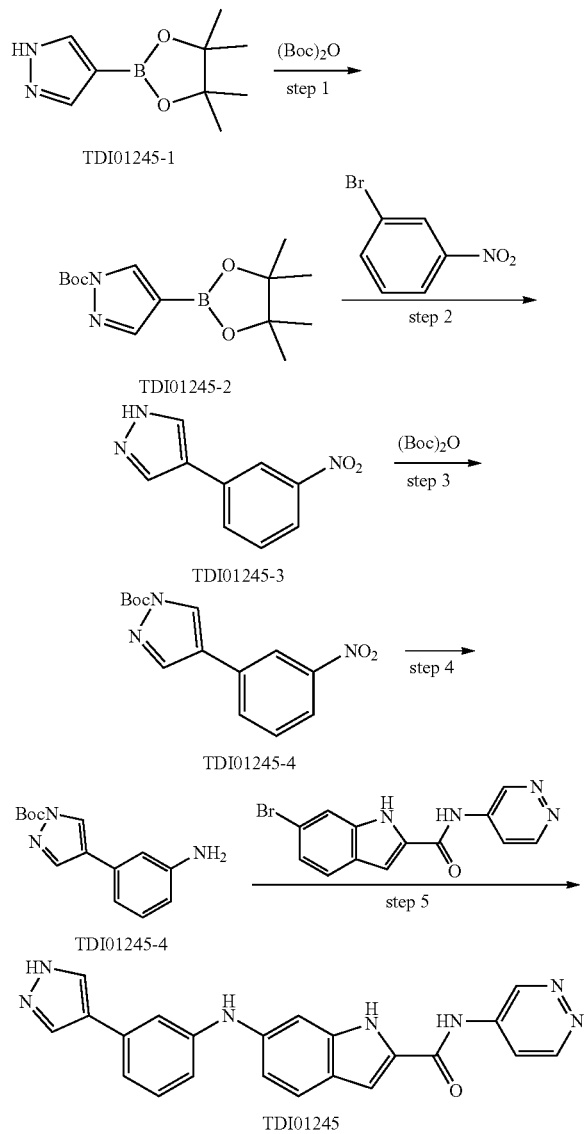

Step 1:

Compound TDI01245-1 (5.0 g, 25.77 mmol) was dissolved in dichloromethane (100 ml), diisopropylethylamine (13.30 g, 100.08 mmol) and 4-dimethylaminopyridine (1.57 g, 12.88 mmol) were added, and di-tert-butyl dicarbonate (11.24 g, 51.55 mmol) was added after the reaction was stirred at room temperature for 10 minutes. Thin layer chromatography (petroleum ether:ethyl acetate=3:1) indicated the reaction was complete. The reaction solution was dissolved in dichloromethane (400 ml), and successively washed with water (500 ml*2) and saturated brine (500 ml). The organic phase was dried over anhydrous sodium sulfate, concentrated, and purified by column chromatography (petroleum ether:ethyl acetate=1:0 to 10:1), to afford compound TDI01245-2 (4.58 g, white solid).

¹H NMR (400 MHz, CDCl₃) δ 8.42-8.34 (m, 1H), 7.93 (s, 1H), 1.65 (s, 9H), 1.34 (s, 12H).

Step 2:

Compound TDI01245-2 (5.0 g, 17.01 mmol) and 1-bromo-3-nitrobenzene (2.863 g, 14.17 mmol) were dissolved in a mixed solution of 1,4-dioxane/water (8:1) (500 mL), potassium carbonate (3.91 g, 28.34 mmol) and Pd(dppf)Cl₂ (497 mg, 0.708 mmol) were added, purge with argon was performed for 3 times, and the reaction was placed in an oil bath at 110° C. overnight. LC-MS indicated the reaction was complete. The reaction solution was cooled to room temperature, filtered, and concentrated under reduced pressure. The residue was dissolved in dichloromethane (500 mL), and successively washed with water (500 ml*2) and saturated brine (500 ml). The organic phase was dried over anhydrous sodium sulfate, concentrated, and purified by column chromatography (dichloromethane:methanol=1:0 to 50:1) to afford compound TDI01245-3 (850 mg, yellow solid).

¹H NMR (400 MHz, DMSO-d₆) δ 13.14 (s, 1H), 8.44 (d, J=11.2 Hz, 2H), 8.20-8.06 (m, 2H), 8.03 (dd, J=8.0, 1.6 Hz, 1H), 7.65 (t, J=8.0 Hz, 1H). MS m/z (ESI): 190.3 [M+H].

Step 3:

Compound TDI01245-3 (850 mg, 4.497 mmol) was dissolved in dichloromethane (100 ml), diisopropylethylamine (2.32 g, 17.989 mmol) and 4-dimethylaminopyridine (274 mg, 2.249 mmol) were added, and di-tert-butyl dicarbonate (1.96 g, 8.995 mmol) was added after the reaction was stirred at room temperature for 10 minutes. Thin layer chromatography (dichloromethane) indicated the reaction was complete. The reaction solution was dissolved in dichloromethane (400 ml), and successively washed with water (250 ml*2) and saturated brine (250 ml). The organic phase was dried over anhydrous sodium sulfate, concentrated, and purified by column chromatography (petroleum ether:dichloromethane=10:1 to 1:1), to afford compound TDI01245-4 (820 mg, white solid).

¹H NMR (400 MHz, CDCl₃) δ 8.43 (s, 1H), 8.38 (t, J=1.6 Hz, 1H), 8.16 (dd, J=8.0, 1.2 Hz, 1H), 7.85 (d, J=7.6 Hz, 1H), 7.59 (t, J=8.0 Hz, 1H), 7.26 (s, 1H), 1.70 (s, 9H).

Step 4:

Compound TDI01245-4 (820 mg, 2.837 mmol) was dissolved in methanol (100 ml), palladium/carbon (100 mg) was added, purge with hydrogen was performed for 3 times, and the reaction was placed in an oil bath at 35° C. overnight. LC-MS indicated the reaction was complete. The reaction solution was cooled to room temperature, filtered, concentrated under reduced pressure, and purified by column chromatography (dichloromethane:methanol=1:0 to 100:1) to afford compound TDI01245-5 (650 mg, off-white solid).

¹H NMR (400 MHz, CDCl₃) δ 8.25 (s, 1H), 7.95 (s, 1H), 7.18 (t, J=7.6 Hz, 1H), 6.92 (d, J=7.6 Hz, 1H), 6.84 (s, 1H), 6.63 (d, J=8.0 Hz, 1H), 3.71 (s, 2H), 1.67 (s, 9H). MS m/z (ESI): 249.0 [M–H].

Step 5:

Compound TDI01245-5 (300 mg, 1.158 mmol) and 6-bromo-N-(pyridazin-4-yl)-1H-indole-2-carboxamide (the preparation method thereof is as described in Example 5) (366 mg, 1.158 mmol) were dissolved in tert-butanol (8 mL). Pd₂(dba)₃ (110 mg, 0.116 mmol), t-BuXPhos (753 mg, 2.316 mmol) and cesium carbonate (245.5 mg, 0.579 mmol) were added, and the reaction was performed under microwave radiation at 115° C. and the protection of argon for 2 hours. LC-MS indicated the reaction was complete. The reaction solution was rotary evaporated to dryness, slurried in dichloromethane (20 ml), and filtered. The residue was purified by liquid chromatography to afford compound TDI01245 (53.25 mg, brownish red solid).

$^1$H NMR (400 MHz, DMSO-$d_6$) δ 11.55 (s, 1H), 10.81 (s, 1H), 9.56 (s, 1H), 9.13 (s, 1H), 8.23 (s, 2H), 7.98 (s, 2H), 7.58 (d, J=8.8 Hz, 1H), 7.47 (s, 1H), 7.37 (s, 1H), 7.25 (s, 2H), 7.09 (d, J=7.6 Hz, 1H), 6.93 (dd, J=21.2, 7.9 Hz, 2H). MS m/z (ESI): 396.2 [M−H].

Example 10: Preparation of 2-(5-(4-((1H-indazol-5-yl)amino)pyrimidin-2-yl)isoindolin-2-yl)-N-(pyridazin-4-yl)acetamide (TDI01238)

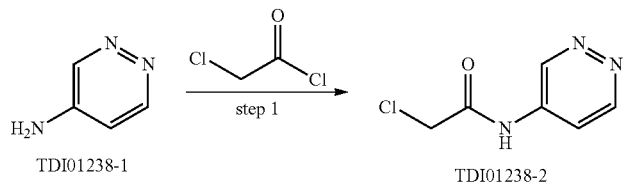

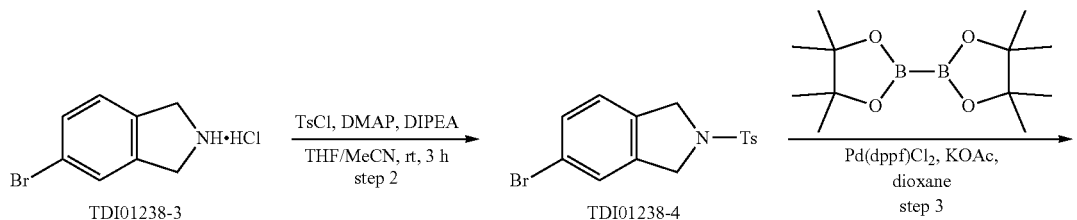

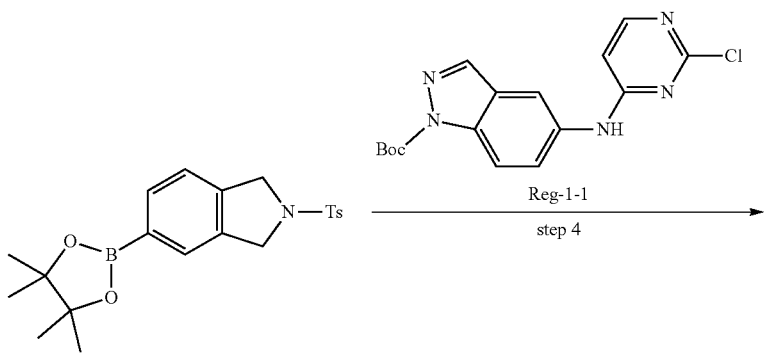

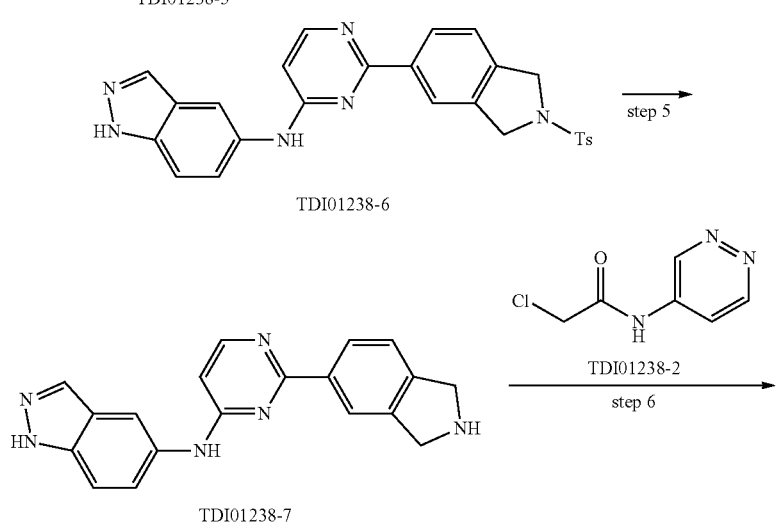

-continued

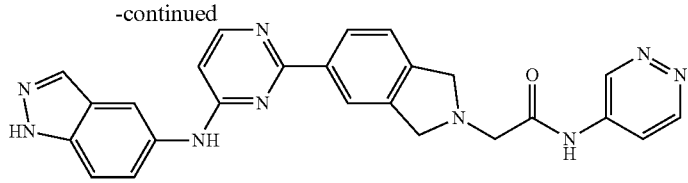

TDI01238

Step 1:

Compound TDI01238-1 (1 g, 10.526 mmol), chloroacetyl chloride (1.3 g, 11.504 mmol) and triethylamine (1.17 g, 11.584 mmol) were dissolved in dichloromethane (10 mL), and the reaction was performed at room temperature for 3 hours. LC-MS indicated the reaction was complete. Water (25 mL) and dichloromethane (30 mL) were added to the reaction solution, and precipitation occurred. The filter cake was obtained after filtration, washed with water and n-hexane, and dried to afford compound TDI01238-2 (950 mg, brown solid, yield: 52.78%).

$^1$H NMR (400 MHz, DMSO-d$_6$) δ 10.97 (s, 1H), 9.30 (dd, 1H), 9.07 (dd, 1H), 7.92 (dd, 1H), 4.37 (s, 2H). MS m/z (ESI): 172.1 [M+H].

Step 2:

Compound TDI01238-3 (500 mg, 2.132 mmol), 4-tosyl chloride (447 mg, 2.345 mmol), 4-dimethylaminopyridine (78 mg, 0.6396 mmol), diisopropylethylamine (825 mg, 6.396 mmol) and tetrahydrofuran/acetonitrile (20/8 mL) were mixed, and reacted at room temperature for 16 h. After the reaction was complete, the reaction solution was concentrated to dryness, and the residue was added with water, followed by extraction with ethyl acetate (20 mL*2). The organic phase was combined, washed with saturated brine, dried over anhydrous sodium sulfate, and then concentrated to dryness. The residue was rinsed with petroleum ether to afford compound TDI01238-4 (700 mg, white solid, yield: 93.58%).

$^1$H NMR (400 MHz, CDCl$_3$) δ 7.76 (d, 2H), 7.33 (dd, 4H), 7.03 (d, 1H), 4.57 (d, 4H), 2.41 (s, 3H). MS m/z (ESI): 352.1 [M+H].

Step 3:

Compound TDI01238-4 (700 mg, 1.988 mmol) and bis(pinacolato)diboron (757 mg, 2.983 mmol) were dissolved in 1,4-dioxane (20 mL), potassium acetate (584 mg, 5.964 mmol) and Pd(dppf)Cl$_2$ (146 mg, 0.199 mmol) were added, purge with argon was performed for 3 times, and the reaction was placed in an oil bath at 105° C., and allowed to proceed for 4 h. After the reaction was complete, the reaction solution was filtered, and the filtrate was concentrated under reduced pressure to dryness. The residue was added with water, and extracted with dichloromethane (20 mL*2). The organic phase was combined, washed with saturated brine, dried over anhydrous sodium sulfate, and then concentrated to dryness. The residue was purified by column chromatography (petroleum ether:ethyl acetate=10:1) to afford compound TDI01238-5 (740 mg, white solid, yield: 93.3%).

$^1$H NMR (400 MHz, CDCl$_3$) δ 7.76 (d, 2H), 7.67 (d, 1H), 7.61 (s, 1H), 7.30 (d, 2H), 7.17 (d, 1H), 4.62 (d, 4H), 2.39 (s, 3H), 1.32 (s, 12H). MS m/z (ESI): 400.2 [M+H].

Step 4:

Compound TDI01238-5 (0.5 g, 1.253 mmol) and Reg-1-1 (288 mg, 0.835 mmol) were dissolved in a mixed solution of ethanol/water (8/1 mL), sodium carbonate (266 mg, 2.505 mmol) and Pd(PPh$_3$)$_2$Cl$_2$ (59 mg, 0.0835 mmol) were added, purge with argon was performed for 3 times, the reaction was placed in an oil bath at 100° C., and allowed to proceed for 2 h. After the reaction was complete, the reaction solution was filtered, and the filtrate was concentrated under reduced pressure to dryness. The residue was added with water, and extracted with ethyl acetate (20 mL*3). The organic phase was combined, washed with saturated brine, dried over anhydrous sodium sulfate, and then concentrated to dryness. The residue was purified by column chromatography (dichloromethane:methanol=30:1-20:1) to afford compound TDI01238-6 (260 mg, yellow oil, yield: 64.68%).

$^1$H NMR (400 MHz, CDCl$_3$) δ 8.30 (dd, 1H), 8.20 (s, 0.5H), 8.09 (d, 1H), 7.77 (dd, 2.5H), 7.68 (m, 1H), 7.55 (dd, 1H), 7.47 (d, 0.5H), 7.32 (m, 5H), 7.17 (d, 0.3H), 7.02 (s, 0.4H), 6.49 (dd, 0.7H), 4.65 (dd, 4H), 2.40 (d, 3H). MS m/z (ESI): 483.3 [M+H].

Step 5:

Compound TDI01238-6 (245 mg, 0.508 mmol) and hydrobromic acid (5 mL) were placed in an oil bath at 95° C., and reacted for 6 h. After the reaction was complete, the reaction solution was concentrated under reduced pressure to dryness, toluene (10 mL) was added to dissolve the residue, and the resulted solution was then concentrated under reduced pressure to dryness, to afford compound TDI01238-7 (150 mg, yellow solid, yield: 90.36%).

$^1$H NMR (400 MHz, DMSO-d$_6$) δ 11.47 (s, 1H), 9.69 (s, 2H), 9.48 (s, 1H), 8.40 (d, 1H), 8.19 (s, 2H), 7.70 (m, 2H), 7.49 (d, 1H), 7.13 (d, 1H), 4.67 (s, 3H), 4.53 (t, 2H). MS m/z (ESI): 329.2 [M+H].

Step 6:

Compound TDI01238-7 (100 mg, 0.244 mmol), TDI01238-2 (37 mg, 0.219 mmol) and N,N-diisopropylethylamine (94 mg, 0.732 mmol) were dissolved in acetonitrile (4 mL), and the reaction was performed in an oil bath at 70° C. for 3 h. After the reaction was complete, insoluble was removed by filtration, the filtrate was evaporated to dryness, and the residue was purified by preparative thin layer chromatography (dichloromethane:methanol=10:1), to give a crude product (50 mg), which was further purified by high-performance liquid chromatography to afford compound TDI01238 (13.17 mg, yellow solid, yield: 11.65%).

$^1$H NMR (400 MHz, DMSO-d$_6$) δ 13.07 (s, 1H), 11.30 (s, 1H), 9.92 (s, 1H), 9.36 (s, 1H), 9.14 (d, 1H), 8.36 (m, 2H), 8.19 (s, 1H), 8.11 (s, 1H), 7.97 (m, 1H), 7.57 (dd, 2H), 6.75 (d, 1H), 4.84 (s, 3H), 4.60 (s, 1H). MS m/z (ESI): 464.3 [M+H].

Example 11: Preparation of 5-(4-((1H-indazol-5-yl)amino)pyrimidin-2-yl)-N-(pyridazin-4-yl)isoindoline-2-carboxamide (TDI01237)

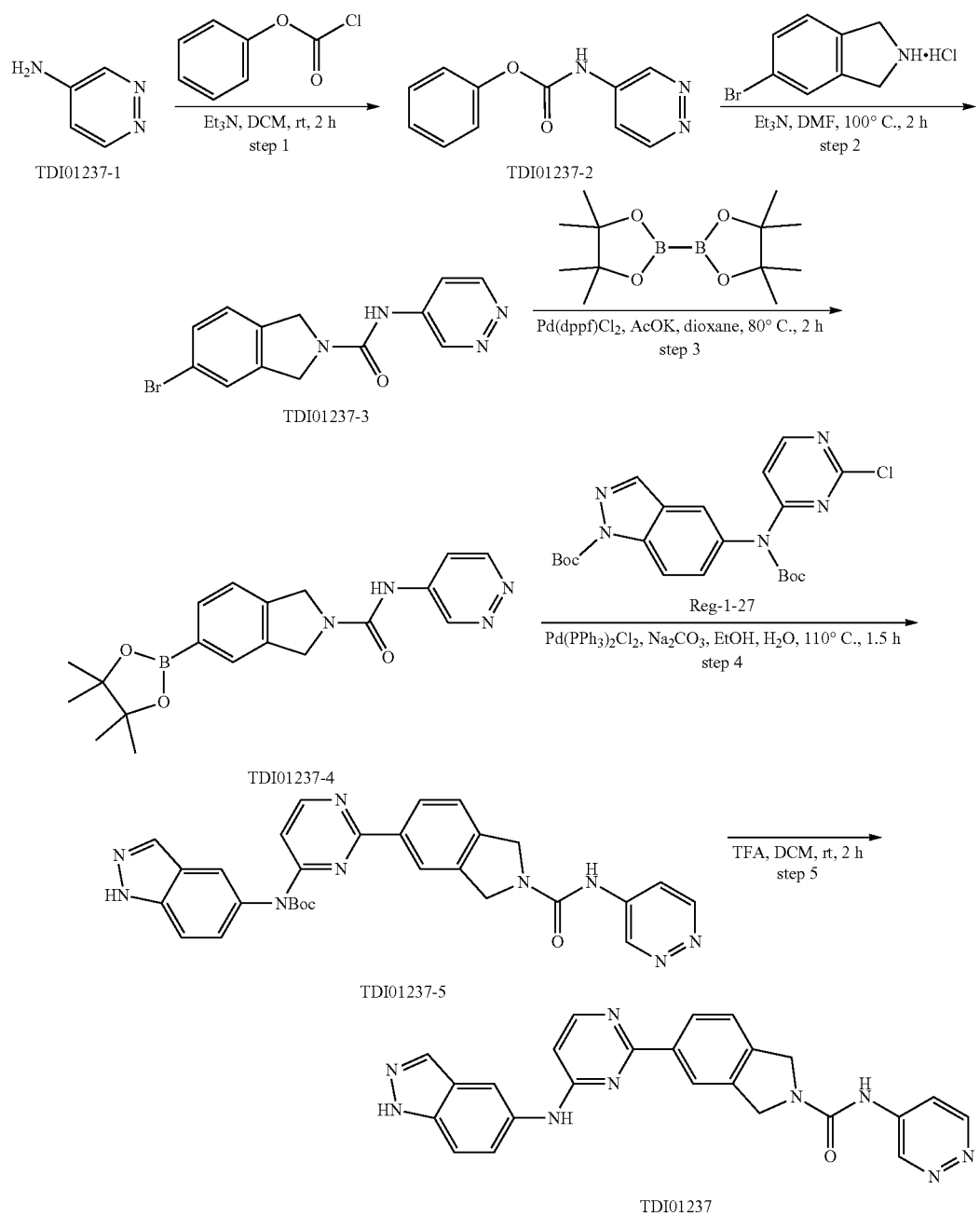

Step 1:
Under ice bath cooling, phenyl chloroformate (1.24 g, 7.89 mmol) was added to a solution of TDI01237-1 (500 mg, 5.27 mmol) and triethylamine (1.06 g, 10.54 mmol) in dichloromethane (10 mL), and the reaction was performed at room temperature for 2 h. LC-MS indicated the reaction was complete. The reaction was quenched by adding water (15 mL), extracted with dichloromethane (30 mL), washed with saturated brine (15 mL), dried, and concentrated to afford TDI01237-2 (600 mg, crude product). MS m/z (ESI): 216.1 [M+H].

Step 2:
Compound TDI01237-2 (410 mg, 1.91 mmol) and 5-bromoisoindoline hydrochloride (895 mg, 3.82 mmol) were dissolved in N,N-dimethylformamide (5 mL), triethylamine (2 mL) was added, and the reaction was performed in an oil bath at 100° C. for 1 h. LC-MS indicated the reaction was complete. Water (15 mL) was slowly added to the reaction solution, and a large amount of solid precipitated. The mixture was stirred for 30 min, filtered, and the solid thus obtained was TDI01237-3 (380 mg, wine red solid, yield: 62.56%). MS m/z (ESI): 319.2 [M+H].

Step 3:
Compound TDI01237-3 (350 mg, 1.09 mmol) and bis(pinacolato)diboron (558 mg, 2.19 mmol) were dissolved in dioxane (12 mL), potassium acetate (323 mg, 3.29 mmol) and Pd(dppf)Cl$_2$ (81 mg, 0.11 mmol) were added, purge with argon was performed for 3 times, the reaction was placed in an oil bath, and allowed to proceed overnight. Thin layer chromatography (dichloromethane/methanol=10:1) indicated the reaction was complete. The reaction solution was cooled to room temperature, concentrated under reduced pressure, and the residue was separated by column chromatography (dichloromethane/methanol=20:1), to afford compound TDI01237-4 (120 mg, yellow solid, yield: 30.08%). MS m/z (ESI): 367.2 [M+H].

Step 4:

Compound TDI01237-4 (100 mg, 0.273 mmol) and Reg-1-27 (80 mg, 0.182 mmol) were dissolved in ethanol/water=5/2 (7 mL), sodium carbonate (58 mg, 0.546 mmol) and Pd(PPh$_3$)$_2$ (13 mg, 0.018 mmol) were added, purge with argon was performed for 3 times, and the reaction was performed under microwave radiation at 110° C. for 1.5 h. LC-MS indicated the reaction was complete. The reaction solution was cooled to room temperature, filtered, and concentrated followed by addition of water (5 mL). The solution was extracted with dichloromethane (15 mL), washed with saturated brine (5 mL), dried over anhydrous sodium sulfate, and concentrated followed by purification by thin layer chromatography (dichloromethane:methanol=10:1) to afford compound TDI01237-5 (30 mg, yellow solid, yield: 30.03%). MS m/z (ESI): 550.3 [M+H].

Step 5:

Trifluoroacetic acid (1 mL) was added to a solution of TDI01237-5 (30 mg, 0.055 mmol) in dichloromethane (3 mL), and the reaction was performed at room temperature for 2 hours. LC-MS indicated the reaction was complete. The reaction solution was cooled to room temperature, concentrated under reduced pressure, and the residue was purified by liquid chromatography to afford compound TDI01237 (2.13 mg, yellow solid, yield: 8.53%).

$^1$H NMR (400 MHz, DMSO-d$_6$) δ 10.09 (s, 1H), 9.79 (s, 1H), 9.46 (d, J=2.3 Hz, 1H), 9.11 (d, J=6.4 Hz, 1H), 8.36 (d, J=6.2 Hz, 1H), 8.29 (d, J=8.1 Hz, 2H), 8.19 (dd, J=7.4, 4.8 Hz, 2H), 8.12 (s, 1H), 7.62-7.53 (m, 3H), 6.76 (d, J=6.2 Hz, 1H), 4.95 (s, 4H). MS m/z (ESI): 450.2 [M+H].

Example 12: Preparation of 2-(6-(4-((1H-indazol-5-yl)amino)pyrimidin-2-yl)-1-oxoisoindolin-2-yl)-N-(pyridazin-4-yl)acetamide (TDI01239)

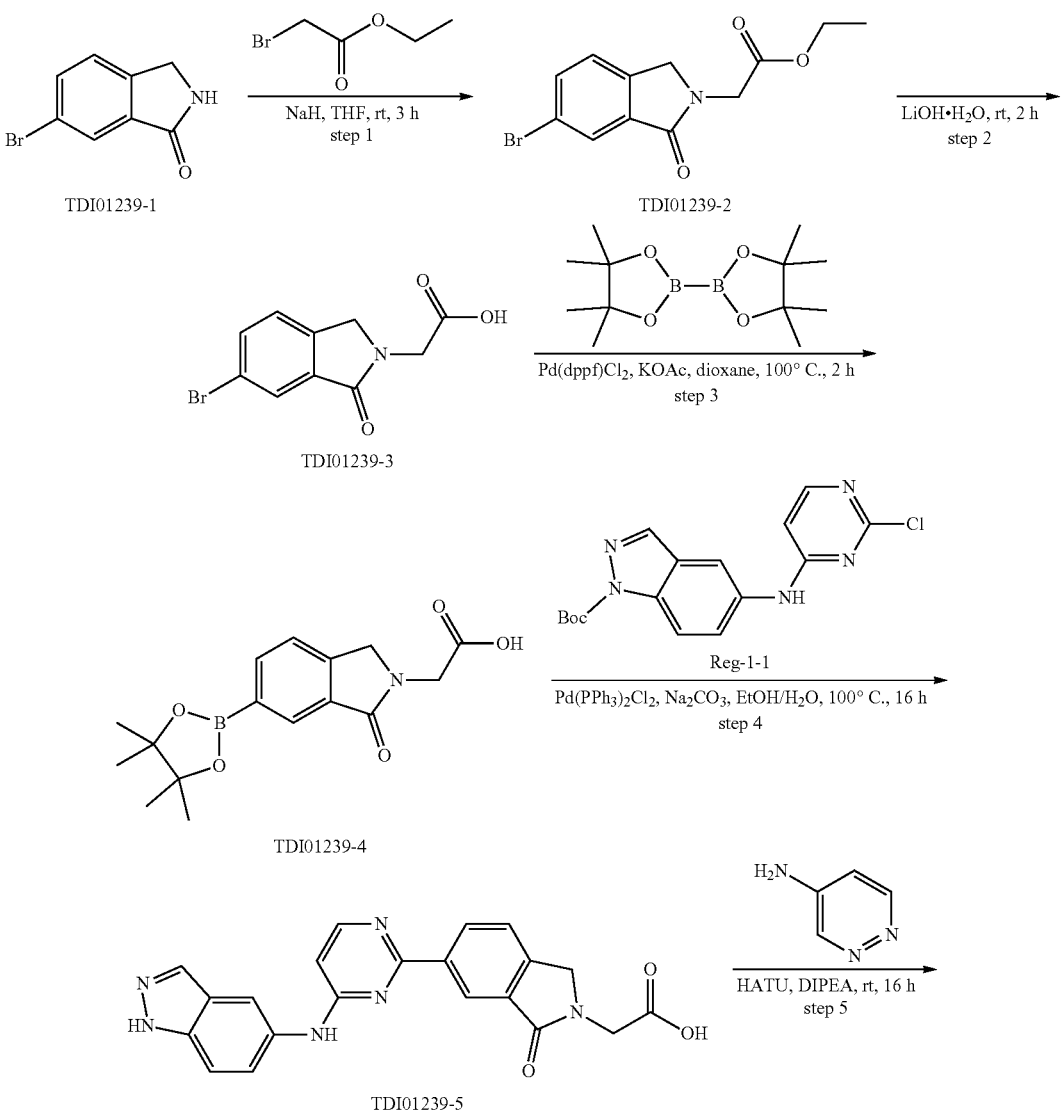

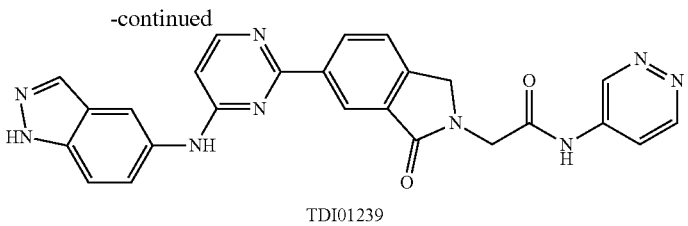

TDI01239

Step 1:

TDI01239-1 (500 mg, 2.358 mmol) was dissolved in tetrahydrofuran (24 mL), and cooled to 0° C. Under the protection of nitrogen, 60% NaH (236 mg, 5.895 mmol) was added to the above reaction solution, and the reaction was performed at room temperature for 1 h after the addition. Bromoethyl acetate was then added at 0° C., and the reaction was continued at room temperature for 2 h. LC-MS indicated the reaction was complete. After completion of the reaction, ice water and 1N HCl solution was added to quench the reaction, and the aqueous phase was extracted with ethyl acetate (15 mL). The combined organic phase was washed with saturated brine, dried over anhydrous sodium sulfate and concentrated to dryness to afford TDI01239-2 (700 mg, yellow solid, yield: 99.57%). MS m/z (ESI): 298.1 [M+H].

Step 2:

TDI01239-2 (700 mg, 2.357 mmol), lithium hydroxide monohydrate (297 mg, 7.071 mmol) were added to a mixed solution of tetrahydrofuran (10 ml) and water (10 ml), and the reaction was stirred at room temperature for 2 h. LC-MS indicated the reaction was complete. After pH was adjusted to 3 with dilute hydrochloric acid, the solution was extracted with ethyl acetate (2 mL). The organic phase was combined, washed with saturated brine, dried over anhydrous sodium sulfate, and concentrated to afford TDI01239-3 (600 mg, yellow solid, yield: 94.64%). MS m/z (ESI): 270.1 [M+H].

Step 3:

TDI01239-3 (0.3 g, 1.115 mmol) and bis(pinacolato)diboron (425 mg, 1.673 mmol) were dissolved in 1,4-dioxane (10 mL), potassium acetate (328 mg, 3.345 mmol) and Pd(dppf)Cl$_2$ (82 mg, 0.1115 mmol) were added, purge with argon was performed for 3 times, and the reaction was placed in an oil bath at 100° C., and allowed to proceed for 3 h. LC-MS indicated the reaction was complete. After the reaction was complete, the solution was filtered, and the filtrate was concentrated to afford TDI01239-4 (350 mg, black oil, crude product).

$^1$H NMR (400 MHz, DMSO-d$_6$) δ 7.96 (s, 1H), 7.90 (d, 1H), 7.64 (d, 1H), 4.55 (s, 2H), 4.27 (s, 2H), 1.32 (s, 12H). MS m/z (ESI): 318.2 [M+H].

Step 4:

TDI01239-4 (350 mg, 1.104 mmol) and Reg-1-1 (254 mg, 0.736 mmol) were dissolved in a mixed solution of ethanol (10 ml) and water (1.25 ml), sodium carbonate (234 mg, 2.208 mmol) and Pd(PPh$_3$)$_2$Cl$_2$ (52 mg, 0.0736 mmol) were added, purge with argon was performed for 3 times, and the reaction was placed in an oil bath at 100° C., and allowed to proceed for 16 h. LC-MS indicated the reaction was complete. The reaction solution was filtered, the filtrate was evaporated to dryness, and the residue was purified by column chromatography (dichloromethane:methanol=20:1-1:1) to afford TDI01239-5 (130 mg, light yellow solid, yield: 29.48%).

$^1$H NMR (400 MHz, CDCl$_3$) δ 9.88 (s, 1H), 8.63 (s, 1H), 8.55 (d, 1H), 8.36 (d, J=5.9 Hz, 1H), 8.20 (s, 1H), 8.04 (s, 1H), 7.69 (d, 1H), 7.57 (s, 2H), 6.75 (d, 1H), 4.62 (s, 2H), 3.87 (s, 2H). MS m/z (ESI): 401.2 [M+H].

Step 5:

TDI01239-5 (70 mg, 0.175 mmol) and 4-aminopyridazine (20 mg, 0.21 mmol) were dissolved in N,N-dimethylformamide (2 mL), HATU (66 mg, 0.175 mmol) and diisopropylethylamine (68 mg, 0.525 mmol) were added, and the reaction was performed at room temperature for 16 h. LC-MS indicated the reaction was complete. The solvent was evaporated to dryness, and the residue was purified by preparative chromatograph (dichloromethane:methanol:aqueous ammonia=8:1:10 drops) to give a crude product, which was purified by high-performance liquid chromatography to afford compound TDI01239 (5.29 mg, yellow solid, yield: 6.37%).

$^1$H NMR (400 MHz, DMSO-d$_6$) δ 11.10 (s, 1H), 10.32 (s, 1H), 9.33 (d, 1H), 9.11 (d, 1H), 8.65 (s, 1H), 8.55 (dd, 1H), 8.39 (d, 1H), 8.15 (s, 1H), 8.10 (s, 1H), 8.00 (dd, 1H), 7.84 (d, 1H), 7.62 (d, 1H), 7.55 (d, 1H), 6.81 (d, 1H), 4.70 (s, 2H), 4.56 (s, 2H). MS m/z (ESI): 478.2 [M+H].

Biological Assay

The kinase IC$_{50}$ was determined by a commercialized CISBIO kinase detection kit, HTRF KinEASE-STK S2 kit (62ST2PEC). ROCK2 (01-119) employed in the reaction was purchased from Carna Biosciences.

Before the assay, the following working solutions as needed were formulated with corresponding reagents according to the instruction of the kinase detection kit: 1×kinase buffer, 5×STK-S2 substrate working solution (1.5 µM) and 5×ATP working solution (1.5 µM), 5×ROCK2 kinase working solution, 4×Streptavidin-XL665 working solution, and 4×STK-Ab-Cryptate 2 detection solution. Then the assay was performed according to the following procedure.

A solution of a compound at a concentration of 10000 nM was prepared with the 1×kinase buffer containing 2.5% DMSO. Gradient dilution of the solution of the compound was performed with the kinase buffer containing DMSO, so as to obtain solutions of a test compound at 9 different concentrations. In addition to wells of test compounds, a positive well (containing all the reagents except the compound) and a negative well (containing all the reagents except the test compound and kinase) were set. Except for the control wells (positive and negative wells), a solution of a test compound (4 µL) was added to each of the reaction wells, and a solution of 2.5% DMSO was added to the control wells. Then the substrate (2 µM, i.e., 2 µL 5×STK-S2 substrate working solution) was added to each of the reaction wells. The 5×ROCK2 kinase working solution (2 µL, containing 1.4 ng ROCK2 kinase) was added to each of the reaction wells except for the negative well, the volume of which was made up with the 1×kinase buffer (2 µL). The 5×ATP working solution (2 µL) was added to each of the reaction wells, and the mixtures were incubated at room temperature for 2 hours. After the kinase reaction was complete, the 4×Streptavidin-XL665 working solution was added to each of the reaction wells, the solutions were mixed, followed by immediate addition of the 4×STK-Ab-Cryptate 2 detection solution (5 μL), and the mixtures were incubated at room temperature for 1 hour. The fluorescence signal was read on ENVISION (Perkinelmer) (excitation wavelength: 320 nm, and emission wavelength: 665 nm and 615 nm). The inhibitory rate in each well was calculated based on the fluorescence intensity value: ER (Emission Ratio)=(fluorescence intensity at 665 nm/fluorescence intensity at 615 nm); inhibitory rate=$(ER_{positive}-ER_{test\ compound})/(ER_{positive}-ER_{negative})*100\%$. Curves were plotted and fitted to obtain the median inhibitory concentration ($IC_{50}$) of each test compound with the PRISM 5.0 software. $IC_{50}$ value of each compound is as shown in the following table.

| Compound No. | ROCK2 $IC_{50}$ (nM) |
| --- | --- |
| TDI01116 | 236 |
| TDI01152 | 88 |
| TDI01164 | 438 |
| TDI01167 | 223 |
| TDI01175 | 197 |
| TDI01178 | 168 |
| TDI01180 | 37 |
| TDI01181 | 92 |
| TDI01188 | 123 |
| TDI01191 | 225 |
| TDI01201 | 48 |
| TDI01213 | 255 |
| TDI01232 | 295 |
| TDI01236 | 135 |
| TDI01237 | 171 |
| TDI01250 | 208 |
| TDI01251 | 101 |
| TDI01276 | 113 |
| TDI01347 | 356 |

Various modifications of the invention in addition to those described herein will become apparent to those skilled in the art from the foregoing description. Such modifications are intended to fall within the scope of the appended claims. Each reference, including all patents, applications, journal articles, books and any other disclosure, referred to herein is hereby incorporated by reference in its entirety.

What is claimed is:

1. A compound or a pharmaceutically acceptable salt, ester, stereoisomer, N-oxide, or isotopically labeled compound thereof, wherein the compound has the structure of Formula (I):

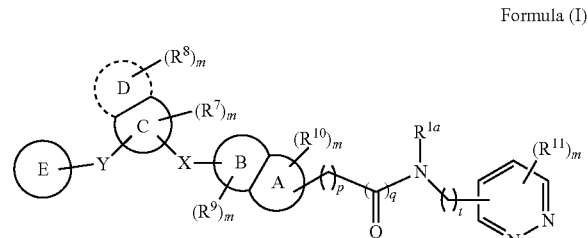

Formula (I)

wherein:
X and Y are each independently selected from the group consisting of a direct bond, C(=O), O, S(=O)$_i$ and NR;

R is selected from the group consisting of H, $C_{1-6}$ alkyl, $C_{2-6}$ alkenyl, $C_{2-6}$ alkynyl, saturated or partially unsaturated $C_{3-10}$ cyclic hydrocarbyl, saturated or partially unsaturated 3- to 10-membered heterocyclyl, $C_{6-10}$ aryl, 5- to 14-membered heteroaryl and $C_{6-12}$ aralkyl, and at most 2 ring members in the cyclic hydrocarbyl and heterocyclyl are C(=O);

ring A and ring B are each independently selected from the group consisting of saturated or partially unsaturated $C_{3-10}$ hydrocarbon ring, saturated or partially unsaturated 3- to 10-membered heterocycle, $C_{6-10}$ aromatic ring and 5- to 14-membered heteroaromatic ring, and at most 2 ring members in the hydrocarbon ring and heterocycle are C(=O);

ring C is selected from the group consisting of saturated or partially unsaturated $C_{3-10}$ hydrocarbon ring, saturated or partially unsaturated 3- to 10-membered heterocycle, $C_{6-10}$ aromatic ring and 5- to 14-membered heteroaromatic ring, and at most 2 ring members in the hydrocarbon ring and heterocycle are C(=O);

ring D is absent, or is selected from the group consisting of saturated or partially unsaturated $C_{3-10}$ hydrocarbon ring, saturated or partially unsaturated 3- to 10-membered heterocycle, $C_{6-10}$ aromatic ring and 5- to 14-membered heteroaromatic ring, and at most 2 ring members in the hydrocarbon ring and heterocycle are C(=O);

ring E is selected from the group consisting of

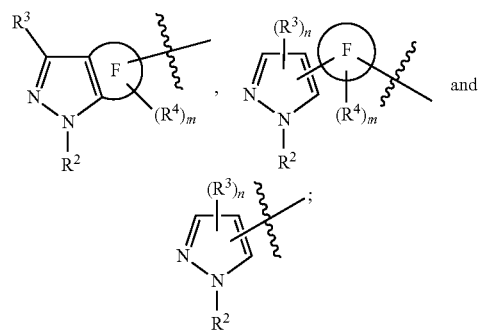

ring F is selected from the group consisting of saturated or partially unsaturated $C_{3-10}$ hydrocarbon ring, saturated or partially unsaturated 3- to 10-membered heterocycle, $C_{6-10}$ aromatic ring and 5- to 14-membered heteroaromatic ring, and at most 2 ring members in the hydrocarbon ring and heterocycle are C(=O);

$R^{1a}$ is selected from the group consisting of H, halogen, amino, cyano, nitro, $C_{1-6}$ alkyl, $C_{2-6}$ alkenyl, $C_{2-6}$ alkynyl, $C_{3-10}$ cyclic hydrocarbyl, 3- to 10-membered heterocyclyl, $C_{6-10}$ aryl, 5- to 14-membered heteroaryl, $C_{6-12}$ aralkyl, —C(=O)$R^5$, —OC(=O)$R^5$, —C(=O)OR$^5$, —OR$^5$, —SR$^5$, —S(=O)$R^5$, —S(=O)$_2R^5$, —S(=O)$_2NR^5R^6$, —NR$^5R^6$, —C(=O)NR$^5R^6$, —NR$^5$—C(=O)$R^6$, —NR$^5$—C(=O)OR$^6$, —NR$^5$—S(=O)$_2$—R$^6$, —NR$^5$—C(=O)—NR$^5R^6$, —C$_{1-6}$ alkylene-NR$^5R^6$, —C$_{1-6}$ alkylene-OR$^5$ and —O—C$_{1-6}$ alkylene-NR$^5R^6$;

$R^2$, $R^3$, $R^4$, $R^7$, $R^8$, $R^9$, $R^{10}$ and $R^{11}$, at each occurrence, are each independently selected from the group consisting of H, halogen, amino, cyano, nitro, $C_{1-6}$ alkyl, $C_{2-6}$ alkenyl, $C_{2-6}$ alkynyl, $C_{3-10}$ cyclic hydrocarbyl, 3- to 10-membered heterocyclyl, $C_{6-10}$ aryl, 5- to 14-membered heteroaryl, $C_{6-12}$ aralkyl, —C(=O)$R^5$, —OC(=O)R⁵, —C(=O)OR⁵, —OR⁵, —SR⁵, —S(=O)R⁵, —S(=O)₂R⁵, —S(=O)₂NR⁵R⁶, —NR⁵R⁶, —C(=O)NR⁵R⁶, —NR⁵—C(=O)R⁶, —NR⁵—C(=O)OR⁶, —NR⁵—S(=O)₂—R⁶, —NR⁵—C(=O)—NR⁵R⁶, —C₁₋₆ alkylene-NR⁵R⁶ and —O—C₁₋₆ alkylene-NR⁵R⁶;

alternatively, when the pyridazine ring in Formula (I) is substituted with two R¹¹, and the two R¹¹ are at ortho positions on the pyridazine ring, the two R¹¹ together with the carbon atoms to which they are attached form C₄₋₁₀ cyclic hydrocarbyl, 4- to 10-membered heterocyclyl, C₆₋₁₀ aryl, or 5- to 14-membered heteroaryl;

R⁵ and R⁶, at each occurrence, are each independently selected from the group consisting of H, C₁₋₆ alkyl, C₃₋₁₀ cyclic hydrocarbyl, 3- to 10-membered heterocyclyl, C₆₋₁₀ aryl, 5- to 14-membered heteroaryl and C₆₋₁₂ aralkyl;

the above alkyl, alkylene, alkenyl, alkynyl, cyclic hydrocarbyl, hydrocarbon ring, heterocyclyl, heterocycle, aryl, aromatic ring, heteroaryl, heteroaromatic ring and aralkyl, at each occurrence, are each optionally substituted with one or more substituents independently selected from the group consisting of: halogen, hydroxyl, oxo, amino, cyano, nitro, C₁₋₆ alkyl, C₃₋₆ cyclic hydrocarbyl, 3- to 10-membered heterocyclyl, C₆₋₁₀ aryl, 5- to 14-membered heteroaryl, C₆₋₁₂ aralkyl, —C(=O)R⁵, —OC(=O)R⁵, —C(=O)OR⁵, —OR⁵, —SR⁵, —S(=O)R⁵, —S(=O)₂R⁵, —S(=O)₂NR⁵R⁶, —NR⁵R⁶, —C(=O)NR⁵R⁶, —NR⁵—C(=O)R⁶, —NR⁵—C(=O)OR⁶, —NR⁵—S(=O)₂—R⁶, —NR⁵—C(=O)—NR⁵R⁶, —C₁₋₆ alkylene-NR⁵R⁶ and —O—C₁₋₆ alkylene-NR⁵R⁶, and the alkyl, cyclic hydrocarbyl, heterocyclyl, aryl, heteroaryl and aralkyl are further optionally substituted with one or more substituents independently selected from the group consisting of: halogen, hydroxyl, oxo, amino, cyano, nitro, C₁₋₆ alkyl, C₃₋₆ cyclic hydrocarbyl, 3- to 10-membered heterocyclyl, C₆₋₁₀ aryl, 5- to 14-membered heteroaryl and C₆₋₁₂ aralkyl;

m, at each occurrence, is each independently an integer of 0, 1, 2 or 3;

n is an integer of 0, 1 or 2;

i is an integer of 0, 1 or 2;

p is an integer of 0, 1, 2 or 3;

q is an integer of 0 or 1; and t is an integer of 0, 1, 2, or 3.

2. The compound according to claim 1, or a pharmaceutically acceptable salt, ester, stereoisomer, N-oxide, or isotopically labeled compound thereof, wherein X and Y are each independently selected from the group consisting of a direct bond, C(=O), O, S, S(=O), S(=O)₂ and NH, and at least one of X and Y is a direct bond.

3. The compound according to claim 1, or a pharmaceutically acceptable salt, ester, stereoisomer, N-oxide, or isotopically labeled compound thereof, wherein at least one of ring A and ring B is selected from the group consisting of saturated or partially unsaturated 3- to 10-membered heterocycle and 5- to 14-membered heteroaromatic ring, at most 2 ring members in the heterocycle are C(=O), and when ring B is a heterocycle containing a nitrogen atom, ring B is not attached to X via the nitrogen atom; and R⁹ and R¹⁰, at each occurrence, are each independently selected from the group consisting of methyl, ethyl, propyl and —CH₂CH₂—N(CH₃)₂.

4. The compound according to claim 1, or a pharmaceutically acceptable salt, ester, stereoisomer, N-oxide, or isotopically labeled compound thereof, wherein

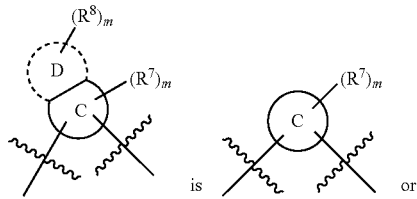

is

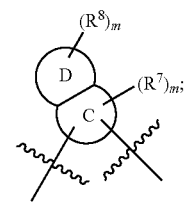

or and;

R⁷ and R⁸, at each occurrence, are each independently selected from the group consisting of F, Cl, Br, I, cyano, methyl, ethyl, propyl, trifluoromethyl, phenyl, —O—CH₂CH₂—N(CH₃)₂ and —CH₂CH₂—N(CH₃)₂.

5. The compound according to claim 1, or a pharmaceutically acceptable salt, ester, stereoisomer, N-oxide, or isotopically labeled compound thereof, wherein ring E is

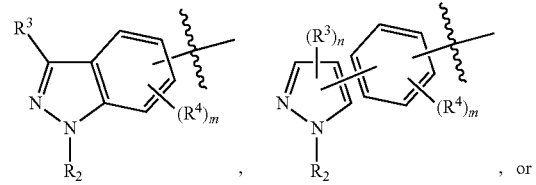

, or

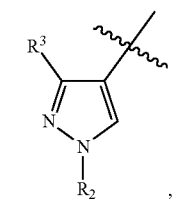

,

R³ and R⁴, at each occurrence, are each independently selected from the group consisting of H, F, Cl, Br, I, methyl, ethyl, propyl, methoxy, —O-ethylene-N(CH₃)₂.

6. The compound according to claim 1, or a pharmaceutically acceptable salt, ester, stereoisomer, N-oxide, or isotopically labeled compound thereof, wherein

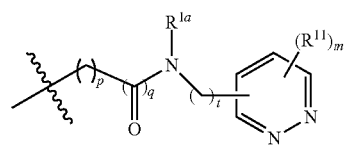

is selected from the group consisting of

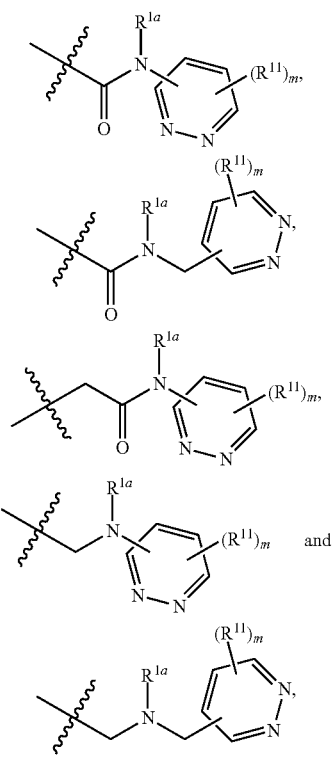

and

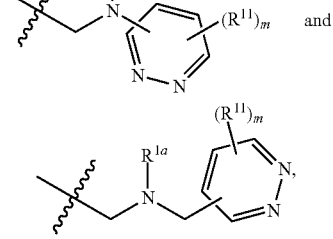

three $R^{11}$ are present, each independently selected from the group consisting of H, halogen, amino, cyano, nitro, $C_{1-6}$ alkyl, $C_{2-6}$ alkenyl, $C_{2-6}$ alkynyl, $C_{3-10}$ cyclic hydrocarbyl, 3- to 10-membered heterocyclyl, $C_{6-10}$ aryl, 5- to 14-membered heteroaryl, $C_{6-12}$ aralkyl, $-C(=O)R^5$, $-OC(=O)R^5$, $-C(=O)OR^5$, $-OR^5$, $-SR^5$, $-S(=O)R^5$, $-S(=O)_2R^5$, $-S(=O)_2NR^5R^6$, $-NR^5R^6$, $-C(=O)NR^5R^6$, $-NR^5-C(=O)R^6$, $-NR^5-C(=O)OR^6$, $-NR^5-S(=O)_2-R^6$, $-NR^5-C(=O)-NR^5R^6$, $-C_{1-6}$ alkylene-$NR^5R^6$ and $-O-C_{1-6}$ alkylene-$NR^5R^6$;

alternatively, two $R^{11}$ are present and together with the carbon atoms to which they are attached form $C_{4-10}$ cyclic hydrocarbyl, 4- to 10-membered heterocyclyl, $C_{6-10}$ aryl, or 5- to 14-membered heteroaryl.

7. The compound according to claim 1, or a pharmaceutically acceptable salt, ester, stereoisomer, N-oxide, or isotopically labeled compound thereof, wherein three $R^{11}$ are each independently selected from the group consisting of H, F, Cl, Br, methyl, trifluoromethyl, methoxy, N-methylpiperazinyl, and dimethyl amino;

alternatively, two $R^{11}$ together with the carbon atoms to which they are attached form phenyl.

8. The compound according to claim 1, or a pharmaceutically acceptable salt, ester, stereoisomer, N-oxide, or isotopically labeled compound thereof, wherein the compound has the structure of any of the following formulae:

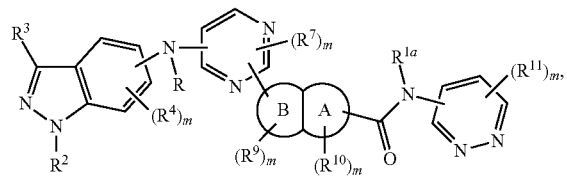

(II)

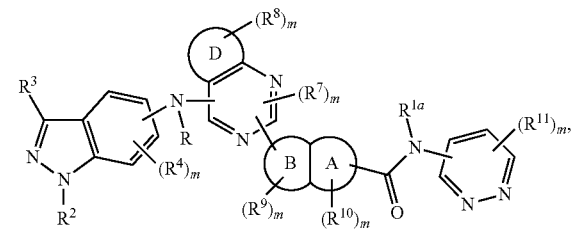

(II')

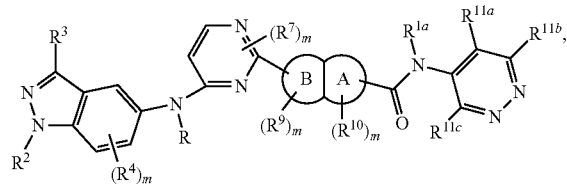

(III)

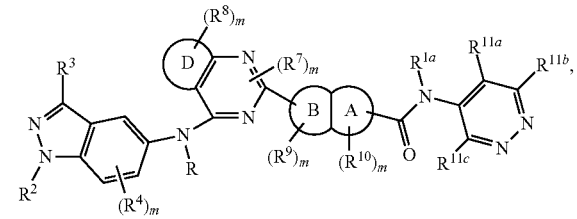

(III')

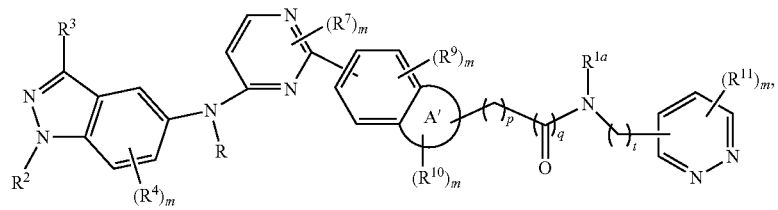

(IV)

-continued
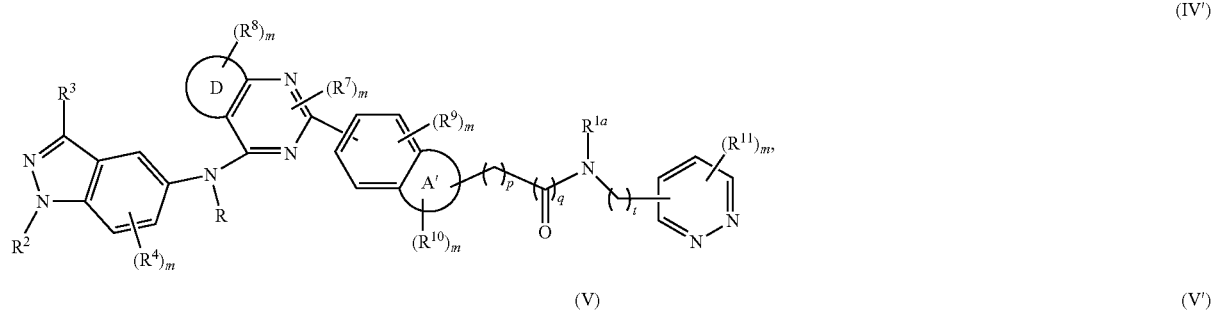
(IV')
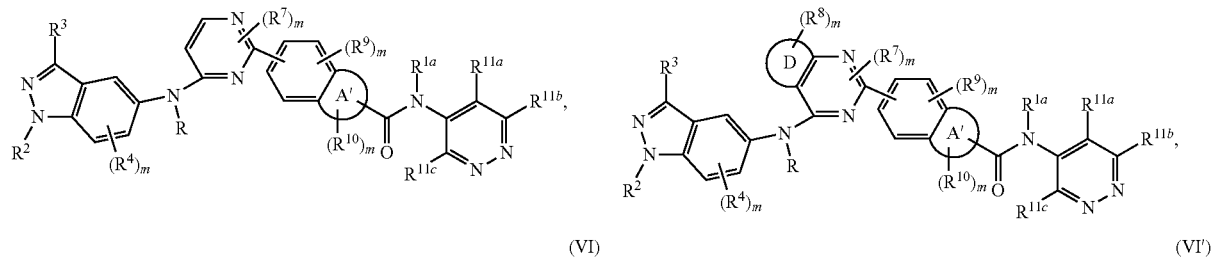
(V) (V')
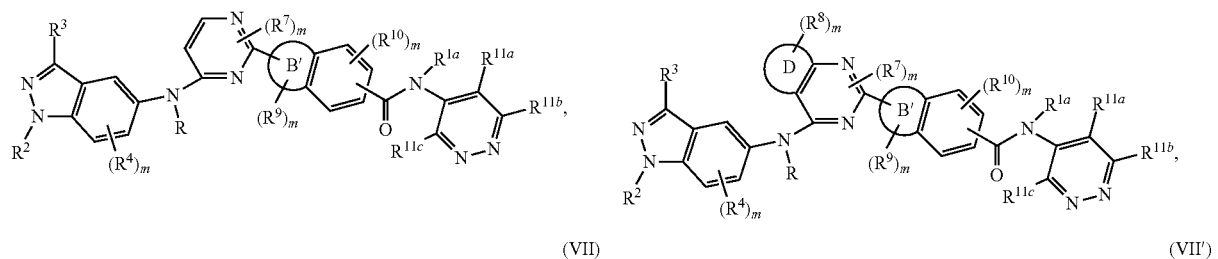
(VI) (VI')
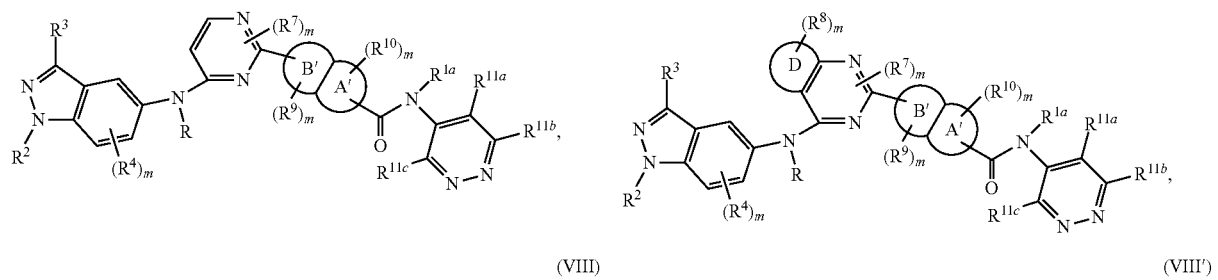
(VII) (VII')
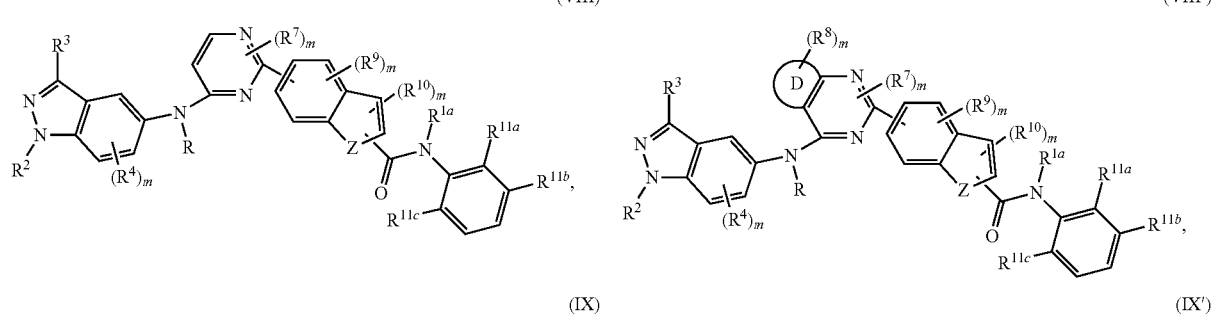
(VIII) (VIII')
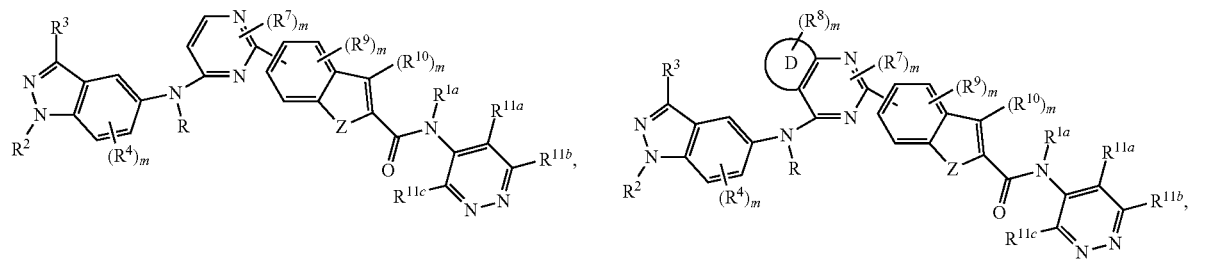
(IX) (IX')

173

-continued (X)

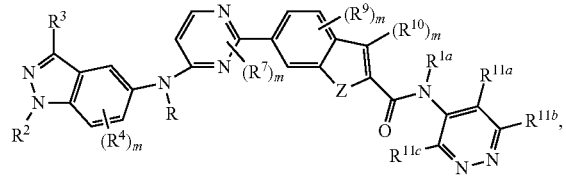

(X')

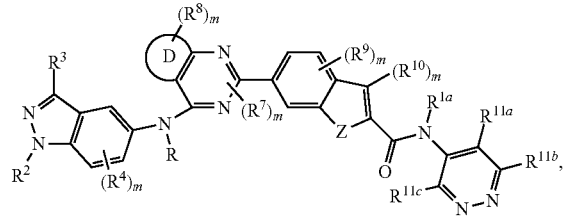

(XI)

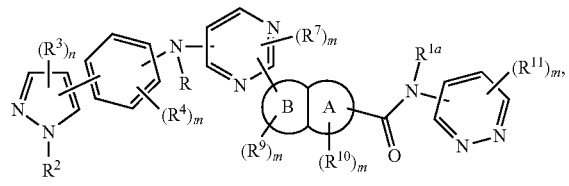

(XI')

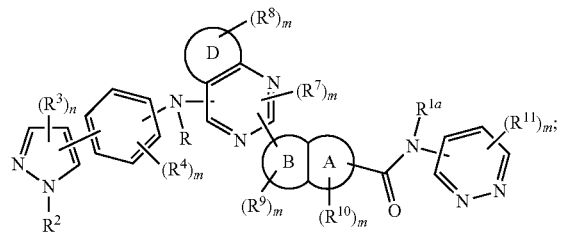

wherein:
Z is selected from the group consisting of O, S(=O)$_i$ and NR;
each of the remaining groups is as defined in claim 1.

174

9. The compound according to claim 1, or a pharmaceutically acceptable salt, ester, stereoisomer, N-oxide, or isotopically labeled compound thereof, wherein the compound has the following structure:

| Serial Number | No. | Compound Structure |
|---|---|---|
| 1. | TDI01116 | 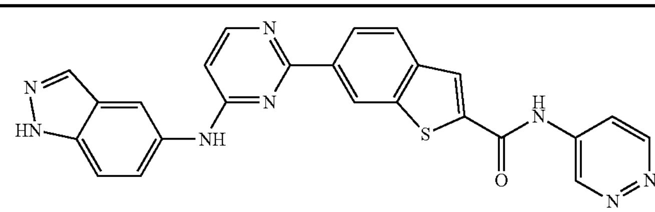 |
| 2. | TDI01152 | 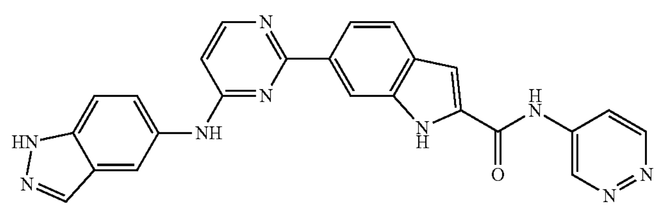 [SMILES: O=C(Nc1ccnnc1)c1cc2ccc(-c3nccc(Nc4ccc5[nH]ncc5c4)n3)cc2[nH]1] |
| 3. | TDI01154 | 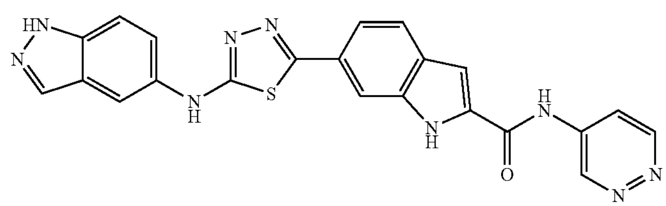 [SMILES: O=C(Nc1ccnnc1)c1cc2ccc(-c3nnc(Nc4ccc5[nH]ncc5c4)s3)cc2[nH]1] |
| 4 | TDI01162 | 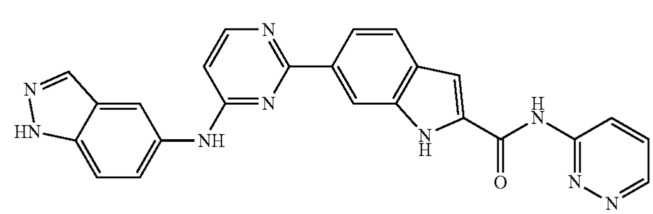 [SMILES: O=C(Nc1cccnn1)c1cc2ccc(-c3nccc(Nc4ccc5[nH]ncc5c4)n3)cc2[nH]1] |

-continued

| Serial Number | No. | Compound Structure |
|---|---|---|
| 5. | TDI01164 | 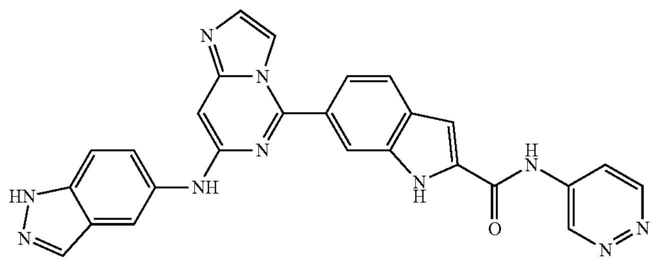 [SMILES: O=C(Nc1ccnnc1)c1cc2ccc(-c3nc(Nc4ccc5[nH]ncc5c4)cc4nccn34)cc2[nH]1] |
| 6. | TDI01165 | 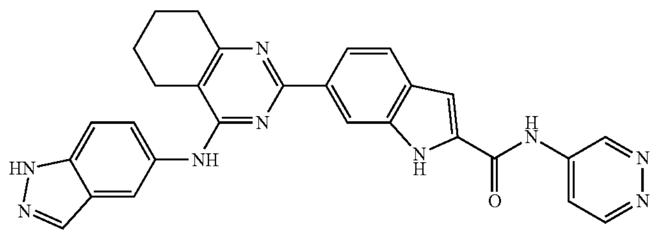 [SMILES: O=C(Nc1ccnnc1)c1cc2ccc(-c3nc4c(c(Nc5ccc6[nH]ncc6c5)n3)CCCC4)cc2[nH]1] |
| 7. | TDI01166 | 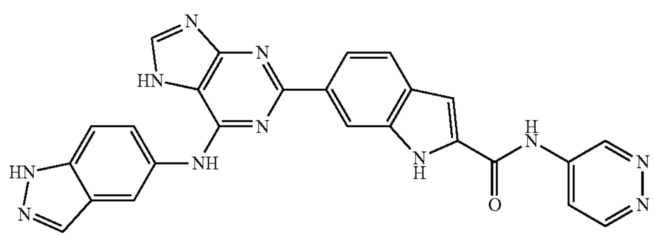 [SMILES: O=C(Nc1ccnnc1)c1cc2ccc(-c3nc(Nc4ccc5[nH]ncc5c4)c4[nH]cnc4n3)cc2[nH]1] |
| 8. | TDI01167 | 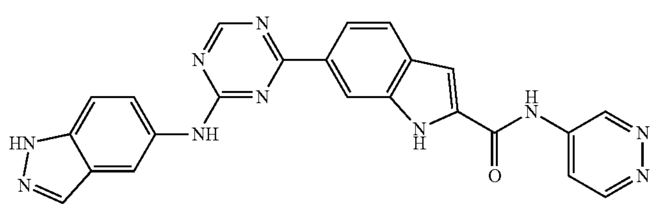 [SMILES: O=C(Nc1ccnnc1)c1cc2ccc(-c3ncnc(Nc4ccc5[nH]ncc5c4)n3)cc2[nH]1] |
| 9. | TDI01168 | 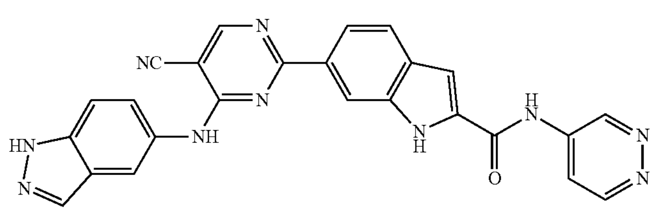 [SMILES: N#Cc1cnc(-c2ccc3cc(C(=O)Nc4ccnnc4)[nH]c3c2)nc1Nc1ccc2[nH]ncc2c1] |
| 10. | TDI01169 | 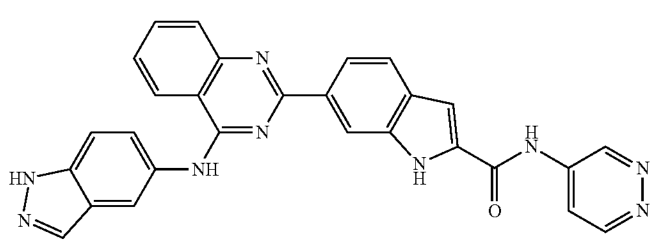 [SMILES: O=C(Nc1ccnnc1)c1cc2ccc(-c3nc(Nc4ccc5[nH]ncc5c4)c4ccccc4n3)cc2[nH]1] |

-continued
| Serial Number | No. | Compound Structure |
|---|---|---|
| 11. | TDI01172 | 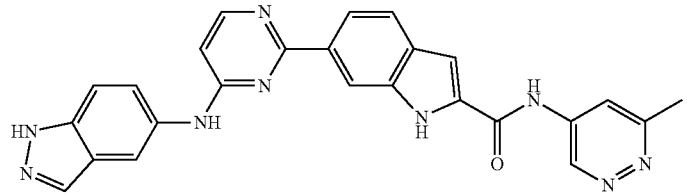 [SMILES: Cc1cc(NC(=O)c2cc3ccc(-c4nccc(Nc5ccc6[nH]ncc6c5)n4)cc3[nH]2)cnn1] |
| 12. | TDI01174 | 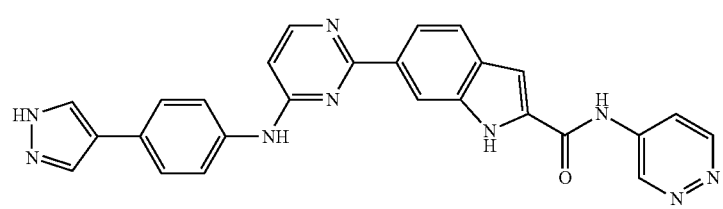 [SMILES: O=C(Nc1ccnnc1)c1cc2ccc(-c3nccc(Nc4ccc(-c5cn[nH]c5)cc4)n3)cc2[nH]1] |
| 13. | TDI01175 | 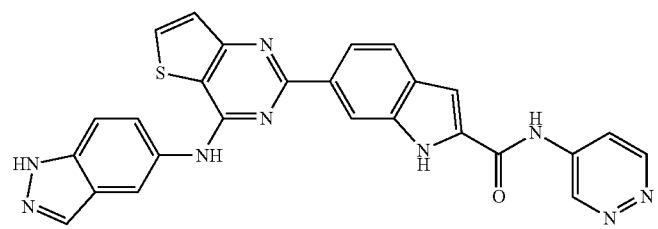 [SMILES: O=C(Nc1ccnnc1)c1cc2ccc(-c3nc(Nc4ccc5[nH]ncc5c4)c4sccc4n3)cc2[nH]1] |
| 14. | TDI01178 | 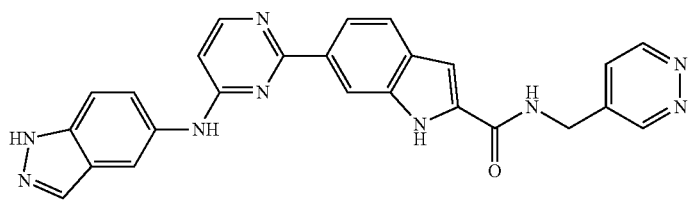 [SMILES: O=C(NCc1ccnnc1)c1cc2ccc(-c3nccc(Nc4ccc5[nH]ncc5c4)n3)cc2[nH]1] |
| 15. | TDI01179 | 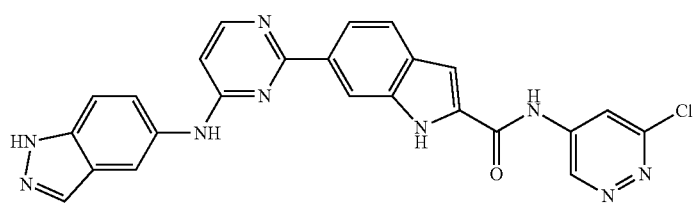 [SMILES: O=C(Nc1cnnc(Cl)c1)c1cc2ccc(-c3nccc(Nc4ccc5[nH]ncc5c4)n3)cc2[nH]1] |
| 16. | TDI01180 | 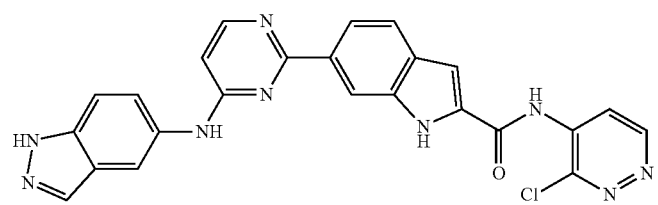 |
| 17. | TDI01181 | 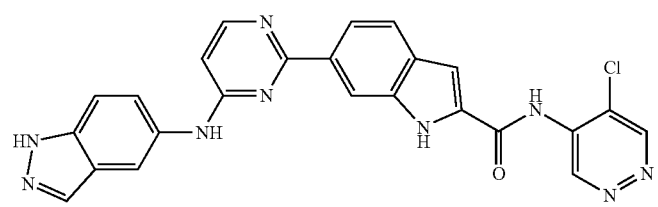 [SMILES: O=C(Nc1cnncc1Cl)c1cc2ccc(-c3nccc(Nc4ccc5[nH]ncc5c4)n3)cc2[nH]1] |

-continued

| Serial Number | No. | Compound Structure |
|---|---|---|
| 18. | TDI01185 | 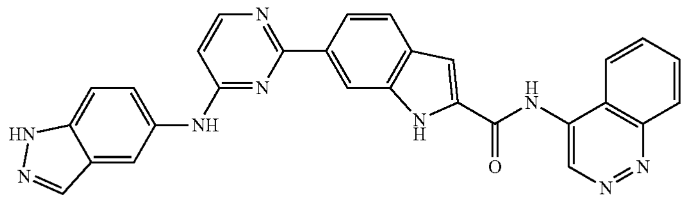 [SMILES: O=C(Nc1cnnc2ccccc12)c1cc2ccc(-c3nccc(Nc4ccc5[nH]ncc5c4)n3)cc2[nH]1] |
| 19. | TDI01187 | 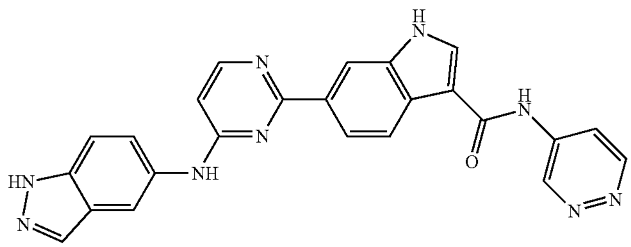 [SMILES: O=C(Nc1ccnnc1)c1c[nH]c2cc(-c3nccc(Nc4ccc5[nH]ncc5c4)n3)ccc12] |
| 20. | TDI01188 | 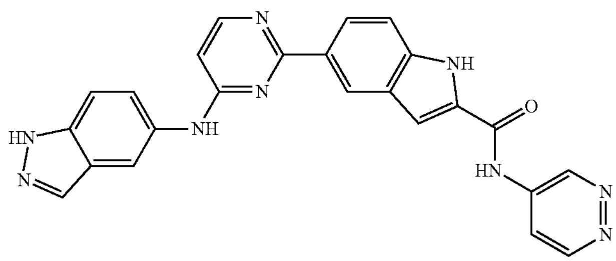 [SMILES: O=C(Nc1ccnnc1)c1cc2cc(-c3nccc(Nc4ccc5[nH]ncc5c4)n3)ccc2[nH]1] |
| 21. | TDI01189 | 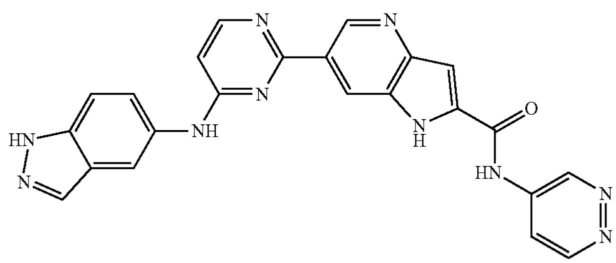 [SMILES: O=C(Nc1ccnnc1)c1cc2ncc(-c3nccc(Nc4ccc5[nH]ncc5c4)n3)cc2[nH]1] |
| 22. | TDI01190 | 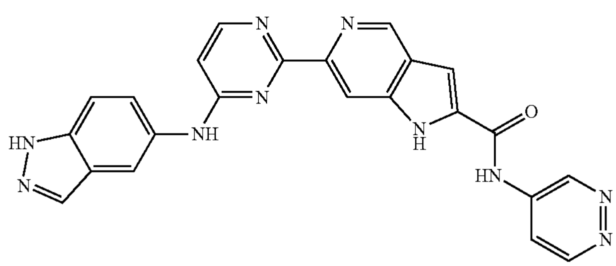 [SMILES: O=C(Nc1ccnnc1)c1cc2cnc(-c3nccc(Nc4ccc5[nH]ncc5c4)n3)cc2[nH]1] |
| 23. | TDI01191 | 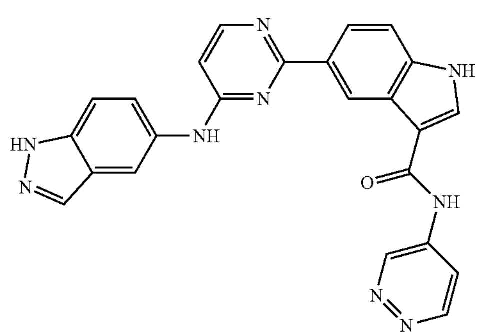 [SMILES: O=C(Nc1ccnnc1)c1c[nH]c2ccc(-c3nccc(Nc4ccc5[nH]ncc5c4)n3)cc12] |

-continued

| Serial Number | No. | Compound Structure |
|---|---|---|
| 24. | TDI01192 | 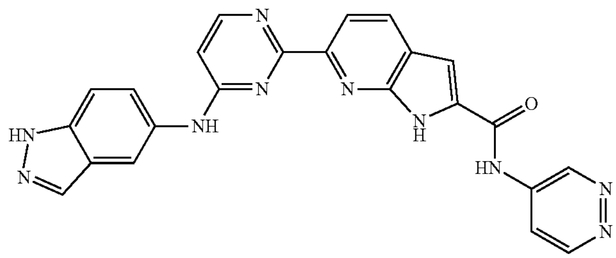 [SMILES: O=C(Nc1ccnnc1)c1cc2ccc(-c3nccc(Nc4ccc5[nH]ncc5c4)n3)nc2[nH]1] |
| 25. | TDI01193 | 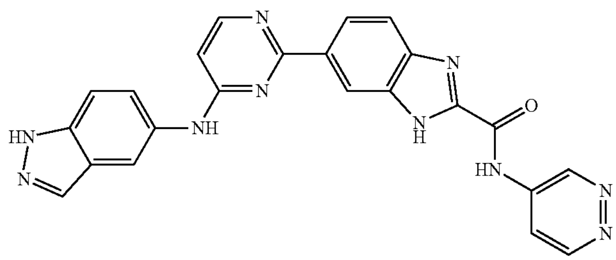 [SMILES: O=C(Nc1ccnnc1)c1nc2ccc(-c3nccc(Nc4ccc5[nH]ncc5c4)n3)cc2[nH]1] |
| 26. | TDI01194 | 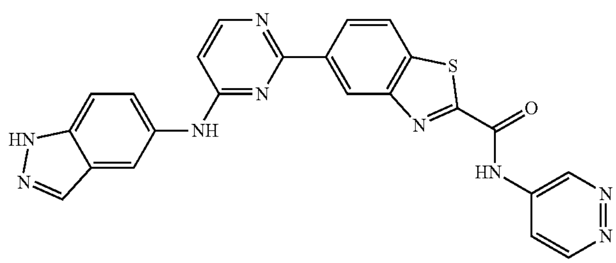 [SMILES: O=C(Nc1ccnnc1)c1nc2cc(-c3nccc(Nc4ccc5[nH]ncc5c4)n3)ccc2s1] |
| 27. | TDI01195 | 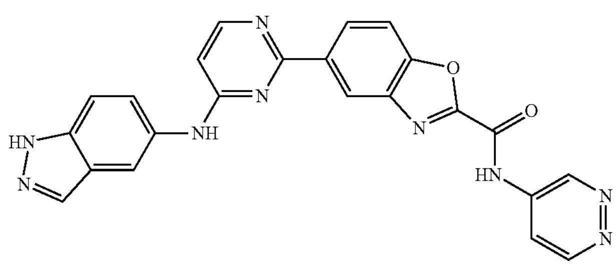 [SMILES: O=C(Nc1ccnnc1)c1nc2cc(-c3nccc(Nc4ccc5[nH]ncc5c4)n3)ccc2o1] |
| 28. | TDI01196 | 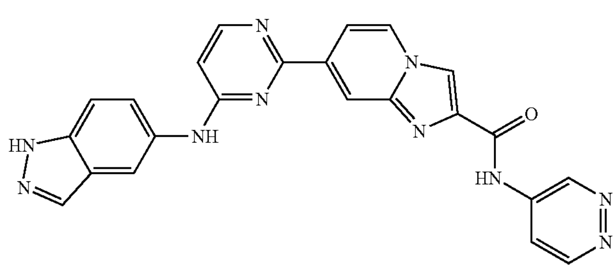 [SMILES: O=C(Nc1ccnnc1)c1cn2ccc(-c3nccc(Nc4ccc5[nH]ncc5c4)n3)cc2n1] |
| 29. | TDI01197 | 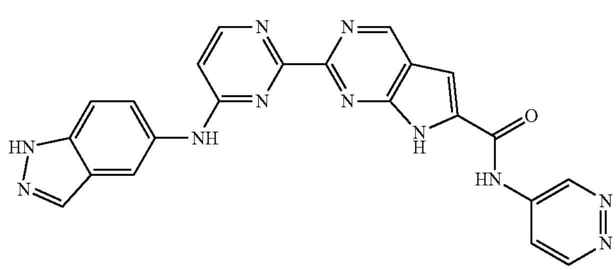 [SMILES: O=C(Nc1ccnnc1)c1cc2cnc(-c3nccc(Nc4ccc5[nH]ncc5c4)n3)nc2[nH]1] |

-continued

| Serial Number | No. | Compound Structure |
|---|---|---|
| 30. | TDI01198 | 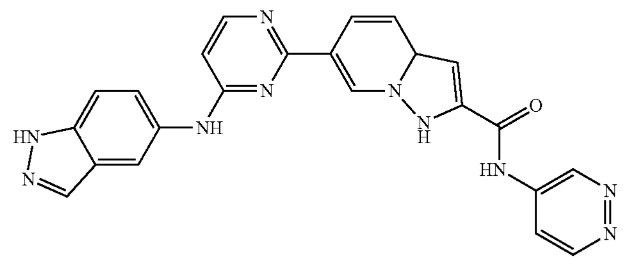 [SMILES: O=C(Nc1ccnnc1)C1=CC2C=CC(c3nccc(Nc4ccc5[nH]ncc5c4)n3)=CN2N1] |
| 31. | TDI01201 | 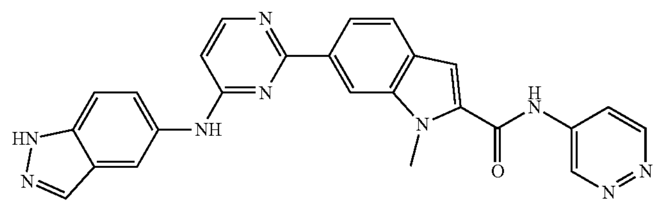 [SMILES: Cn1c(C(=O)Nc2ccnnc2)cc2ccc(-c3nccc(Nc4ccc5[nH]ncc5c4)n3)cc21] |
| 32. | TDI01209 | 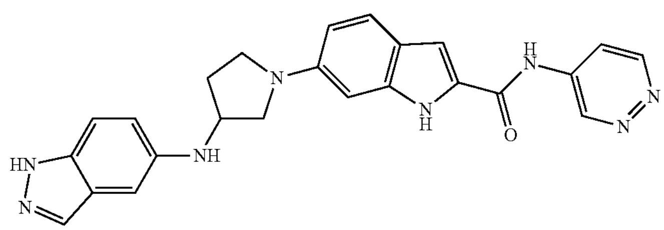 [SMILES: O=C(Nc1ccnnc1)c1cc2ccc(N3CCC(Nc4ccc5[nH]ncc5c4)C3)cc2[nH]1] |
| 33. | TDI01211 | 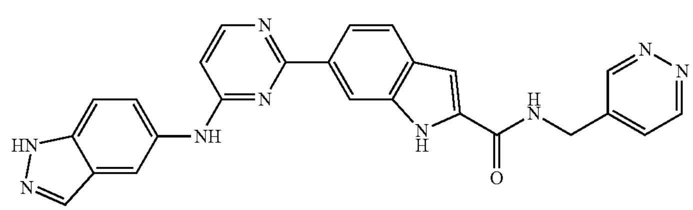 [SMILES: O=C(NCc1ccnnc1)c1cc2ccc(-c3nccc(Nc4ccc5[nH]ncc5c4)n3)cc2[nH]1] |
| 34. | TDI01212 | 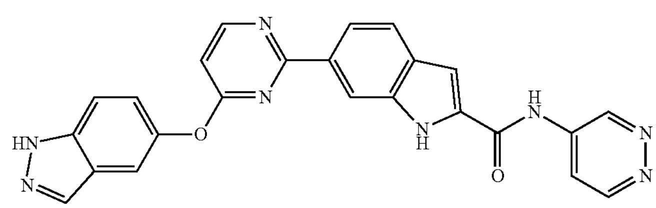 [SMILES: O=C(Nc1ccnnc1)c1cc2ccc(-c3nccc(Oc4ccc5[nH]ncc5c4)n3)cc2[nH]1] |
| 35. | TDI01213 | 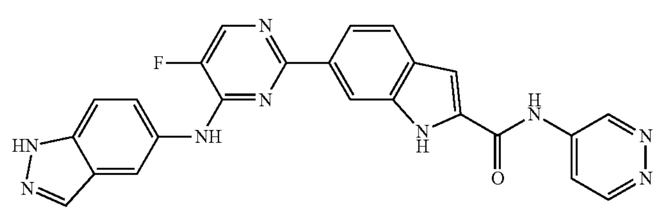 [SMILES: O=C(Nc1ccnnc1)c1cc2ccc(-c3ncc(F)c(Nc4ccc5[nH]ncc5c4)n3)cc2[nH]1] |
| 36. | TDI01214 | 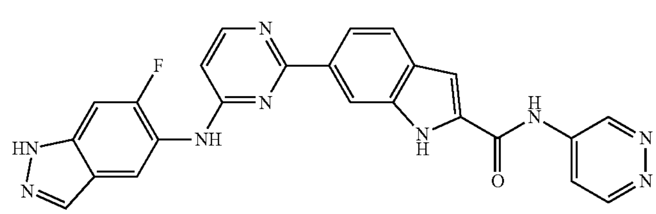 [SMILES: O=C(Nc1ccnnc1)c1cc2ccc(-c3nccc(Nc4cc5cn[nH]c5cc4F)n3)cc2[nH]1] |

-continued
| Serial Number | No. | Compound Structure |
|---|---|---|
| 37. | TDI01216 | 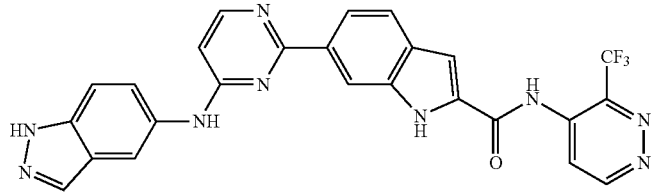 [SMILES: O=C(Nc1ccnnc1C(F)(F)F)c1cc2ccc(-c3nccc(Nc4ccc5[nH]ncc5c4)n3)cc2[nH]1] |
| 38. | TDI01217 | 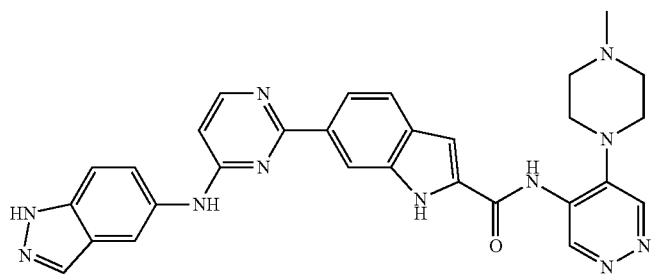 [SMILES: CN1CCN(c2cnncc2NC(=O)c2cc3ccc(-c4nccc(Nc5ccc6[nH]ncc6c5)n4)cc3[nH]2)CC1] |
| 39. | TDI01223 | 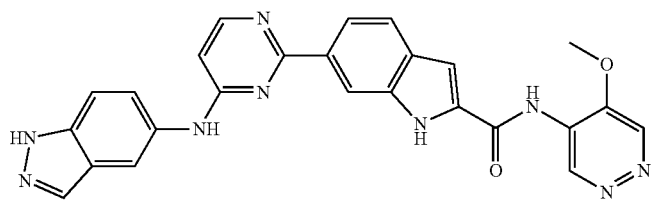 [SMILES: COc1cnncc1NC(=O)c1cc2ccc(-c3nccc(Nc4ccc5[nH]ncc5c4)n3)cc2[nH]1] |
| 40. | TDI01224 | 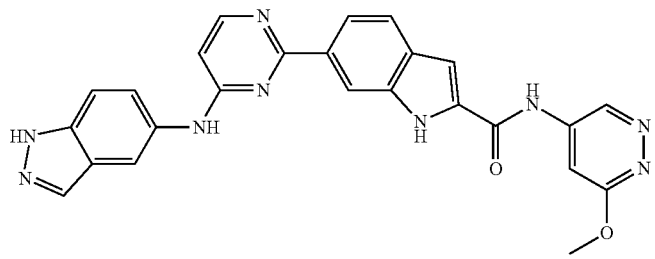 [SMILES: COc1cc(NC(=O)c2cc3ccc(-c4nccc(Nc5ccc6[nH]ncc6c5)n4)cc3[nH]2)cnn1] |
| 41. | TDI01225 | 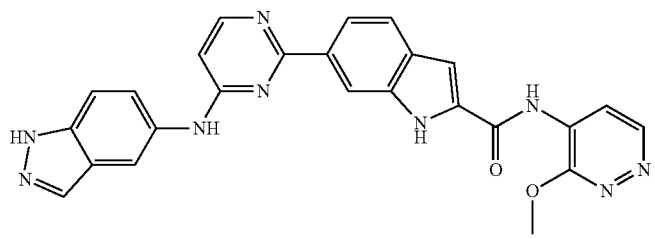 [SMILES: COc1nnccc1NC(=O)c1cc2ccc(-c3nccc(Nc4ccc5[nH]ncc5c4)n3)cc2[nH]1] |
| 42. | TDI01226 | 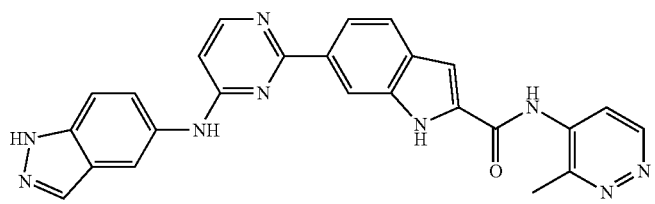 [SMILES: Cc1nnccc1NC(=O)c1cc2ccc(-c3nccc(Nc4ccc5[nH]ncc5c4)n3)cc2[nH]1] |

-continued

| Serial Number | No. | Compound Structure |
|---|---|---|
| 43. | TDI01227 | 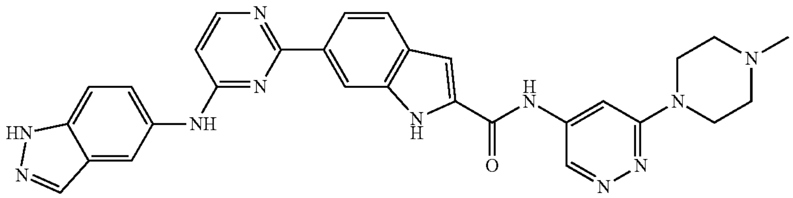 [SMILES: CN1CCN(c2cc(NC(=O)c3cc4ccc(-c5nccc(Nc6ccc7[nH]ncc7c6)n5)cc4[nH]3)cnn2)CC1] |
| 44. | TDI01228 | 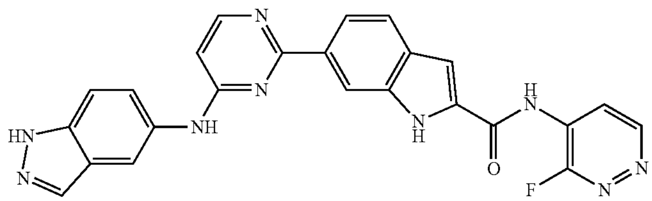 [SMILES: O=C(Nc1ccnnc1F)c1cc2ccc(-c3nccc(Nc4ccc5[nH]ncc5c4)n3)cc2[nH]1] |
| 45. | TDI01231 | 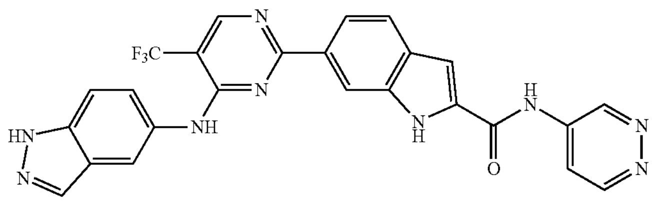 [SMILES: O=C(Nc1ccnnc1)c1cc2ccc(-c3ncc(C(F)(F)F)c(Nc4ccc5[nH]ncc5c4)n3)cc2[nH]1] |
| 46. | TDI01232 | 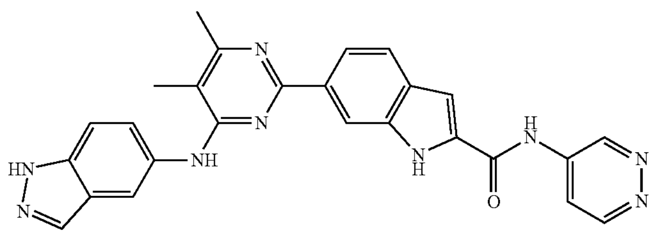 [SMILES: Cc1nc(-c2ccc3cc(C(=O)Nc4ccnnc4)[nH]c3c2)nc(Nc2ccc3[nH]ncc3c2)c1C] |
| 47. | TDI01233 | 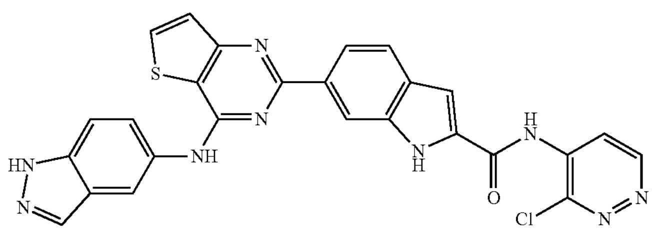 [SMILES: O=C(Nc1ccnnc1Cl)c1cc2ccc(-c3nc(Nc4ccc5[nH]ncc5c4)c4sccc4n3)cc2[nH]1] |
| 48. | TDI01234 | 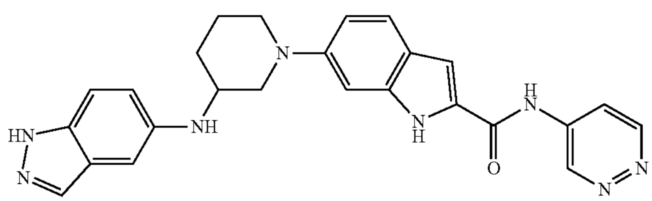 [SMILES: O=C(Nc1ccnnc1)c1cc2ccc(N3CCCC(Nc4ccc5[nH]ncc5c4)C3)cc2[nH]1] |
| 49. | TDI01235 | 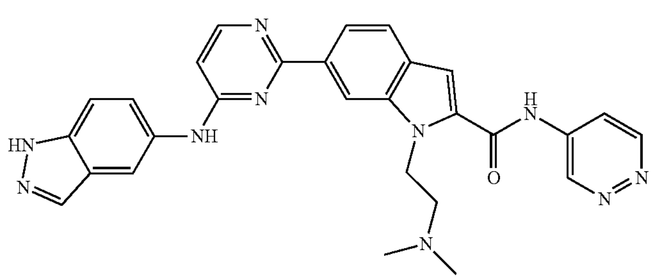 [SMILES: CN(C)CCn1c(C(=O)Nc2ccnnc2)cc2ccc(-c3nccc(Nc4ccc5[nH]ncc5c4)n3)cc21] |

-continued
| Serial Number | No. | Compound Structure |
|---|---|---|
| 50. | TDI01236 | 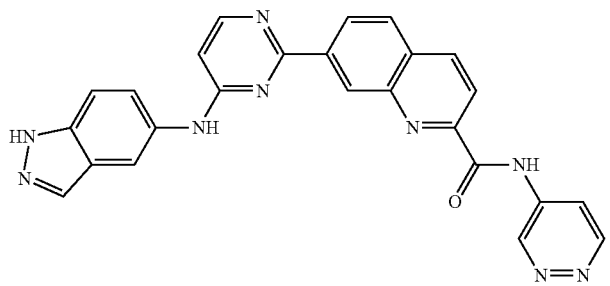 [SMILES: O=C(Nc1ccnnc1)c1ccc2ccc(-c3nccc(Nc4ccc5[nH]ncc5c4)n3)cc2n1] |
| 51. | TDI01237 | 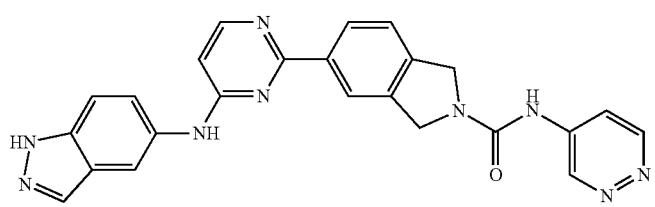 [SMILES: O=C(Nc1ccnnc1)N1Cc2ccc(-c3nccc(Nc4ccc5[nH]ncc5c4)n3)cc2C1] |
| 52. | TDI01238 | 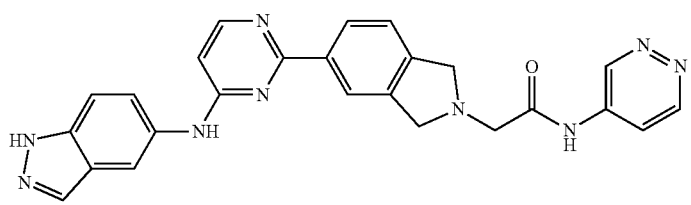 [SMILES: O=C(CN1Cc2ccc(-c3nccc(Nc4ccc5[nH]ncc5c4)n3)cc2C1)Nc1ccnnc1] |
| 53. | TDI01239 | 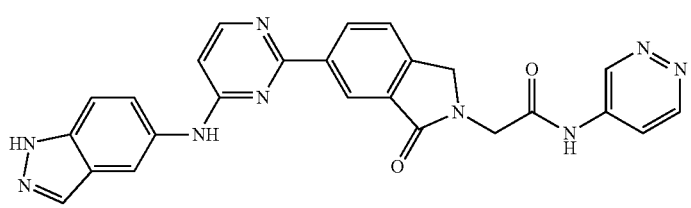 [SMILES: O=C(CN1Cc2ccc(-c3nccc(Nc4ccc5[nH]ncc5c4)n3)cc2C1=O)Nc1ccnnc1] |
| 54. | TDI01240 | 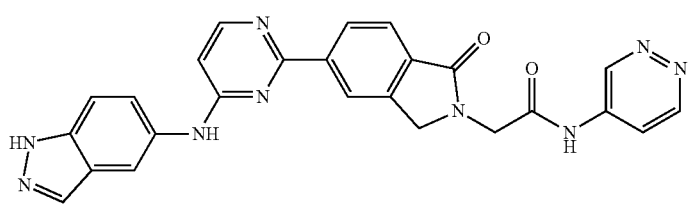 [SMILES: O=C(CN1Cc2cc(-c3nccc(Nc4ccc5[nH]ncc5c4)n3)ccc2C1=O)Nc1ccnnc1] |
| 55. | TDI01242 | 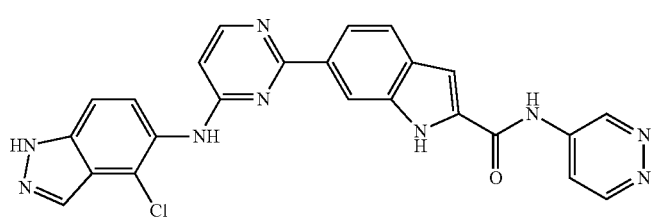 |

-continued

| Serial Number | No. | Compound Structure |
|---|---|---|
| 56. | TDI01243 | 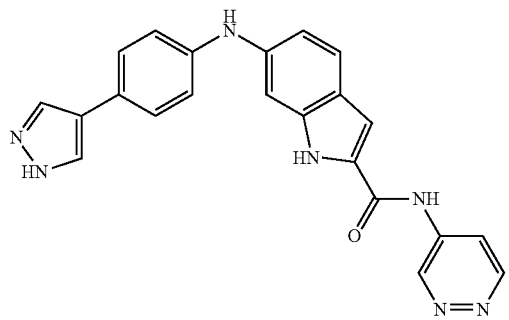 [SMILES: O=C(Nc1ccnnc1)c1cc2ccc(Nc3ccc(-c4cn[nH]c4)cc3)cc2[nH]1] |
| 57. | TDI01244 | 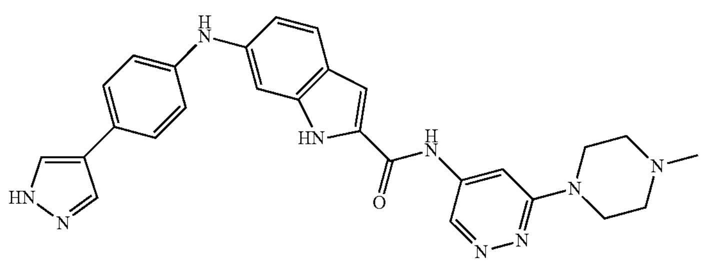 [SMILES: CN1CCN(c2cc(NC(=O)c3cc4ccc(Nc5ccc(-c6cn[nH]c6)cc5)cc4[nH]3)cnn2)CC1] |
| 58. | TDI01245 | 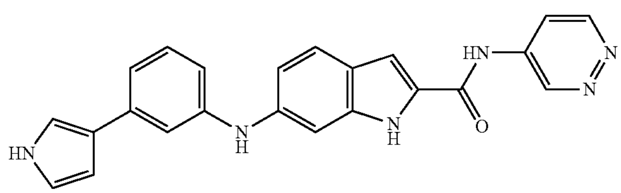 [SMILES: O=C(Nc1ccnnc1)c1cc2ccc(Nc3cccc(-c4cc[nH]c4)c3)cc2[nH]1] |
| 59. | TDI01246 | 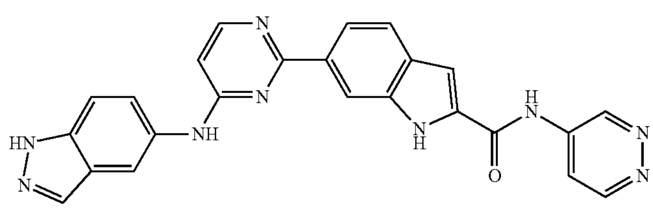 [SMILES: O=C(Nc1ccnnc1)c1cc2ccc(-c3nccc(Nc4ccc5[nH]ncc5c4)n3)cc2[nH]1] |
| 60. | TDI01249 | 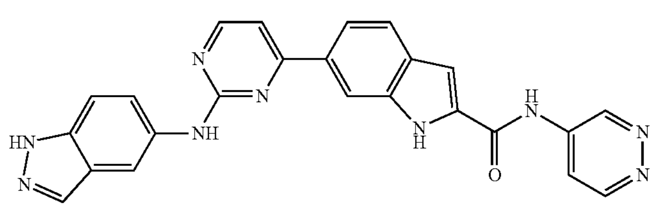 [SMILES: O=C(Nc1ccnnc1)c1cc2ccc(-c3ccnc(Nc4ccc5[nH]ncc5c4)n3)cc2[nH]1] |
| 61. | TDI01250 | 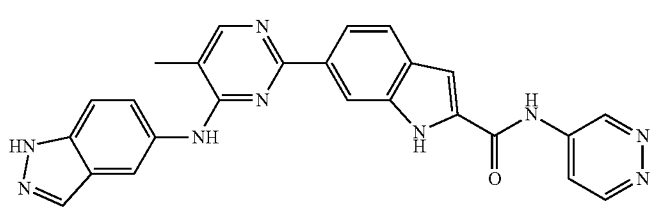 [SMILES: Cc1cnc(-c2ccc3cc(C(=O)Nc4ccnnc4)[nH]c3c2)nc1Nc1ccc2[nH]ncc2c1] |

-continued

| Serial Number | No. | Compound Structure |
|---|---|---|
| 62. | TDI01251 | 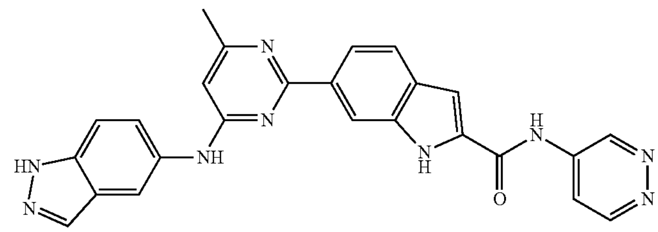 [SMILES: Cc1cc(Nc2ccc3[nH]ncc3c2)nc(-c2ccc3cc(C(=O)Nc4ccnnc4)[nH]c3c2)n1] |
| 63. | TDI01257 | 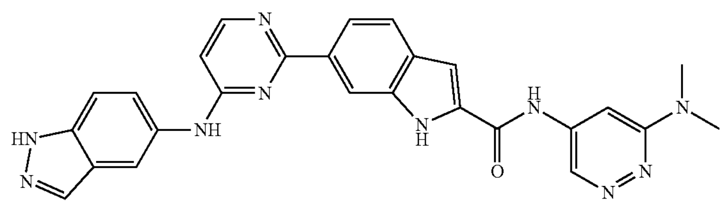 [SMILES: CN(C)c1cc(NC(=O)c2cc3ccc(-c4nccc(Nc5ccc6[nH]ncc6c5)n4)cc3[nH]2)cnn1] |
| 64. | TDI01261 | 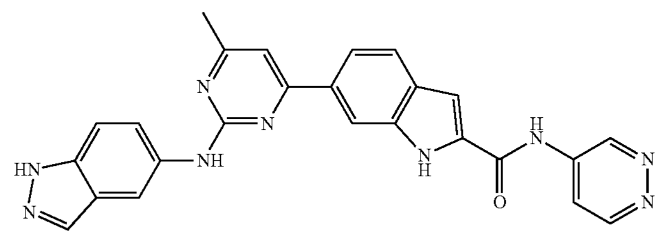 [SMILES: Cc1cc(-c2ccc3cc(C(=O)Nc4ccnnc4)[nH]c3c2)nc(Nc2ccc3[nH]ncc3c2)n1] |
| 65. | TDI01275 | 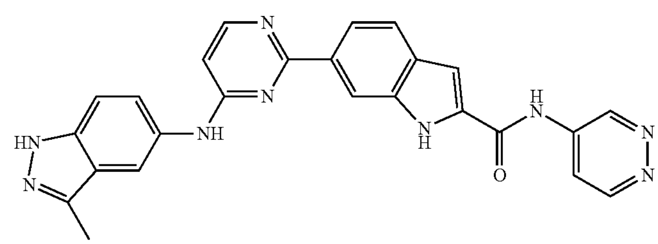 [SMILES: Cc1n[nH]c2ccc(Nc3ccnc(-c4ccc5cc(C(=O)Nc6ccnnc6)[nH]c5c4)n3)cc12] |
| 66. | TDI01276 | 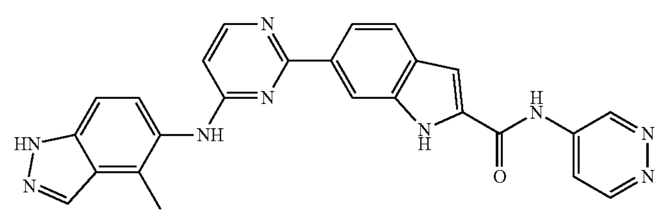 [SMILES: Cc1c(Nc2ccnc(-c3ccc4cc(C(=O)Nc5ccnnc5)[nH]c4c3)n2)ccc2[nH]ncc12] |
| 67. | TDI01277 | 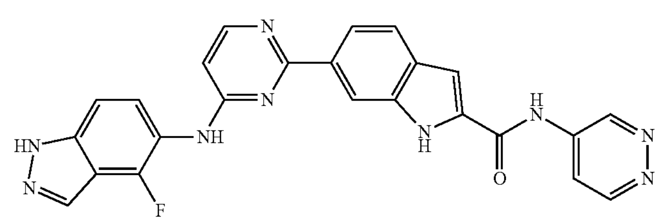 [SMILES: O=C(Nc1ccnnc1)c1cc2ccc(-c3nccc(Nc4ccc5[nH]ncc5c4F)n3)cc2[nH]1] |
| 68. | TDI01278 | 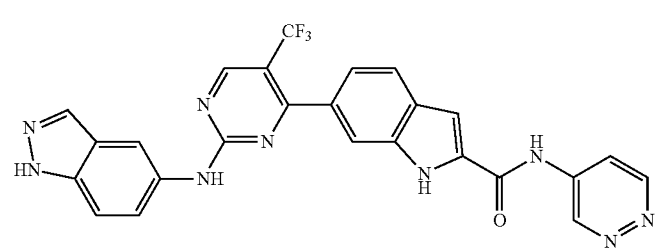 [SMILES: O=C(Nc1ccnnc1)c1cc2ccc(-c3nc(Nc4ccc5[nH]ncc5c4)ncc3C(F)(F)F)cc2[nH]1] |

| Serial Number | No. | Compound Structure |
|---|---|---|
| 69. | TDI01282 | 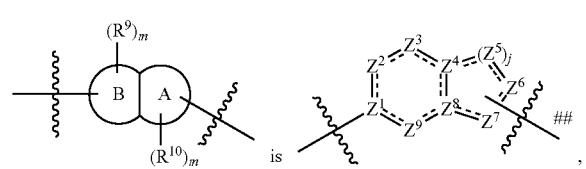 |
| 70. | TDI01314 | 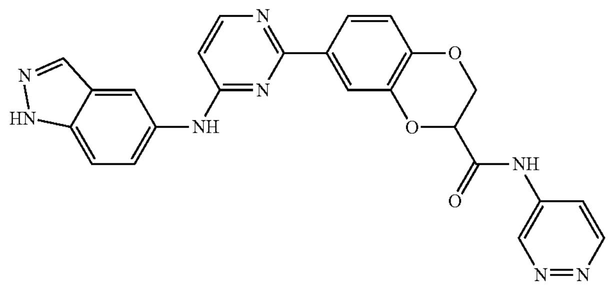 [SMILES: O=C(Nc1ccnnc1)C1COc2ccc(-c3nccc(Nc4ccc5[nH]ncc5c4)n3)cc2O1] |
| 71. | TDI01347 | 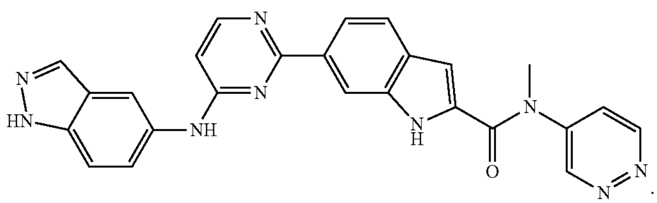 [SMILES: CN(C(=O)c1cc2ccc(-c3nccc(Nc4ccc5[nH]ncc5c4)n3)cc2[nH]1)c1ccnnc1] |

10. A pharmaceutical composition comprising a prophylactically or therapeutically effective amount of the compound according to claim 1 or a pharmaceutically acceptable salt, ester, stereoisomer, N-oxide, or isotopically labeled compound thereof, and a pharmaceutically acceptable carrier.

11. The compound according to claim 3, or a pharmaceutically acceptable salt, ester, stereoisomer, N-oxide, or isotopically labeled compound thereof, wherein

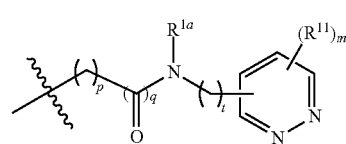

the above group is attached to X at either of the two positions labeled # or ##, and is attached to wherein:

---- represents either a single or a double bond, and the adjacent bonds are not double bonds simultaneously;

$Z^1$, $Z^2$, $Z^3$, $Z^4$, $Z^5$, $Z^6$, $Z^7$, $Z^8$ and $Z^9$, at each occurrence, are each independently selected from the group consisting of C, $CR^9$, $C(R^9)_2$, $CR^{10}$, $C(R^{10})_2$, $C(=O)$, N, $NR^9$, $NR^{10}$, O and S; and j is 0, 1, 2, 3 or 4;

provided that at most two groups among $Z^1$-$Z^9$ are simultaneously $C(=O)$, and the atom attached to X is not a nitrogen atom.

12. The compound according to claim 11, or a pharmaceutically acceptable salt, ester, stereoisomer, N-oxide, or isotopically labeled compound thereof, wherein $Z^1$, $Z^2$, $Z^3$, $Z^4$, $Z^5$, $Z^6$, $Z^7$, $Z^8$ and $Z^9$, at each occurrence, are each independently selected from the group consisting of C, CH, $CCH_3$, $CH_2$, $C(=O)$, N, NH, $NCH_3$, $NCH_2CH_2$—$N(CH_3)_2$, O and S.

13. The compound according to claim 3, or a pharmaceutically acceptable salt, ester, stereoisomer, N-oxide, or isotopically labeled compound thereof, wherein

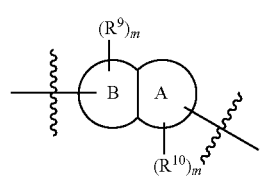

is at the other position,

-continued

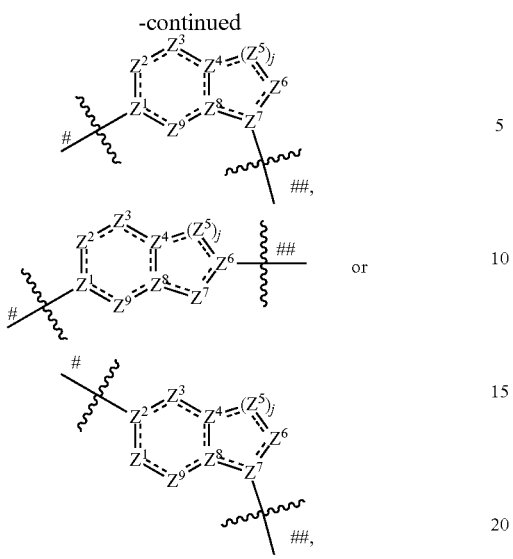

and the above group is attached to X at either of the two positions labeled # or ##, and is attached to

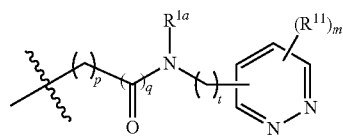

at the other position,
wherein:
---- represents either a single or a double bond, and the adjacent bonds are not double bonds simultaneously;

$Z^1$, $Z^2$, $Z^3$, $Z^4$, $Z^5$, $Z^6$, $Z^7$, $Z^8$ and $Z^9$, at each occurrence, are each independently selected from the group consisting of C, $CR^9$, $C(R^9)_2$, $CR^{10}$, $C(R^{10})_2$, $C(=O)$, N, $NR^9$, $NR^{10}$, O and S; and j is 0, 1, 2, 3 or 4;
provided that at most two groups among $Z^1$-$Z^9$ are simultaneously $C(=O)$, and the atom attached to X is not a nitrogen atom.

14. The compound according to claim 13, or a pharmaceutically acceptable salt, ester, stereoisomer, N-oxide, or isotopically labeled compound thereof, wherein $Z^1$, $Z^2$, $Z^3$, $Z^4$, $Z^5$, $Z^6$, $Z^7$, $Z^8$ and $Z^9$, at each occurrence, are each independently selected from the group consisting of C, CH, $CCH_3$, $CH_2$, $C(=O)$, N, NH, $NCH_3$, $NCH_2CH_2$—$N(CH_3)_2$, O and S.

15. The compound according to claim 3, or a pharmaceutically acceptable salt, ester, stereoisomer, N-oxide, or isotopically labeled compound thereof, wherein

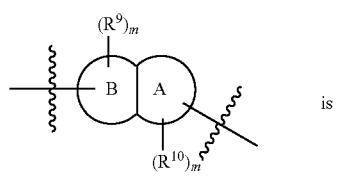

-continued

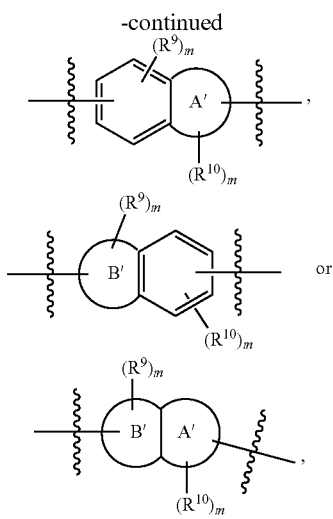

wherein ring A' and ring B' are each independently selected from the group consisting of saturated or partially unsaturated 3- to 10-membered heterocycle and 5- to 14-membered heteroaromatic ring, and at most 2 ring members in the heterocycle are $C(=O)$; provided that when ring B' is a heterocycle containing a nitrogen atom, ring B' is not attached to X via the nitrogen atom.

16. The compound according to claim 15, or a pharmaceutically acceptable salt, ester, stereoisomer, N-oxide, or isotopically labeled compound thereof, wherein

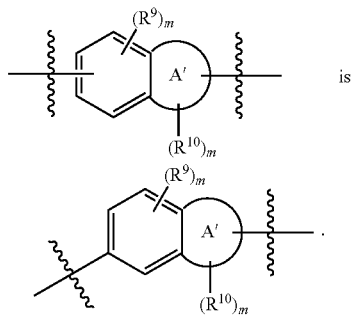

17. The compound according to claim 15, or a pharmaceutically acceptable salt, ester, stereoisomer, N-oxide, or isotopically labeled compound thereof, wherein

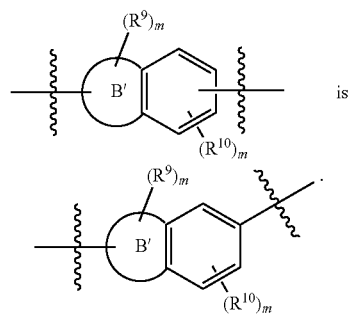

18. The compound according to claim 3, or a pharmaceutically acceptable salt, ester, stereoisomer, N-oxide, or isotopically labeled compound thereof, wherein

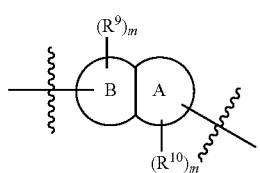
is selected from the group consisting of
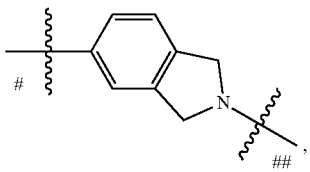
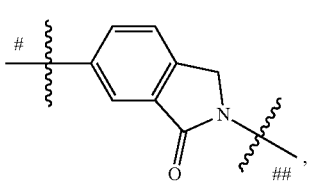
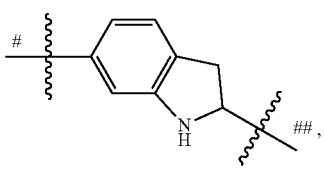
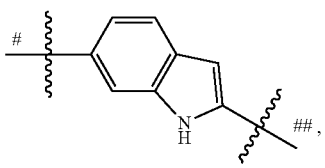
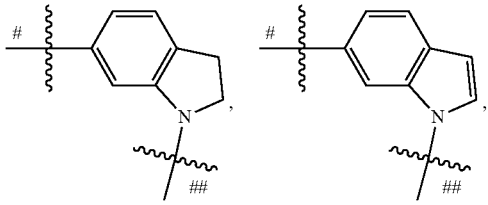
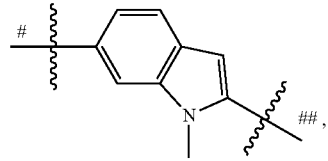
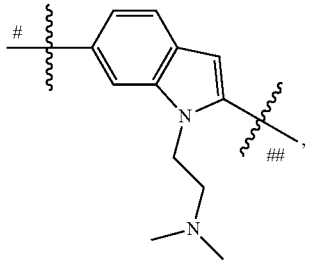
-continued
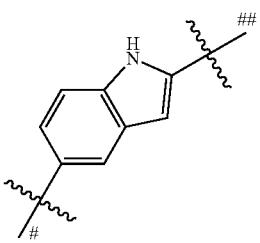

201
-continued
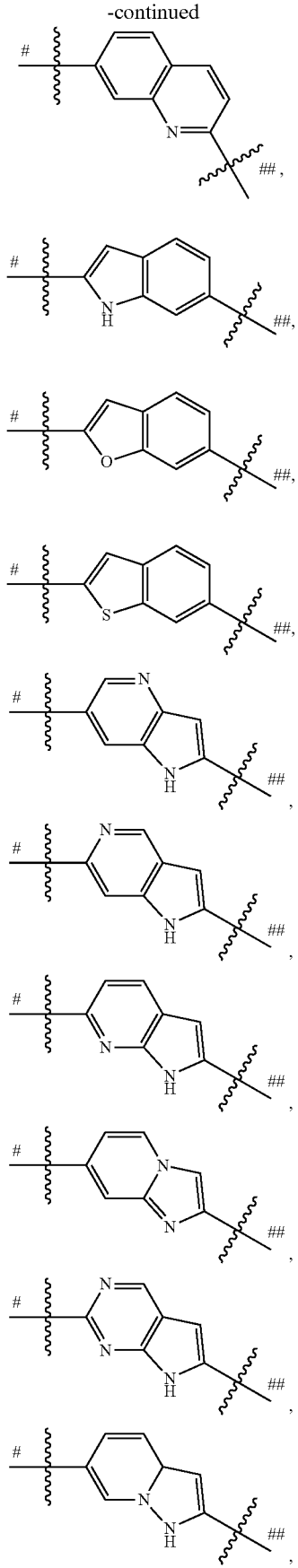
202
-continued
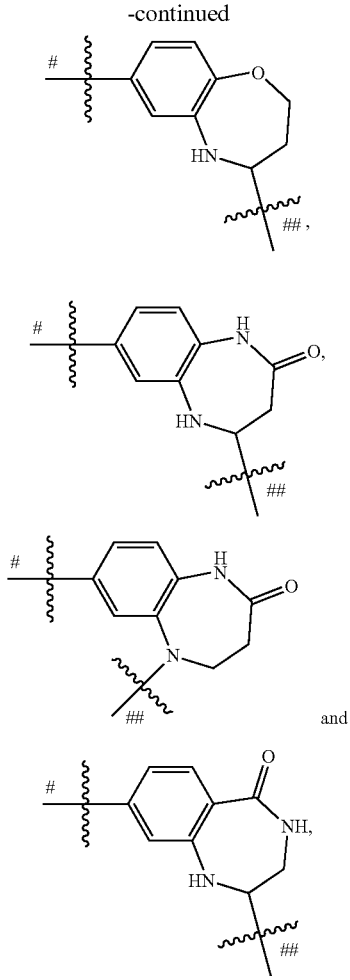
the above group is attached to X at either of the two positions labeled # or ##, and is attached to
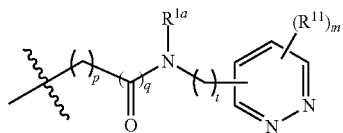
at the other position, provided that the atom attached to X is not a nitrogen atom.
19. The compound according to claim 4, or a pharmaceutically acceptable salt, ester, stereoisomer, N-oxide, or isotopically labeled compound thereof, wherein
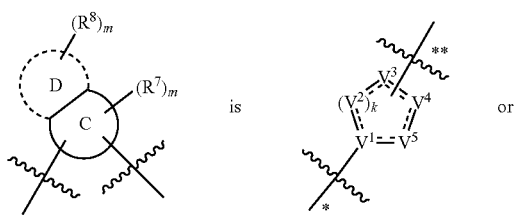

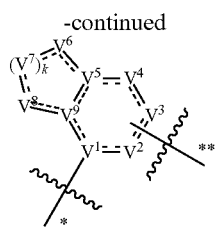

the above group is attached to Y at either of the two positions labeled * or **, and is attached to X at the other position, wherein:
---- represents either a single or a double bond, and the adjacent bonds are not double bonds simultaneously;
$V^1, V^2, V^3, V^4, V^5, V^6, V^7, V^8$ and $V^9$, at each occurrence, are each independently selected from the group consisting of C, $CR^7$, $C(R^7)_2$, $CR^8$, $C(R^8)_2$, $C(=O)$, N, $NR^7$, $NR^8$, O and S; and
k is 0, 1, 2, 3 or 4;
provided that at most two groups among $V^1$-$V^9$ are simultaneously $C(=O)$.

20. The compound according to claim 19, or a pharmaceutically acceptable salt, ester, stereoisomer, N-oxide, or isotopically labeled compound thereof, wherein $V^1$, $V^2$, $V^3$, $V^4$, $V^5$, $V^6$, $V^7$, $V^8$ and $V^9$, at each occurrence, are each independently selected from the group consisting of C, CH, CF, CCN, $CCH_3$, $CCF_3$, $—CO—CH_2CH_2—N(CH_3)_2$, $CH_2$, $C(=O)$, N, NH, $NCH_3$, N-Ph, $—N—CH_2CH_2—N(CH_3)_2$, O and S.

21. The compound according to claim 4, or a pharmaceutically acceptable salt, ester, stereoisomer, N-oxide, or isotopically labeled compound thereof, wherein

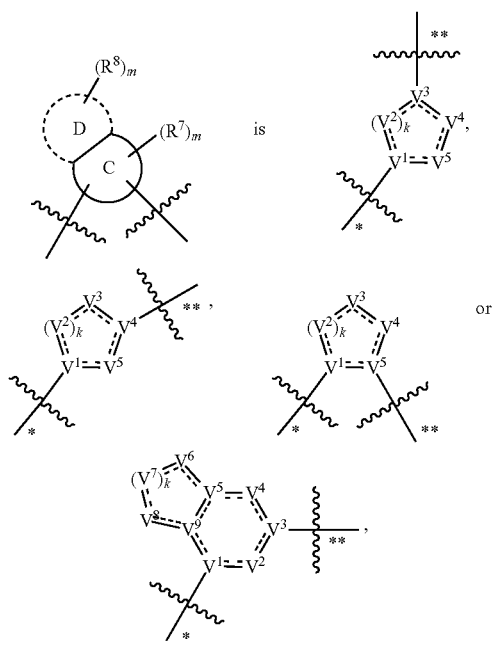

the above group is attached to Y at either of the two positions labeled * or **, and is attached to X at the other position, wherein:
---- represents either a single or a double bond, and the adjacent bonds are not double bonds simultaneously;
$V^1, V^2, V^3, V^4, V^5, V^6, V^7, V^8$ and $V^9$, at each occurrence, are each independently selected from the group consisting of C, $CR^7$, $C(R^7)_2$, $CR^8$, $C(R^8)_2$, $C(=O)$, N, $NR^7$, $NR^8$, O and S; and
k is 0, 1, 2, 3 or 4;
provided that at most two groups among $V^1$-$V^9$ are simultaneously $C(=O)$.

22. The compound according to claim 21, or a pharmaceutically acceptable salt, ester, stereoisomer, N-oxide, or isotopically labeled compound thereof, wherein $V^1$, $V^2$, $V^3$, $V^4$, $V^5$, $V^6$, $V^7$, $V^8$ and $V^9$, at each occurrence, are each independently selected from the group consisting of C, CH, CF, CCN, $CCH_3$, $CCF_3$, $—CO—CH_2CH_2—N(CH_3)_2$, $CH_2$, $C(=O)$, N, NH, $NCH_3$, N-Ph, $—N—CH_2CH_2—N(CH_3)_2$, O and S.

23. The composition according to claim 4, or a pharmaceutically acceptable salt, ester, stereoisomer, N-oxide, or isotopically labeled compound thereof, wherein

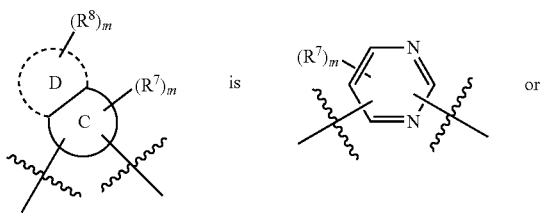

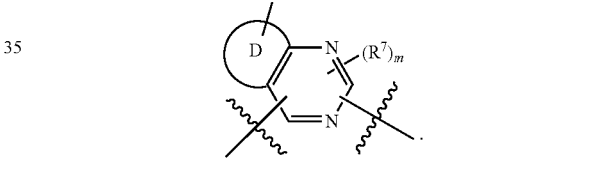

24. The composition according to claim 4, or a pharmaceutically acceptable salt, ester, stereoisomer, N-oxide, or isotopically labeled compound thereof, wherein

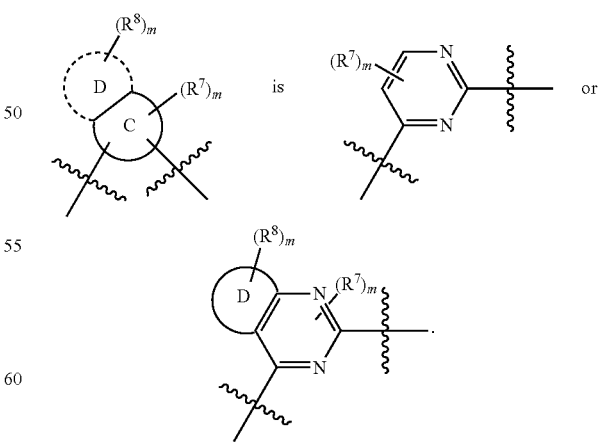

25. The composition according to claim 4, or a pharmaceutically acceptable salt, ester, stereoisomer, N-oxide, or isotopically labeled compound thereof, wherein

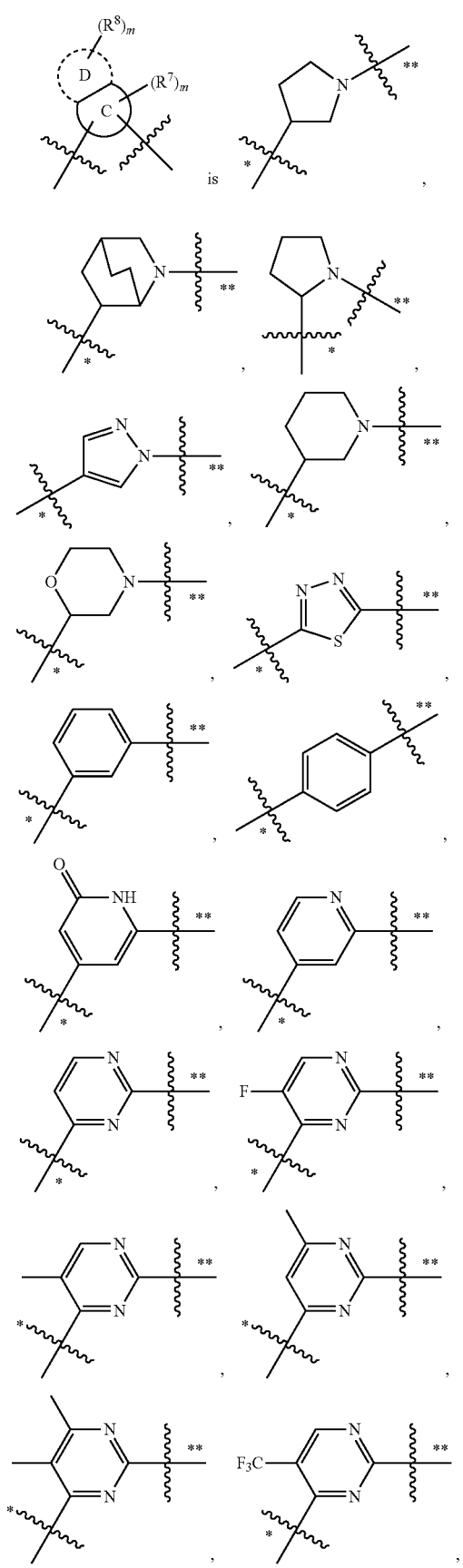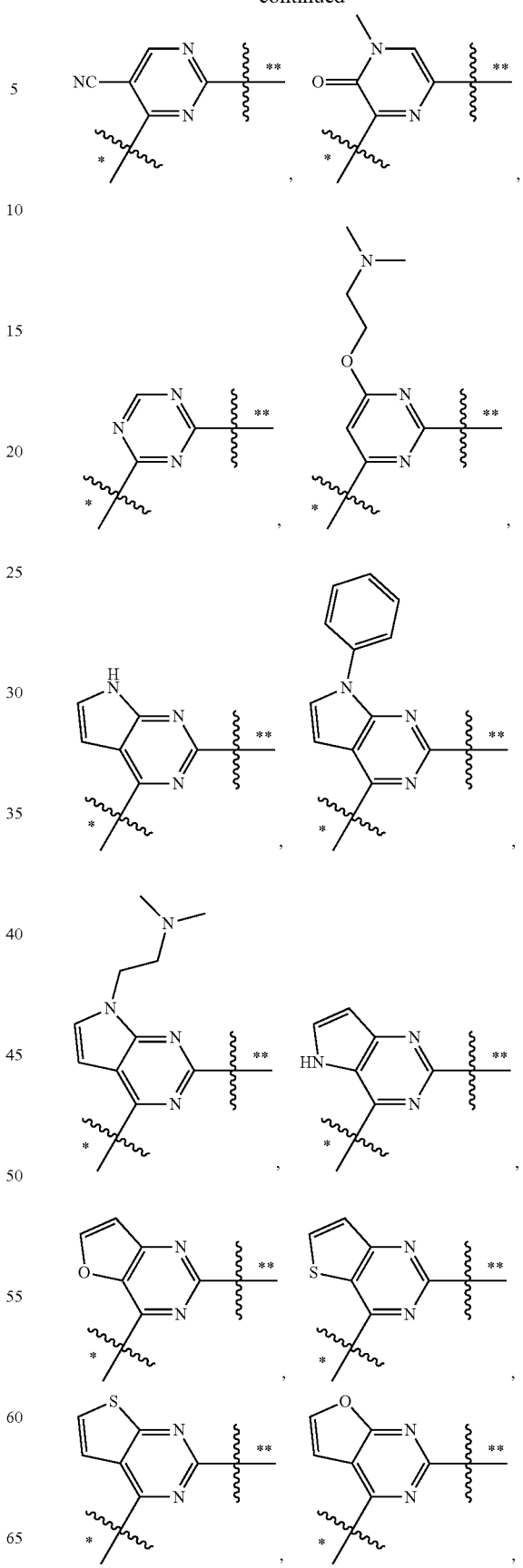

-continued

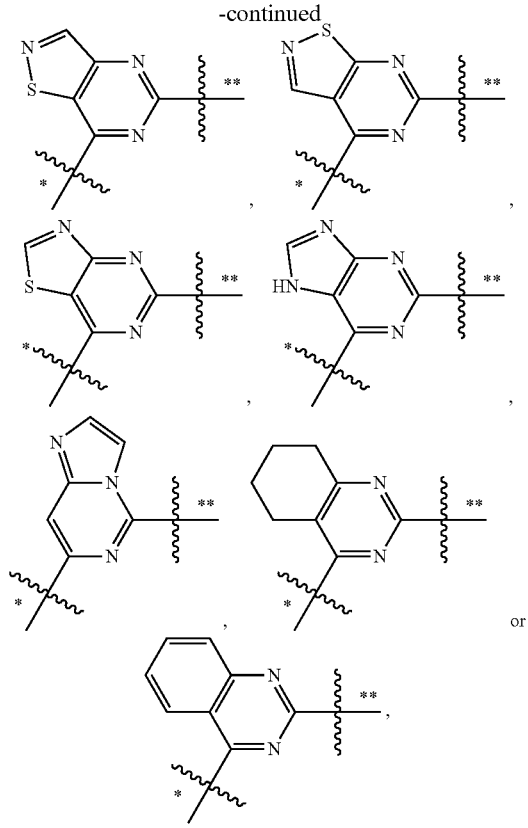

the above group is attached to Y at either of the two positions labeled * or **, and is attached to X at the other position.

26. The composition according to claim 5, or a pharmaceutically acceptable salt, ester, stereoisomer, N-oxide, or isotopically labeled compound thereof, wherein ring E is

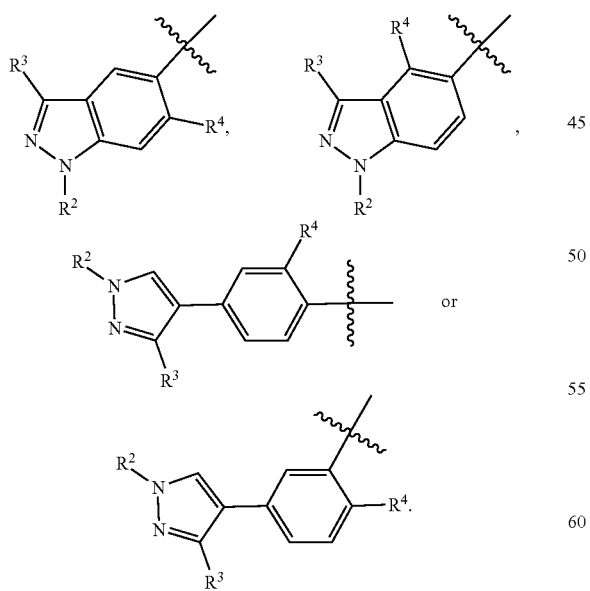

27. The composition according to claim 5, or a pharmaceutically acceptable salt, ester, stereoisomer, N-oxide, or isotopically labeled compound thereof, wherein ring E is

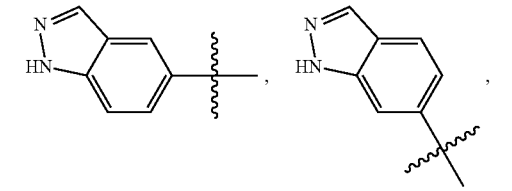

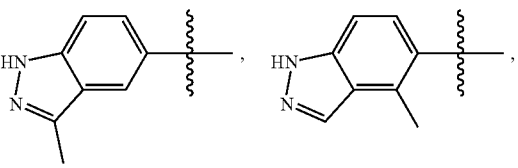

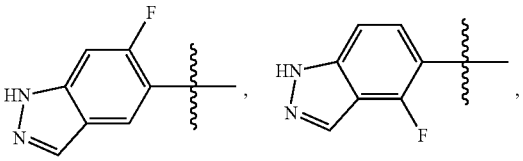

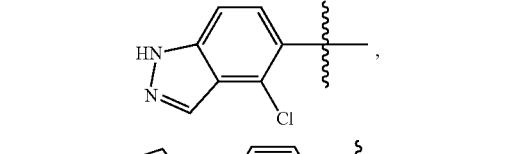

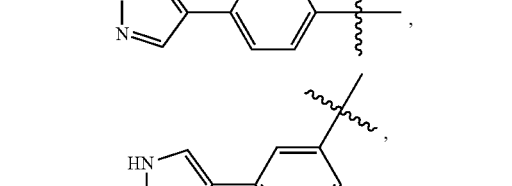

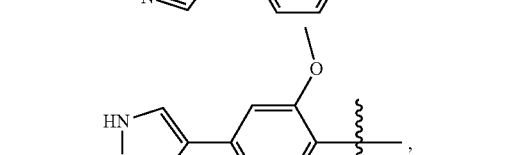

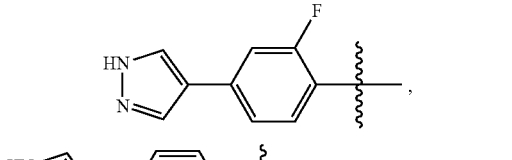

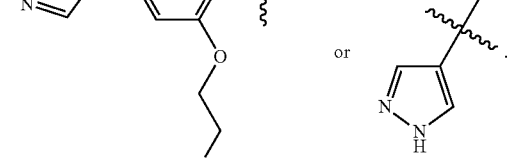

28. The composition according to claim 6, or a pharmaceutically acceptable salt, ester, stereoisomer, N-oxide, or isotopically labeled compound thereof, wherein

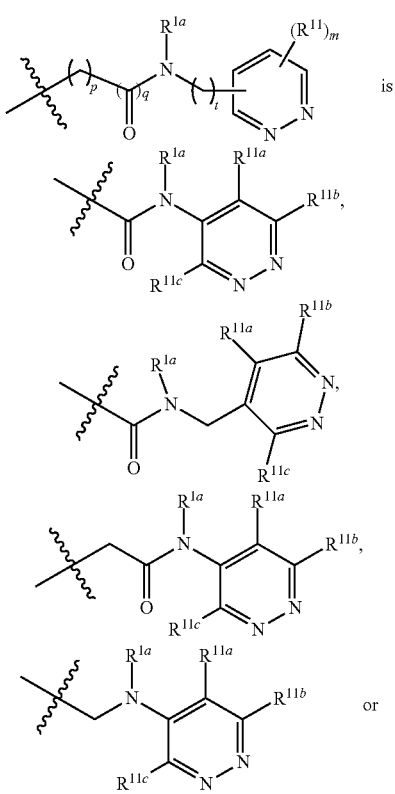

is

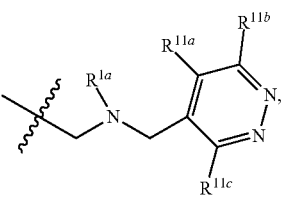

wherein $R^{11a}$, $R^{11b}$ and $R^{1c}$ are each independently selected from the group consisting of H, halogen, amino, cyano, nitro, $C_{1-6}$ alkyl, $C_{2-6}$ alkenyl, $C_{2-6}$ alkynyl, $C_{3-10}$ cyclic hydrocarbyl, 3- to 10-membered heterocyclyl, $C_{6-10}$ aryl, 5- to 14-membered heteroaryl, $C_{6-12}$ aralkyl, —C(=O)$R^5$, —OC(=O)$R^5$, —C(=O)O$R^5$, —O$R^5$, —S$R^5$, —S(=O)$R^5$, —S(=O)$_2R^5$, —S(=O)$_2$N$R^5R^6$, —N$R^5R^6$, —C(=O)N$R^5R^6$, —N$R^5$—C(=O)$R^6$, —N$R^5$—C(=O)O$R^6$, —N$R^5$—S(=O)$_2$—$R^6$, —N$R^5$—C(=O)—N$R^5R^6$, —$C_{1-6}$ alkylene-N$R^5R^6$ and —O—$C_{1-6}$ alkylene-N$R^5R^6$;

alternatively, $R^{11a}$ and $R^{11b}$ together with the carbon atoms to which they are attached form $C_{4-10}$ cyclic hydrocarbyl, 4- to 10-membered heterocyclyl, $C_{6-10}$ aryl, or 5- to 14-membered heteroaryl.

29. The pharmaceutical composition according to claim 10, wherein said pharmaceutical composition is in the form of a solid, semi-solid, liquid, or gas preparation.

* * * * *